(12) United States Patent  
Duggan et al.

(10) Patent No.: US 11,046,651 B2  
(45) Date of Patent: Jun. 29, 2021

(54) PIPERAZINE SUBSTITUTED AZAPINE DERIVATIVES AND USES THEREOF

(71) Applicant: Alairion, Inc., Belmont, MA (US)

(72) Inventors: Mark E. Duggan, Tequesta, FL (US); Dale M. Edgar, Augustine, FL (US)

(73) Assignee: ALAIRION, INC., Belmont, MA (US)

( * ) Notice: Subject to any disclaimer, the term of this patent is extended or adjusted under 35 U.S.C. 154(b) by 0 days.

(21) Appl. No.: 17/075,468

(22) Filed: Oct. 20, 2020

(65) Prior Publication Data

US 2021/0114989 A1 Apr. 22, 2021

Related U.S. Application Data

(60) Provisional application No. 62/923,762, filed on Oct. 21, 2019, provisional application No. 63/002,096, filed on Mar. 30, 2020.

(51) Int. Cl.
| | |
|---|---|
| *A61K 31/55* | (2006.01) |
| *A61K 31/551* | (2006.01) |
| *A61K 31/553* | (2006.01) |
| *A61K 31/554* | (2006.01) |
| *A61P 43/00* | (2006.01) |

(Continued)

(52) U.S. Cl.
CPC ......... *C07D 223/20* (2013.01); *C07D 267/18* (2013.01)

(58) Field of Classification Search
CPC ....... A61P 43/00; A61K 31/55; A61K 31/551; A61K 31/553; A61K 31/554; C07D 417/04; C07D 417/14; C07D 413/04; C07D 413/14; C07D 403/04; C07D 403/14; C07D 281/16; C07D 267/20; C07D 243/38; C07D 223/20
See application file for complete search history.

(56) References Cited

U.S. PATENT DOCUMENTS

| 5,344,828 A | 9/1994 | Sawanishi et al. |
| 7,317,026 B2 | 1/2008 | Edgar et al. |

(Continued)

FOREIGN PATENT DOCUMENTS

| JP | H03184963 A | 8/1991 |
| JP | H05163245 A | 6/1993 |

(Continued)

OTHER PUBLICATIONS

Carley, D. W., "Efficacy of Mirtazapine in Obstructive Sleep Apnea Syndrome", Sleep, 2007, vol. 30, No. 1, p. 35-41.

(Continued)

*Primary Examiner* — Brenda L Coleman

(74) *Attorney, Agent, or Firm* — Seed IP Law Group LLP

(57) ABSTRACT

The present disclosure relates to compounds of Formula (I) and (II):

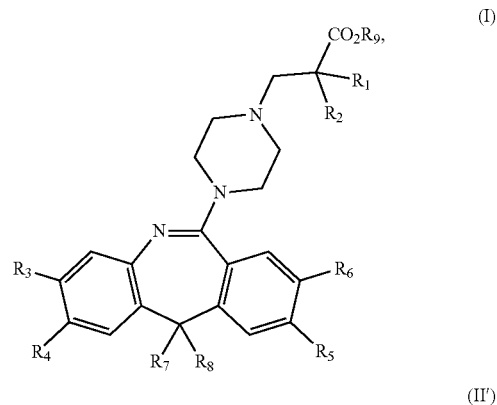

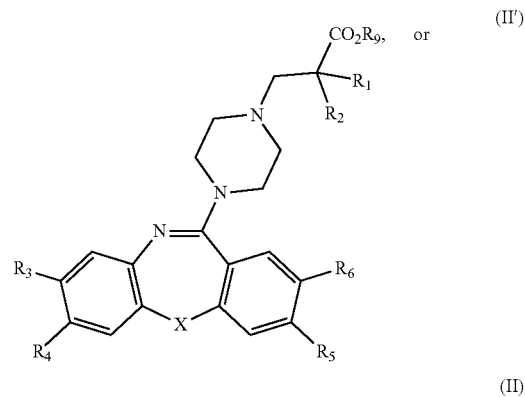

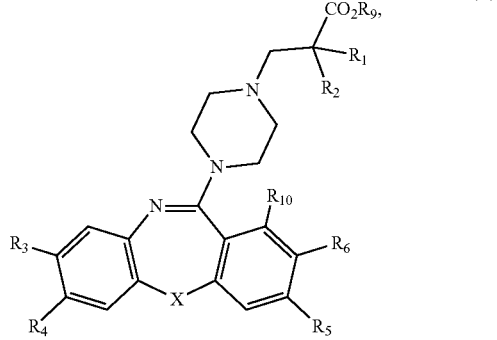

and to their prodrugs, pharmaceutically acceptable salts, pharmaceutical compositions, methods of use, and methods for their preparation. The compounds disclosed herein are useful for modulating H1 and 5-$HT_{2A}$ receptors and are to be used in the treatment of sleep disorders, such as sleep fragmentation, disturbed sleep/arousals, and arousal threshold.

22 Claims, 5 Drawing Sheets

(51) Int. Cl.

| | |
|---|---|
| *C07D 223/20* | (2006.01) |
| *C07D 243/38* | (2006.01) |
| *C07D 267/20* | (2006.01) |
| *C07D 281/16* | (2006.01) |
| *C07D 403/04* | (2006.01) |
| *C07D 403/14* | (2006.01) |
| *C07D 413/04* | (2006.01) |
| *C07D 413/14* | (2006.01) |
| *C07D 417/04* | (2006.01) |
| *C07D 417/14* | (2006.01) |
| *C07D 267/18* | (2006.01) |

(56) References Cited

U.S. PATENT DOCUMENTS

| | | | |
|---|---|---|---|
| 7,563,785 B2 * | 7/2009 | Edgar | A61K 31/554 514/211.13 |
| 7,592,333 B2 | 9/2009 | Edgar et al. | |
| 2006/0094705 A1 | 5/2006 | Edgar et al. | |
| 2008/0090805 A1 | 4/2008 | Olsson et al. | |
| 2012/0129834 A1 * | 5/2012 | Hughes | A61P 25/28 514/211.13 |

FOREIGN PATENT DOCUMENTS

| | | |
|---|---|---|
| WO | WO 2004/026030 A2 | 4/2004 |
| WO | WO 2004/056182 A1 | 7/2004 |
| WO | WO 2005/063254 A2 | 7/2005 |
| WO | WO 2006/088786 A2 | 8/2006 |
| WO | WO 2006/107948 A2 | 10/2006 |
| WO | WO 2007/047737 A1 | 4/2007 |
| WO | WO 2007/047776 A1 | 4/2007 |
| WO | WO 2007/053618 A1 | 5/2007 |
| WO | WO 2008/021463 A2 | 2/2008 |
| WO | WO 2008/118141 A2 | 10/2008 |
| WO | WO 2009/073154 A1 | 6/2009 |
| WO | WO 2014/116684 A1 | 7/2014 |
| WO | WO 2019/042889 A1 | 3/2019 |
| WO | WO 2019/245047 A1 | 12/2019 |

OTHER PUBLICATIONS

Edgar et al., "Modafinil Induces Wakefulness Without Intensifying Motor Activity or Subsequent Rebound Hypersomnolence in the Rat", Journal of Pharmacology & Experimental Therapeutics, 1997, vol. 283, p. 757-769.

Edgar et al., "CCD-3693: An Orally Bioavailable Analog of the Endogenous Neuroactive Steroid, Pregnanolone, Demonstrates Potent Sedative Hypnotic Actions in the Rat", Journal of Pharmacology & Experimental Therapeutics, 1997, vol. 282, p. 420-429.

Edgar et al., "Triazolam-induced sleep in the rat: influence of prior sleep, circadian time, and light/ dark cycles", Psychopharmacology 1991, vol. 105, p. 374-380.

Gilmour et al., "In vitro characterisation of the novel positive allosteric modulators of the mGlu5 receptor, LSN2463359 and LSN2814617, and their effects on sleep architecture and operant responding in the rat", Neuropharmacology 2012, vol. 64, p. 224-239.

Marek, G., et al. "Synergistic Action of 5-HT2A Antagonists and Selective Serotonin Reuptake Inhibitors in Neuropsychiatric Disorders", Neuropsychopharmacology, 2003, vol. 28, p. 402-412.

McCarthy et al., "REM sleep homeostasis in the absence of REM sleep: Effects of antidepressants", Neuropharmacology, 2016, vol. 108, p. 415-425.

Olive et al., "Compensatory Sleep Responses to Wakefulness Induced by the Dopamine Autoreceptor Antagonist (-)DS121", Journal of Pharmacology & Experimental Therapeutics, 1998, vol. 285, No. 3, p. 1073-1083.

Phillips et al. "Differential effects of NMDA antagonists on high frequency and gamma EEG oscillations in a neurodevelopmental model of schizophrenia", Neuropharmacology, 2012, vol. 62, p. 1359-1370.

Seidel et al., "Alpha-2 Adrenergic Modulation of Sleep: Time-of-Day-Dependent Pharmacodynamic Profiles of Dexmedetomidine and Clonidine in the Rat", Journal of Pharmacology & Experimental Therapeutics, 1995, vol. 275, No. 1, p. 263-273.

Van Gelder et al. "Real-Time Automated Sleep Scoring: Validation of a Microcomputer-Based System for Mice", Sleep 1991, vol. 14, Issue 1, p. 48-55.

* cited by examiner

PIPERAZINE SUBSTITUTED AZAPINE DERIVATIVES AND USES THEREOF

RELATED APPLICATIONS

This application claims priority to, and the benefit of, U.S. Application Nos. 62/923,762, filed Oct. 21, 2019, and 63/002,096, filed Mar. 30, 2020, the entire contents of each of which are incorporated herein by reference.

FIELD OF THE DISCLOSURE

The present disclosure relates to piperazine substituted azapine derivatives, prodrugs, and pharmaceutically acceptable salts thereof, which may possess dual acting H1 inverse agonist and 5-$HT_{2A}$ antagonist (H1/5-$HT_{2A}$) activity and are accordingly useful in methods of treatment of the human or animal body. The present disclosure also relates to processes for the preparation of these compounds, to pharmaceutical compositions comprising them and to their use in the treatment of sleep disorders, such as sleep fragmentation, disturbed sleep/arousals, and arousal threshold.

BACKGROUND

Breakthroughs in the field of sleep disorders research has brought about widespread scientific and popular appreciation for the health benefits of restful and restorative sleep. Sleep is now recognized, along with diet and exercise, as one of the three pillars of good health. The overall prevalence of current or previous sleep disorders in adults is estimated at 52.4% of the population. Almost two-thirds (i.e. 64%) of the population report sleep difficulties at least a few times a week (National Sleep Foundation, "2012 Sleep in America" Poll, 2012). The International Classification of Sleep Disorders distinguishes over 80 different disorders and each can have profound health and economic implications. Whilst the daytime impairment caused by poor sleep has long been appreciated, poor sleep also has cascading negative impact upon alertness, cognition, learning and memory, vigilance, performance, and a broad range of co-morbid health conditions including acute and chronic pain and pain disorders, psychiatric conditions, neurodegenerative disease, developmental disorders, metabolic disease and diabetes, obesity, cardiovascular disease, immunological disorders, and many other medical conditions.

Sleep disorder subjects are now readily segmented into a broader range of sleep disorder categories and conditions that are more amenable to new and tailored therapies that hold promise for delivering better subject outcomes. Objective measures of sleep can play a vital role toward understanding poor sleep and its amelioration. Despite sleeping 7-8 hours or more, subjects whose sleep is frequently interrupted or "fragmented", suffer all the consequences of sleep deprivation. Indeed sleep consolidation is necessary for the restorative physiological benefits of sleep to be realized and comorbid conditions.

Pharmacological options are limited for the treatment of sleep fragmentation. In response to the lack of pharmacological options, there exists an urgent unmet clinical need to develop new methods of treating sleep fragmentation, including pharmacological methods of treatment.

SUMMARY

In one aspect, the present disclosure provides, inter alia, a compound of Formula (I), (II), or (II'):

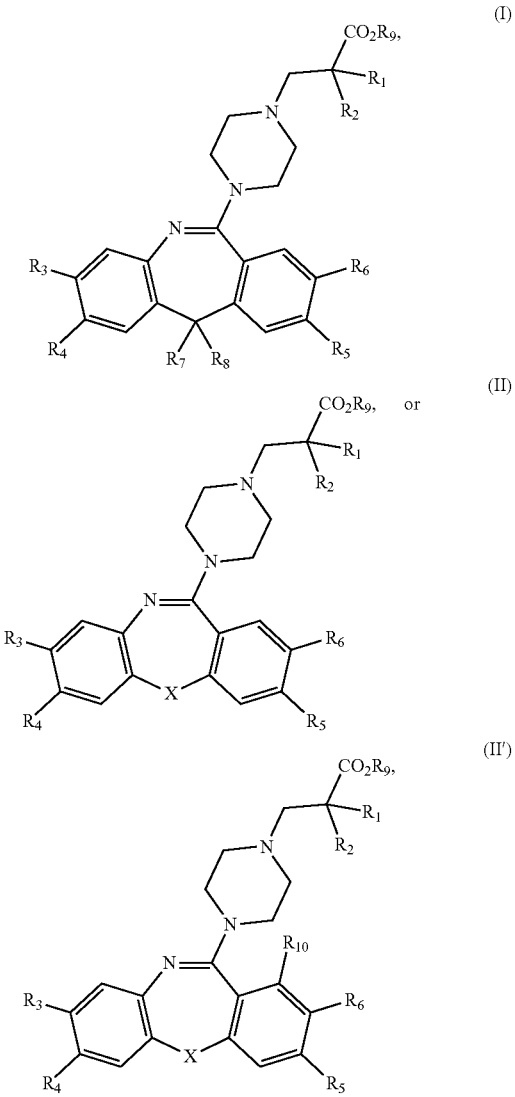

or a prodrug, solvate, or pharmaceutically acceptable salt thereof.

In one aspect, the present disclosure provides a compound obtainable by, or obtained by, a method for preparing a compound as described herein (e.g., a method comprising one or more steps described in Schemes 1-3).

In one aspect, the present disclosure provides a pharmaceutical composition comprising a compound of the present disclosure, or a pharmaceutically acceptable salt thereof, and a pharmaceutically acceptable diluent or carrier.

In one aspect, the present disclosure provides an intermediate as described herein, being suitable for use in a method for preparing a compound as described herein (e.g., the intermediate is selected from the intermediates described in the synthesis of Examples 1-24).

In one aspect, the present disclosure provides a method of modulating H1/5-$HT_{2A}$ activity (e.g., in vitro or in vivo), comprising contacting a cell with an effective amount of a compound of the present disclosure or a pharmaceutically acceptable salt thereof. In one aspect, the present disclosure provides a method of treating or preventing a disease or disorder disclosed herein in a subject in need thereof, by administering to the subject a therapeutically effective amount of a compound of the present disclosure or a pharmaceutically acceptable salt thereof, or a pharmaceutical composition of the present disclosure.

In one aspect, the present disclosure provides a method of treating a disease or disorder disclosed herein in a subject in need thereof, by administering to the subject a therapeutically effective amount of a compound of the present disclosure or a pharmaceutically acceptable salt thereof, or a pharmaceutical composition of the present disclosure.

In one aspect, the present disclosure provides a compound of the present disclosure or a pharmaceutically acceptable salt thereof for use in modulating H1/5-HT$_{2A}$ activity (e.g., in vitro or in vivo). In one aspect, the present disclosure provides a compound of the present disclosure or a pharmaceutically acceptable salt thereof for use in treating or preventing a disease or disorder disclosed herein.

In one aspect, the present disclosure provides a compound of the present disclosure or a pharmaceutically acceptable salt thereof for use in treating a disease or disorder disclosed herein.

In one aspect, the present disclosure provides use of a compound of the present disclosure or a pharmaceutically acceptable salt thereof in the manufacture of a medicament for modulating H1/5-HT$_{2A}$ activity (e.g., in vitro or in vivo).

In one aspect, the present disclosure provides use of a compound of the present disclosure or a pharmaceutically acceptable salt thereof in the manufacture of a medicament for treating or preventing a disease or disorder disclosed herein.

In one aspect, the present disclosure provides use of a compound of the present disclosure or a pharmaceutically acceptable salt thereof in the manufacture of a medicament for treating a disease or disorder disclosed herein.

In one aspect, the disease or disorder to be treated is a sleep disorder.

In some embodiments, the sleep disorder is increased disturbed sleep, increased sleep fragmentation, increased arousals, or decreased arousal threshold.

In some embodiments, the sleep disorder is cause by or co-morbid with a medical condition, wherein the medical condition causes or worsens the sleep disorder.

In some embodiments, the sleep disorder is caused by a medical condition, wherein the medical condition causes or worsens the sleep disorder.

In some embodiments, the sleep disorder is co-morbid with a medical condition, wherein the medical condition causes or worsens the sleep disorder.

In one aspect, the present disclosure provides a method of preparing a compound of the present disclosure.

In one aspect, the present disclosure provides a method of preparing a compound, comprising one or more steps described herein.

Unless otherwise defined, all technical and scientific terms used herein have the same meaning as commonly understood by one of ordinary skill in the art to which this disclosure belongs. In the specification, the singular forms also include the plural unless the context clearly dictates otherwise. Although methods and materials similar or equivalent to those described herein can be used in the practice or testing of the present disclosure, suitable methods and materials are described below. All publications, patent applications, patents and other references mentioned herein are incorporated by reference. The references cited herein are not admitted to be prior art to the claimed invention. In the case of conflict, the present specification, including definitions, will control. In addition, the materials, methods and examples are illustrative only and are not intended to be limiting. In the case of conflict between the chemical structures and names of the compounds disclosed herein, the chemical structures will control.

Other features and advantages of the disclosure will be apparent from the following detailed description and claims.

DETAILED DESCRIPTION

Figure 1:
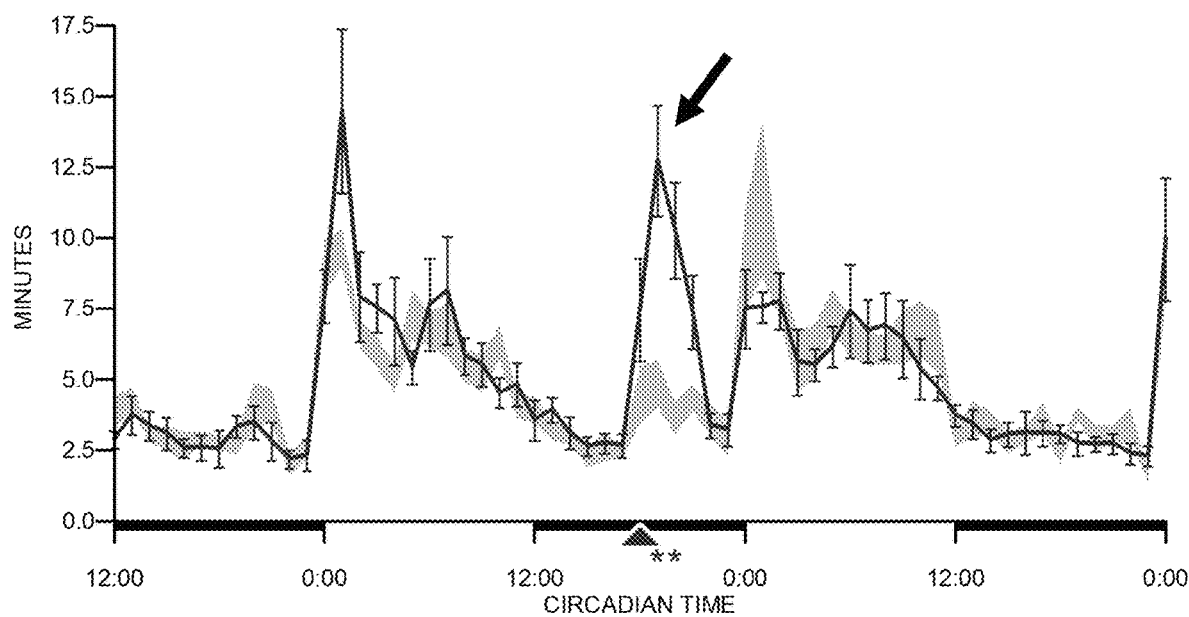
FIG. 1 depicts average aligned sleep bout each hour after administration of compound 8, wherein the thin line depicts compound 8 administration at 10 mg/kg PO (CT-18, n=9), and the thick line depicts administration of the control, methylcellulose, at 1 mL/kg PO (CT-18, n=10).

Compounds described herein are generally designed to modulate H1/5-HT$_{2A}$ function, and therefore act as H1/5-

HT$_{2A}$ receptor antagonists for the treatment and prevention of sleep disorders in a subject. Modulation, as used herein, refers to dual acting H1 inverse agonist and 5-HT$_{2A}$ antagonist activity.

A compound as described herein acts, in certain embodiments, as a dual acting H1 inverse agonist and 5-HT$_{2A}$ antagonist, e.g., effecting the H1/5-HT$_{2A}$ receptors in either a positive or negative manner.

5-HT$_2$ receptors are a subclass of serotonin receptors, which are a group of G protein-coupled receptors and ligand-gated ion channels. The 5-HT$_{2A}$ receptor, found in the central nervous system, mediates excitatory neurotransmission. A 5-HT$_{2A}$ antagonist blocks the excitatory neurotransmissions. Without wishing to be bound by theory, blocking excitatory neurotransmission may be associated with promoting better sleep (e.g., treating a sleep disorder). H1 receptors, which are G protein-coupled receptors, are known to induce wakefulness upon agonism. Without wishing to be bound by theory, H1 inverse agonists may induce sleepiness (e.g., treat a sleep disorder).

The present disclosure is directed to compounds that are especially well suited to treat sleep disorders characterized in whole or in part by sleep fragmentation.

Accordingly, the compounds and pharmaceutical compositions provided herein find use as therapeutics for preventing or treating sleep disorders in subjects such as mammals including humans and non-human mammals. The compounds and pharmaceutical compositions provided herein find use as therapeutics for treating sleep disorders in subjects such as mammals including humans and non-human mammals. The present disclosure includes within its scope, and extends to, the recited methods of treatment, as well as to the compounds for such methods, and to the use of such compounds for the preparation of medicaments useful for such methods.

The disclosure relates to compounds useful for the modulation of H1/5-HT$_{2A}$. In particular, compounds with improved physicochemical, pharmacological and pharmaceutical properties to existing H1/5-HT$_{2A}$-modulating compounds are desired.

In some embodiments, the present disclosure provides a method of modulating H1/5-HT$_{2A}$ function (e.g., dual acting H1 inverse agonist and 5-HT$_{2A}$ antagonist activity, e.g., in vitro or in vivo), comprising contacting a cell with an effective amount of a compound of the present disclosure or a pharmaceutically acceptable salt thereof. In some embodiments, the present disclosure provides a method of alleviating a symptom of, treating or preventing a disease or disorder disclosed herein in a subject in need thereof, by administering to the subject a therapeutically effective amount of a compound of the present disclosure or a pharmaceutically acceptable salt thereof, or a pharmaceutical composition of the present disclosure.

Definitions

Unless otherwise stated, the following terms used in the specification and claims have the following meanings set out below.

As used herein, "alkyl", "$C_1$, $C_2$, $C_3$, $C_4$, $C_5$ or $C_6$ alkyl" or "$C_1$-$C_6$ alkyl" is intended to include $C_1$, $C_2$, $C_3$, $C_4$, $C_5$ or $C_6$ straight chain (linear) saturated aliphatic hydrocarbon groups and $C_2$, $C_3$, $C_4$, $C_5$ or $C_6$ branched saturated aliphatic hydrocarbon groups. For example, $C_1$-$C_6$ alkyl is intends to include $C_1$, $C_2$, $C_3$, $C_4$, $C_5$ and $C_6$ alkyl groups. Examples of alkyl include, moieties having from one to six carbon atoms, such as, but not limited to, methyl, ethyl, n-propyl, i-propyl, n-butyl, s-butyl, t-butyl, n-pentyl, i-pentyl, or n-hexyl. In some embodiments, a straight chain or branched alkyl has six or fewer carbon atoms (e.g., $C_1$-$C_6$ for straight chain, $C_3$-$C_6$ for branched chain), and in another embodiment, a straight chain or branched alkyl has four or fewer carbon atoms.

As used herein, the term "optionally substituted alkyl" refers to unsubstituted alkyl or alkyl having designated substituents replacing one or more hydrogen atoms on one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulphhydryl, alkylthio, arylthio, thiocarboxylate, sulphates, alkylsulphinyl, sulphonato, sulphamoyl, sulphonamido, nitro, trifluoromethyl, cyano, azido, heterocyclyl, alkylaryl, or an aromatic or heteroaromatic moiety.

As used herein, the term "alkenyl" includes unsaturated aliphatic groups analogous in length and possible substitution to the alkyls described above, but that contain at least one double bond. For example, the term "alkenyl" includes straight chain alkenyl groups (e.g., ethenyl, propenyl, butenyl, pentenyl, hexenyl, heptenyl, octenyl, nonenyl, decenyl), and branched alkenyl groups. In certain embodiments, a straight chain or branched alkenyl group has six or fewer carbon atoms in its backbone (e.g., $C_2$-$C_6$ for straight chain, $C_3$-$C_6$ for branched chain). The term "$C_2$-$C_6$" includes alkenyl groups containing two to six carbon atoms. The term "$C_3$-$C_6$" includes alkenyl groups containing three to six carbon atoms.

As used herein, the term "optionally substituted alkenyl" refers to unsubstituted alkenyl or alkenyl having designated substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulphhydryl, alkylthio, arylthio, thiocarboxylate, sulphates, alkylsulphinyl, sulphonato, sulphamoyl, sulphonamido, nitro, trifluoromethyl, cyano, heterocyclyl, alkylaryl, or an aromatic or heteroaromatic moiety.

As used herein, the term "alkynyl" includes unsaturated aliphatic groups analogous in length and possible substitution to the alkyls described above, but which contain at least one triple bond. For example, "alkynyl" includes straight chain alkynyl groups (e.g., ethynyl, propynyl, butynyl, pentynyl, hexynyl, heptynyl, octynyl, nonynyl, decynyl), and branched alkynyl groups. In certain embodiments, a straight chain or branched alkynyl group has six or fewer carbon atoms in its backbone (e.g., $C_2$-$C_6$ for straight chain, $C_3$-$C_6$ for branched chain). The term "$C_2$-$C_6$" includes alkynyl groups containing two to six carbon atoms. The term "$C_3$-$C_6$" includes alkynyl groups containing three to six carbon atoms. As used herein, "$C_2$-$C_6$ alkenylene linker" or "$C_2$-$C_6$ alkynylene linker" is intended to include $C_2$, $C_3$, $C_4$, $C_5$ or C₆ chain (linear or branched) divalent unsaturated aliphatic hydrocarbon groups. For example, $C_2$-$C_6$ alkenylene linker is intended to include $C_2$, $C_3$, $C_4$, $C_5$ and $C_6$ alkenylene linker groups.

As used herein, the term "optionally substituted alkynyl" refers to unsubstituted alkynyl or alkynyl having designated substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulphhydryl, alkylthio, arylthio, thiocarboxylate, sulphates, alkylsulphinyl, sulphonato, sulphamoyl, sulphonamido, nitro, trifluoromethyl, cyano, azido, heterocyclyl, alkylaryl, or an aromatic or heteroaromatic moiety.

Other optionally substituted moieties (such as optionally substituted cycloalkyl, heterocycloalkyl, aryl, or heteroaryl) include both the unsubstituted moieties and the moieties having one or more of the designated substituents. For example, substituted heterocycloalkyl includes those substituted with one or more alkyl groups, such as 2,2,6,6-tetramethyl-piperidinyl and 2,2,6,6-tetramethyl-1,2,3,6-tetrahydropyridinyl.

As used herein, the term "cycloalkyl" refers to a saturated or partially unsaturated hydrocarbon monocyclic or polycyclic (e.g., fused, bridged, or spiro rings) system having 3 to 30 carbon atoms (e.g., $C_3$-$C_{12}$, $C_3$-$C_{10}$, or $C_3$-$C_8$). Examples of cycloalkyl include, but are not limited to, cyclopropyl, cyclobutyl, cyclopentyl, cyclohexyl, cycloheptyl, cyclooctyl, cyclopentenyl, cyclohexenyl, cycloheptenyl, 1,2,3,4-tetrahydronaphthalenyl, and adamantyl. In the case of polycyclic cycloalkyl, only one of the rings in the cycloalkyl needs to be non-aromatic.

As used herein, the term "heterocycloalkyl" refers to a saturated or partially unsaturated 3-8 membered monocyclic, 7-12 membered bicyclic (fused, bridged, or spiro rings), or 11-14 membered tricyclic ring system (fused, bridged, or spiro rings) having one or more heteroatoms (such as O, N, S, P, or Se), e.g., 1 or 1-2 or 1-3 or 1-4 or 1-5 or 1-6 heteroatoms, or e.g., 1, 2, 3, 4, 5, or 6 heteroatoms, independently selected from the group consisting of nitrogen, oxygen and sulphur, unless specified otherwise. Examples of heterocycloalkyl groups include, but are not limited to, piperidinyl, piperazinyl, pyrrolidinyl, dioxanyl, tetrahydrofuranyl, isoindolinyl, indolinyl, imidazolidinyl, pyrazolidinyl, oxazolidinyl, isoxazolidinyl, triazolidinyl, oxiranyl, azetidinyl, oxetanyl, thietanyl, 1,2,3,6-tetrahydropyridinyl, tetrahydropyranyl, dihydropyranyl, pyranyl, morpholinyl, tetrahydrothiopyranyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, 1,4-dioxa-8-azaspiro[4.5]decanyl, 1,4-dioxaspiro[4.5]decanyl, 1-oxaspiro[4.5]decanyl, 1-azaspiro[4.5]decanyl, 3'H-spiro[cyclohexane-1,1'-isobenzofuran]-yl, 7'H-spiro[cyclohexane-1,5'-furo[3,4-b]pyridin]-yl, 3'H-spiro[cyclohexane-1,1'-furo[3,4-c]pyridin]-yl, 3-azabicyclo[3.1.0]hexanyl, 3-azabicyclo[3.1.0]hexan-3-yl, 1,4,5,6-tetrahydropyrrolo[3,4-c]pyrazolyl, 3,4,5,6,7,8-hexahydropyrido[4,3-d]pyrimidinyl, 4,5,6,7-tetrahydro-1H-pyrazolo[3,4-c]pyridinyl, 5,6,7,8-tetrahydropyrido[4,3-d]pyrimidinyl, 2-azaspiro[3.3]heptanyl, 2-methyl-2-azaspiro[3.3]heptanyl, 2-azaspiro[3.5]nonanyl, 2-methyl-2-azaspiro[3.5]nonanyl, 2-azaspiro[4.5]decanyl, 2-methyl-2-azaspiro[4.5]decanyl, 2-oxa-azaspiro[3.4]octanyl, 2-oxa-azaspiro[3.4]octan-6-yl, and the like. In the case of multicyclic heterocycloalkyl, only one of the rings in the heterocycloalkyl needs to be non-aromatic (e.g., 4,5,6,7-tetrahydrobenzo[c]isoxazolyl).

As used herein, the term "aryl" includes groups with aromaticity, including "conjugated," or multicyclic systems with one or more aromatic rings and do not contain any heteroatom in the ring structure. The term aryl includes both monovalent species and divalent species. Examples of aryl groups include, but are not limited to, phenyl, biphenyl, naphthyl and the like. Conveniently, an aryl is phenyl.

As used herein, the term "heteroaryl" is intended to include a stable 5-, 6-, or 7-membered monocyclic or 7-, 8-, 9-, 10-, 11- or 12-membered bicyclic aromatic heterocyclic ring which consists of carbon atoms and one or more heteroatoms, e.g., 1 or 1-2 or 1-3 or 1-4 or 1-5 or 1-6 heteroatoms, or e.g., 1, 2, 3, 4, 5, or 6 heteroatoms, independently selected from the group consisting of nitrogen, oxygen and sulphur. The nitrogen atom may be substituted or unsubstituted (i.e., N or NR wherein R is H or an other substituent, as defined). The nitrogen and sulphur heteroatoms may optionally be oxidised (i.e., N→O and $S(O)_p$, where p=1 or 2). It is to be noted that total number of S and O atoms in the aromatic heterocycle is not more than 1. Examples of heteroaryl groups include pyrrole, furan, thiophene, thiazole, isothiazole, imidazole, triazole, tetrazole, pyrazole, oxazole, isoxazole, pyridine, pyrazine, pyridazine, pyrimidine, and the like. Heteroaryl groups can also be fused or bridged with alicyclic or heterocyclic rings, which are not aromatic so as to form a multicyclic system (e.g., 4,5,6,7-tetrahydrobenzo[c]isoxazolyl).

Furthermore, the terms "aryl" and "heteroaryl" include multicyclic aryl and heteroaryl groups, e.g., tricyclic, bicyclic, e.g., naphthalene, benzoxazole, benzodioxazole, benzothiazole, benzoimidazole, benzothiophene, quinoline, isoquinoline, naphthrydine, indole, benzofuran, purine, benzofuran, deazapurine, indolizine.

The cycloalkyl, heterocycloalkyl, aryl, or heteroaryl ring can be substituted at one or more ring positions (e.g., the ring-forming carbon or heteroatom such as N) with such substituents as described above, for example, alkyl, alkenyl, alkynyl, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulphhydryl, alkylthio, arylthio, thiocarboxylate, sulphates, alkylsulphinyl, sulphonato, sulphamoyl, sulphonamido, nitro, trifluoromethyl, cyano, azido, heterocyclyl, alkylaryl, or an aromatic or heteroaromatic moiety. Aryl and heteroaryl groups can also be fused or bridged with alicyclic or heterocyclic rings, which are not aromatic so as to form a multicyclic system (e.g., tetralin, methylenedioxyphenyl such as benzo[d][1,3]dioxole-5-yl).

As used herein, the term "substituted," means that any one or more hydrogen atoms on the designated atom is replaced with a selection from the indicated groups, provided that the designated atom's normal valency is not exceeded, and that the substitution results in a stable compound. When a substituent is oxo or keto (i.e., =O), then 2 hydrogen atoms on the atom are replaced. Keto substituents are not present on aromatic moieties. Ring double bonds, as used herein, are double bonds that are formed between two adjacent ring atoms (e.g., C=C, C=N or N=N). "Stable compound" and "stable structure" are meant to indicate a compound that is sufficiently robust to survive isolation to a useful degree of purity from a reaction mixture, and formulation into an efficacious therapeutic agent.

When a bond to a substituent is shown to cross a bond connecting two atoms in a ring, then such substituent may be bonded to any atom in the ring. When a substituent is listed without indicating the atom via which such substituent is bonded to the rest of the compound of a given formula, then such substituent may be bonded via any atom in such formula. Combinations of substituents and/or variables are permissible, but only if such combinations result in stable compounds.

When any variable (e.g., R) occurs more than one time in any constituent or formula for a compound, its definition at each occurrence is independent of its definition at every other occurrence. Thus, for example, if a group is shown to be substituted with 0-2 R moieties, then the group may optionally be substituted with up to two R moieties and R at each occurrence is selected independently from the definition of R. Also, combinations of substituents and/or variables are permissible, but only if such combinations result in stable compounds.

As used herein, the term "hydroxy" or "hydroxyl" includes groups with an —OH or —O⁻.

As used herein, the term "halo" or "halogen" refers to fluoro, chloro, bromo and iodo.

As used herein, the term "optionally substituted haloalkyl" refers to unsubstituted haloalkyl having designated substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulphhydryl, alkylthio, arylthio, thiocarboxylate, sulphates, alkylsulphinyl, sulphonato, sulphamoyl, sulphonamido, nitro, trifluoromethyl, cyano, azido, heterocyclyl, alkylaryl, or an aromatic or heteroaromatic moiety.

As used herein, the expressions "one or more of A, B, or C," "one or more A, B, or C," "one or more of A, B, and C," "one or more A, B, and C," "selected from the group consisting of A, B, and C", "selected from A, B, and C", and the like are used interchangeably and all refer to a selection from a group consisting of A, B, and/or C, i.e., one or more As, one or more Bs, one or more Cs, or any combination thereof, unless indicated otherwise.

It is to be understood that the present disclosure provides methods for the synthesis of the compounds of any of the Formulae described herein. The present disclosure also provides detailed methods for the synthesis of various disclosed compounds of the present disclosure according to the following schemes as well as those shown in the Examples.

It is to be understood that, throughout the description, where compositions are described as having, including, or comprising specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the invention remains operable. Moreover, two or more steps or actions can be conducted simultaneously.

It is to be understood that the synthetic processes of the disclosure can tolerate a wide variety of functional groups, therefore various substituted starting materials can be used. The processes generally provide the desired final compound at or near the end of the overall process, although it may be desirable in certain instances to further convert the compound to a pharmaceutically acceptable salt thereof.

It is to be understood that compounds of the present disclosure can be prepared in a variety of ways using commercially available starting materials, compounds known in the literature, or from readily prepared intermediates, by employing standard synthetic methods and procedures either known to those skilled in the art, or which will be apparent to the skilled artisan in light of the teachings herein. Standard synthetic methods and procedures for the preparation of organic molecules and functional group transformations and manipulations can be obtained from the relevant scientific literature or from standard textbooks in the field. Although not limited to any one or several sources, classic texts such as Smith, M. B., March, J., *March's Advanced Organic Chemistry: Reactions, Mechanisms, and Structure,* $5^{th}$ edition, John Wiley & Sons: New York, 2001; Greene, T. W., Wuts, P. G. M., *Protective Groups in Organic Synthesis,* $3^{rd}$ edition, John Wiley & Sons: New York, 1999; R. Larock, *Comprehensive Organic Transformations,* VCH Publishers (1989); L. Fieser and M. Fieser, *Fieser and Fieser's Reagents for Organic Synthesis,* John Wiley and Sons (1994); and L. Paquette, ed., *Encyclopedia of Reagents for Organic Synthesis,* John Wiley and Sons (1995), incorporated by reference herein, are useful and recognised reference textbooks of organic synthesis known to those in the art One of ordinary skill in the art will note that, during the reaction sequences and synthetic schemes described herein, the order of certain steps may be changed, such as the introduction and removal of protecting groups. One of ordinary skill in the art will recognise that certain groups may require protection from the reaction conditions via the use of protecting groups. Protecting groups may also be used to differentiate similar functional groups in molecules. A list of protecting groups and how to introduce and remove these groups can be found in Greene, T. W., Wuts, P. G. M., *Protective Groups in Organic Synthesis,* $3^{rd}$ edition, John Wiley & Sons: New York, 1999.

It is to be understood that, unless otherwise stated, any description of a method of treatment includes use of the compounds to provide such treatment or prophylaxis as is described herein, as well as use of the compounds to prepare a medicament to treat or prevent such condition. It is to be understood that, unless otherwise stated, any description of a method of treatment includes use of the compounds to provide such treatment or prophylaxis as is described herein, as well as use of the compounds to prepare a medicament to treat such condition. The treatment includes treatment of human or non-human animals including rodents and other disease models.

As used herein, the term "subject" is interchangeable with the term "subject in need thereof", both of which refer to a subject having a disease or disorder or having an increased risk of developing the disease or disorder. In some embodiments, the subject has a sleep disorder or has an increased risk of developing a sleep disorder. A "subject" includes a mammal. The mammal can be e.g., a human or appropriate non-human mammal, such as primate, mouse, rat, dog, cat, cow, horse, goat, camel, sheep or a pig. The subject can also be a bird or fowl. In one embodiment, the mammal is a human. A subject in need thereof can be one who has been previously diagnosed or identified as having a disease or disorder disclosed herein. A subject in need thereof can also be one who is suffering from a disease or disorder disclosed herein. Alternatively, a subject in need thereof can be one who has an increased risk of developing such disease or disorder relative to the population at large (i.e., a subject who is predisposed to developing such disorder relative to the population at large). A subject in need thereof can have a refractory or resistant a disease or disorder disclosed herein (i.e., a disease or disorder disclosed herein that does not respond or has not yet responded to treatment). The subject may be resistant at start of treatment or may become resistant during treatment. In some embodiments, the subject in need thereof received and failed all known effective therapies for a disease or disorder disclosed herein. In some embodiments, the subject in need thereof received at least one prior therapy.

As used herein, the term "treating" or "treat" describes the management and care of a subject for the purpose of combating a disease, condition, or disorder and includes the administration of a compound of the present disclosure, or a pharmaceutically acceptable salt, polymorph or solvate thereof, to alleviate the symptoms or complications of a disease, condition or disorder, or to eliminate the disease, condition or disorder. The term "treat" can also include treatment of a cell in vitro or an animal model.

It is to be appreciated that references to "treating" or "treatment" include the alleviation of established symptoms of a condition. "Treating" or "treatment" of a state, disorder or condition therefore includes: (1) delaying the appearance of clinical symptoms of the state, disorder or condition developing in a human that may be afflicted with or predisposed to the state, disorder or condition but does not yet experience or display clinical or subclinical symptoms of the state, disorder or condition, (2) inhibiting the state, disorder or condition, i.e., arresting, reducing or delaying the development of the disease or a relapse thereof (in case of maintenance treatment) or at least one clinical or subclinical symptom thereof, or (3) relieving or attenuating the disease, i.e., causing regression of the state, disorder or condition or at least one of its clinical or subclinical symptoms.

It is to be understood that a compound of the present disclosure, or a pharmaceutically acceptable salt, polymorph or solvate thereof, can or may also be used to prevent a relevant disease, condition or disorder, or used to identify suitable candidates for such purposes.

As used herein, the term "preventing," "prevent," or "protecting against" describes reducing or eliminating the onset of the symptoms or complications of such disease, condition or disorder.

It is to be understood that one skilled in the art may refer to general reference texts for detailed descriptions of known techniques discussed herein or equivalent techniques. These texts include Ausubel et al., *Current Protocols in Molecular Biology*, John Wiley and Sons, Inc. (2005); Sambrook et al., *Molecular Cloning, A Laboratory Manual* (3$^{rd}$ edition), Cold Spring Harbor Press, Cold Spring Harbor, N.Y. (2000); Coligan et al., *Current Protocols in Immunology*, John Wiley & Sons, N.Y.; Enna et al., *Current Protocols in Pharmacology*, John Wiley & Sons, N.Y.; Fingl et al., *The Pharmacological Basis of Therapeutics* (1975), *Remington's Pharmaceutical Sciences*, Mack Publishing Co., Easton, Pa., 18$^{th}$ edition (1990). These texts can, of course, also be referred to in making or using an aspect of the disclosure.

It is to be understood that the present disclosure also provides pharmaceutical compositions comprising any compound described herein in combination with at least one pharmaceutically acceptable excipient or carrier.

As used herein, the term "pharmaceutical composition" is a formulation containing the compounds of the present disclosure in a form suitable for administration to a subject. In one embodiment, the pharmaceutical composition is in bulk or in unit dosage form. The unit dosage form is any of a variety of forms, including, for example, a capsule, an IV bag, a tablet, a single pump on an aerosol inhaler or a vial. The quantity of active ingredient (e.g., a formulation of the disclosed compound or salt, hydrate, solvate or isomer thereof) in a unit dose of composition is an effective amount and is varied according to the particular treatment involved. One skilled in the art will appreciate that it is sometimes necessary to make routine variations to the dosage depending on the age and condition of the subject. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this disclosure include powders, sprays, ointments, pastes, creams, lotions, gels, solutions, patches and inhalants. In one embodiment, the active compound is mixed under sterile conditions with a pharmaceutically acceptable carrier, and with any preservatives, buffers, or propellants that are required.

As used herein, the term "pharmaceutically acceptable" refers to those compounds, anions, cations, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

It is to be understood that a pharmaceutical composition of the disclosure is formulated to be compatible with its intended route of administration. Examples of routes of administration include parenteral, e.g., intravenous, intradermal, subcutaneous, oral (e.g., ingestion), inhalation, transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulphite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

It is to be understood that a compound or pharmaceutical composition of the disclosure can be administered to a subject in many of the well-known methods. As a non-limiting example a compound of the present disclosure may be administered as an injection, orally, or applied through the skin with patches. The dose chosen should be sufficient to constitute effective treatment but not so high as to cause unacceptable side effects. The state of the disease condition (e.g., a disease or disorder disclosed herein) and the health of the subject should preferably be closely monitored during and for a reasonable period after treatment.

As used herein, the term "effective amount", refers to an amount of a pharmaceutical agent to treat, ameliorate, or prevent an identified disease, disorder, or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician.

As used herein, the term "therapeutically effective amount", refers to an amount of a pharmaceutical agent to treat or ameliorate an identified disease, disorder, or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician. A "therapeutically effective amount" may be administered to a subject for treating a disease or disorder. The "therapeutically effective amount" will vary depending on the compound, the disease and its severity and the age, weight, etc., of the subject to be treated.

It is to be understood that, for any compound, the therapeutically effective amount can be estimated initially either in cell culture assays, e.g., neoplastic cells, or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are preferred. The dosage may vary within this range depending upon the dosage form employed, sensitivity of the subject, and the route of administration.

Dosage and administration are adjusted to provide sufficient levels of the active agent(s) or to maintain the desired effect. Factors which may be taken into account include the severity of the state of the disease or disorder, general health of the subject, age, weight, and gender of the subject, diet, time and frequency of administration, drug combination(s), reaction sensitivities, and tolerance/response to therapy.

The pharmaceutical compositions containing active compounds of the present disclosure may be manufactured in a manner that is generally known, e.g., by means of conventional mixing, dissolving, granulating, dragee-making, levigating, emulsifying, encapsulating, entrapping, or lyophilising processes. Pharmaceutical compositions may be formulated in a conventional manner using one or more pharmaceutically acceptable carriers comprising excipients and/or auxiliaries that facilitate processing of the active compounds into preparations that can be used pharmaceutically. Of course, the appropriate formulation is dependent upon the route of administration chosen.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol and sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilisation. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible pharmaceutically acceptable carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser, which contains a suitable propellant, e.g., a gas such as carbon dioxide, or a nebuliser.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives.

Transmucosal administration can be accomplished through the use of nasal sprays or suppositories. For transdermal administration, the active compounds are formulated into ointments, salves, gels, or creams as generally known in the art.

The active compounds can be prepared with pharmaceutically acceptable carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the disclosure are dictated by and directly dependent on the unique characteristics of the active compound and the particular therapeutic effect to be achieved.

In therapeutic applications, the dosages of the pharmaceutical compositions used in accordance with the disclosure vary depending on the agent, the age, weight, and clinical condition of the recipient subject, and the experience and judgment of the clinician or practitioner administering the therapy, among other factors affecting the selected dosage. Generally, the dose should be sufficient to result in slowing, and preferably regressing, the symptoms of the disease or disorder disclosed herein and also preferably causing complete regression of the disease or disorder. An effective amount of a pharmaceutical agent is that which provides an objectively identifiable improvement as noted by the clinician or other qualified observer. Improvement in disturbed sleep, sleep fragmentation, arousals, or arousal threshold indicates regression. As used herein, the term "dosage effective manner" refers to amount of an active compound to produce the desired biological effect in a subject or cell.

It is to be understood that the pharmaceutical compositions can be included in a container, pack, or dispenser together with instructions for administration.

It is to be understood that, for the compounds of the present disclosure being capable of further forming salts, all of these forms are also contemplated within the scope of the claimed disclosure.

As used herein, the term "pharmaceutically acceptable salts" refer to derivatives of the compounds of the present disclosure wherein the parent compound is modified by making acid or base salts thereof. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulphonic, acetic, ascorbic, benzene sulphonic, benzoic, bicarbonic, carbonic, citric, edetic, ethane disulphonic, 1,2-ethane sulphonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulphonic, maleic, malic, mandelic, methane sulphonic, napsylic, nitric, oxalic, pamoic, pantothenic, phenylacetic, phosphoric, polygalacturonic, propionic, salicylic, stearic, subacetic, succinic, sulphamic, sulphanilic, sulphuric, tannic, tartaric, toluene sulphonic, and the commonly occurring amine acids, e.g., glycine, alanine, phenylalanine, arginine, etc.

In some embodiments, the pharmaceutically acceptable salt is a sodium salt, a potassium salt, a calcium salt, a magnesium salt, a diethylamine salt, a choline salt, a meglumine salt, a benzathine salt, a tromethamine salt, an ammonia salt, an arginine salt, or a lysine salt.

Other examples of pharmaceutically acceptable salts include hexanoic acid, cyclopentane propionic acid, pyruvic acid, malonic acid, 3-(4-hydroxybenzoyl)benzoic acid, cinnamic acid, 4-chlorobenzenesulphonic acid, 2-naphthalenesulphonic acid, 4-toluenesulphonic acid, camphorsulphonic acid, 4-methylbicyclo-[2.2.2]-oct-2-ene-1-carboxylic acid, 3-phenylpropionic acid, trimethylacetic acid, tertiary butylacetic acid, muconic acid, and the like. The present disclosure also encompasses salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. In the salt form, it is understood that the ratio of the compound to the cation or anion of the salt can be 1:1, or any ratio other than 1:1, e.g., 3:1, 2:1, 1:2, or 1:3.

It is to be understood that all references to pharmaceutically acceptable salts include solvent addition forms (solvates) or crystal forms (polymorphs) as defined herein, of the same salt.

The compounds, or pharmaceutically acceptable salts thereof, are administered orally, nasally, transdermally, pulmonary, inhalationally, buccally, sublingually, intraperitoneally, subcutaneously, intramuscularly, intravenously, rectally, intrapleurally, intrathecally and parenterally. In one embodiment, the compound is administered orally. One skilled in the art will recognise the advantages of certain routes of administration.

A salt, for example, can be formed between an anion and a positively charged group (e.g., amino) on a substituted compound disclosed herein. Suitable anions include chloride, bromide, iodide, sulphate, bisulphate, sulphamate, nitrate, phosphate, citrate, methanesulphonate, trifluoroacetate, glutamate, glucuronate, glutarate, malate, maleate, succinate, fumarate, tartrate, tosylate, salicylate, lactate, naphthalenesulphonate, and acetate (e.g., trifluoroacetate).

As used herein, the term "pharmaceutically acceptable anion" refers to an anion suitable for forming a pharmaceutically acceptable salt. Likewise, a salt can also be formed between a cation and a negatively charged group (e.g., carboxylate) on a substituted compound disclosed herein. Suitable cations include sodium ion, potassium ion, magnesium ion, calcium ion, and an ammonium cation such as tetramethylammonium ion or diethylamine ion. The substituted compounds disclosed herein also include those salts containing quaternary nitrogen atoms.

It is to be understood that the compounds of the present disclosure, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

As used herein, the term "solvate" means solvent addition forms that contain either stoichiometric or non-stoichiometric amounts of solvent. Some compounds have a tendency to trap a fixed molar ratio of solvent molecules in the crystalline solid state, thus forming a solvate.

If the solvent is water the solvate formed is a hydrate; and if the solvent is alcohol, the solvate formed is an alcoholate. Hydrates are formed by the combination of one or more molecules of water with one molecule of the substance in which the water retains its molecular state as $H_2O$.

As used herein, the term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar or comparable in function and appearance, but not in structure or origin to the reference compound.

As used herein, the term "derivative" refers to compounds that have a common core structure and are substituted with various groups as described herein.

As used herein, the term "bioisostere" refers to a compound resulting from the exchange of an atom or of a group of atoms with another, broadly similar, atom or group of atoms. The objective of a bioisosteric replacement is to create a new compound with similar biological properties to the parent compound. The bioisosteric replacement may be physicochemically or topologically based. Examples of carboxylic acid bioisosteres include, but are not limited to, acyl sulphonamides, tetrazoles, sulphonates and phosphonates. See, e.g., Patani and LaVoie, Chem. Rev. 96, 3147-3176, 1996.

As used herein, "2HPβCD" refers to (2-hydroxypropyl)-β-cyclodextrin.

As used herein, "REM" refers to the rapid eye movement sleep stage.

As used herein, "SEM" refers to standard error of the mean.

As used herein, "CT" refers to circadian time.

As used herein, "sleep continuity" refers to the measurement of sleep-bout length.

As used herein, the "depth" of sleep is characterized by EEG slow wave activity, which may subserve sleep continuity or sleep consolidation, which is one of several determinants of sleep quality.

As used here, "SWA" refers to slow wave activity, which may be exemplified as EEG delta power by use of Fourier analysis.

As used herein, the term "rat" and "laboratory rat" are used interchangeably.

As use herein, the phrase "compound of the disclosure" refers to those compounds which are disclosed herein, both generically and specifically.

"Uninterrupted bouts of sleep" (average sleep bout duration) is defined herein as the average duration of all bouts of uninterrupted sleep that occurred each hour, measured in minutes. "Interruption" is defined as 2 or more consecutive 10 sec epochs of wakefulness. The value for the length of a bout that extends into the subsequent hour is assigned to the hour in which it begins. An analogous quantification may be carried out for bouts of wakefulness. Sleep bout length is of particular interest because it may reflect the human tendency to awaken periodically through the night (such awakenings are normally not recalled), which in turn may be an important factor in determining the restorative value of sleep in humans. Pre-clinical measures of sleep bout duration are also strong predictors of soporific efficacy in humans.

"Number of transitions to wake" (number of transitions from sleep to wakefulness) is a count of the number of times sleep (including any objectively determined stage of sleep) was followed by wake (including any objectively determined stage of wakefulness) each hour. For purposes of this definition, a single qualifying 10 second epoch of wakefulness that immediately follows sleep constitutes a transition from sleep to wake. One or more consecutive 10 second epochs of wakefulness that immediately follows one or more 10 second epoch of sleep or sleep is also counted as a transition from sleep to wake. A 10 second epoch containing a minimum of 50% wakefulness content (determined by the EEG and EMG within that epoch) could be classified as wake for the entire epoch. Number of transitions to wake are of interest as they provide a direct measure of the number of arousals (transitions from sleep to wake) each hour. Number of arousals are a useful measure of sleep fragmentation in animals and humans. Drugs that improve sleep fragmentation have been shown to improve the restorative benefits of sleep.

"LMA intensity" is defined as LMA counts per minute of EEG-defined wakefulness. This variate allows an assessment of LMA that is independent of the amount of time awake; thus, it may be used to quantify the specificity of a wake- or sleep-promoting effect.

As used herein, "temporal proximity" means that administration of one therapeutic agent occurs within a time period before or after the administration of another therapeutic agent, such that the therapeutic effect of the one therapeutic agent overlaps with the therapeutic effect of the another therapeutic agent. In some embodiments, the therapeutic effect of the one therapeutic agent completely overlaps with the therapeutic effect of the other therapeutic agent. In some embodiments, "temporal proximity" means that administration of one therapeutic agent occurs within a time period before or after the administration of another therapeutic agent, such that there is a synergistic effect between the one therapeutic agent and the other therapeutic agent. "Temporal proximity" may vary according to various factors, including but not limited to, the age, gender, weight, genetic background, medical condition, disorder, disease history, and treatment history of the subject to which the therapeutic agents are to be administered; the disease, disorder, or condition to be treated or ameliorated; the therapeutic outcome to be achieved; the dosage, dosing frequency, and dosing duration of the therapeutic agents; the pharmacokinetics and pharmacodynamics of the therapeutic agents; and the route(s) through which the therapeutic agents are administered. In some embodiments, "temporal proximity" means within 15 minutes, within 30 minutes, within an hour, within two hours, within four hours, within six hours, within eight hours, within 12 hours, within 18 hours, within 24 hours, within 36 hours, within 2 days, within 3 days, within 4 days, within 5 days, within 6 days, within a week, within 2 weeks, within 3 weeks, within 4 weeks, with 6 weeks, or within 8 weeks. In some embodiments, multiple administration of one therapeutic agent can occur in temporal proximity to a single administration of another therapeutic agent. In some embodiments, temporal proximity may change during a treatment cycle or within a dosing regimen.

Unless explicitly indicated otherwise, the terms "approximately" and "about" are synonymous. In some embodiments, "approximately" and "about" refer to the recited amount, value, dose or duration ±20%, ±15%, ±10%, ±8%, ±6%, 5%, ±4%, ±2%, ±1%, or ±0.5%. In another embodiment, "approximately" and "about" refer to the listed amount or duration ±10%, ±8%, ±6%, ±5%, ±4%, or ±2%. In some embodiments, "approximately" and "about" refer to the listed amount, value, dose, or duration ±5%. In some embodiments, "approximately" and "about" refer to the listed amount, value, dose, or duration ±2%. In some embodiments, "approximately" and "about" refer to the listed amount, value, dose, or duration ±1%.

It is also to be understood that certain compounds of any one of the Formulae disclosed herein may exist in solvated as well as unsolvated forms such as, for example, hydrated forms. A suitable pharmaceutically acceptable solvate is, for example, a hydrate such as hemi-hydrate, a mono-hydrate, a di-hydrate or a tri-hydrate. It is to be understood that the disclosure encompasses all such solvated forms that possess H1/5-HT$_{2A}$ modulation activity.

It is also to be understood that certain compounds of any one of the Formulae disclosed herein may exhibit polymorphism, and that the disclosure encompasses all such forms, or mixtures thereof, which possess H1/5-HT$_{2A}$ modulation activity. It is generally known that crystalline materials may be analysed using conventional techniques such as X-Ray Powder Diffraction analysis, Differential Scanning Calorimetry, Thermal Gravimetric Analysis, Diffuse Reflectance Infrared Fourier Transform (DRIFT) spectroscopy, Near Infrared (NIR) spectroscopy, solution and/or solid state nuclear magnetic resonance spectroscopy. The water content of such crystalline materials may be determined by Karl Fischer analysis.

Compounds of any one of the Formulae disclosed herein may exist in a number of different tautomeric forms and references to compounds of Formula (I), (II), and (II') include all such forms. For the avoidance of doubt, where a compound can exist in one of several tautomeric forms, and only one is specifically described or shown, all others are nevertheless embraced by Formula (I), (II), or (II'). Examples of tautomeric forms include keto-, enol-, and enolate-forms, as in, for example, the following tautomeric pairs: keto/enol (illustrated below), imine/enamine, amide/imino alcohol, amidine/amidine, nitroso/oxime, thioketone/enethiol, and nitro/aci-nitro.

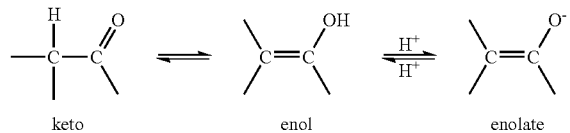

keto            enol            enolate

Compounds of any one of the Formulae disclosed herein containing an amine function may also form N-oxides. A reference herein to a compound of Formula (I), (II), and (II') that contains an amine function also includes the N-oxide. Where a compound contains several amine functions, one or more than one nitrogen atom may be oxidised to form an N-oxide. Particular examples of N-oxides are the N-oxides of a tertiary amine or a nitrogen atom of a nitrogen-containing heterocycle. N-oxides can be formed by treatment of the corresponding amine with an oxidising agent such as hydrogen peroxide or a peracid (e.g. a peroxycarboxylic acid), see for example Advanced Organic Chemistry, by Jerry March, 4th Edition, Wiley Interscience, pages. More particularly, N-oxides can be made by the procedure of L. W. Deady (Syn. Comm. 1977, 7, 509-514) in which the amine compound is reacted with meta-chloroperoxybenzoic acid (mCPBA), for example, in an inert solvent such as dichloromethane.

The compounds of any one of the Formulae disclosed herein may be administered in the form of a prodrug which is broken down in the human or animal body to release a compound of the disclosure. A prodrug may be used to alter the physical properties and/or the pharmacokinetic properties of a compound of the disclosure. A prodrug can be formed when the compound of the disclosure contains a suitable group or substituent to which a property-modifying group can be attached. Examples of prodrugs include derivatives containing in vivo cleavable alkyl or acyl substituents at the ester or amide group in any one of the Formulae disclosed herein.

As used herein, the term "isomerism" means compounds that have identical molecular formulae but differ in the sequence of bonding of their atoms or in the arrangement of their atoms in space. Isomers that differ in the arrangement of their atoms in space are termed "stereoisomers." Stereoisomers that are not mirror images of one another are termed "diastereoisomers," and stereoisomers that are non-superimposable mirror images of each other are termed "enantiomers" or sometimes optical isomers. A mixture containing equal amounts of individual enantiomeric forms of opposite chirality is termed a "racemic mixture."

As used herein, the term "chiral center" refers to an atom bonded to four nonidentical substituents (e.g., a carbon atom).

As used herein, the term "chiral isomer" means a compound with at least one chiral center. Compounds with more than one chiral center may exist either as an individual diastereomer or as a mixture of diastereomers, termed "diastereomeric mixture." When one chiral center is present, a stereoisomer may be characterised by the absolute configuration (R or S) of that chiral center. Absolute configuration refers to the arrangement in space of the substituents attached to the chiral center. The substituents attached to the chiral center under consideration are ranked in accordance with the Sequence Rule of Cahn, Ingold and Prelog. (Cahn et al., *Angew. Chem. Inter. Edit.* 1966, 5, 385; errata 511; Cahn et al., *Angew. Chem.* 1966, 78, 413; Cahn and Ingold, *J. Chem. Soc.* 1951 (London), 612; Cahn et al., *Experientia* 1956, 12, 81; Cahn, *J. Chem. Educ.* 1964, 41, 116).

As used herein, the term "geometric isomer" means the diastereomers that owe their existence to hindered rotation about double bonds or a cycloalkyl linker (e.g., 1,3-cyclobutyl).

These configurations are differentiated in their names by the prefixes cis and trans, or Z and E, which indicate that the groups are on the same or opposite side of the double bond in the molecule according to the Cahn-Ingold-Prelog rules.

It is to be understood that the compounds of the present disclosure may be depicted as different chiral isomers or geometric isomers. It is also to be understood that when compounds have chiral isomeric or geometric isomeric forms, all isomeric forms are intended to be included in the scope of the present disclosure, and the naming of the compounds does not exclude any isomeric forms, it being understood that not all isomers may have the same level of activity.

It is to be understood that the structures and other compounds discussed in this disclosure include all atropic isomers thereof. It is also to be understood that not all atropic isomers may have the same level of activity.

As used herein, the term "atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques, it has been possible to separate mixtures of two atropic isomers in select cases.

As used herein, the term "tautomer" is one of two or more structural isomers that exist in equilibrium and is readily converted from one isomeric form to another. This conversion results in the formal migration of a hydrogen atom accompanied by a switch of adjacent conjugated double bonds. Tautomers exist as a mixture of a tautomeric set in solution. In solutions where tautomerisation is possible, a chemical equilibrium of the tautomers will be reached. The exact ratio of the tautomers depends on several factors, including temperature, solvent and pH. The concept of tautomers that are interconvertible by tautomerisations is called tautomerism. Of the various types of tautomerism that are possible, two are commonly observed. In keto-enol tautomerism a simultaneous shift of electrons and a hydrogen atom occurs. Ring-chain tautomerism arises as a result of the aldehyde group (—CHO) in a sugar chain molecule reacting with one of the hydroxy groups (—OH) in the same molecule to give it a cyclic (ring-shaped) form as exhibited by glucose.

It is to be understood that the compounds of the present disclosure may be depicted as different tautomers. It should also be understood that when compounds have tautomeric forms, all tautomeric forms are intended to be included in the scope of the present disclosure, and the naming of the compounds does not exclude any tautomer form. It will be understood that certain tautomers may have a higher level of activity than others.

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterised by the absolute configuration of its asymmetric center and is described by the R- and S-sequencing rules of Cahn and Prelog, or by the manner in which the molecule rotates the plane of polarised light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of this disclosure may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 2001), for example by synthesis from optically active starting materials or by resolution of a racemic form. Some of the compounds of the disclosure may have geometric isomeric centers (E- and Z-isomers). It is to be understood that the present disclosure encompasses all optical, diastereoisomers and geometric isomers and mixtures thereof that possess H1/5-HT$_{2A}$-modulation activity Accordingly, the present disclosure includes those compounds of any one of the Formulae disclosed herein as defined hereinbefore when made available by organic synthesis and when made available within the human or animal body by way of cleavage of a prodrug thereof. Accordingly, the present disclosure includes those compounds of any one of the Formulae disclosed herein that are produced by organic synthetic means and also such compounds that are produced in the human or animal body by way of metabolism of a precursor compound, that is a compound of any one of the Formulae disclosed herein may be a synthetically-produced compound or a metabolically-produced compound.

A suitable pharmaceutically acceptable prodrug of a compound of any one of the Formulae disclosed herein is one that is based on reasonable medical judgment as being suitable for administration to the subject without undesirable pharmacological activities and without undue toxicity. Various forms of prodrug have been described, for example in the following documents: a) Methods in Enzymology, Vol. 42, p. 309-396, edited by K. Widder, et al. (Academic Press, 1985); b) Design of Pro-drugs, edited by H. Bundgaard, (Elsevier, 1985); c) A Textbook of Drug Design and Development, edited by Krogsgaard-Larsen and H. Bundgaard, Chapter 5 "Design and Application of Pro-drugs", by H. Bundgaard p. 113-191 (1991); d) H. Bundgaard, Advanced Drug Delivery Reviews, 8, 1-38 (1992); e) H. Bundgaard, et al., Journal of Pharmaceutical Sciences, 77, 285 (1988); f) N. Kakeya, et al., Chem. Pharm. Bull., 32, 692 (1984); g) T. Higuchi and V. Stella, "Pro-Drugs as Novel Delivery Systems", A.C.S. Symposium Series, Volume 14; and h) E. Roche (editor), "Bioreversible Carriers in Drug Design", Pergamon Press, 1987.

A suitable pharmaceutically acceptable prodrug of a compound of any one of the Formulae disclosed herein that possesses a hydroxy group is, for example, an in vivo cleavable ester or ether thereof. An in vivo cleavable ester or ether of a compound of any one of the Formulae disclosed herein containing a hydroxy group is, for example, a pharmaceutically acceptable ester or ether which is cleaved in the subject to produce the parent hydroxy compound. Suitable pharmaceutically acceptable ester forming groups for a hydroxy group include inorganic esters such as phosphate esters (including phosphoramidic cyclic esters). Further suitable pharmaceutically acceptable ester forming groups for a hydroxy group include $C_1$-$C_{10}$ alkanoyl groups such as acetyl, benzoyl, phenylacetyl and substituted benzoyl and phenylacetyl groups, $C_1$-$C_{10}$ alkoxycarbonyl groups such as ethoxycarbonyl, N,N—($C_1$-$C_6$ alkyl)2carbamoyl, 2-dialkylaminoacetyl and 2-carboxyacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-($C_1$-$C_4$ alkyl)piperazin-1-ylmethyl. Suitable pharmaceutically acceptable ether forming groups for a hydroxy group include α-acyloxyalkyl groups such as acetoxymethyl and pivaloyloxymethyl groups.

A suitable pharmaceutically acceptable prodrug of a compound of any one of the Formulae disclosed herein that possesses a carboxy group is, for example, an in vivo cleavable amide thereof, for example an amide formed with an amine such as ammonia, a $C_{1-4}$alkylamine such as methylamine, a ($C_1$-$C_4$ alkyl)$_2$amine such as dimethylamine, N-ethyl-N-methylamine or diethylamine, a $C_1$-$C_4$ alkoxy-$C_2$-$C_4$ alkylamine such as 2-methoxyethylamine, a phenyl-$C_1$-$C_4$ alkylamine such as benzylamine and amino acids such as glycine or an ester thereof.

A suitable pharmaceutically acceptable prodrug of a compound of any one of the Formulae disclosed herein that possesses an amino group is, for example, an in vivo cleavable amide derivative thereof. Suitable pharmaceutically acceptable amides from an amino group include, for example an amide formed with $C_1$-$C_{10}$ alkanoyl groups such as an acetyl, benzoyl, phenylacetyl and substituted benzoyl and phenylacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-($C_1$-$C_4$ alkyl)piperazin-1-ylmethyl.

The dosage regimen utilising the compounds is selected in accordance with a variety of factors including type, species, age, weight, sex and medical condition of the subject; the severity of the condition to be treated; the route of administration; the renal and hepatic function of the subject; and the particular compound or salt thereof employed. An ordinarily skilled physician or veterinarian can readily determine and prescribe the effective amount of the drug required to prevent, counter, or arrest the progress of the condition. An ordinarily skilled physician or veterinarian can readily determine and prescribe the effective amount of the drug required to counter or arrest the progress of the condition.

Techniques for formulation and administration of the disclosed compounds of the disclosure can be found in *Remington: the Science and Practice of Pharmacy*, 19$^{th}$ edition, Mack Publishing Co., Easton, Pa. (1995). In an embodiment, the compounds described herein, and the pharmaceutically acceptable salts thereof, are used in pharmaceutical preparations in combination with a pharmaceutically acceptable carrier or diluent. Suitable pharmaceutically acceptable carriers include inert solid fillers or diluents and sterile aqueous or organic solutions. The compounds will be present in such pharmaceutical compositions in amounts sufficient to provide the desired dosage amount in the range described herein.

All percentages and ratios used herein, unless otherwise indicated, are by weight. Other features and advantages of the present disclosure are apparent from the different examples. The provided examples illustrate different components and methodology useful in practicing the present disclosure. The examples do not limit the claimed disclosure. Based on the present disclosure the skilled artisan can identify and employ other components and methodology useful for practicing the present disclosure.

In the synthetic schemes described herein, compounds may be drawn with one particular configuration for simplicity. Such particular configurations are not to be construed as limiting the disclosure to one or another isomer, tautomer, regioisomer or stereoisomer, nor does it exclude mixtures of isomers, tautomers, regioisomers or stereoisomers; however, it will be understood that a given isomer, tautomer, regioisomer or stereoisomer may have a higher level of activity than another isomer, tautomer, regioisomer or stereoisomer.

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

Compounds of the Present Disclosure

In some aspects, the present disclosure provides, inter alia, a compound of Formula (I):

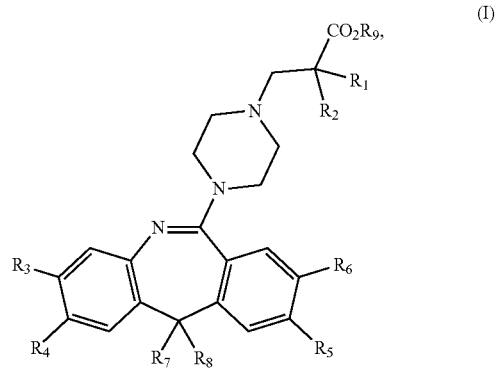

or a prodrug, solvate, or pharmaceutically acceptable salt thereof, wherein:

$R_1$ is $C_1$-$C_6$ alkyl, $C_2$-$C_6$ alkenyl, $C_2$-$C_6$ alkynyl, $C_1$-$C_6$ haloalkyl, $C_1$-$C_6$ alkoxyl, or $C_3$-$C_6$ cycloalkyl;

$R_2$ is $C_1$-$C_6$ alkyl, $C_2$-$C_6$ alkenyl, $C_2$-$C_6$ alkynyl, $C_1$-$C_6$ haloalkyl, $C_1$-$C_6$ alkoxyl, or $C_3$-$C_6$ cycloalkyl; or $R_1$ and $R_2$ together with the atoms to which they are attached form a $C_3$-$C_6$ saturated or partially unsaturated cycloalkyl or a 3- to 14-membered saturated or partially unsaturated heterocycle comprising 1-5 heteroatoms selected from N, O, and S;

$R_3$ is H, halogen, —S($C_1$-$C_6$ alkyl), —N($C_1$-$C_6$ alkyl)$_2$, —NH($C_1$-$C_6$ alkyl), —NH$_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxyl, $C_1$-$C_6$ haloalkoxyl, or $C_3$-$C_6$ cycloalkyl;

$R_4$ is H, halogen, —S($C_1$-$C_6$ alkyl), —N($C_1$-$C_6$ alkyl)$_2$, —NH($C_1$-$C_6$ alkyl), —NH$_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxyl, $C_1$-$C_6$ haloalkoxyl, or $C_3$-$C_6$ cycloalkyl;

$R_5$ is H, halogen, —S($C_1$-$C_6$ alkyl), —N($C_1$-$C_6$ alkyl)$_2$, —NH($C_1$-$C_6$ alkyl), —NH$_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxyl, $C_1$-$C_6$ haloalkoxyl, or $C_3$-$C_6$ cycloalkyl;

$R_6$ is H, halogen, —S($C_1$-$C_6$ alkyl), —N($C_1$-$C_6$ alkyl)$_2$, —NH($C_1$-$C_6$ alkyl), —NH$_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxyl, $C_1$-$C_6$ haloalkoxyl, or $C_3$-$C_6$ cycloalkyl;

$R_7$ is H, deuterium, $C_1$-$C_6$ alkyl, $C_2$-$C_6$ alkenyl, or $C_2$-$C_6$ alkynyl;

$R_8$ is H, deuterium, $C_1$-$C_6$ alkyl, $C_2$-$C_6$ alkenyl, or $C_2$-$C_6$ alkynyl; and $R_9$ is H, $C_1$-$C_6$ alkyl, $C_2$-$C_6$ alkenyl, $C_2$-$C_6$ alkynyl, $C_1$-$C_6$ haloalkyl, or $C_3$-$C_6$ cycloalkyl, provided that at least one of $R_3$, $R_4$, $R_5$, and $R_6$ is H.

In some aspects, the present disclosure provides, inter alia, a compound of Formula (II):

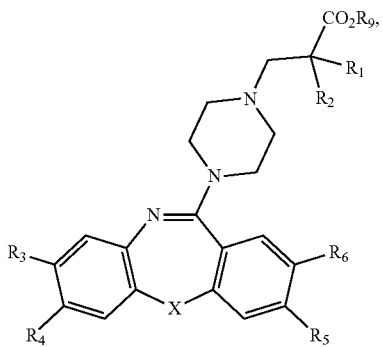

(II)

or a prodrug, solvate, or pharmaceutically acceptable salt thereof, wherein:

X is $CR_7R_8$, O, S, or $NR_7$;

$R_1$ is $C_1$-$C_6$ alkyl, $C_2$-$C_6$ alkenyl, $C_2$-$C_6$ alkynyl, $C_1$-$C_6$ haloalkyl, $C_1$-$C_6$ alkoxyl, or $C_3$-$C_6$ cycloalkyl;

$R_2$ is $C_1$-$C_6$ alkyl, $C_2$-$C_6$ alkenyl, $C_2$-$C_6$ alkynyl, $C_1$-$C_6$ haloalkyl, $C_1$-$C_6$ alkoxyl, or $C_3$-$C_6$ cycloalkyl; or $R_1$ and $R_2$ together with the atoms to which they are attached form a $C_3$-$C_6$ saturated or partially unsaturated cycloalkyl or a 3- to 14-membered saturated or partially unsaturated heterocycle comprising 1-5 heteroatoms selected from N, O, and S;

$R_3$ is H, halogen, —S($C_1$-$C_6$ alkyl), —N($C_1$-$C_6$ alkyl)$_2$, —NH($C_1$-$C_6$ alkyl), —NH$_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxyl, $C_1$-$C_6$ haloalkoxyl, or $C_3$-$C_6$ cycloalkyl;

$R_4$ is H, halogen, —S($C_1$-$C_6$ alkyl), —N($C_1$-$C_6$ alkyl)$_2$, —NH($C_1$-$C_6$ alkyl), —NH$_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxyl, $C_1$-$C_6$ haloalkoxyl, or $C_3$-$C_6$ cycloalkyl;

$R_5$ is H, halogen, —S($C_1$-$C_6$ alkyl), —N($C_1$-$C_6$ alkyl)$_2$, —NH($C_1$-$C_6$ alkyl), —NH$_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxyl, $C_1$-$C_6$ haloalkoxyl, or $C_3$-$C_6$ cycloalkyl;

$R_6$ is H, halogen, —S($C_1$-$C_6$ alkyl), —N($C_1$-$C_6$ alkyl)$_2$, —NH($C_1$-$C_6$ alkyl), —NH$_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxyl, $C_1$-$C_6$ haloalkoxyl, or $C_3$-$C_6$ cycloalkyl;

$R_7$ is H, deuterium, $C_1$-$C_6$ alkyl, $C_2$-$C_6$ alkenyl, or $C_2$-$C_6$ alkynyl;

$R_8$ is H, deuterium, $C_1$-$C_6$ alkyl, $C_2$-$C_6$ alkenyl, or $C_2$-$C_6$ alkynyl; and $R_9$ is H, $C_1$-$C_6$ alkyl, $C_2$-$C_6$ alkenyl, $C_2$-$C_6$ alkynyl, $C_1$-$C_6$ haloalkyl, or $C_3$-$C_6$ cycloalkyl, provided that:

(a) when $R_5$ is H then X is $CR_7R_8$ or S;

(b) when $R_5$ halogen, $R_4$ is H, then $R_3$ is not methyl, methoxyl, or Br and X is $CR_7R_8$ or S; and (c) when $R_5$ is methoxyl or methyl then $R_4$ is not H.

In some aspects, the present disclosure provides, inter alia, a compound of Formula (II'):

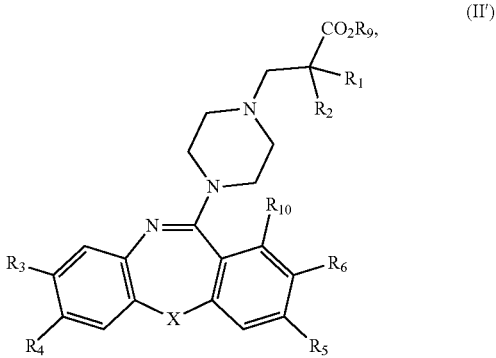

(II')

or a prodrug, solvate, or pharmaceutically acceptable salt thereof, wherein:

X is $CR_7R_8$, O, S, or $NR_7$;

$R_1$ is $C_1$-$C_6$ alkyl, $C_2$-$C_6$ alkenyl, $C_2$-$C_6$ alkynyl, $C_1$-$C_6$ haloalkyl, $C_1$-$C_6$ alkoxyl, or $C_3$-$C_6$ cycloalkyl;

$R_2$ is $C_1$-$C_6$ alkyl, $C_2$-$C_6$ alkenyl, $C_2$-$C_6$ alkynyl, $C_1$-$C_6$ haloalkyl, $C_1$-$C_6$ alkoxyl, or $C_3$-$C_6$ cycloalkyl; or $R_1$ and $R_2$ together with the atoms to which they are attached form a $C_3$-$C_6$ saturated or partially unsaturated cycloalkyl or a 3- to 14-membered saturated or partially unsaturated heterocycle comprising 1-5 heteroatoms selected from N, O, and S;

$R_3$ is H, halogen, —S($C_1$-$C_6$ alkyl), —N($C_1$-$C_6$ alkyl)$_2$, —NH($C_1$-$C_6$ alkyl), —NH$_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxyl, $C_1$-$C_6$ haloalkoxyl, or $C_3$-$C_6$ cycloalkyl;

$R_4$ is H, halogen, —S($C_1$-$C_6$ alkyl), —N($C_1$-$C_6$ alkyl)$_2$, —NH($C_1$-$C_6$ alkyl), —NH$_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxyl, $C_1$-$C_6$ haloalkoxyl, or $C_3$-$C_6$ cycloalkyl;

$R_5$ is H, halogen, —S($C_1$-$C_6$ alkyl), —N($C_1$-$C_6$ alkyl)$_2$, —NH($C_1$-$C_6$ alkyl), —NH$_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxyl, $C_1$-$C_6$ haloalkoxyl, or $C_3$-$C_6$ cycloalkyl;

$R_6$ is H, halogen, —S($C_1$-$C_6$ alkyl), —N($C_1$-$C_6$ alkyl)$_2$, —NH($C_1$-$C_6$ alkyl), —NH$_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxyl, $C_1$-$C_6$ haloalkoxyl, or $C_3$-$C_6$ cycloalkyl;

$R_7$ is H, deuterium, $C_1$-$C_6$ alkyl, $C_2$-$C_6$ alkenyl, or $C_2$-$C_6$ alkynyl;

$R_8$ is H, deuterium, $C_1$-$C_6$ alkyl, $C_2$-$C_6$ alkenyl, or $C_2$-$C_6$ alkynyl;

$R_9$ is H, $C_1$-$C_6$ alkyl, $C_2$-$C_6$ alkenyl, $C_2$-$C_6$ alkynyl, $C_1$-$C_6$ haloalkyl, or $C_3$-$C_6$ cycloalkyl; and $R_{10}$ is H or halogen, provided that:

(a) (i) when $R_5$ is H then X is $CR_7R_8$ or S, or (ii) when $R_5$ is H and X is O then $R_{10}$ is halogen;

(b) when $R_5$ halogen, $R_4$ is H, then $R_3$ is not methyl, methoxyl, or Br and X is $CR_7R_8$ or S; and (c) when $R_5$ is methoxyl or methyl then $R_4$ is not H.

It is understood that, for a compound of Formula (I), (II), and (II'), X, $R_1$, $R_2$, $R_3$, $R_4$, $R_5$, $R_6$, $R_7$, $R_8$, $R_9$, and $R_{10}$ can each be, where applicable, selected from the groups described herein, and any group described herein for any of X, $R_1$, $R_2$, $R_3$, $R_4$, $R_5$, $R_6$, $R_7$, $R_8$, $R_9$, and $R_{10}$ can be combined, where applicable, with any group described herein for one or more of the remainder X, $R_1$, $R_2$, $R_3$, $R_4$, $R_5$, $R_6$, $R_7$, $R_8$, $R_9$, and $R_{10}$.

For a compound of Formula (I), (II), or (II'), where applicable:

In some embodiments, X is $CR_7R_8$, O, S, or $NR_7$. In some embodiments, X is $CR_7R_8$, O, or S. In some embodiments, X is $CR_7R_8$ or S. In some embodiments, X is $CR_7R_8$ or O. In some embodiments, X is $CR_7R_8$. In some embodiments, X is O. In some embodiments, X is S. In some embodiments, X is $NR_7$.

In some embodiments, X is $CH_2$.

In some embodiments, $R_1$ is $C_1$-$C_6$ alkyl, $C_2$-$C_6$ alkenyl, $C_2$-$C_6$ alkynyl, $C_1$-$C_6$ haloalkyl, $C_1$-$C_6$ alkoxyl, or $C_3$-$C_6$ cycloalkyl.

In some embodiments, $R_1$ is $C_1$-$C_6$ alkyl, $C_2$-$C_6$ alkenyl, $C_2$-$C_6$ alkynyl, $C_1$-$C_6$ haloalkyl, $C_1$-$C_6$ alkoxyl, or $C_3$-$C_6$ cycloalkyl.

In some embodiments, $R_1$ is $C_1$-$C_6$ alkyl, $C_2$-$C_6$ alkenyl, or $C_2$-$C_6$ alkynyl.

In some embodiments, $R_1$ is $C_1$-$C_6$ alkyl. In some embodiments, $R_1$ is methyl. In some embodiments, $R_1$ is ethyl. In some embodiments, $R_1$ is propyl. In some embodiments, $R_1$ is butyl. In some embodiments, $R_1$ is isopropyl. In some embodiments, $R_1$ is iso-butyl. In some embodiments, $R_1$ is sec-butyl. In some embodiments, $R_1$ is tert-butyl. In some embodiments, $R_1$ is pentyl. In some embodiments, $R_1$ is iso-pentyl. In some embodiments, $R_1$ is hexyl. In some embodiments, $R_1$ is iso-hexyl.

In some embodiments, $R_1$ is $C_2$-$C_6$ alkenyl. In some embodiments, $R_1$ is $C_2$ alkenyl. In some embodiments, $R_1$ is $C_3$ alkenyl. In some embodiments, $R_1$ is $C_4$ alkenyl. In some embodiments, $R_1$ is $C_5$ alkenyl. In some embodiments, $R_1$ is $C_6$ alkenyl.

In some embodiments, $R_1$ is $C_2$-$C_6$ alkynyl. In some embodiments, $R_1$ is $C_2$ alkynyl. In some embodiments, $R_1$ is $C_3$ alkynyl. In some embodiments, $R_1$ is $C_4$ alkynyl. In some embodiments, $R_1$ is $C_5$ alkynyl. In some embodiments, $R_1$ is $C_6$ alkynyl.

In some embodiments, $R_1$ is $C_1$-$C_6$ haloalkyl, $C_1$-$C_6$ alkoxyl, or $C_3$-$C_6$ cycloalkyl.

In some embodiments, $R_1$ is $C_3$-$C_6$ cycloalkyl. In some embodiments, $R_1$ is cyclopropyl. In some embodiments, $R_1$ is cyclobutyl. In some embodiments, $R_1$ is cyclopentyl. In some embodiments, $R_1$ is cyclohexyl.

In some embodiments, $R_1$ is $C_1$-$C_6$ haloalkyl. In some embodiments, $R_1$ is halomethyl. In some embodiments, $R_1$ is haloethyl. In some embodiments, $R_1$ is halopropyl. In some embodiments, $R_1$ is halobutyl. In some embodiments, $R_1$ is halopentyl. In some embodiments, $R_1$ is halohexyl.

In some embodiments, $R_1$ is $C_1$-$C_6$ alkoxyl. In some embodiments, $R_1$ is methoxyl. In some embodiments, $R_1$ is ethoxyl. In some embodiments, $R_1$ is propoxyl. In some embodiments, $R_1$ is butoxyl. In some embodiments, $R_1$ is pentoxyl. In some embodiments, $R_1$ is hexoxyl.

In some embodiments, $R_2$ is $C_1$-$C_6$ alkyl, $C_2$-$C_6$ alkenyl, $C_2$-$C_6$ alkynyl, $C_1$-$C_6$ haloalkyl, $C_1$-$C_6$ alkoxyl, or $C_3$-$C_6$ cycloalkyl.

In some embodiments, $R_2$ is $C_1$-$C_6$ alkyl, $C_2$-$C_6$ alkenyl, or $C_2$-$C_6$ alkynyl.

In some embodiments, $R_2$ is $C_1$-$C_6$ alkyl. In some embodiments, $R_2$ is methyl. In some embodiments, $R_2$ is ethyl. In some embodiments, $R_2$ is propyl. In some embodiments, $R_2$ is butyl. In some embodiments, $R_2$ is isopropyl. In some embodiments, $R_2$ is iso-butyl. In some embodiments, $R_2$ is sec-butyl. In some embodiments, $R_2$ is tert-butyl. In some embodiments, $R_2$ is pentyl. In some embodiments, $R_2$ is iso-pentyl. In some embodiments, $R_2$ is hexyl. In some embodiments, $R_2$ is iso-hexyl.

In some embodiments, $R_2$ is $C_2$-$C_6$ alkenyl. In some embodiments, $R_2$ is $C_2$ alkenyl. In some embodiments, $R_2$ is $C_3$ alkenyl. In some embodiments, $R_2$ is $C_4$ alkenyl. In some embodiments, $R_2$ is $C_5$ alkenyl. In some embodiments, $R_2$ is $C_6$ alkenyl.

In some embodiments, $R_2$ is $C_2$-$C_6$ alkynyl. In some embodiments, $R_2$ is $C_2$ alkynyl. In some embodiments, $R_2$ is $C_3$ alkynyl. In some embodiments, $R_2$ is $C_4$ alkynyl. In some embodiments, $R_2$ is $C_5$ alkynyl. In some embodiments, $R_2$ is $C_6$ alkynyl.

In some embodiments, $R_2$ is $C_1$-$C_6$ haloalkyl, $C_1$-$C_6$ alkoxyl, or $C_3$-$C_6$ cycloalkyl.

In some embodiments, $R_2$ is $C_3$-$C_6$ cycloalkyl. In some embodiments, $R_2$ is cyclopropyl. In some embodiments, $R_2$ is cyclobutyl. In some embodiments, $R_2$ is cyclopentyl. In some embodiments, $R_2$ is cyclohexyl.

In some embodiments, $R_2$ is $C_1$-$C_6$ haloalkyl. In some embodiments, $R_2$ is halomethyl. In some embodiments, $R_2$ is haloethyl. In some embodiments, $R_2$ is halopropyl. In some embodiments, $R_2$ is halobutyl. In some embodiments, $R_2$ is halopentyl. In some embodiments, $R_2$ is halohexyl.

In some embodiments, $R_2$ is $C_1$-$C_6$ alkoxyl. In some embodiments, $R_2$ is methoxyl. In some embodiments, $R_2$ is ethoxyl. In some embodiments, $R_2$ is propoxyl. In some embodiments, $R_2$ is butoxyl. In some embodiments, $R_2$ is pentoxyl. In some embodiments, $R_2$ is hexoxyl.

In some embodiments, $R_1$ and $R_2$ together with the atoms to which they are attached form a $C_3$-$C_6$ saturated or partially unsaturated cycloalkyl or a 3- to 14-membered saturated or partially unsaturated heterocycle comprising 1-5 heteroatoms selected from N, O, and S.

In some embodiments, $R_1$ and $R_2$ together with the atoms to which they are attached form a $C_3$-$C_6$ saturated or partially unsaturated cycloalkyl.

In some embodiments, $R_1$ and $R_2$ together with the atoms to which they are attached form a $C_3$ saturated or partially unsaturated cycloalkyl.

In some embodiments, $R_1$ and $R_2$ together with the atoms to which they are attached form a $C_4$ saturated or partially unsaturated cycloalkyl.

In some embodiments, $R_1$ and $R_2$ together with the atoms to which they are attached form a $C_5$ saturated or partially unsaturated cycloalkyl.

In some embodiments, $R_1$ and $R_2$ together with the atoms to which they are attached form a $C_6$ saturated or partially unsaturated cycloalkyl.

In some embodiments, $R_1$ and $R_2$ together with the atoms to which they are attached form a $C_3$-$C_6$ saturated cycloalkyl.

In some embodiments, $R_1$ and $R_2$ together with the atoms to which they are attached form a $C_3$ saturated cycloalkyl.

In some embodiments, $R_1$ and $R_2$ together with the atoms to which they are attached form a $C_4$ saturated cycloalkyl.

In some embodiments, $R_1$ and $R_2$ together with the atoms to which they are attached form a $C_5$ saturated cycloalkyl.

In some embodiments, $R_1$ and $R_2$ together with the atoms to which they are attached form a $C_6$ saturated cycloalkyl.

In some embodiments, $R_1$ and $R_2$ together with the atoms to which they are attached form a $C_3$-$C_6$ partially unsaturated cycloalkyl.

In some embodiments, $R_1$ and $R_2$ together with the atoms to which they are attached form a $C_3$ partially unsaturated cycloalkyl.

In some embodiments, $R_1$ and $R_2$ together with the atoms to which they are attached form a $C_4$ partially unsaturated cycloalkyl.

In some embodiments, $R_1$ and $R_2$ together with the atoms to which they are attached form a $C_5$ partially unsaturated cycloalkyl.

In some embodiments, $R_1$ and $R_2$ together with the atoms to which they are attached form a $C_6$ partially unsaturated cycloalkyl.

In some embodiments, $R_1$ and $R_2$ together with the atoms to which they are attached form a cyclopropyl. In some embodiments, $R_1$ and $R_2$ together with the atoms to which they are attached form a cyclobutyl. In some embodiments, $R_1$ and $R_2$ together with the atoms to which they are attached form a cyclopentyl. In some embodiments, $R_1$ and $R_2$ together with the atoms to which they are attached form a cyclohexyl.

In some embodiments, $R_1$ and $R_2$ together with the atoms to which they are attached form a 3- to 14-membered saturated or partially unsaturated heterocycle comprising 1-5 heteroatoms selected from N, O, and S.

In some embodiments, $R_1$ and $R_2$ together with the atoms to which they are attached form a 3-membered saturated or partially unsaturated heterocycle comprising 1-5 heteroatoms selected from N, O, and S.

In some embodiments, $R_1$ and $R_2$ together with the atoms to which they are attached form a 4-membered saturated or partially unsaturated heterocycle comprising 1-5 heteroatoms selected from N, O, and S.

In some embodiments, $R_1$ and $R_2$ together with the atoms to which they are attached form a 5-membered saturated or partially unsaturated heterocycle comprising 1-5 heteroatoms selected from N, O, and S.

In some embodiments, $R_1$ and $R_2$ together with the atoms to which they are attached form a 6-membered saturated or partially unsaturated heterocycle comprising 1-5 heteroatoms selected from N, O, and S.

In some embodiments, $R_1$ and $R_2$ together with the atoms to which they are attached form a 7-membered saturated or partially unsaturated heterocycle comprising 1-5 heteroatoms selected from N, O, and S.

In some embodiments, $R_1$ and $R_2$ together with the atoms to which they are attached form a 8-membered saturated or partially unsaturated heterocycle comprising 1-5 heteroatoms selected from N, O, and S.

In some embodiments, $R_1$ and $R_2$ together with the atoms to which they are attached form a 9-membered saturated or partially unsaturated heterocycle comprising 1-5 heteroatoms selected from N, O, and S.

In some embodiments, $R_1$ and $R_2$ together with the atoms to which they are attached form a 10-membered saturated or partially unsaturated heterocycle comprising 1-5 heteroatoms selected from N, O, and S.

In some embodiments, $R_1$ and $R_2$ together with the atoms to which they are attached form a 11-membered saturated or partially unsaturated heterocycle comprising 1-5 heteroatoms selected from N, O, and S.

In some embodiments, $R_1$ and $R_2$ together with the atoms to which they are attached form a 12-membered saturated or partially unsaturated heterocycle comprising 1-5 heteroatoms selected from N, O, and S.

In some embodiments, $R_1$ and $R_2$ together with the atoms to which they are attached form a 13-membered saturated or partially unsaturated heterocycle comprising 1-5 heteroatoms selected from N, O, and S.

In some embodiments, $R_1$ and $R_2$ together with the atoms to which they are attached form a 14-membered saturated or partially unsaturated heterocycle comprising 1-5 heteroatoms selected from N, O, and S.

In some embodiments, $R_1$ and $R_2$ together with the atoms to which they are attached form a 3- to 14-membered saturated heterocycle comprising 1-5 heteroatoms selected from N, O, and S.

In some embodiments, $R_1$ and $R_2$ together with the atoms to which they are attached form a 3-membered saturated heterocycle comprising 1-5 heteroatoms selected from N, O, and S.

In some embodiments, $R_1$ and $R_2$ together with the atoms to which they are attached form a 4-membered saturated heterocycle comprising 1-5 heteroatoms selected from N, O, and S.

In some embodiments, $R_1$ and $R_2$ together with the atoms to which they are attached form a 5-membered saturated heterocycle comprising 1-5 heteroatoms selected from N, O, and S.

In some embodiments, $R_1$ and $R_2$ together with the atoms to which they are attached form a 6-membered saturated heterocycle comprising 1-5 heteroatoms selected from N, O, and S.

In some embodiments, $R_1$ and $R_2$ together with the atoms to which they are attached form a 7-membered saturated heterocycle comprising 1-5 heteroatoms selected from N, O, and S.

In some embodiments, $R_1$ and $R_2$ together with the atoms to which they are attached form a 8-membered saturated heterocycle comprising 1-5 heteroatoms selected from N, O, and S.

In some embodiments, $R_1$ and $R_2$ together with the atoms to which they are attached form a 9-membered saturated heterocycle comprising 1-5 heteroatoms selected from N, O, and S.

In some embodiments, $R_1$ and $R_2$ together with the atoms to which they are attached form a 10-membered saturated heterocycle comprising 1-5 heteroatoms selected from N, O, and S.

In some embodiments, $R_1$ and $R_2$ together with the atoms to which they are attached form a 11-membered saturated heterocycle comprising 1-5 heteroatoms selected from N, O, and S.

In some embodiments, $R_1$ and $R_2$ together with the atoms to which they are attached form a 12-membered saturated heterocycle comprising 1-5 heteroatoms selected from N, O, and S.

In some embodiments, $R_1$ and $R_2$ together with the atoms to which they are attached form a 13-membered saturated heterocycle comprising 1-5 heteroatoms selected from N, O, and S.

In some embodiments, $R_1$ and $R_2$ together with the atoms to which they are attached form a 14-membered saturated heterocycle comprising 1-5 heteroatoms selected from N, O, and S.

In some embodiments, $R_1$ and $R_2$ together with the atoms to which they are attached form a 3- to 14-membered partially unsaturated heterocycle comprising 1-5 heteroatoms selected from N, O, and S.

In some embodiments, $R_1$ and $R_2$ together with the atoms to which they are attached form a 3-membered partially unsaturated heterocycle comprising 1-5 heteroatoms selected from N, O, and S.

In some embodiments, $R_1$ and $R_2$ together with the atoms to which they are attached form a 4-membered partially unsaturated heterocycle comprising 1-5 heteroatoms selected from N, O, and S.

In some embodiments, $R_1$ and $R_2$ together with the atoms to which they are attached form a 5-membered partially unsaturated heterocycle comprising 1-5 heteroatoms selected from N, O, and S.

In some embodiments, $R_1$ and $R_2$ together with the atoms to which they are attached form a 6-membered partially unsaturated heterocycle comprising 1-5 heteroatoms selected from N, O, and S.

In some embodiments, $R_1$ and $R_2$ together with the atoms to which they are attached form a 7-membered partially unsaturated heterocycle comprising 1-5 heteroatoms selected from N, O, and S.

In some embodiments, $R_1$ and $R_2$ together with the atoms to which they are attached form a 8-membered partially unsaturated heterocycle comprising 1-5 heteroatoms selected from N, O, and S.

In some embodiments, $R_1$ and $R_2$ together with the atoms to which they are attached form a 9-membered partially unsaturated heterocycle comprising 1-5 heteroatoms selected from N, O, and S.

In some embodiments, $R_1$ and $R_2$ together with the atoms to which they are attached form a 10-membered partially unsaturated heterocycle comprising 1-5 heteroatoms selected from N, O, and S.

In some embodiments, $R_1$ and $R_2$ together with the atoms to which they are attached form a 11-membered partially unsaturated heterocycle comprising 1-5 heteroatoms selected from N, O, and S.

In some embodiments, $R_1$ and $R_2$ together with the atoms to which they are attached form a 12-membered partially unsaturated heterocycle comprising 1-5 heteroatoms selected from N, O, and S.

In some embodiments, $R_1$ and $R_2$ together with the atoms to which they are attached form a 13-membered partially unsaturated heterocycle comprising 1-5 heteroatoms selected from N, O, and S.

In some embodiments, $R_1$ and $R_2$ together with the atoms to which they are attached form a 14-membered partially unsaturated heterocycle comprising 1-5 heteroatoms selected from N, O, and S.

In some embodiments, $R_1$ and $R_2$ together with the atoms to which they are attached form a 3- to 14-membered saturated or partially unsaturated heterocycle comprising 1 heteroatom selected from N, O, and S.

In some embodiments, $R_1$ and $R_2$ together with the atoms to which they are attached form a 3- to 14-membered saturated or partially unsaturated heterocycle comprising 2 heteroatoms selected from N, O, and S.

In some embodiments, $R_1$ and $R_2$ together with the atoms to which they are attached form a 3- to 14-membered saturated or partially unsaturated heterocycle comprising 3 heteroatoms selected from N, O, and S.

In some embodiments, $R_1$ and $R_2$ together with the atoms to which they are attached form a 3- to 14-membered saturated or partially unsaturated heterocycle comprising 4 heteroatoms selected from N, O, and S.

In some embodiments, $R_1$ and $R_2$ together with the atoms to which they are attached form a 3- to 14-membered saturated or partially unsaturated heterocycle comprising 5 heteroatoms selected from N, O, and S.

In some embodiments, $R_3$ is H, halogen, —S($C_1$-$C_6$ alkyl), —N($C_1$-$C_6$ alkyl)$_2$, —NH($C_1$-$C_6$ alkyl), —NH$_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxyl, $C_1$-$C_6$ haloalkoxyl, or $C_3$-$C_6$ cycloalkyl.

In some embodiments, $R_3$ is H.

In some embodiments, $R_3$ is halogen, —S($C_1$-$C_6$ alkyl), —N($C_1$-$C_6$ alkyl)$_2$, —NH($C_1$-$C_6$ alkyl), —NH$_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxyl, $C_1$-$C_6$ haloalkoxyl, or $C_3$-$C_6$ cycloalkyl.

In some embodiments, $R_3$ is halogen. In some embodiments, $R_3$ is F, Cl, Br, or I. In some embodiments, $R_3$ is F, Cl, or Br. In some embodiments, $R_3$ is F or Cl. In some embodiments, $R_3$ is F. In some embodiments, $R_3$ is Cl. In some embodiments, $R_3$ is Br. In some embodiments, $R_3$ is I.

In some embodiments, $R_3$ is $C_1$-$C_6$ alkyl, $C_2$-$C_6$ alkenyl, or $C_2$-$C_6$ alkynyl.

In some embodiments, $R_3$ is $C_1$-$C_6$ alkyl. In some embodiments, $R_3$ is methyl. In some embodiments, $R_3$ is ethyl. In some embodiments, $R_3$ is propyl. In some embodiments, $R_3$ is butyl.

In some embodiments, $R_3$ is isopropyl. In some embodiments, $R_3$ is iso-butyl. In some embodiments, $R_3$ is sec-butyl. In some embodiments, $R_3$ is tert-butyl. In some embodiments, $R_3$ is pentyl. In some embodiments, $R_3$ is iso-pentyl. In some embodiments, $R_3$ is hexyl. In some embodiments, $R_3$ is iso-hexyl.

In some embodiments, $R_3$ is $C_2$-$C_6$ alkenyl. In some embodiments, $R_3$ is $C_2$ alkenyl. In some embodiments, $R_3$ is $C_3$ alkenyl. In some embodiments, $R_3$ is $C_4$ alkenyl. In some embodiments, $R_3$ is $C_5$ alkenyl. In some embodiments, $R_3$ is $C_6$ alkenyl.

In some embodiments, $R_3$ is $C_2$-$C_6$ alkynyl. In some embodiments, $R_3$ is $C_2$ alkynyl. In some embodiments, $R_3$ is $C_3$ alkynyl. In some embodiments, $R_3$ is $C_4$ alkynyl. In some embodiments, $R_3$ is $C_5$ alkynyl. In some embodiments, $R_3$ is $C_6$ alkynyl.

In some embodiments, $R_3$ is $C_1$-$C_6$ haloalkyl, $C_1$-$C_6$ alkoxyl, $C_1$-$C_6$ haloalkoxyl, or $C_3$-$C_6$ cycloalkyl.

In some embodiments, $R_3$ is $C_1$-$C_6$ haloalkyl. In some embodiments, $R_3$ is halomethyl. In some embodiments, $R_3$ is haloethyl. In some embodiments, $R_3$ is halopropyl. In some embodiments, $R_3$ is halobutyl. In some embodiments, $R_3$ is halopentyl. In some embodiments, $R_3$ is halohexyl.

In some embodiments, $R_3$ is $C_1$-$C_6$ alkoxyl. In some embodiments, $R_3$ is methoxyl. In some embodiments, $R_3$ is ethoxyl. In some embodiments, $R_3$ is propoxyl. In some embodiments, $R_3$ is butoxyl. In some embodiments, $R_3$ is pentoxyl. In some embodiments, $R_3$ is hexoxyl.

In some embodiments, $R_3$ is $C_1$-$C_6$ haloalkoxyl. In some embodiments, $R_3$ is halomethoxyl. In some embodiments, $R_3$ is haloethoxyl. In some embodiments, $R_3$ is halopropoxyl. In some embodiments, $R_3$ is halobutoxyl. In some embodiments, $R_3$ is halopentoxyl. In some embodiments, $R_3$ is halohexoxyl.

In some embodiments, $R_3$ is $C_3$-$C_6$ cycloalkyl. In some embodiments, $R_3$ is cyclopropyl. In some embodiments, $R_3$ is cyclobutyl. In some embodiments, $R_3$ is cyclopentyl. In some embodiments, $R_3$ is cyclohexyl.

In some embodiments, $R_3$ is —S($C_1$-$C_6$ alkyl), —N($C_1$-$C_6$ alkyl)$_2$, or —NH($C_1$-$C_6$ alkyl).

In some embodiments, $R_3$ is —S($C_1$-$C_6$ alkyl). In some embodiments, $R_3$ is —S(methyl). In some embodiments, $R_3$ is —S(ethyl). In some embodiments, $R_3$ is —S(propyl). In some embodiments, $R_3$ is —S(butyl). In some embodiments, $R_3$ is —S(pentyl). In some embodiments, $R_3$ is —S(hexyl).

In some embodiments, $R_3$ is —N($C_1$-$C_6$ alkyl)$_2$, —NH($C_1$-$C_6$ alkyl), or —NH$_2$.

In some embodiments, $R_3$ is —NH$_2$.

In some embodiments, $R_3$ is —N($C_1$-$C_6$ alkyl)$_2$. In some embodiments, $R_3$ is —N(methyl)$_2$. In some embodiments, $R_3$ is —N(ethyl)$_2$. In some embodiments, $R_3$ is —N(propyl)$_2$. In some embodiments, $R_3$ is —N(butyl)$_2$. In some embodiments, $R_3$ is —N(pentyl)$_2$. In some embodiments, $R_3$ is —N(hexyl)$_2$.

In some embodiments, $R_3$ is —NH($C_1$-$C_6$ alkyl). In some embodiments, $R_3$ is —NH(methyl). In some embodiments, $R_3$ is —NH(ethyl). In some embodiments, $R_3$ is —NH(propyl). In some embodiments, $R_3$ is —NH(butyl). In some embodiments, $R_3$ is —NH(pentyl). In some embodiments, $R_3$ is —NH(hexyl).

In some embodiments, $R_3$ is H, F, Cl, methyl, or methoxyl.

In some embodiments, $R_4$ is H, halogen, —S($C_1$-$C_6$ alkyl), —N($C_1$-$C_6$ alkyl)$_2$, —NH($C_1$-$C_6$ alkyl), —NH$_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxyl, $C_1$-$C_6$ haloalkoxyl, or $C_3$-$C_6$ cycloalkyl.

In some embodiments, $R_4$ is H.

In some embodiments, $R_4$ is halogen, —S($C_1$-$C_6$ alkyl), —N($C_1$-$C_6$ alkyl)$_2$, —NH($C_1$-$C_6$ alkyl), —NH$_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxyl, $C_1$-$C_6$ haloalkoxyl, or $C_3$-$C_6$ cycloalkyl.

In some embodiments, $R_4$ is halogen. In some embodiments, $R_4$ is F, Cl, Br, or I. In some embodiments, $R_4$ is F, Cl, or Br. In some embodiments, $R_4$ is F or Cl. In some embodiments, $R_4$ is F. In some embodiments, $R_4$ is Cl. In some embodiments, $R_4$ is Br. In some embodiments, $R_4$ is I.

In some embodiments, $R_4$ is $C_1$-$C_6$ alkyl, $C_2$-$C_6$ alkenyl, or $C_2$-$C_6$ alkynyl. In some embodiments, $R_4$ is $C_1$-$C_6$ alkyl. In some embodiments, $R_4$ is methyl. In some embodiments, $R_4$ is ethyl. In some embodiments, $R_4$ is propyl. In some embodiments, $R_4$ is butyl. In some embodiments, $R_4$ is isopropyl. In some embodiments, $R_4$ is iso-butyl. In some embodiments, $R_4$ is sec-butyl. In some embodiments, $R_4$ is tert-butyl. In some embodiments, $R_4$ is pentyl. In some embodiments, $R_4$ is iso-pentyl. In some embodiments, $R_4$ is hexyl. In some embodiments, $R_4$ is iso-hexyl.

In some embodiments, $R_4$ is $C_2$-$C_6$ alkenyl. In some embodiments, $R_4$ is $C_2$ alkenyl. In some embodiments, $R_4$ is $C_3$ alkenyl. In some embodiments, $R_4$ is $C_4$ alkenyl. In some embodiments, $R_4$ is $C_5$ alkenyl. In some embodiments, $R_4$ is $C_6$ alkenyl.

In some embodiments, $R_4$ is $C_2$-$C_6$ alkynyl. In some embodiments, $R_4$ is $C_2$ alkynyl. In some embodiments, $R_4$ is $C_3$ alkynyl. In some embodiments, $R_4$ is $C_4$ alkynyl. In some embodiments, $R_4$ is $C_5$ alkynyl. In some embodiments, $R_4$ is $C_6$ alkynyl.

In some embodiments, $R_4$ is $C_1$-$C_6$ haloalkyl, $C_1$-$C_6$ alkoxyl, $C_1$-$C_6$ haloalkoxyl, or $C_3$-$C_6$ cycloalkyl.

In some embodiments, $R_4$ is $C_1$-$C_6$ haloalkyl. In some embodiments, $R_4$ is halomethyl. In some embodiments, $R_4$ is haloethyl. In some embodiments, $R_4$ is halopropyl. In some embodiments, $R_4$ is halobutyl. In some embodiments, $R_4$ is halopentyl. In some embodiments, $R_4$ is halohexyl.

In some embodiments, $R_4$ is $C_1$-$C_6$ alkoxyl. In some embodiments, $R_4$ is methoxyl. In some embodiments, $R_4$ is ethoxyl. In some embodiments, $R_4$ is propoxyl. In some embodiments, $R_4$ is butoxyl. In some embodiments, $R_4$ is pentoxyl. In some embodiments, $R_4$ is hexoxyl.

In some embodiments, $R_4$ is $C_1$-$C_6$ haloalkoxyl. In some embodiments, $R_4$ is halomethoxyl. In some embodiments, $R_4$ is haloethoxyl. In some embodiments, $R_4$ is halopropoxyl. In some embodiments, $R_4$ is halobutoxyl. In some embodiments, $R_4$ is halopentoxyl. In some embodiments, $R_4$ is halohexoxyl.

In some embodiments, $R_4$ is $C_3$-$C_6$ cycloalkyl. In some embodiments, $R_4$ is cyclopropyl. In some embodiments, $R_4$ is cyclobutyl. In some embodiments, $R_4$ is cyclopentyl. In some embodiments, $R_4$ is cyclohexyl.

In some embodiments, $R_4$ is —S($C_1$-$C_6$ alkyl), —N($C_1$-$C_6$ alkyl)$_2$, or —NH($C_1$-$C_6$ alkyl).

In some embodiments, $R_4$ is —S($C_1$-$C_6$ alkyl). In some embodiments, $R_4$ is —S(methyl). In some embodiments, $R_4$ is —S(ethyl). In some embodiments, $R_4$ is —S(propyl). In some embodiments, $R_4$ is —S(butyl). In some embodiments, $R_4$ is —S(pentyl). In some embodiments, $R_4$ is —S(hexyl).

In some embodiments, $R_4$ is —N($C_1$-$C_6$ alkyl)$_2$, —NH($C_1$-$C_6$ alkyl), or —NH$_2$.

In some embodiments, $R_4$ is —NH$_2$.

In some embodiments, $R_4$ is —N($C_1$-$C_6$ alkyl)$_2$. In some embodiments, $R_4$ is —N(methyl)$_2$. In some embodiments, $R_4$ is —N(ethyl)$_2$. In some embodiments, $R_4$ is —N(propyl)$_2$. In some embodiments, $R_4$ is —N(butyl)$_2$. In some embodiments, $R_4$ is —N(pentyl)$_2$. In some embodiments, $R_4$ is —N(hexyl)$_2$.

In some embodiments, $R_4$ is —NH($C_1$-$C_6$ alkyl). In some embodiments, $R_4$ is —NH(methyl). In some embodiments, $R_4$ is —NH(ethyl). In some embodiments, $R_4$ is —NH(propyl). In some embodiments, $R_4$ is —NH(butyl). In some embodiments, $R_4$ is —NH(pentyl). In some embodiments, $R_4$ is —NH(hexyl).

In some embodiments, $R_4$ is H, F, Cl, methyl, or $CHF_2$.

In some embodiments, $R_5$ is H, halogen, —S($C_1$-$C_6$ alkyl), —N($C_1$-$C_6$ alkyl)$_2$, —NH($C_1$-$C_6$ alkyl), —NH$_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxyl, $C_1$-$C_6$ haloalkoxyl, or $C_3$-$C_6$ cycloalkyl.

In some embodiments, $R_5$ is H.

In some embodiments, $R_5$ is halogen, —S($C_1$-$C_6$ alkyl), —N($C_1$-$C_6$ alkyl)$_2$, —NH($C_1$-$C_6$ alkyl), —NH$_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxyl, $C_1$-$C_6$ haloalkoxyl, or $C_3$-$C_6$ cycloalkyl.

In some embodiments, $R_5$ is halogen. In some embodiments, $R_5$ is F, Cl, Br, or I. In some embodiments, $R_5$ is F, Cl, or Br. In some embodiments, $R_5$ is F or Cl. In some embodiments, $R_5$ is F. In some embodiments, $R_5$ is Cl. In some embodiments, $R_5$ is Br. In some embodiments, $R_5$ is I.

In some embodiments, $R_5$ is $C_1$-$C_6$ alkyl, $C_2$-$C_6$ alkenyl, or $C_2$-$C_6$ alkynyl.

In some embodiments, $R_5$ is $C_1$-$C_6$ alkyl. In some embodiments, $R_5$ is methyl. In some embodiments, $R_5$ is ethyl. In some embodiments, $R_5$ is propyl. In some embodiments, $R_5$ is butyl.

In some embodiments, $R_5$ is isopropyl. In some embodiments, $R_5$ is iso-butyl. In some embodiments, $R_5$ is sec-butyl. In some embodiments, $R_5$ is tert-butyl. In some embodiments, $R_5$ is pentyl. In some embodiments, $R_5$ is iso-pentyl. In some embodiments, $R_5$ is hexyl. In some embodiments, $R_5$ is iso-hexyl.

In some embodiments, $R_5$ is $C_2$-$C_6$ alkenyl. In some embodiments, $R_5$ is $C_2$ alkenyl. In some embodiments, $R_5$ is $C_3$ alkenyl. In some embodiments, $R_5$ is $C_4$ alkenyl. In some embodiments, $R_5$ is $C_5$ alkenyl. In some embodiments, $R_5$ is $C_6$ alkenyl.

In some embodiments, $R_5$ is $C_2$-$C_6$ alkynyl. In some embodiments, $R_5$ is $C_2$ alkynyl. In some embodiments, $R_5$ is $C_3$ alkynyl. In some embodiments, $R_5$ is $C_4$ alkynyl. In some embodiments, $R_5$ is $C_5$ alkynyl. In some embodiments, $R_5$ is $C_6$ alkynyl.

In some embodiments, $R_5$ is $C_1$-$C_6$ haloalkyl, $C_1$-$C_6$ alkoxyl, $C_1$-$C_6$ haloalkoxyl, or $C_3$-$C_6$ cycloalkyl.

In some embodiments, $R_5$ is $C_1$-$C_6$ haloalkyl. In some embodiments, $R_5$ is halomethyl. In some embodiments, $R_5$ is haloethyl. In some embodiments, $R_5$ is halopropyl. In some embodiments, $R_5$ is halobutyl. In some embodiments, $R_5$ is halopentyl. In some embodiments, $R_5$ is halohexyl.

In some embodiments, $R_5$ is $C_1$-$C_6$ alkoxyl. In some embodiments, $R_5$ is methoxyl. In some embodiments, $R_5$ is ethoxyl. In some embodiments, $R_5$ is propoxyl. In some embodiments, $R_5$ is butoxyl. In some embodiments, $R_5$ is pentoxyl. In some embodiments, $R_5$ is hexoxyl.

In some embodiments, $R_5$ is $C_1$-$C_6$ haloalkoxyl. In some embodiments, $R_5$ is halomethoxyl. In some embodiments, $R_5$ is haloethoxyl. In some embodiments, $R_5$ is halopropoxyl. In some embodiments, $R_5$ is halobutoxyl. In some embodiments, $R_5$ is halopentoxyl. In some embodiments, $R_5$ is halohexoxyl.

In some embodiments, $R_5$ is $C_3$-$C_6$ cycloalkyl. In some embodiments, $R_5$ is cyclopropyl.

In some embodiments, $R_5$ is cyclobutyl. In some embodiments, $R_5$ is cyclopentyl. In some embodiments, $R_5$ is cyclohexyl.

In some embodiments, $R_5$ is —S($C_1$-$C_6$ alkyl), —N($C_1$-$C_6$ alkyl)$_2$, or —NH($C_1$-$C_6$ alkyl).

In some embodiments, $R_5$ is —S($C_1$-$C_6$ alkyl). In some embodiments, $R_5$ is —S(methyl). In some embodiments, $R_5$ is —S(ethyl). In some embodiments, $R_5$ is —S(propyl). In some embodiments, $R_5$ is —S(butyl). In some embodiments, $R_5$ is —S(pentyl). In some embodiments, $R_5$ is —S(hexyl).

In some embodiments, $R_5$ is —N($C_1$-$C_6$ alkyl)$_2$, —NH($C_1$-$C_6$ alkyl), or —NH$_2$.

In some embodiments, $R_5$ is —NH$_2$.

In some embodiments, $R_5$ is —N($C_1$-$C_6$ alkyl)$_2$. In some embodiments, $R_5$ is —N(methyl)$_2$.

In some embodiments, $R_5$ is —N(ethyl)$_2$. In some embodiments, $R_5$ is —N(propyl)$_2$. In some embodiments, $R_5$ is —N(butyl)$_2$. In some embodiments, $R_5$ is —N(pentyl)$_2$. In some embodiments, $R_5$ is —N(hexyl)$_2$.

In some embodiments, $R_5$ is —NH($C_1$-$C_6$ alkyl). In some embodiments, $R_5$ is —NH(methyl). In some embodiments, $R_5$ is —NH(ethyl). In some embodiments, $R_5$ is —NH(propyl).

In some embodiments, $R_5$ is —NH(butyl). In some embodiments, $R_5$ is —NH(pentyl). In some embodiments, $R_5$ is —NH(hexyl).

In some embodiments, $R_5$ is H, F, Cl, methyl, ethyl, iso-propyl, n-propyl, methoxyl, methylthiyl, or CHF$_2$.

In some embodiments, $R_6$ is H, halogen, —S($C_1$-$C_6$ alkyl), —N($C_1$-$C_6$ alkyl)$_2$, —NH($C_1$-$C_6$ alkyl), —NH$_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxyl, $C_1$-$C_6$ haloalkoxyl, or $C_3$-$C_6$ cycloalkyl.

In some embodiments, $R_6$ is H.

In some embodiments, $R_6$ is halogen, —S($C_1$-$C_6$ alkyl), —N($C_1$-$C_6$ alkyl)$_2$, —NH($C_1$-$C_6$ alkyl), —NH$_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxyl, $C_1$-$C_6$ haloalkoxyl, or $C_3$-$C_6$ cycloalkyl.

In some embodiments, $R_6$ is halogen. In some embodiments, $R_6$ is F, Cl, Br, or I. In some embodiments, $R_6$ is F, Cl, or Br. In some embodiments, $R_6$ is F or Cl. In some embodiments, $R_6$ is F. In some embodiments, $R_6$ is Cl. In some embodiments, $R_6$ is Br. In some embodiments, $R_6$ is I.

In some embodiments, $R_6$ is $C_1$-$C_6$ alkyl, $C_2$-$C_6$ alkenyl, or $C_2$-$C_6$ alkynyl.

In some embodiments, $R_6$ is $C_1$-$C_6$ alkyl. In some embodiments, $R_6$ is methyl. In some embodiments, $R_6$ is ethyl. In some embodiments, $R_6$ is propyl. In some embodiments, $R_6$ is butyl. In some embodiments, $R_6$ is isopropyl. In some embodiments, $R_6$ is iso-butyl. In some embodiments, $R_6$ is sec-butyl. In some embodiments, $R_6$ is tert-butyl. In some embodiments, $R_6$ is pentyl. In some embodiments, $R_6$ is iso-pentyl. In some embodiments, $R_6$ is hexyl. In some embodiments, $R_6$ is iso-hexyl.

In some embodiments, $R_6$ is $C_2$-$C_6$ alkenyl. In some embodiments, $R_6$ is $C_2$ alkenyl. In some embodiments, $R_6$ is $C_3$ alkenyl. In some embodiments, $R_6$ is $C_4$ alkenyl. In some embodiments, $R_6$ is $C_5$ alkenyl. In some embodiments, $R_6$ is $C_6$ alkenyl.

In some embodiments, $R_6$ is $C_2$-$C_6$ alkynyl. In some embodiments, $R_6$ is $C_2$ alkynyl. In some embodiments, $R_6$ is $C_3$ alkynyl. In some embodiments, $R_6$ is $C_4$ alkynyl. In some embodiments, $R_6$ is $C_5$ alkynyl. In some embodiments, $R_6$ is $C_6$ alkynyl.

In some embodiments, $R_6$ is $C_1$-$C_6$ haloalkyl, $C_1$-$C_6$ alkoxyl, $C_1$-$C_6$ haloalkoxyl, or $C_3$-$C_6$ cycloalkyl.

In some embodiments, $R_6$ is $C_1$-$C_6$ haloalkyl. In some embodiments, $R_6$ is halomethyl. In some embodiments, $R_6$ is haloethyl. In some embodiments, $R_6$ is halopropyl. In some embodiments, $R_6$ is halobutyl. In some embodiments, $R_6$ is halopentyl. In some embodiments, $R_6$ is halohexyl.

In some embodiments, $R_6$ is $C_1$-$C_6$ alkoxyl. In some embodiments, $R_6$ is methoxyl. In some embodiments, $R_6$ is ethoxyl. In some embodiments, $R_6$ is propoxyl. In some embodiments, $R_6$ is butoxyl. In some embodiments, $R_6$ is pentoxyl. In some embodiments, $R_6$ is hexoxyl.

In some embodiments, $R_6$ is $C_1$-$C_6$ haloalkoxyl. In some embodiments, $R_6$ is halomethoxyl. In some embodiments, $R_6$ is haloethoxyl. In some embodiments, $R_6$ is halopropoxyl. In some embodiments, $R_6$ is halobutoxyl. In some embodiments, $R_6$ is halopentoxyl. In some embodiments, $R_6$ is halohexoxyl.

In some embodiments, $R_6$ is $C_3$-$C_6$ cycloalkyl. In some embodiments, $R_6$ is cyclopropyl.

In some embodiments, $R_6$ is cyclobutyl. In some embodiments, $R_6$ is cyclopentyl. In some embodiments, $R_6$ is cyclohexyl.

In some embodiments, $R_6$ is —S($C_1$-$C_6$ alkyl), —N($C_1$-$C_6$ alkyl)$_2$, or —NH($C_1$-$C_6$ alkyl).

In some embodiments, $R_6$ is —S($C_1$-$C_6$ alkyl). In some embodiments, $R_6$ is —S(methyl). In some embodiments, $R_6$ is —S(ethyl). In some embodiments, $R_6$ is —S(propyl). In some embodiments, $R_6$ is —S(butyl). In some embodiments, $R_6$ is —S(pentyl). In some embodiments, $R_6$ is —S(hexyl).

In some embodiments, $R_6$ is —N($C_1$-$C_6$ alkyl)$_2$, —NH($C_1$-$C_6$ alkyl), or —NH$_2$.

In some embodiments, $R_6$ is —NH$_2$.

In some embodiments, $R_6$ is —N($C_1$-$C_6$ alkyl)$_2$. In some embodiments, $R_6$ is —N(methyl)$_2$.

In some embodiments, $R_6$ is —N(ethyl)$_2$. In some embodiments, $R_6$ is —N(propyl)$_2$. In some embodiments, $R_6$ is —N(butyl)$_2$. In some embodiments, $R_6$ is —N(pentyl)$_2$. In some embodiments, $R_6$ is —N(hexyl)$_2$.

In some embodiments, $R_6$ is —NH($C_1$-$C_6$ alkyl). In some embodiments, $R_6$ is —NH(methyl). In some embodiments, $R_6$ is —NH(ethyl). In some embodiments, $R_6$ is —NH(propyl).

In some embodiments, $R_6$ is —NH(butyl). In some embodiments, $R_6$ is —NH(pentyl). In some embodiments, $R_6$ is —NH(hexyl).

In some embodiments, $R_6$ is H, methyl, or methoxyl.

In some embodiments, $R_7$ is H, deuterium, $C_1$-$C_6$ alkyl, $C_2$-$C_6$ alkenyl, or $C_2$-$C_6$ alkynyl.

In some embodiments, $R_7$ is H, $C_1$-$C_6$ alkyl, $C_2$-$C_6$ alkenyl, or $C_2$-$C_6$ alkynyl.

In some embodiments, $R_7$ is H or deuterium.

In some embodiments, $R_7$ is H. In some embodiments, $R_7$ is deuterium.

In some embodiments, $R_7$ is $C_1$-$C_6$ alkyl, $C_2$-$C_6$ alkenyl, or $C_2$-$C_6$ alkynyl.

In some embodiments, $R_7$ is $C_1$-$C_6$ alkyl. In some embodiments, $R_7$ is methyl. In some embodiments, $R_7$ is ethyl. In some embodiments, $R_7$ is propyl. In some embodiments, $R_7$ is butyl.

In some embodiments, $R_7$ is isopropyl. In some embodiments, $R_7$ is iso-butyl. In some embodiments, $R_7$ is sec-butyl. In some embodiments, $R_7$ is tert-butyl. In some embodiments, $R_7$ is pentyl. In some embodiments, $R_7$ is iso-pentyl. In some embodiments, $R_7$ is hexyl. In some embodiments, $R_7$ is iso-hexyl.

In some embodiments, $R_7$ is $C_2$-$C_6$ alkenyl. In some embodiments, $R_7$ is $C_2$ alkenyl. In some embodiments, $R_7$ is $C_3$ alkenyl. In some embodiments, $R_7$ is $C_4$ alkenyl. In some embodiments, $R_7$ is $C_5$ alkenyl. In some embodiments, $R_7$ is $C_6$ alkenyl.

In some embodiments, $R_7$ is $C_2$-$C_6$ alkynyl. In some embodiments, $R_7$ is $C_2$ alkynyl. In some embodiments, $R_7$ is $C_3$ alkynyl. In some embodiments, $R_7$ is $C_4$ alkynyl. In some embodiments, $R_7$ is $C_5$ alkynyl. In some embodiments, $R_7$ is $C_6$ alkynyl.

In some embodiments, $R_8$ is H, deuterium, $C_1$-$C_6$ alkyl, $C_2$-$C_6$ alkenyl, or $C_2$-$C_6$ alkynyl.

In some embodiments, $R_8$ is H, $C_1$-$C_6$ alkyl, $C_2$-$C_6$ alkenyl, or $C_2$-$C_6$ alkynyl.

In some embodiments, $R_8$ is H or deuterium.

In some embodiments, $R_8$ is H. In some embodiments, $R_8$ is deuterium.

In some embodiments, $R_8$ is $C_1$-$C_6$ alkyl, $C_2$-$C_6$ alkenyl, or $C_2$-$C_6$ alkynyl.

In some embodiments, $R_8$ is $C_1$-$C_6$ alkyl. In some embodiments, $R_8$ is methyl. In some embodiments, $R_8$ is ethyl. In some embodiments, $R_8$ is propyl. In some embodiments, $R_8$ is butyl.

In some embodiments, $R_8$ is isopropyl. In some embodiments, $R_8$ is iso-butyl. In some embodiments, $R_8$ is sec-butyl. In some embodiments, $R_8$ is tert-butyl. In some embodiments, $R_8$ is pentyl. In some embodiments, $R_8$ is iso-pentyl. In some embodiments, $R_8$ is hexyl. In some embodiments, $R_8$ is iso-hexyl.

In some embodiments, $R_8$ is $C_2$-$C_6$ alkenyl. In some embodiments, $R_8$ is $C_2$ alkenyl. In some embodiments, $R_8$ is $C_3$ alkenyl. In some embodiments, $R_8$ is $C_4$ alkenyl. In some embodiments, $R_8$ is $C_5$ alkenyl. In some embodiments, $R_8$ is $C_6$ alkenyl.

In some embodiments, $R_8$ is $C_2$-$C_6$ alkynyl. In some embodiments, $R_8$ is $C_2$ alkynyl. In some embodiments, $R_8$ is $C_3$ alkynyl. In some embodiments, $R_8$ is $C_4$ alkynyl. In some embodiments, $R_8$ is $C_5$ alkynyl. In some embodiments, $R_8$ is $C_6$ alkynyl.

In some embodiments, $R_9$ is H, $C_1$-$C_6$ alkyl, $C_2$-$C_6$ alkenyl, $C_2$-$C_6$ alkynyl, $C_1$-$C_6$ haloalkyl, or $C_3$-$C_6$ cycloalkyl.

In some embodiments, $R_9$ is H.

In some embodiments, $R_9$ is $C_1$-$C_6$ alkyl, $C_2$-$C_6$ alkenyl, or $C_2$-$C_6$ alkynyl.

In some embodiments, $R_9$ is $C_1$-$C_6$ alkyl. In some embodiments, $R_9$ is methyl. In some embodiments, $R_9$ is ethyl. In some embodiments, $R_9$ is propyl. In some embodiments, $R_9$ is butyl.

In some embodiments, $R_9$ is isopropyl. In some embodiments, $R_9$ is iso-butyl. In some embodiments, $R_9$ is sec-butyl. In some embodiments, $R_9$ is tert-butyl. In some embodiments, $R_9$ is pentyl. In some embodiments, $R_9$ is iso-pentyl. In some embodiments, $R_9$ is hexyl. In some embodiments, $R_9$ is iso-hexyl.

In some embodiments, $R_9$ is $C_2$-$C_6$ alkenyl. In some embodiments, $R_9$ is $C_2$ alkenyl. In some embodiments, $R_9$ is $C_3$ alkenyl. In some embodiments, $R_9$ is $C_4$ alkenyl. In some embodiments, $R_9$ is $C_5$ alkenyl. In some embodiments, $R_8$ is $C_6$ alkenyl.

In some embodiments, $R_9$ is $C_2$-$C_6$ alkynyl. In some embodiments, $R_9$ is $C_2$ alkynyl. In some embodiments, $R_9$ is $C_3$ alkynyl. In some embodiments, $R_9$ is $C_4$ alkynyl. In some embodiments, $R_9$ is $C_5$ alkynyl. In some embodiments, $R_9$ is $C_6$ alkynyl.

In some embodiments, $R_9$ is $C_1$-$C_6$ haloalkyl or $C_3$-$C_6$ cycloalkyl.

In some embodiments, $R_9$ is $C_1$-$C_6$ haloalkyl. In some embodiments, $R_9$ is halomethyl. In some embodiments, $R_9$ is haloethyl. In some embodiments, $R_9$ is halopropyl. In some embodiments, $R_9$ is halobutyl. In some embodiments, $R_9$ is halopentyl. In some embodiments, $R_9$ is halohexyl.

In some embodiments, $R_9$ is $C_3$-$C_6$ cycloalkyl. In some embodiments, $R_9$ is cyclopropyl.

In some embodiments, $R_9$ is cyclobutyl. In some embodiments, $R_9$ is cyclopentyl. In some embodiments, $R_9$ is cyclohexyl.

In some embodiments, at least one of $R_3$, $R_4$, $R_5$, and $R_6$ is H.

In some embodiment, at least one of $R_3$, $R_4$, $R_5$, and $R_6$ is not H.

In some embodiments, at least one of $R_3$ and $R_4$ is H.

In some embodiments, at least one of $R_5$ and $R_6$ is H.

In some embodiments, X is $CR_7R_8$ or S and $R_5$ is H.

In some embodiments, X is $CR_7R_8$ and $R_5$ is H.

In some embodiments, X is $CH_2$ and $R_5$ is H.

In some embodiments, X is S and $R_5$ is H.

In some embodiments, when $R_5$ is halogen and $R_4$ is H, then $R_3$ is not methyl, methoxyl, or Br and X is $CR_7R_8$ or S.

In some embodiments, $R_5$ is halogen, $R_4$ is H, X is $CR_7R_8$ or S, and $R_3$ is H, F, Cl, I, —S($C_1$-$C_6$ alkyl), —N($C_1$-$C_6$ alkyl)$_2$, —NH($C_1$-$C_6$ alkyl), —NH$_2$, $C_2$-$C_6$ alkyl, $C_2$-$C_6$ alkenyl, $C_2$-$C_6$ alkynyl, $C_1$-$C_6$ haloalkyl, $C_2$-$C_6$ alkoxyl, $C_1$-$C_6$ haloalkoxyl, or $C_3$-$C_6$ cycloalkyl.

In some embodiments, when $R_5$ is halogen and $R_4$ is H then X is S and $R_3$ is not methyl, methoxyl, or Br.

In some embodiments, $R_5$ is halogen, $R_4$ is H, X is S, and $R_3$ is H, F, Cl, I, —S($C_1$-$C_6$ alkyl), —N($C_1$-$C_6$ alkyl)$_2$, —NH($C_1$-$C_6$ alkyl), —NH$_2$, $C_2$-$C_6$ alkyl, $C_2$-$C_6$ alkenyl, $C_2$-$C_6$ alkynyl, $C_1$-$C_6$ haloalkyl, $C_2$-$C_6$ alkoxyl, $C_1$-$C_6$ haloalkoxyl, or $C_3$-$C_6$ cycloalkyl.

In some embodiments, when $R_5$ is halogen and $R_4$ is H then X is $CR_7R_8$ and $R_3$ is not methyl, methoxyl, or Br.

In some embodiments, $R_5$ is halogen, $R_4$ is H, X is $CR_7R_8$, and $R_3$ is H, F, Cl, I, —S($C_1$-$C_6$ alkyl), —N($C_1$-$C_6$ alkyl)$_2$, —NH($C_1$-$C_6$ alkyl), —NH$_2$, $C_2$-$C_6$ alkyl, $C_2$-$C_6$ alkenyl, $C_2$-$C_6$ alkynyl, $C_1$-$C_6$ haloalkyl, $C_2$-$C_6$ alkoxyl, $C_1$-$C_6$ haloalkoxyl, or $C_3$-$C_6$ cycloalkyl.

In some embodiments, when $R_5$ is halogen and $R_4$ is H, then X is $CH_2$ and $R_3$ is not methyl, methoxyl, or Br.

In some embodiments, $R_5$ is halogen, $R_4$ is H, X is $CH_2$, and $R_3$ is H, F, Cl, I, —S($C_1$-$C_6$ alkyl), —N($C_1$-$C_6$ alkyl)$_2$, —NH($C_1$-$C_6$ alkyl), —NH$_2$, $C_2$-$C_6$ alkyl, $C_2$-$C_6$ alkenyl, $C_2$-$C_6$ alkynyl, $C_1$-$C_6$ haloalkyl, $C_2$-$C_6$ alkoxyl, $C_1$-$C_6$ haloalkoxyl, or $C_3$-$C_6$ cycloalkyl.

In some embodiments, when $R_5$ is halogen and $R_4$ is H, then X is not O and $R_3$ is not methyl, methoxyl, or Br.

In some embodiments, $R_5$ is halogen, $R_4$ is H, X is not 0, and $R_3$ is H, F, Cl, I, —S($C_1$-$C_6$ alkyl), —N($C_1$-$C_6$ alkyl)$_2$, —NH($C_1$-$C_6$ alkyl), —NH$_2$, $C_2$-$C_6$ alkyl, $C_2$-$C_6$ alkenyl, $C_2$-$C_6$ alkynyl, $C_1$-$C_6$ haloalkyl, $C_2$-$C_6$ alkoxyl, $C_1$-$C_6$ haloalkoxyl, or $C_3$-$C_6$ cycloalkyl.

In some embodiments, $R_5$ is halogen, $R_4$ is H, X is $CR_7R_8$ or S, and $R_3$ is H, F, or Cl.

In some embodiments, $R_5$ is halogen, $R_4$ is H, X is $CR_7R_8$, and $R_3$ is H, F, or Cl.

In some embodiments, $R_5$ is halogen, $R_4$ is H, X is $CH_2$, and $R_3$ is H, F, or Cl.

In some embodiments, $R_5$ is methoxyl or methyl and $R_4$ is not H.

In some embodiments, $R_5$ is methoxyl and $R_4$ is not H.

In some embodiments, $R_5$ is methyl and $R_4$ is not H.

In some embodiments, $R_5$ is methoxyl or methyl and $R_4$ is halogen, —S($C_1$-$C_6$ alkyl), —N($C_1$-$C_6$ alkyl)$_2$, —NH($C_1$-$C_6$ alkyl), —NH$_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxyl, $C_1$-$C_6$ haloalkoxyl, or $C_3$-$C_6$ cycloalkyl.

In some embodiments, $R_5$ is methoxyl or methyl and $R_4$ is F, Cl, methyl, or $CHF_2$.

In some embodiments, $R_{10}$ is H or halogen. In some embodiments, $R_{10}$ is H. In some embodiments $R_{10}$ is halogen. In some embodiments, $R_{10}$ is F, Cl, Br, or I. In some embodiments, $R_{10}$ is F, Cl, or Br. In some embodiments, $R_{10}$ is F or Cl. In some embodiments, $R_{10}$ is F. In some embodiments, $R_{10}$ is Cl. In some embodiments, $R_{10}$ is Br. In some embodiments, $R_{10}$ is I.

In some embodiments, X is O and $R_9$ is H.

In some embodiments, X is O, $R_9$ is H, and $R_1$ is $C_1$-$C_6$ alkyl.

In some embodiments, X is O, $R_9$ is H, and $R_1$ is methyl.

In some embodiments, X is O, $R_9$ is H, $R_1$ is methyl, and $R_2$ is $C_1$-$C_6$ alkyl.

In some embodiments, X is O, $R_9$ is H, $R_1$ is methyl, and $R_2$ is methyl.

In some embodiments, X is O, $R_9$ is H, $R_1$ is methyl, $R_2$ is methyl, and $R_3$ is H.

In some embodiments, X is O, $R_9$ is H, $R_1$ is methyl, $R_2$ is methyl, and $R_3$ is halogen, $C_1$-$C_6$ alkyl, $C_1$-$C_6$ haloalkyl, or $C_1$-$C_6$ alkoxyl.

In some embodiments, X is O, $R_9$ is H, $R_1$ is methyl, $R_2$ is methyl, and $R_3$ is F, Cl, methyl, $CHF_2$, or methoxyl.

In some embodiments, X is O, $R_9$ is H, $R_1$ is methyl, $R_2$ is methyl, and $R_4$ is H.

In some embodiments, X is O, $R_9$ is H, $R_1$ is methyl, $R_2$ is methyl, and $R_4$ is halogen, $C_1$-$C_6$ alkyl, or $C_1$-$C_6$ haloalkyl.

In some embodiments, X is O, $R_9$ is H, $R_1$ is methyl, $R_2$ is methyl, and $R_4$ is F, Cl, methyl, or $CHF_2$.

In some embodiments, X is O, $R_9$ is H, $R_1$ is methyl, $R_2$ is methyl, and $R_5$ is H.

In some embodiments, X is O, $R_9$ is H, $R_1$ is methyl, $R_2$ is methyl, and $R_5$ is halogen, $C_1$-$C_6$ alkyl, $C_1$-$C_6$ haloalkyl, $C_1$-$C_6$ alkoxyl, or S($C_1$-$C_6$ alkyl).

In some embodiments, X is O, $R_9$ is H, $R_1$ is methyl, $R_2$ is methyl, and $R_5$ is F, Cl, methyl, ethyl, n-propyl, iso-propyl, $CHF_2$, methoxyl, or methylthiyl.

In some embodiments, X is O, $R_9$ is H, $R_1$ is methyl, $R_2$ is methyl, and $R_6$ is H.

In some embodiments, X is O, $R_9$ is H, $R_1$ is methyl, $R_2$ is methyl, and $R_6$ is $C_1$-$C_6$ alkyl or $C_1$-$C_6$ alkoxyl.

In some embodiments, X is O, $R_9$ is H, $R_1$ is methyl, $R_2$ is methyl, and $R_6$ is methyl or methoxyl.

In some embodiments, X is O, $R_9$ is H, and $R_1$ and $R_2$ together to atoms which they are attached form a $C_3$-$C_6$ saturated or unsaturated cycloalkyl.

In some embodiments, X is O, $R_9$ is H, and $R_1$ and $R_2$ together to atoms which they are attached form a $C_3$-$C_6$ saturated cycloalkyl.

In some embodiments, X is O, $R_9$ is H, $R_1$ and $R_2$ together to atoms which they are attached form a cyclopropyl.

In some embodiments, X is O, $R_9$ is H, $R_1$ and $R_2$ together to atoms which they are attached form a cyclopropyl, and $R_3$ is H.

In some embodiments, X is O, $R_9$ is H, $R_1$ and $R_2$ together to atoms which they are attached form a cyclopropyl, and $R_4$ is H.

In some embodiments, X is O, $R_9$ is H, $R_1$ and $R_2$ together to atoms which they are attached form a cyclopropyl, and $R_4$ is halogen or $C_1$-$C_6$ alkyl.

In some embodiments, X is O, $R_9$ is H $R_1$ and $R_2$ together to atoms which they are attached form a cyclopropyl, and $R_4$ is F, Cl, or methyl.

In some embodiments, X is O, $R_9$ is H, $R_1$ and $R_2$ together to atoms which they are attached form a cyclopropyl, and $R_5$ is H.

In some embodiments, X is O, $R_9$ is H, $R_1$ and $R_2$ together to atoms which they are attached form a cyclopropyl, and $R_5$ is halogen or $C_1$-$C_6$ alkyl.

In some embodiments, X is O, $R_9$ is H, $R_1$ and $R_2$ together to atoms which they are attached form a cyclopropyl, and $R_5$ is F, methyl, or ethyl.

In some embodiments, X is $CH_2$ and $R_9$ is H.

In some embodiments, X is $CH_2$, $R_9$ is H, and $R_1$ is methyl.

In some embodiments, X is $CH_2$, $R_9$ is H, $R_1$ is methyl, and $R_2$ is methyl.

In some embodiments, X is $CH_2$, $R_9$ is H, $R_1$ is methyl, $R_2$ is methyl, and $R_3$ is H.

In some embodiments, X is $CH_2$, $R_9$ is H, $R_1$ is methyl, $R_2$ is methyl, and $R_4$ is H.

In some embodiments, X is $CH_2$, $R_9$ is H, $R_1$ is methyl, $R_2$ is methyl, and $R_4$ is halogen or $C_1$-$C_6$ alkyl.

In some embodiments, X is $CH_2$, $R_9$ is H, $R_1$ is methyl, $R_2$ is methyl, and $R_4$ is Cl or methyl.

In some embodiments, X is $CH_2$, $R_9$ is H, $R_1$ is methyl, $R_2$ is methyl, and $R_5$ is H.

In some embodiments, X is $CH_2$, $R_9$ is H, $R_1$ is methyl, $R_2$ is methyl, and $R_5$ is halogen or $C_1$-$C_6$ alkyl.

In some embodiments, X is $CH_2$, $R_9$ is H, $R_1$ is methyl, $R_2$ is methyl, and $R_5$ is F, Cl, or methyl.

In some embodiments, X is $CH_2$, $R_9$ is H, and $R_1$ and $R_2$ together to atoms which they are attached form a $C_3$-$C_6$ saturated or unsaturated cycloalkyl.

In some embodiments, X is $CH_2$, $R_9$ is H, and $R_1$ and $R_2$ together to atoms which they are attached form a $C_3$-$C_6$ saturated cycloalkyl.

In some embodiments, X is $CH_2$, $R_9$ is H, $R_1$ and $R_2$ together to atoms which they are attached form a cyclopropyl.

In some embodiments, X is $CH_2$, $R_9$ is H, $R_1$ and $R_2$ together to atoms which they are attached form a cyclopropyl, and $R_3$ is H.

In some embodiments, X is $CH_2$, $R_9$ is H, $R_1$ and $R_2$ together to atoms which they are attached form a cyclopropyl, and $R_4$ is H.

In some embodiments, X is $CH_2$, $R_9$ is H, $R_1$ and $R_2$ together to atoms which they are attached form a cyclopropyl, and $R_4$ is halogen or $C_1$-$C_6$ alkyl.

In some embodiments, X is $CH_2$, $R_9$ is H, $R_1$ and $R_2$ together to atoms which they are attached form a cyclopropyl, and $R_4$ is Cl or methyl.

In some embodiments, X is $CH_2$, $R_9$ is H, $R_1$ and $R_2$ together to atoms which they are attached form a cyclopropyl, and $R_5$ is H.

In some embodiments, X is $CH_2$, $R_9$ is H, $R_1$ and $R_2$ together to atoms which they are attached form a cyclopropyl, and $R_5$ is $C_1$-$C_6$ alkyl.

In some embodiments, X is $CH_2$, $R_9$ is H, $R_1$ and $R_2$ together to atoms which they are attached form a cyclopropyl, and $R_5$ is methyl.

In some embodiments, when $R_5$ is H and X is O then $R_{10}$ is halogen.

In some embodiments, when $R_{10}$ is not H then X is O. In some embodiments, when $R_{10}$ is halogen then X is O.

In some embodiments, a compound of Formula (I) is a compound of Formula (Ia):

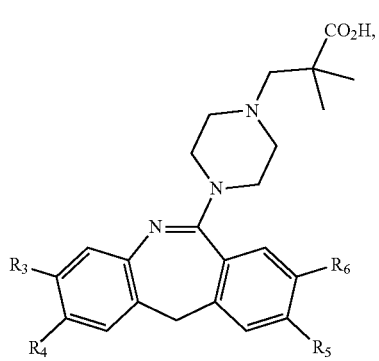

(Ia)

or a prodrug, solvate, or pharmaceutically acceptable salt thereof, wherein $R_3$, $R_4$, $R_5$, and $R_6$, are as described herein for Formula (I).

In some embodiments, a compound of Formula (I) is a compound of Formula (Ib):

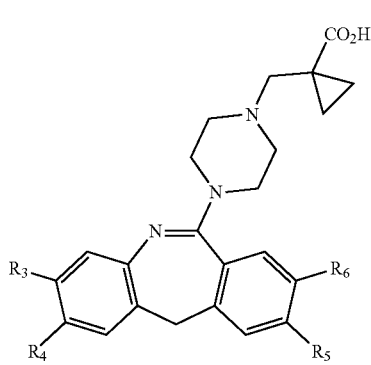

(Ib)

or a prodrug, solvate, or pharmaceutically acceptable salt thereof, wherein $R_3$, $R_4$, $R_5$, and $R_6$, are as described herein for Formula (I).

In some embodiments, a compound of Formula (II) is a compound of Formula (IIa):

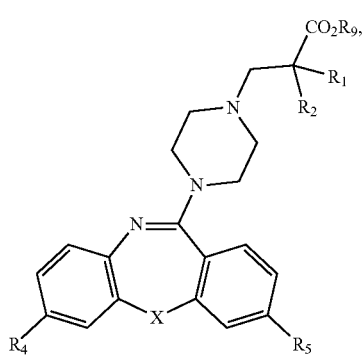

(IIa)

or a prodrug, solvate, or pharmaceutically acceptable salt thereof, wherein X, $R_1$, $R_2$, $R_4$, $R_5$, and $R_9$ are as described herein for Formula (II).

In some embodiments, a compound of Formula (II) is a compound of Formula (IIa-1):

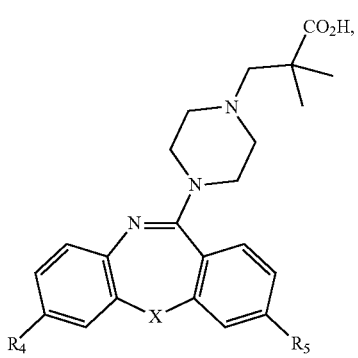

(IIa-1)

or a prodrug, solvate, or pharmaceutically acceptable salt thereof, wherein X, $R_4$, and $R_5$ are as described herein for Formula (II).

In some embodiments, a compound of Formula (II) is a compound of Formula (IIa-2):

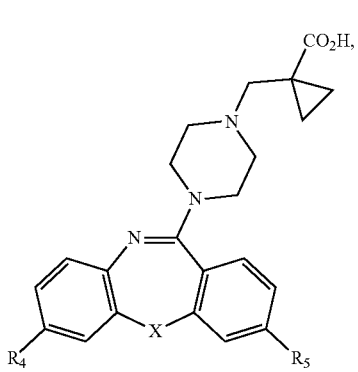

(IIa-1)

or a prodrug, solvate, or pharmaceutically acceptable salt thereof, wherein X, $R_4$, and $R_5$ are as described herein for Formula (II).

In some embodiments, a compound of Formula (II) is a compound of Formula (IIb):

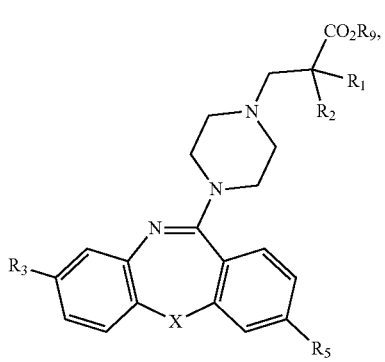

(IIb)

or a prodrug, solvate, or pharmaceutically acceptable salt thereof, wherein X, $R_1$, $R_2$, $R_3$, $R_5$, and $R_9$ are as described herein for Formula (II).

In some embodiments, a compound of Formula (II) is a compound of Formula (IIb-1):

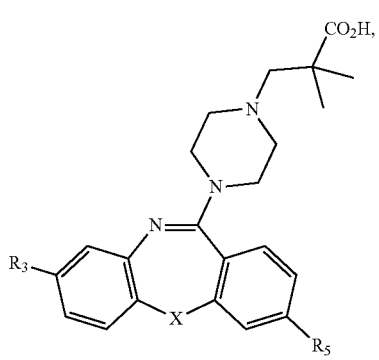

(IIb-1)

or a prodrug, solvate, or pharmaceutically acceptable salt thereof, wherein X, $R_3$, and $R_5$ are as described herein for Formula (II).

In some embodiments, a compound of Formula (II) is a compound of Formula (IIb-2):

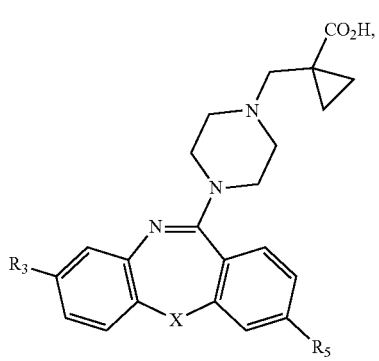

(IIb-2)

or a prodrug, solvate, or pharmaceutically acceptable salt thereof, wherein X, $R_3$, and $R_5$ are as described herein for Formula (II).

In some embodiments, a compound of Formula (II) is a compound of Formula (IIc):

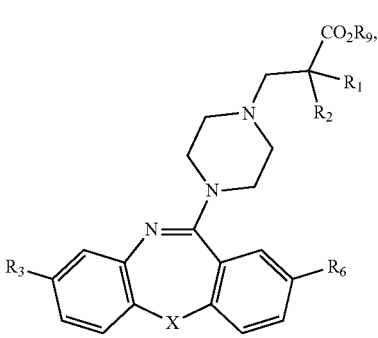

(IIc)

or a prodrug, solvate, or pharmaceutically acceptable salt thereof, wherein X, $R_1$, $R_2$, $R_3$, $R_6$, and $R_9$ are as described herein for Formula (II).

In some embodiments, a compound of Formula (II) is a compound of Formula (IIc-1):

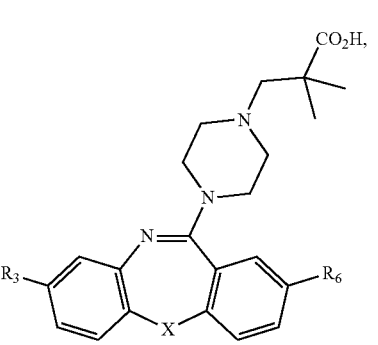

(IIc-1)

or a prodrug, solvate, or pharmaceutically acceptable salt thereof, wherein X, $R_3$, and $R_6$ are as described herein for Formula (II).

In some embodiments, a compound of Formula (II) is a compound of Formula (IIc-2):

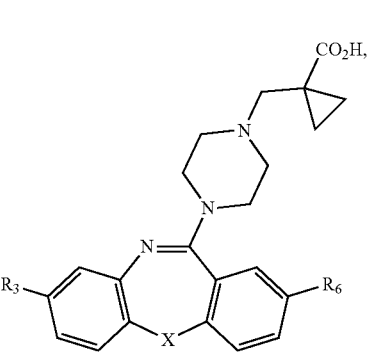

(IIc-2)

or a prodrug, solvate, or pharmaceutically acceptable salt thereof, wherein X, $R_3$, and $R_6$ are as described herein for Formula (II).

In some embodiments, a compound of Formula (II') is a compound of Formula (II'a):

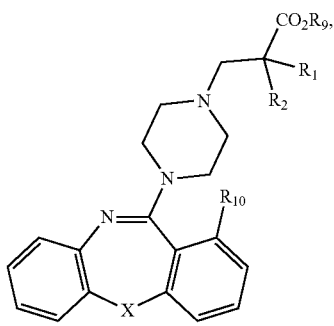

(II'a)

or a prodrug, solvate, or pharmaceutically acceptable salt thereof, wherein X, $R_1$, $R_2$, $R_9$, and $R_{10}$ are as described herein for Formula (II').

It is understood that, for a compound of any one of the formulae described herein, X, $R_1$, $R_2$, $R_3$, $R_4$, $R_5$, $R_6$, $R_7$, $R_8$, $R_9$, and $R_{10}$ can each be, where applicable, selected from the groups described herein, and any group described herein for any X, $R_1$, $R_2$, $R_3$, $R_4$, $R_5$, $R_6$, $R_7$, $R_8$, $R_9$, and $R_{10}$ can be combined, where applicable, with any group described herein for one or more of the remainder of X, $R_1$, $R_2$, $R_3$, $R_4$, $R_5$, $R_6$, $R_7$, $R_8$, $R_9$, and $R_{10}$.

In some embodiments, the compound is selected from the compounds described in Table 1 or 2 and prodrugs and pharmaceutically acceptable salts thereof.

In some embodiments, the compound is selected from the compounds described in Table 1 or 2 and pharmaceutically acceptable salts thereof.

In some embodiments, the compound is selected from the prodrugs of compounds described in Table 1 or 2 and pharmaceutically acceptable salts thereof.

In some embodiments, the compound is selected from the compounds described in Table 1 or 2.

TABLE 1

(Formula A)

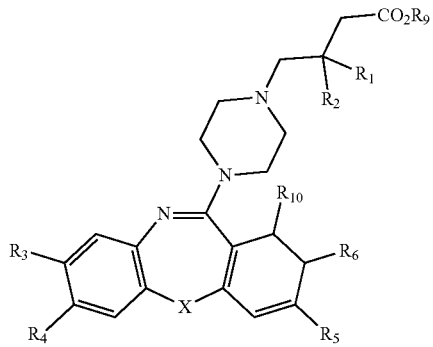

| Compound No. | $R_1$, $R_2$ | $R_3$ | $R_4$ | $R_5$ | $R_6$ | $R_{10}$ | X |
|---|---|---|---|---|---|---|---|
| 1 | methyl, methyl | H | Cl | methyl | H | H | O |
| 2 | methyl, methyl | H | Cl | iso-propyl | H | H | O |
| 3 | methyl, methyl | H | Cl | ethyl | H | H | O |
| 4 | methyl, methyl | H | Cl | methylthiyl | H | H | O |
| 5 | methyl, methyl | H | Cl | n-propyl | H | H | O |
| 6 | methyl, methyl | H | F | methyl | H | H | O |
| 7 | methyl, methyl | H | methyl | methyl | H | H | O |
| 8 | methyl, methyl | H | H | H | H | H | $CH_2$ |
| 9 | cyclopropyl | H | methyl | methyl | H | H | O |
| 10 | cyclopropyl | H | F | F | H | H | O |
| 11 | methyl, methyl | H | F | F | H | H | O |
| 12 | cyclopropyl | H | H | H | H | H | $CH_2$ |
| 13 | cyclopropyl | H | Cl | methyl | H | H | O |
| 14 | cyclopropyl | H | methyl | ethyl | H | H | O |
| 15 | methyl, methyl | H | methyl | $CHF_2$ | H | H | O |
| 16 | methyl, methyl | H | $CHF_2$ | methyl | H | H | O |
| 17 | methyl, methyl | H | methyl | F | H | H | O |
| 18 | cyclopropyl | H | F | methyl | H | H | O |
| 19 | cyclopropyl | H | methyl | F | H | H | O |
| 20 | methyl, methyl | H | Cl | methoxyl | H | H | O |
| 21 | methyl, methyl | H | F | methoxyl | H | H | O |
| 22 | methyl, methyl | H | Cl | methyl | H | H | C |
| 23 | cyclopropyl | H | Cl | methyl | H | H | $CH_2$ |
| 24 | methyl, methyl | H | methyl | methyl | H | H | $CH_2$ |
| 25 | cyclopropyl | H | methyl | methyl | H | H | $CH_2$ |
| 26 | methyl, methyl | H | H | Cl | H | H | $CH_2$ |
| 27 | methyl, methyl | H | H | F | H | H | $CH_2$ |
| 28 | methyl, methyl | F | H | methyl | H | H | O |
| 29 | methyl, methyl | Cl | H | methyl | H | H | O |
| 30 | methyl, methyl | Cl | H | F | H | H | O |
| 31 | methyl, methyl | F | H | F | H | H | O |
| 32 | methyl, methyl | methoxyl | H | $CHF_2$ | H | H | O |
| 33 | methyl, methyl | methyl | H | $CHF_2$ | H | H | O |
| 34 | methyl, methyl | Cl | H | H | methyl | H | O |

TABLE 1-continued

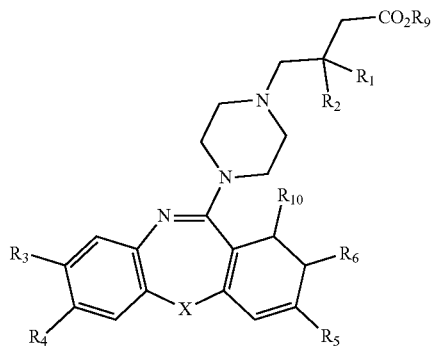

(Formula A)

| Compound No. | $R_1$, $R_2$ | $R_3$ | $R_4$ | $R_5$ | $R_6$ | $R_{10}$ | X |
|---|---|---|---|---|---|---|---|
| 35 | methyl, methyl | Cl | H | H | methoxyl | H | O |
| 36 | methyl, methyl | H | H | $CHF_2$ | H | H | O |
| 37 | methyl, methyl | H | H | F | H | H | $CH_2$ |
| 38 | methyl, methyl | H | methyl | H | H | H | $CH_2$ |
| 39 | methyl, methyl | H | H | H | H | F | O |

TABLE 2

| Compound No. | Structure | Structure name |
|---|---|---|
| 1 | 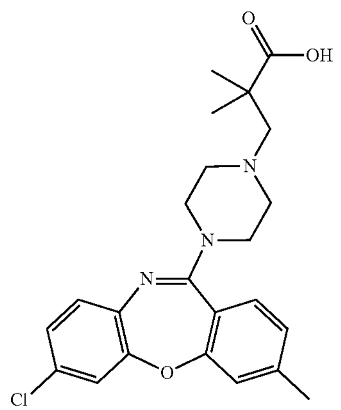 [SMILES: Cc1ccc2c(c1)Oc1cc(Cl)ccc1N=C2N1CCN(CC(C)(C)C(=O)O)CC1] | 3-(4-(7-chloro-3-methyldibenzo[b,f][1,4]oxazepin-11-yl)piperazin-1-yl)-2,2-dimethylpropanoic acid |
| 2 | 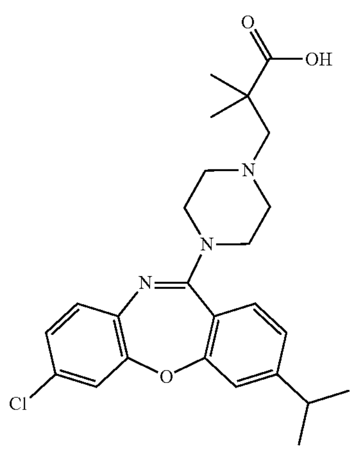 [SMILES: CC(C)c1ccc2c(c1)Oc1cc(Cl)ccc1N=C2N1CCN(CC(C)(C)C(=O)O)CC1] | 3-(4-(7-chloro-3-isopropyldibenzo[b,f][1,4]oxazepin-11-yl)piperazin-1-yl)-2,2-dimethylpropanoic acid |

TABLE 2-continued
| Compound No. | Structure | Structure name |
|---|---|---|
| 3 | 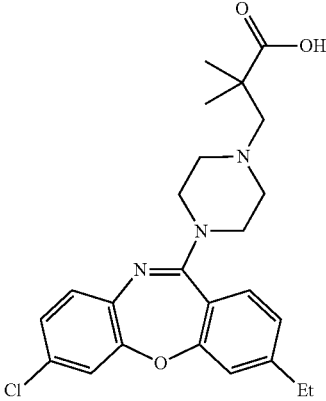 [SMILES: CCc1ccc2c(c1)Oc1cc(Cl)ccc1N=C2N1CCN(CC(C)(C)C(=O)O)CC1] | 3-(4-(7-chloro-3-ethyldibenzo[b,f][1,4]oxazepin-11-yl)piperazin-1-yl)-2,2-dimethylpropanoic acid |
| 4 | 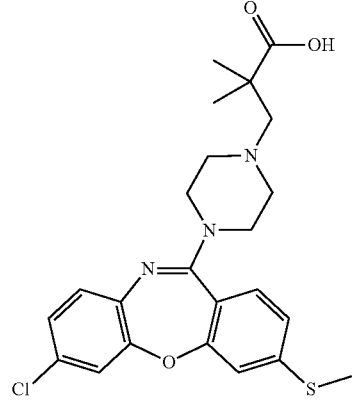 [SMILES: CSc1ccc2c(c1)Oc1cc(Cl)ccc1N=C2N1CCN(CC(C)(C)C(=O)O)CC1] | 3-(4-(7-chloro-3-(methylthio)dibenzo[b,f][1,4]oxazepin-11-yl)piperazin-1-yl)-2,2-dimethylpropanoic acid |
| 5 | 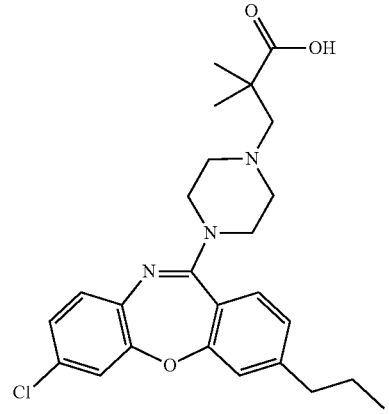 [SMILES: CCCc1ccc2c(c1)Oc1cc(Cl)ccc1N=C2N1CCN(CC(C)(C)C(=O)O)CC1] | 3-(4-(7-chloro-3-propyldibenzo[b,f][1,4]oxazepin-11-yl)piperazin-1-yl)-2,2-dimethylpropanoic acid |

TABLE 2-continued
| Compound No. | Structure | Structure name |
|---|---|---|
| 6 | 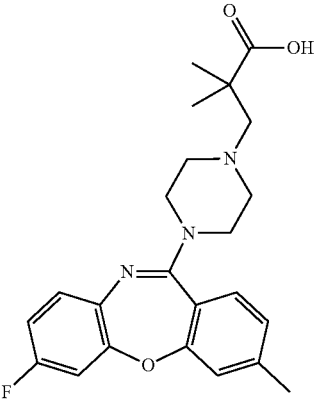 | 3-(4-(7-fluoro-3-methyldibenzo[b,f][1,4]oxazepin-11-yl)piperazin-1-yl)-2,2-dimethylpropanoic acid |
| 7 | 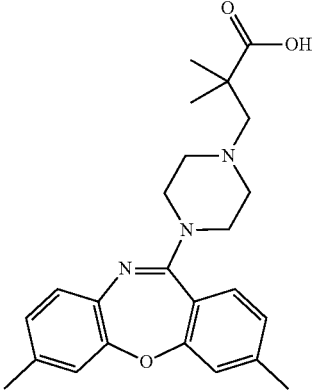 [SMILES: Cc1ccc2c(c1)Oc1cc(C)ccc1C(N1CCN(CC(C)(C)C(=O)O)CC1)=N2] | 3-(4-(3,7-dimethyldibenzo[b,f][1,4]oxazepin-11-yl)piperazin-1-yl)-2,2-dimethylpropanoic acid |
| 8 | 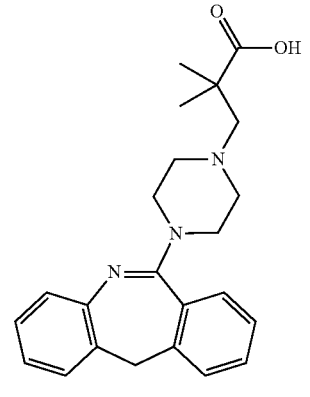 [SMILES: CC(C)(CN1CCN(C2=Nc3ccccc3Cc3ccccc32)CC1)C(=O)O] | 3-(4-(11H-dibenzo[b,e]azepin-6-yl)piperazin-1-yl)-2,2-dimethylpropanoic acid |
| 9 | 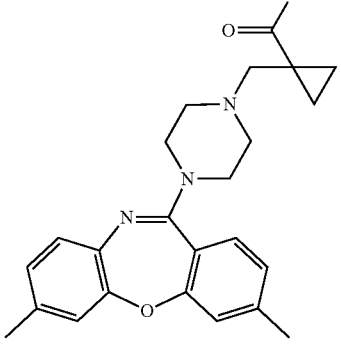 | 1-((4-(3,7-dimethyldibenzo[b,f][1,4]oxazepin-11-yl)piperazin-1-yl)methyl)cyclopropane-1-carboxylic acid |

TABLE 2-continued

| Compound No. | Structure | Structure name |
| --- | --- | --- |
| 10 | 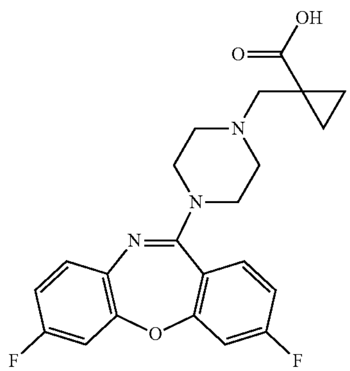 [SMILES: O=C(O)C1(CN2CCN(C3=Nc4ccc(F)cc4Oc4cc(F)ccc43)CC2)CC1] | 1-((4-(3,7-difluorodibenzo[b,f][1,4]oxazepin-11-yl)piperazin-1-yl)methyl)cyclopropane-1-carboxylic acid |
| 11 | 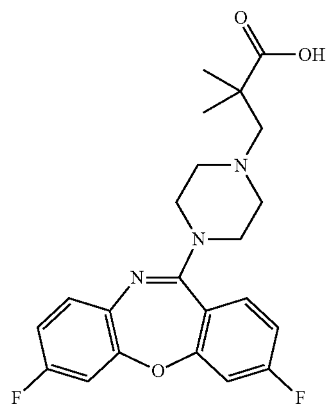 | 3-(4-(3,7-difluorodibenzo[b,f][1,4]oxazepin-11-yl)piperazin-1-yl)-2,2-dimethylpropanoic acid |
| 12 | 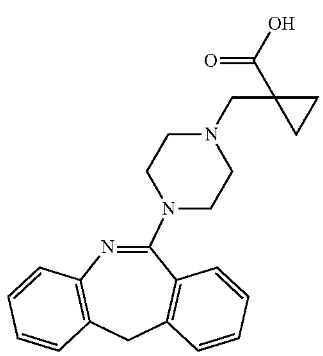 [SMILES: O=C(O)C1(CN2CCN(C3=Nc4ccccc4Cc4ccccc43)CC2)CC1] | 1-((4-(11H-dibenzo[b,e]azepin-6-yl)piperazin-1-yl)methyl)cyclopropane-1-carboxylic acid |
| 13 | 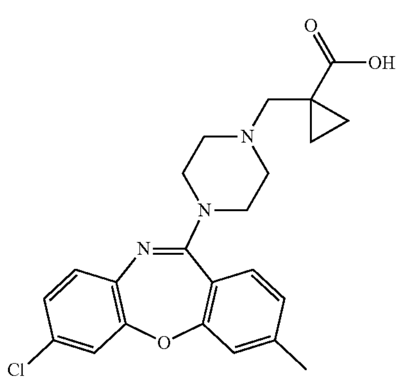 [SMILES: Cc1ccc2c(c1)Oc1cc(Cl)ccc1N=C2N1CCN(CC2(C(=O)O)CC2)CC1] | 1-((4-(7-chloro-3-methyldibenzo[b,f][1,4]oxazepin-11-yl)piperazin-1-yl)methyl)cyclopropane-1-carboxylic acid |

TABLE 2-continued

| Compound No. | Structure | Structure name |
|---|---|---|
| 14 | 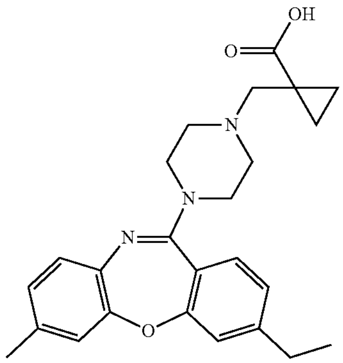 [SMILES: CCc1ccc2c(c1)Oc1cc(C)ccc1N=C2N1CCN(CC2(C(=O)O)CC2)CC1] | 1-((4-(3-ethyl-7-methyldibenzo[b,f][1,4]oxazepin-11-yl)piperazin-1-yl)methyl)cyclopropane-1-carboxylic acid |
| 15 | 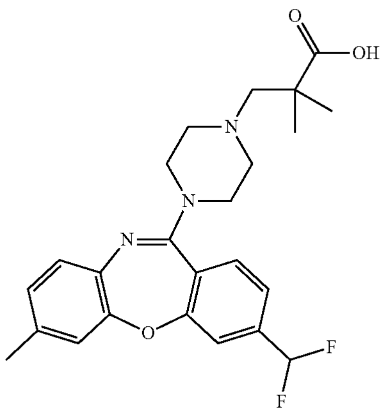 [SMILES: Cc1ccc2c(c1)Oc1cc(C(F)F)ccc1C(N1CCN(CC(C)(C)C(=O)O)CC1)=N2] | 3-(4-(3-(difluoromethyl)-7-methyldibenzo[b,f][1,4]oxazepin-11-yl)piperazin-1-yl)-2,2-dimethylpropanoic acid |
| 16 | 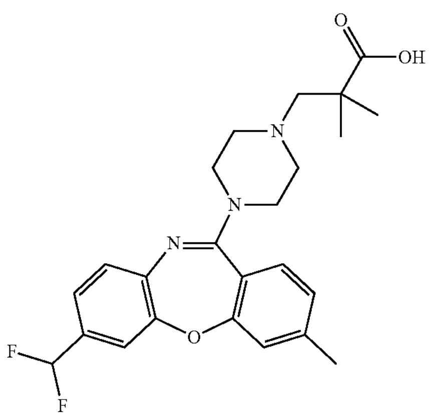 [SMILES: Cc1ccc2c(c1)Oc1cc(C(F)F)ccc1N=C2N1CCN(CC(C)(C)C(=O)O)CC1] | 3-(4-(7-(difluoromethyl)-3-methyldibenzo[b,f][1,4]oxazepin-11-yl)piperazin-1-yl)-2,2-dimethylpropanoic acid |
| 17 | 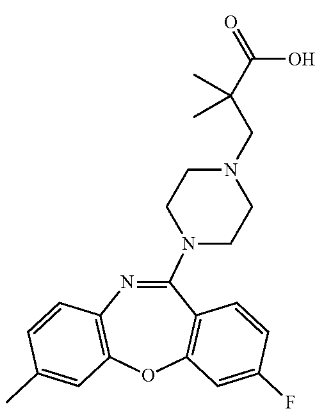 [SMILES: Cc1ccc2c(c1)Oc1cc(F)ccc1C(N1CCN(CC(C)(C)C(=O)O)CC1)=N2] | 3-(4-(3-fluoro-7-methyldibenzo[b,f][1,4]oxazepin-11-yl)piperazin-1-yl)-2,2-dimethylpropanoic acid |

TABLE 2-continued
| Compound No. | Structure | Structure name |
|---|---|---|
| 18 | 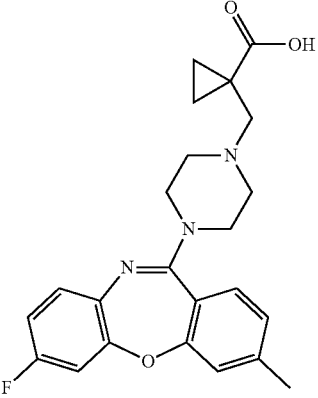 [SMILES: Cc1ccc2c(c1)Oc1cc(F)ccc1N=C2N1CCN(CC2(C(=O)O)CC2)CC1] | 1-((4-(7-fluoro-3-methyldibenzo[b,f][1,4]oxazepin-11-yl)piperazin-1-yl)methyl)cyclopropane-1-carboxylic acid |
| 19 | 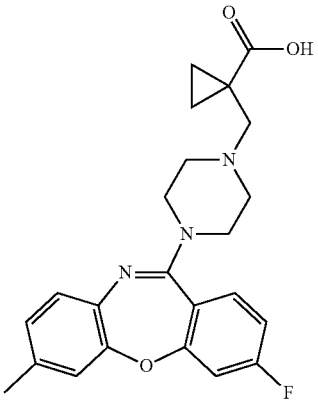 [SMILES: Cc1ccc2c(c1)Oc1cc(F)ccc1C(N1CCN(CC3(C(=O)O)CC3)CC1)=N2] | 1-((4-(3-fluoro-7-methyldibenzo[b,f][1,4]oxazepin-11-yl)piperazin-1-yl)methyl)cyclopropane-1-carboxylic acid |
| 20 | 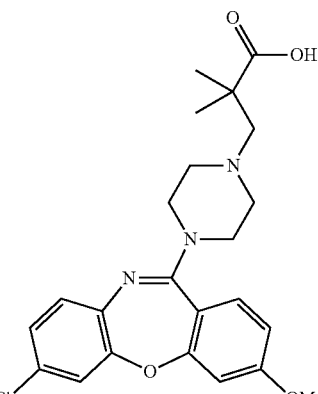 | 3-(4-(7-chloro-3-methoxydibenzo[b,f][1,4]oxazepin-11-yl)piperazin-1-yl)-2,2-dimethylpropanoic acid |

TABLE 2-continued
| Compound No. | Structure | Structure name |
|---|---|---|
| 21 | 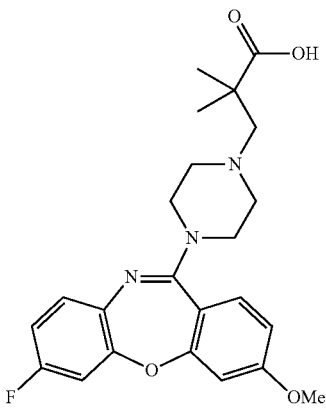 [SMILES: COc1ccc2c(c1)Oc1cc(F)ccc1N=C2N1CCN(CC(C)(C)C(=O)O)CC1] | 3-(4-(7-fluoro-3-methoxydibenzo[b,f][1,4]oxazepin-11-yl)piperazin-1-yl)-2,2-dimethylpropanoic acid |
| 22 | 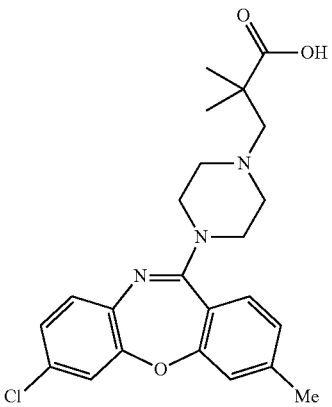 [SMILES: Cc1ccc2c(c1)Oc1cc(Cl)ccc1N=C2N1CCN(CC(C)(C)C(=O)O)CC1] | 3-(4-(2-chloro-9-methyl-11H-dibenzo[b,e]azepin-6-yl)piperazin-1-yl)-2,2-dimethylpropanoic acid |
| 23 | 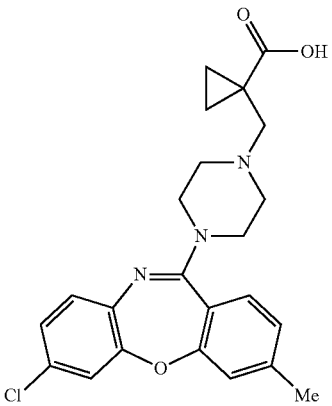 [SMILES: Cc1ccc2c(c1)Oc1cc(Cl)ccc1N=C2N1CCN(CC2(C(=O)O)CC2)CC1] | 1-((4-(2-chloro-9-methyl-11H-dibenzo[b,e]azepin-6-yl)piperazin-1-yl)methyl)cyclopropane-1-carboxylic acid |

TABLE 2-continued
| Compound No. | Structure | Structure name |
|---|---|---|
| 24 | 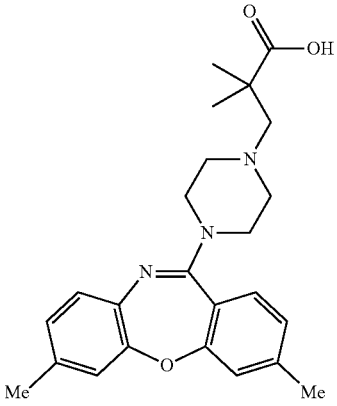 [SMILES: Cc1ccc2c(c1)Oc1cc(C)ccc1C(N1CCN(CC(C)(C)C(=O)O)CC1)=N2] | 3-(4-(2,9-dimethyl-11H-dibenzo[b,e]azepin-6-yl)piperazin-1-yl)-2,2-dimethylpropanoic acid |
| 25 | 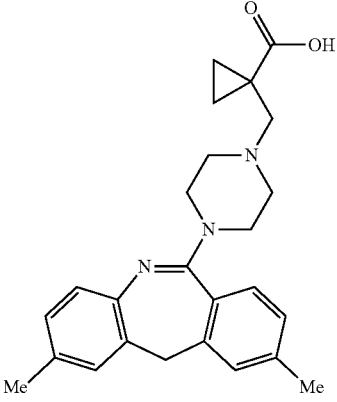 [SMILES: Cc1ccc2c(c1)Cc1cc(C)ccc1C(N1CCN(CC3(C(=O)O)CC3)CC1)=N2] | 1-((4-(2,9-dimethyl-11H-dibenzo[b,e]azepin-6-yl)piperazin-1-yl)methyl)cyclopropane-1-carboxylic acid |
| 26 | 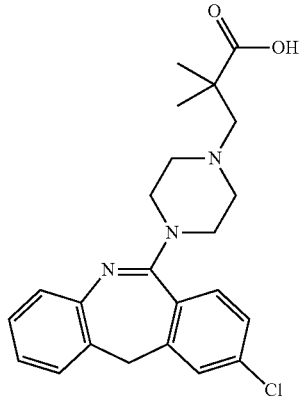 [SMILES: CC(C)(CN1CCN(C2=Nc3ccccc3Cc3cc(Cl)ccc32)CC1)C(=O)O] | 3-(4-(9-chloro-11H-dibenzo[b,e]azepin-6-yl)piperazin-1-yl)-2,2-dimethylpropanoic acid |

| Compound No. | Structure | Structure name |
|---|---|---|
| 27 | 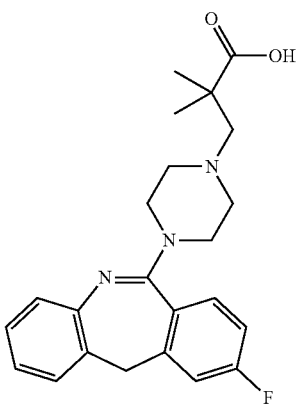 [SMILES: CC(C)(CN1CCN(C2=Nc3ccccc3Cc3cc(F)ccc32)CC1)C(=O)O] | 3-(4-(9-fluoro-11H-dibenzo[b,e]azepin-6-yl)piperazin-1-yl)-2,2-dimethylpropanoic acid |
| 28 | 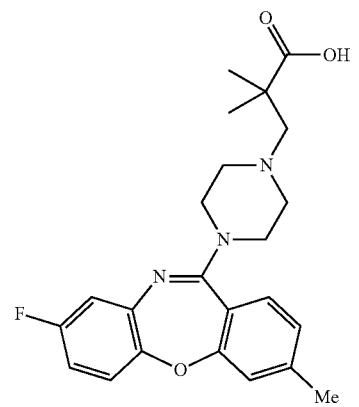 [SMILES: Cc1ccc2c(c1)Oc1ccc(F)cc1N=C2N1CCN(CC(C)(C)C(=O)O)CC1] | 3-(4-(8-fluoro-3-methyldibenzo[b,f][1,4]oxazepin-11-yl)piperazin-1-yl)-2,2-dimethylpropanoic acid |
| 29 | 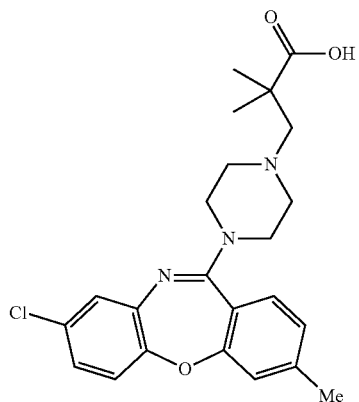 [SMILES: Cc1ccc2c(c1)Oc1ccc(Cl)cc1N=C2N1CCN(CC(C)(C)C(=O)O)CC1] | 3-(4-(8-chloro-3-methyldibenzo[b,f][1,4]oxazepin-11-yl)piperazin-1-yl)-2,2-dimethylpropanoic acid |

TABLE 2-continued

| Compound No. | Structure | Structure name |
|---|---|---|
| 30 | 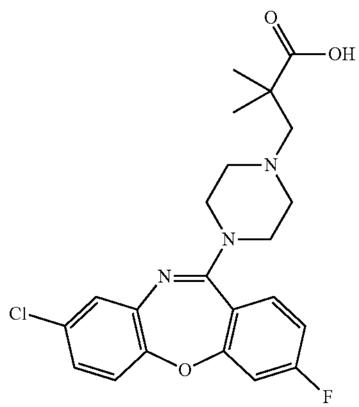 [SMILES: CC(C)(CN1CCN(C2=Nc3cc(Cl)ccc3Oc3cc(F)ccc32)CC1)C(=O)O] | 3-(4-(8-chloro-3-fluorodibenzo[b,f][1,4]oxazepin-11-yl)piperazin-1-yl)-2,2-dimethylpropanoic acid |
| 31 | 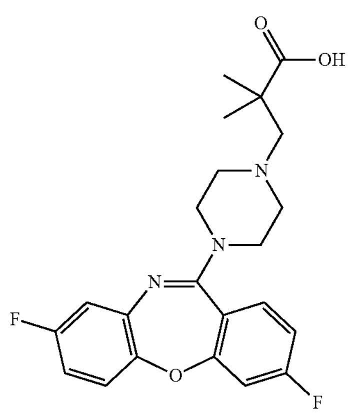 [SMILES: CC(C)(CN1CCN(C2=Nc3cc(F)ccc3Oc3cc(F)ccc32)CC1)C(=O)O] | 3-(4-(3,8-difluorodibenzo[b,f][1,4]oxazepin-11-yl)piperazin-1-yl)-2,2-dimethylpropanoic acid |
| 32 | 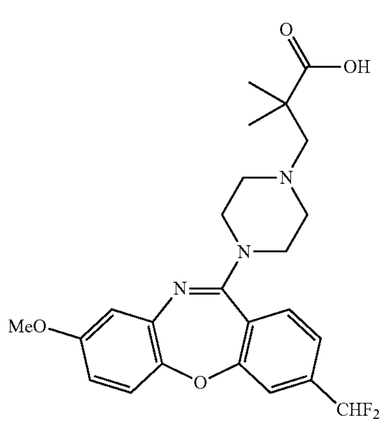 [SMILES: COc1ccc2c(c1)N=C(N1CCN(CC(C)(C)C(=O)O)CC1)c1ccc(C(F)F)cc1O2] | 3-(4-(3-(difluoromethyl)-8-methoxydibenzo[b,f][1,4]oxazepin-11-yl)piperazin-1-yl)-2,2-dimethylpropanoic acid |

TABLE 2-continued

| Compound No. | Structure | Structure name |
|---|---|---|
| 33 | 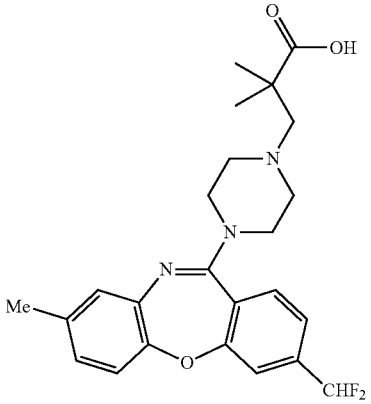 [SMILES: Cc1ccc2c(c1)N=C(N1CCN(CC(C)(C)C(=O)O)CC1)c1ccc(C(F)F)cc1O2] | 3-(4-(3-(difluoromethyl)-8-methyldibenzo[b,f][1,4]oxazepin-11-yl)piperazin-1-yl)-2,2-dimethylpropanoic acid |
| 34 | 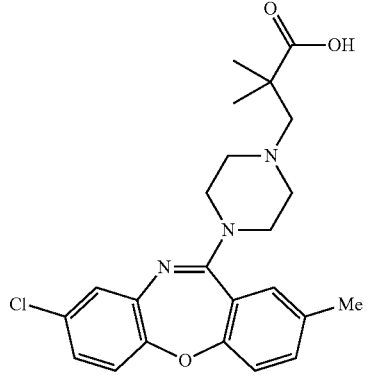 [SMILES: Cc1ccc2c(c1)C(N1CCN(CC(C)(C)C(=O)O)CC1)=Nc1cc(Cl)ccc1O2] | 3-(4-(8-chloro-2-methyldibenzo[b,f][1,4]oxazepin-11-yl)piperazin-1-yl)-2,2-dimethylpropanoic acid |
| 35 | 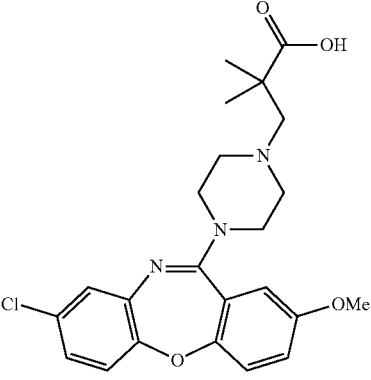 [SMILES: COc1ccc2c(c1)C(N1CCN(CC(C)(C)C(=O)O)CC1)=Nc1cc(Cl)ccc1O2] | 3-(4-(8-chloro-2-methoxydibenzo[b,f][1,4]oxazepin-11-yl)piperazin-1-yl)-2,2-dimethylpropanoic acid |
| 36 | 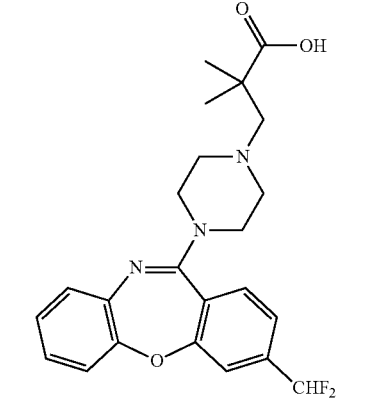 [SMILES: CC(C)(CN1CCN(C2=Nc3ccccc3Oc3cc(C(F)F)ccc32)CC1)C(=O)O] | 3-(4-(3-(difluoromethyl)dibenzo[b,f][1,4]oxazepin-11-yl)piperazin-1-yl)-2,2-dimethylpropanoic acid |

TABLE 2-continued

| Compound No. | Structure name |
|---|---|
| 37 | 3-(4-(9-fluoro-11H-dibenzo[b,e]azepin-6-yl)piperazin-1-yl)-2,2-dimethylpropanoic acid |
| 38 | 2,2-dimethyl-3-(4-(2-methyl-11H-dibenzo[b,e]azepin-6-yl)piperazin-1-yl)propanoic acid |
| 39 | 3-(4-(1-fluorodibenzo[b,f][1,4]oxazepin-11-yl)piperazin-1-yl)-2,2-dimethylpropanoic acid |

In some aspects, the present disclosure provides a compound being an isotopic derivative (e.g., isotopically labeled compound) of any one of the compounds of the Formulae disclosed herein.

In some embodiments, the compounds from Table 1 or 2 are of Formula (I).

In some embodiments, the compounds from Table 1 or 2 are of Formula (II).

In some embodiments, the compounds from Table 1 or 2 are of Formula (II').

In some embodiments, the compound is compound 1, 2, 3, 4, 5, 6, 7, 8, 9, 10, 11, 12, 13, 14, 15, 16, 17, 18, 19, 20, 21, 22, 23, 24, 25, 26, 27, 28, 29, 32, 33, 36, 37, 38, or 39, or a pharmaceutically acceptable salt thereof.

In some embodiments, the compound is compound 1, 2, 3, 4, 5, 6, 7, 8, 9, 10, 11, 12, 13, 14, 15, 16, 17, 18, 19, 20, 21, 22, 23, 24, 25, 26, 27, 28, 29, 32, 33, 36, 37, or 38, or a pharmaceutically acceptable salt thereof.

In some embodiments, the compound is compound 1, 2, 3, 4, 5, 6, 7, 8, 9, 10, 11, 12, 13, 14, 15, 16, 17, 18, 19, 20, 21, 22, 23, 24, 25, 26, 27, 28, 29, 32, 33, or 36, or a pharmaceutically acceptable salt thereof.

In some embodiments, the compound is compound 1, 2, 3, 4, 5, 6, 7, 8, 9, 10, 11, 12, 13, 14, 15, 16, 17, 18, 19, 20, 21, 22, 23, 24, 25, 26, 27, 28, 29, 32, or 33, or a pharmaceutically acceptable salt thereof.

In some embodiments, the compound is compound 7, 8, 15, or 17, or a pharmaceutically acceptable salt thereof.

In some embodiments, the compound is compound 7, 8, or 17, or a pharmaceutically acceptable salt thereof.

In some embodiments, the compound is compound 7 or a pharmaceutically acceptable salt thereof.

In some embodiments, the compound is compound 8 or a pharmaceutically acceptable salt thereof.

In some embodiments, the compound is compound 15 or a pharmaceutically acceptable salt thereof.

In some embodiments, the compound is compound 17 or a pharmaceutically acceptable salt thereof.

In some embodiments, the compound is compound 30, 31, 34, or 35, or a pharmaceutically acceptable salt thereof.

In some embodiments, the compound is compound 30 or a pharmaceutically acceptable salt thereof.

In some embodiments, the compound is compound 31 or a pharmaceutically acceptable salt thereof.

In some embodiments, the compound is compound 34 or a pharmaceutically acceptable salt thereof.

In some embodiments, the compound is compound 35 or a pharmaceutically acceptable salt thereof.

In some embodiments, the compound is compound 36 or a pharmaceutically acceptable salt thereof.

In some embodiments, the compound is an isotopic derivative of any one of the compounds described in Table 1 or 2 and prodrugs and pharmaceutically acceptable salts thereof.

In some embodiments, the compound is an isotopic derivative of any one of the compounds described in Table 1 or 2 and pharmaceutically acceptable salts thereof.

In some embodiments, the compound is an isotopic derivative of any one of prodrugs of the compounds described in Table 1 or 2 and pharmaceutically acceptable salts thereof.

In some embodiments, the compound is an isotopic derivative of any one of the compounds described in Table 1 or 2.

It is understood that the isotopic derivative can be prepared using any of a variety of art-recognised techniques. For example, the isotopic derivative can generally be prepared by carrying out the procedures disclosed in the Schemes and/or in the Examples described herein, by substituting an isotopically labeled reagent for a non-isotopically labeled reagent.

In some embodiments, the isotopic derivative is a deuterium labeled compound. In some embodiments, the compound is a $^{18}F$ labeled compound. In some embodiments, the compound is a $^{123}I$ labeled compound, a $^{124}I$ labeled compound, a $^{125}I$ labeled compound, a $^{129}I$ labeled compound, a $^{131}I$ labeled compound, a $^{135}I$ labeled compound, or any combination thereof. In some embodiments, the compound is a $^{33}S$ labeled compound, a $^{34}S$ labeled compound, a $^{35}S$ labeled compound, a $^{36}S$ labeled compound, or any combination thereof.

It is understood that the $^{18}F$, $^{123}I$, $^{124}I$, $^{125}I$, $^{129}I$, $^{131}I$, $^{135}I$, $^{3}S$, $^{34}S$, $^{35}S$, and/or $^{36}S$ labeled compound, can be prepared using any of a variety of art-recognised techniques. For example, the deuterium labeled compound can generally be prepared by carrying out the procedures disclosed in the Schemes and/or in the Examples described herein, by substituting a $^{18}F$, $^{123}I$, $^{124}I$, $^{125}I$, $^{129}I$, $^{131}I$, $^{135}I$, $^{3}S$, $^{34}S$, $^{35}S$, and/or $^{36}S$ labeled reagent for a non-isotope labeled reagent.

A compound of the invention or a pharmaceutically acceptable salt or solvate thereof that contains one or more of the aforementioned $^{18}F$, $^{123}I$, $^{124}I$, $^{125}I$, $^{129}I$, $^{131}I$, $^{135}I$, $^{3}S$, $^{34}S$, $^{35}S$, and $^{36}S$ atom(s) is within the scope of the invention. Further, substitution with isotope (e.g., $^{18}F$, $^{123}I$, $^{124}I$, $^{125}I$, $^{129}I$, $^{131}I$, $^{135}I$, $^{3}S$, $^{34}S$, $^{35}S$, and/or $^{36}S$) may afford certain therapeutic advantages resulting from greater metabolic stability, e.g., increased in vivo half-life or reduced dosage requirements.

For the avoidance of doubt it is to be understood that, where in this specification a group is qualified by "described herein", the said group encompasses the first occurring and broadest definition as well as each and all of the particular definitions for that group.

The various functional groups and substituents making up the compounds of the Formula (I), (II), and (II') are typically chosen such that the molecular weight of the compound does not exceed 1000 daltons. More usually, the molecular weight of the compound will be less than 900, for example less than 800, or less than 750, or less than 700, or less than 650 daltons. More conveniently, the molecular weight is less than 600 and, for example, is 550 daltons or less.

It will be understood that the compounds of any one of the Formulae disclosed herein and any pharmaceutically acceptable salts thereof, comprise stereoisomers, mixtures of stereoisomers, polymorphs of all isomeric forms of said compounds.

The present disclosure also encompasses compounds of the disclosure as defined herein which comprise one or more isotopic substitutions.

It is to be understood that the compounds of any Formula described herein include the compounds themselves, as well as their salts, and their solvates, if applicable.

The in vivo effects of a compound of any one of the Formulae disclosed herein may be exerted in part by one or more metabolites that are formed within the human or animal body after administration of a compound of any one of the Formulae disclosed herein. As stated hereinbefore, the in vivo effects of a compound of any one of the Formulae disclosed herein may also be exerted by way of metabolism of a precursor compound (a prodrug).

Suitably, the present disclosure excludes any individual compounds not possessing the biological activity defined herein.

Methods of Synthesis

In some aspects, the present disclosure provides a method of preparing a compound of the present disclosure.

In some aspects, the present disclosure provides a method of preparing a compound, comprising one or more steps as described herein.

In some aspects, the present disclosure provides a compound obtainable by, or obtained by, or directly obtained by a method for preparing a compound as described herein.

In some aspects, the present disclosure provides an intermediate as described herein, being suitable for use in a method for preparing a compound as described herein.

The compounds of the present disclosure can be prepared by any suitable technique known in the art. Particular processes for the preparation of these compounds are described further in the accompanying examples.

In the description of the synthetic methods described herein and in any referenced synthetic methods that are used to prepare the starting materials, it is to be understood that all proposed reaction conditions, including choice of solvent, reaction atmosphere, reaction temperature, duration of the experiment and workup procedures, can be selected by a person skilled in the art.

It is understood by one skilled in the art of organic synthesis that the functionality present on various portions of the molecule must be compatible with the reagents and reaction conditions utilised.

It will be appreciated that during the synthesis of the compounds of the disclosure in the processes defined herein, or during the synthesis of certain starting materials, it may be desirable to protect certain substituent groups to prevent their undesired reaction. The skilled chemist will appreciate when such protection is required, and how such protecting groups may be put in place, and later removed. For examples of protecting groups see one of the many general texts on the subject, for example, 'Protective Groups in Organic Synthesis' by Theodora Green (publisher: John Wiley & Sons).

Protecting groups may be removed by any convenient method described in the literature or known to the skilled chemist as appropriate for the removal of the protecting group in question, such methods being chosen so as to effect removal of the protecting group with the minimum disturbance of groups elsewhere in the molecule. Thus, if reactants include, for example, groups such as amino, carboxy or hydroxy it may be desirable to protect the group in some of the reactions mentioned herein.

By way of example, a suitable protecting group for an amino or alkylamino group is, for example, an acyl group, for example an alkanoyl group such as acetyl, an alkoxycarbonyl group, for example a methoxycarbonyl, ethoxycarbonyl, or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed by, for example, hydrolysis with a suitable base such as an alkali metal hydroxide, for example lithium or sodium hydroxide. Alternatively an acyl group such as a tert-butoxycarbonyl group may be removed, for example, by treatment with a suitable acid as hydrochloric, sulphuric or phosphoric acid or trifluoroacetic acid and an arylmethoxycarbonyl group such as a benzyloxycarbonyl group may be removed, for example, by hydrogenation over a catalyst such as palladium on carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium, sodium hydroxide or ammonia. Alternatively an arylmethyl group such as a benzyl group may be removed, for example, by hydrogenation over a catalyst such as palladium on carbon.

A suitable protecting group for a carboxy group is, for example, an esterifying group, for example a methyl or an ethyl group which may be removed, for example, by hydrolysis with a base such as sodium hydroxide, or for example a tert-butyl group which may be removed, for example, by treatment with an acid, for example an organic acid such as trifluoroacetic acid, or for example a benzyl group which may be removed, for example, by hydrogenation over a catalyst such as palladium on carbon.

Once a compound of Formula (I), (II), or (II') has been synthesised by any one of the processes defined herein, the processes may then further comprise the additional steps of: (i) removing any protecting groups present; (ii) converting the compound of Formula (I), (II), or (II') into another compound of Formula (I), (II), or (II'); (iii) forming a pharmaceutically acceptable salt, hydrate or solvate thereof; and/or (iv) forming a prodrug thereof.

The resultant compounds of Formula (I), (II), and (II') can be isolated and purified using techniques well known in the art.

Conveniently, the reaction of the compounds is carried out in the presence of a suitable solvent, which is preferably inert under the respective reaction conditions. Examples of suitable solvents comprise but are not limited to hydrocarbons, such as hexane, petroleum ether, benzene, toluene or xylene; chlorinated hydrocarbons, such as trichlorethylene, 1,2-dichloroethane, tetrachloromethane, chloroform or dichloromethane; alcohols, such as methanol, ethanol, isopropanol, n-propanol, n-butanol or tert-butanol; ethers, such as diethyl ether, diisopropyl ether, tetrahydrofuran (THF), 2-methyltetrahydrofuran, cyclopentylmethyl ether (CPME), methyl tert-butyl ether (MTBE) or dioxane; glycol ethers, such as ethylene glycol monomethyl or monoethyl ether or ethylene glycol dimethyl ether (diglyme); ketones, such as acetone, methylisobutylketone (MIBK) or butanone; amides, such as acetamide, dimethylacetamide, dimethylformamide (DMF) or N-methylpyrrolidinone (NMP); nitriles, such as acetonitrile; sulphoxides, such as dimethyl sulphoxide (DMSO); nitro compounds, such as nitromethane or nitrobenzene; esters, such as ethyl acetate or methyl acetate, or mixtures of the said solvents or mixtures with water.

Moreover, by utilising the procedures described herein, in conjunction with ordinary skills in the art, additional compounds of the present disclosure can be readily prepared. Those skilled in the art will readily understand that known variations of the conditions and processes of the following preparative procedures can be used to prepare these compounds.

As will be understood by the person skilled in the art of organic synthesis, compounds of the present disclosure are readily accessible by various synthetic routes, some of which are exemplified in the accompanying examples. The skilled person will easily recognise which kind of reagents and reactions conditions are to be used and how they are to be applied and adapted in any particular instance—wherever necessary or useful—in order to obtain the compounds of the present disclosure. Furthermore, some of the compounds of the present disclosure can readily be synthesised by reacting other compounds of the present disclosure under suitable conditions, for instance, by converting one particular functional group being present in a compound of the present disclosure, or a suitable precursor molecule thereof, into another one by applying standard synthetic methods, like reduction, oxidation, addition or substitution reactions; those methods are well known to the skilled person. Likewise, the skilled person will apply—whenever necessary or useful—synthetic protecting (or protective) groups; suitable protecting groups as well as methods for introducing and removing them are well-known to the person skilled in the art of chemical synthesis and are described, in more detail, in, e.g., P. G. M. Wuts, T. W. Greene, "Greene's Protective Groups in Organic Synthesis", 4th edition (2006) (John Wiley & Sons).

In some embodiments, a compound of the present disclosure is prepared as described in Schemes 1, 2, or 3.

In some embodiments, a compound of the present disclosure is prepared as described in Scheme 1.

In some embodiments, a compound of the present disclosure is prepared as described in Scheme 2.

In some embodiments, a compound of the present disclosure is prepared as described in Scheme 3.

Scheme 1
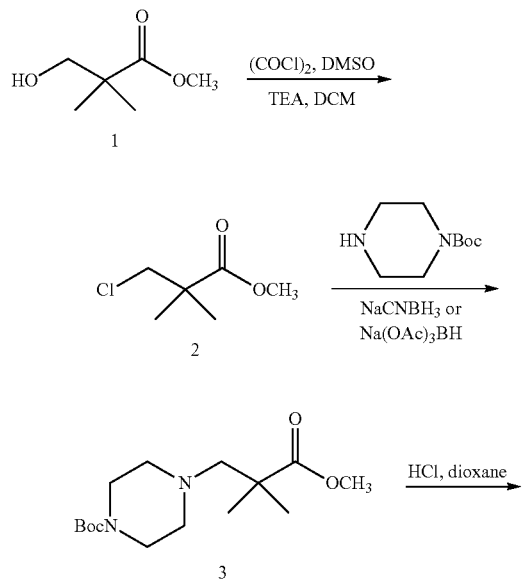
Scheme 1 describes the preparation of methyl 2,2-dimethyl-3-(piperazin-1-yl)propanoate (4), which can be coupled to intermediate 9 in Schemes 2 and 3 by displacement of the chloride, to form compound 10.
Scheme 2
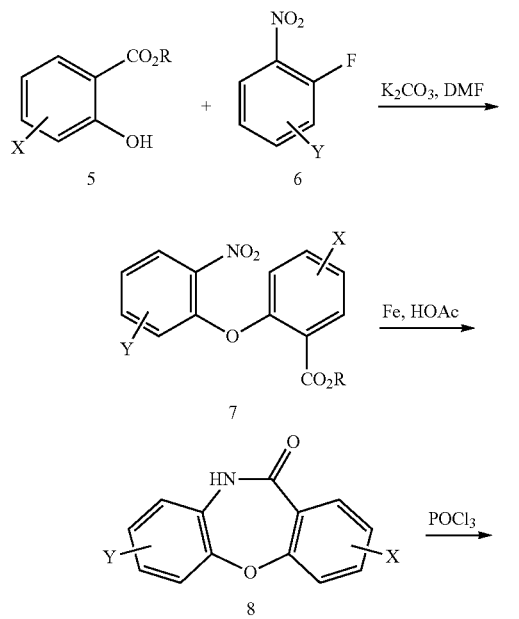
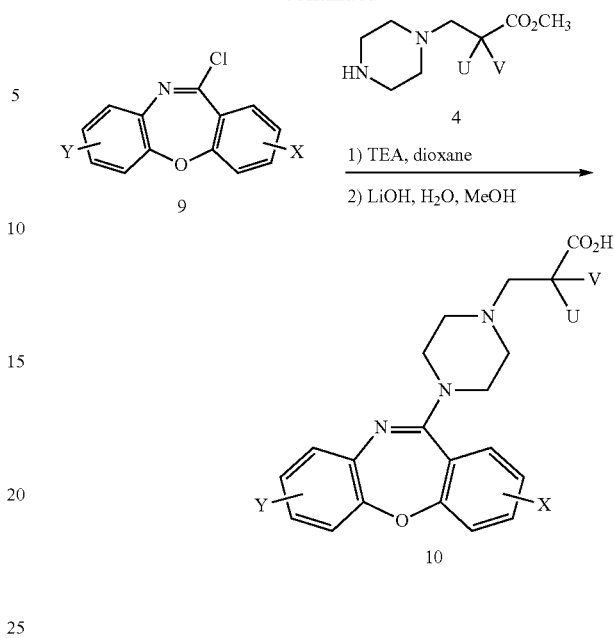
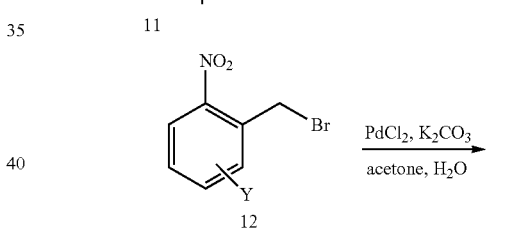
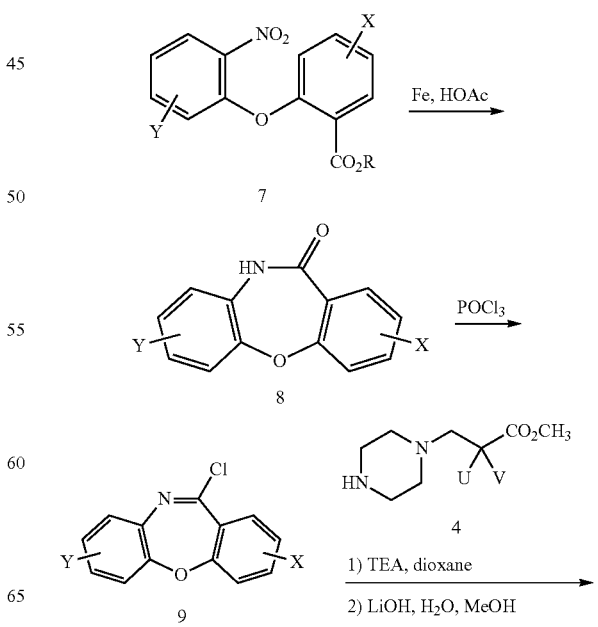

-continued

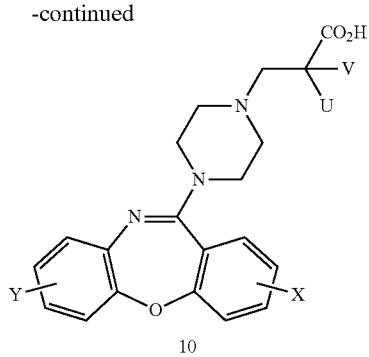

10

Schemes 2 and 3 describe the synthetic routes to prepare the dual H1/5HT$_2$a antagonists exemplified here in. Intermediates 5, and 6 depicted in Scheme 2, can be readily prepared through literature procedures by one practiced in the art. Intermediates 11 and 12 depicted in Scheme 3, can be readily prepared through literature procedures by one practiced in the art.

Biological Assays

Compounds designed, selected and/or optimised by methods described above, once produced, can be characterised using a variety of assays known to those skilled in the art to determine whether the compounds have biological activity. For example, the molecules can be characterised by conventional assays, including but not limited to those assays described below, to determine whether they have a predicted activity, binding activity and/or binding specificity.

Furthermore, high-throughput screening can be used to speed up analysis using such assays. As a result, it can be possible to rapidly screen the molecules described herein for activity, using techniques known in the art. General methodologies for performing high-throughput screening are described, for example, in Devlin (1998) *High Throughput Screening*, Marcel Dekker; and U.S. Pat. No. 5,763,263. High-throughput assays can use one or more different assay techniques including, but not limited to, those described below.

Various in vitro or in vivo biological assays are may be suitable for detecting the effect of the compounds of the present disclosure. These in vitro or in vivo biological assays can include, but are not limited to, enzymatic activity assays, electrophoretic mobility shift assays, reporter gene assays, in vitro cell viability assays, and the assays described herein.

The biological activity of the compounds of the present disclosure may be determined utilizing a binding assay. The binding assay may be for H1 and 5-HT$_{2A}$, 5-HT$_{2C}$, or D2.

The biological activity of the compounds of the present disclosure may be determined utilizing a binding assay. The binding assay may be for H1 and 5-HT$_{2A}$, 5-HT$_{2C}$, or D2.

The biological activity of the compounds of the present disclosure may be determined utilizing a binding assay. The binding assay may be for H1 and 5-HT$_{2A}$. The biological activity of the compounds of the present disclosure may be determined utilizing a binding assay. The binding assay may be for H1. The biological activity of the compounds of the present disclosure may be determined utilizing a binding assay. The binding assay may be for 5-HT$_{2A}$. The binding assay may be for D2.

A compound of the present disclosure may be assayed in comparison to a reference standard (e.g., ketanserin or pyrilamine). The compound of the present disclosure may be transferred to an assay plate for nonspecific binding or total binding. The assay plate may be sealed and shaken. Upon assay completion the reaction mixture may be filtered and washed with buffer. The filter plates may be dried and sealed. Inhibition constants may be calculated using the following equation:

$$\% \text{ inhibition} = \left(1 - \frac{\text{Assay well} - \text{Average } LC}{\text{Average } HC - \text{Average } LC}\right) \times 100$$

and the data was analyzed. The IC$_{50}$ may be calculated and converted to K$_i$.

The biological activity of the compounds of the present disclosure may be determined utilizing a binding assay. The binding assay may be for 5-HT$_{2C}$. A compound of the present disclosure may be assayed in comparison to a reference standard, e.g., SB-206553 (i.e., 5-Methyl-1-(3-pyridylcarbamoyl)-1,2,3,5-tetrahydropyrrolo[2,3-f]indole hydrochloride hydrate). The compound of the present disclosure may be transferred to an assay plate for nonspecific binding or total binding. The assay plate may be sealed and shaken. Upon assay completion the reaction mixture may be filtered and washed with buffer. The filter plates may be dried and sealed. Inhibition constants may be calculated using the following equation:

$$\% \text{ inhibition} = \left(1 - \frac{\text{Assay well} - \text{Average } LC}{\text{Average } HC - \text{Average } LC}\right) \times 100$$

and the data was analyzed. The IC$_{50}$ may be calculated and converted to K$_i$.

The biological activity of the compounds of the present disclosure may be determined utilizing a binding assay. The binding assay may be for D2. A compound of the present disclosure may be assayed in comparison to a reference standard, e.g., droperidol (i.e., 3-[1-[4-(4-fluorophenyl)-4-oxobutyl]-3,6-dihydro-2H-pyridin-4-yl]-1H-benzimidazol-2-one). The compound of the present disclosure may be transferred to an assay plate for nonspecific binding or total binding. The assay plate may be sealed and shaken. Upon assay completion the reaction mixture may be filtered and washed with buffer. The filter plates may be dried and sealed. Inhibition constants may be calculated using the following equation:

$$\% \text{ inhibition} = \left(1 - \frac{\text{Assay well} - \text{Average } LC}{\text{Average } HC - \text{Average } LC}\right) \times 100$$

and the data was analyzed. The IC$_{50}$ may be calculated and converted to K$_i$.

In some embodiments, the compounds of the present disclosure selectively target H1/5-HT$_{2A}$. In some embodiments, the compounds of the present disclosure do not selectively target 5-HT$_{2C}$. In some embodiments, the compounds of the present disclosure target H1/5-HT$_{2A}$ to a greater extent in comparison to 5-HT$_{2C}$ (e.g., the compound targets H1/5-HT$_{2A}$ at a percentage greater than about 10%, about 20%, about 30%, about 40%, about 50%, about 60%, about 70%, about 80%, about 90%, about 95%, or about 99% when compared to 5-HT$_{2C}$).

In some embodiments, the K$_i$ value for 5-HT$_{2A}$ is from about 1 nM to about 150 nM. In some embodiments, the K$_i$ value for 5-HT$_{2A}$ is from about 1 nM to about 125 nM. In some embodiments, the $K_i$ value for 5-HT$_{2A}$ is from about 1 nM to about 100 nM. In some embodiments, the $K_i$ value for 5-HT$_{2A}$ is from about 1 nM to about 75 nM. In some embodiments, the $K_i$ value for 5-HT$_{2A}$ is from about 1 nM to about 50 nM. In some embodiments, the $K_i$ value for 5-HT$_{2A}$ is from about 1 nM to about 40 nM. In some embodiments, the $K_i$ value for 5-HT$_{2A}$ is from about 1 nM to about 30 nM. In some embodiments, the $K_i$ value for 5-HT$_{2A}$ is from about 1 nM to about 20 nM. In some embodiments, the $K_i$ value for 5-HT$_{2A}$ is from about 1 nM to about 10 nM. In some embodiments, the $K_i$ value for 5-HT$_{2A}$ is from about 1 nM to about 5 nM.

In some embodiments, the $K_i$ value for 5-HT$_{2A}$ is about 150 nM. In some embodiments, the $K_i$ value for 5-HT$_{2A}$ is about 125 nM. In some embodiments, the $K_i$ value for 5-HT$_{2A}$ is about 100 nM. In some embodiments, the $K_i$ value for 5-HT$_{2A}$ is about 75 nM. In some embodiments, the $K_i$ value for 5-HT$_{2A}$ is about 50 nM. In some embodiments, the $K_i$ value for 5-HT$_{2A}$ is about 40 nM. In some embodiments, the $K_i$ value for 5-HT$_{2A}$ is about 30 nM. In some embodiments, the $K_i$ value for 5-HT$_{2A}$ is about 20 nM. In some embodiments, the $K_i$ value for 5-HT$_{2A}$ is about 15 nM. In some embodiments, the $K_i$ value for 5-HT$_{2A}$ is about 10 nM. In some embodiments, the $K_i$ value for 5-HT$_{2A}$ is about 9 nM. In some embodiments, the $K_i$ value for 5-HT$_{2A}$ is about 8 nM. In some embodiments, the $K_i$ value for 5-HT$_{2A}$ is about 7 nM. In some embodiments, the $K_i$ value for 5-HT$_{2A}$ is about 6 nM. In some embodiments, the $K_i$ value for 5-HT$_{2A}$ is about 5 nM. In some embodiments, the $K_i$ value for 5-HT$_{2A}$ is about 4 nM. In some embodiments, the $K_i$ value for 5-HT$_{2A}$ is about 3 nM. In some embodiments, the $K_i$ value for 5-HT$_{2A}$ is about 2 nM. In some embodiments, the $K_i$ value for 5-HT$_{2A}$ is about 1 nM.

In some embodiments, the $K_i$ value for H1 is from about 1 nM to about 150 nM. In some embodiments, the $K_i$ value for H1 is from about 1 nM to about 125 nM. In some embodiments, the $K_i$ value for H1 is from about 1 nM to about 100 nM. In some embodiments, the $K_i$ value for H1 is from about 1 nM to about 75 nM. In some embodiments, the $K_i$ value for H1 is from about 1 nM to about 50 nM. In some embodiments, the $K_i$ value for H1 is from about 1 nM to about 40 nM. In some embodiments, the $K_i$ value for H1 is from about 1 nM to about 30 nM. In some embodiments, the $K_i$ value for H1 is from about 1 nM to about 20 nM. In some embodiments, the $K_i$ value for H1 is from about 1 nM to about 10 nM. In some embodiments, the $K_i$ value for H1 is from about 1 nM to about 5 nM.

In some embodiments, the $K_i$ value for H1 is about 150 nM. In some embodiments, the $K_i$ value for H1 is about 125 nM. In some embodiments, the $K_i$ value for H1 is about 100 nM. In some embodiments, the $K_i$ value for H1 is about 90 nM. In some embodiments, the $K_i$ value for H1 is about 80 nM. In some embodiments, the $K_i$ value for H1 is about 70 nM. In some embodiments, the $K_i$ value for H1 is about 60 nM. In some embodiments, the $K_i$ value for H1 is about 50 nM. In some embodiments, the $K_i$ value for H1 is about 40 nM. In some embodiments, the $K_i$ value for H1 is about 30 nM. In some embodiments, the $K_i$ value for H1 is about 20 nM. In some embodiments, the $K_i$ value for H1 is about 15 nM. In some embodiments, the $K_i$ value for H1 is about 10 nM.

In some embodiments, the $K_i$ value for 5-HT$_{2C}$ is from about 500 nM to about 10 μM. In some embodiments, the $K_i$ value for 5-HT$_{2C}$ is about 500 nM. In some embodiments, the $K_i$ value for 5-HT$_{2C}$ is about 750 nM. In some embodiments, the $K_i$ value for 5-HT$_{2C}$ is about 1 μM. In some embodiments, the $K_i$ value for 5-HT$_{2C}$ is about 2 μM. In some embodiments, the $K_i$ value for 5-HT$_{2C}$ is about 3 μM. In some embodiments, the $K_i$ value for 5-HT$_{2C}$ is about 4 μM. In some embodiments, the $K_i$ value for 5-HT$_{2C}$ is about 5 μM. In some embodiments, the $K_i$ value for 5-HT$_{2C}$ is about 6 μM. In some embodiments, the $K_i$ value for 5-HT$_{2C}$ is about 7 μM. In some embodiments, the $K_i$ value for 5-HT$_{2C}$ is about 8 μM. In some embodiments, the $K_i$ value for 5-HT$_{2C}$ is about 9 μM. In some embodiments, the $K_i$ value for 5-HT$_{2C}$ is about 10 μM.

In some embodiments, a compound of the present disclosure has low affinity for 5-HT$_{2C}$ (e.g., a $K_i$ value above about 100 nM, about 200 nM, about 500 nM, about 750 nM, about 1,000 nM, about 1,500 nM, or about 2,000 nM). In some embodiments, Compound No. 7 has low affinity for 5-HT$_{2C}$ (e.g., a $K_i$ value of about 2,200 nM).

In some embodiments, a compound of the present disclosure has an affinity for 5-HT$_{2A}$ (e.g., a $K_i$ value below about 1,500 nM, about 1,000 nM, about 750 nM, about 500 nM, about 250 nM, or about 100 nM). In some embodiments, Compound No. 8 has an affinity for 5-HT$_{2A}$ (e.g., a $K_i$ value of about 87 nM).

In some embodiments, the $K_i$ value for D2 is greater than about 100 nM. In some embodiments, the $K_i$ value for D2 is greater than about 500 nM. In some embodiments, the $K_i$ value for D2 is greater than about 1,000 nM. In some embodiments, the $K_i$ value for D2 is greater than about 10,000 nM. In some embodiments, the $K_i$ value for D2 is greater than about 25,000 nM. In some embodiments, the $K_i$ value for D2 is greater than about 50,000 nM.

In some embodiments, a compound of the present disclosure has low affinity for D2 (e.g., a $K_i$ value above about 100 nM, about 200 nM, about 500 nM, about 750 nM, about 1,000 nM, about 1,500 nM, about 2,000 nM, about 10,000 nM, about 25,000 nM, or about 50,000 nM). In some embodiments, Compound No. 7 has low affinity for D2 (e.g., a $K_i$ value of about above 50,000 nM).

Without wishing to be bound by theory, a non-selective 5-HT$_2$ modulator (e.g., targeting both 5-HT$_{2A}$ and 5-HT$_{2C}$) does not alleviate a symptom of, treat, or prevent a sleep disorder.

Further, without wishing to be bound by theory, modulating 5-HT$_{2C}$ function does not alleviate a symptom of, treat, or prevent a sleep disorder.

The biological activity of the compounds of the present disclosure may be determined utilizing projected human clearance (CL) and half-life in humans. An allometric scaling method, using a single species scaling from monkey clearance was used to project clearance. Human volume of distribution ($V_d$) was projected from animal $V_d$, adjusted for differences in plasma protein binding and assuming similar unbound $V_d$ across species. Human half-life ($T_{1/2}$) was calculated based on a one-compartmental model, using a relationship of $T_{1/2}=0.693\times$(predicted $V_d$/predicted CL).

In some embodiments, the projected human half-life ($t_{1/2}$) is from about 10 hours to about 1 hour. In some embodiments, the projected human half-life is about 10 hours. In some embodiments, the projected human half-life is about 9 hours. In some embodiments, the projected human half-life is about 8 hours. In some embodiments, the projected human half-life is about 7 hours. In some embodiments, the projected human half-life is about 6 hours. In some embodiments, the projected human half-life is about 5 hours. In some embodiments, the projected human half-life is about 4 hours. In some embodiments, the projected human half-life is about 3 hours. In some embodiments, the projected human half-life is about 2 hours. In some embodiments, the projected human half-life is about 1 hour.

A patch clamp electrophysiology system, for example SyncroPatch 384PE (Nanion), may be suitable for obtaining data related to the ionic currents in individual isolated cells.

A microcomputer-based sleep-wake and physiological monitoring system, SCORE™, may be suitable for determining sleep and wakefulness. Validation of the SCORE™ sleepstage identification algorithm in rodents and utility in pre-clinical drug evaluation have been previously described (Van Gelder et al. 1991; Edgar et al., *Psychopharmacology*, 1991, 105: 374-380; Edgar et al., *J Pharmacology & Experimental Therapeutics*, 1997, 283: 757-769; Edgar et al., *J Pharmacol. Exp. Ther*, 1997, 282: 420-429; Seidel et al., *J Pharmacology & Experimental Therapeutics*, 1995, 275: 263-273; Olive et al., *J Pharmacology & Experimental Therapeutics*, 1998, 285: 1073-1083).

The standard recording duration for SCORE data may not be less than 30 hours before and after treatment. The 30 hours pre-treatment baseline recording can itself be preceded by at least 24 hours in which the animal is undisturbed in the home/recording cage. Rats may be randomly assigned to treatments in parallel groups. Some rats may receive more than one active treatment, in which cases at least 7 days "washout" elapse between each treatment.

The subject may be surgically prepared for EEG and EMG recording and administered an analgesic with an antibiotic, followed by therapeutic delivery via intraperitoneal or oral administration. The sleep and wakefulness may be determined using SCORE™.

Statistically significant differences between drug and vehicle may be screened using a post-hoc Student's T-test applied to hourly binned data and adjusted for repeated measures.

The compounds of the present disclosure may exhibit improved sleep fragmentation as assessed by evaluating the sleep architecture and sleep quality endpoints of several dual acting H1 inverse agonist and 5-$HT_{2A}$ antagonist compounds with established affinity and functional activity at this target.

In some embodiments, sleep fragmentation is improved by (i) reducing the number of arousals (as measured by the number of transitions to wake per hour), or (ii) increasing sleep consolidation (as measured by average sleep bout duration per hour). In some embodiments, sleep fragmentation is improved by (i) reducing the number of arousals (as measured by the number of transitions to wake per hour), and (ii) increasing sleep consolidation (as measured by average sleep bout duration per hour). In some embodiments, sleep fragmentation is improved by reducing the number of arousals (as measured by the number of transitions to wake per hour. In some embodiments, sleep fragmentation is improved by increasing sleep consolidation (as measured by average sleep bout duration per hour).

The utility of dual acting H1 inverse agonist and 5-$HT_{2A}$ antagonist molecules to improve sleep fragmentation was assessed by evaluating the sleep architecture and sleep quality endpoints of the compounds of the present disclosure.

The H1 and 5-$HT_{2A}$ binding activity of a compound of the present disclosure may be assessed by utilizing an assay of the present disclosure. In some embodiments, the H1 and 5-$HT_{2A}$ binding activity of a compound of the present disclosure is compared to another compound.

In some embodiments, a compound for comparison may be assayed in comparison to a reference standard (e.g., ketanserin or pyrilamine). The compound for comparison may be transferred to an assay plate for nonspecific binding or total binding. The assay plate may be sealed and shaken. Upon assay completion the reaction mixture may be filtered and washed with buffer. The filter plates may be dried and sealed. Inhibition constants may be calculated using the following equation:

$$\% \text{ inhibition} = \left(1 - \frac{\text{Assay well} - \text{Average } LC}{\text{Average } HC - \text{Average } LC}\right) \times 100$$

and the data was analyzed. The $IC_{50}$ may be calculated and converted to $K_i$.

The 5-$HT_{2C}$ binding activity of a compound of the present disclosure may be assessed by utilizing an assay of the present disclosure. In some embodiments, the 5-$HT_{2C}$ binding activity of a compound of the present disclosure is compared to another compound.

The biological activity of a compounds for comparison may be determined utilizing a binding assay. The binding assay may be for 5-$HT_{2C}$. The compound for comparison may be assayed in comparison to a reference standard, e.g., SB-206553 (i.e., 5-Methyl-1-(3-pyridylcarbamoyl)-1,2,3,5-tetrahydropyrrolo[2,3-f]indole hydrochloride hydrate). The compound for comparison may be transferred to an assay plate for nonspecific binding or total binding. The assay plate may be sealed and shaken. Upon assay completion the reaction mixture may be filtered and washed with buffer. The filter plates may be dried and sealed. Inhibition constants may be calculated using the following equation:

$$\% \text{ inhibition} = \left(1 - \frac{\text{Assay well} - \text{Average } LC}{\text{Average } HC - \text{Average } LC}\right) \times 100$$

and the data was analyzed. The $IC_{50}$ may be calculated and converted to $K_i$.

The D2 binding activity of a compound of the present disclosure may be assessed by utilizing an assay of the present disclosure. In some embodiments, the D2 binding activity of a compound of the present disclosure is compared to another compound.

The biological activity of a compounds for comparison may be determined utilizing a binding assay. The binding assay may be for D2. The compound for comparison may be assayed in comparison to a reference standard, e.g., droperidol (i.e., 3-[1-[4-(4-fluorophenyl)-4-oxobutyl]-3,6-dihydro-2H-pyridin-4-yl]-1H-benzimidazol-2-one). The compound for comparison may be transferred to an assay plate for nonspecific binding or total binding. The assay plate may be sealed and shaken. Upon assay completion the reaction mixture may be filtered and washed with buffer. The filter plates may be dried and sealed. Inhibition constants may be calculated using the following equation:

$$\% \text{ inhibition} = \left(1 - \frac{\text{Assay well} - \text{Average } LC}{\text{Average } HC - \text{Average } LC}\right) \times 100$$

and the data was analyzed. The $IC_{50}$ may be calculated and converted to $K_i$.

Pharmaceutical Compositions

In some aspects, the present disclosure provides a pharmaceutical composition comprising a compound of the present disclosure as an active ingredient. In some embodiments, the present disclosure provides a pharmaceutical composition comprising at least one compound of each of the formulae described herein, or a pharmaceutically acceptable salt or solvate thereof, and one or more pharmaceutically acceptable carriers or excipients. In some embodiments, the present disclosure provides a pharmaceutical composition comprising at least one compound selected from Table 1.

As used herein, the term "composition" is intended to encompass a product comprising the specified ingredients in the specified amounts, as well as any product which results, directly or indirectly, from combination of the specified ingredients in the specified amounts.

The compounds of present disclosure can be formulated for oral administration in forms such as tablets, capsules (each of which includes sustained release or timed release formulations), pills, powders, granules, elixirs, tinctures, suspensions, syrups and emulsions. The compounds of present disclosure on can also be formulated for intravenous (bolus or in-fusion), intraperitoneal, topical, subcutaneous, intramuscular or transdermal (e.g., patch) administration, all using forms well known to those of ordinary skill in the pharmaceutical arts.

The formulation of the present disclosure may be in the form of an aqueous solution comprising an aqueous vehicle. The aqueous vehicle component may comprise water and at least one pharmaceutically acceptable excipient. Suitable acceptable excipients include those selected from the group consisting of a solubility enhancing agent, chelating agent, preservative, tonicity agent, viscosity/suspending agent, buffer, and pH modifying agent, and a mixture thereof.

Any suitable solubility enhancing agent can be used. Examples of a solubility enhancing agent include cyclodextrin, such as those selected from the group consisting of hydroxypropyl-β-cyclodextrin, methyl-β-cyclodextrin, randomly methylated-β-cyclodextrin, ethylated-β-cyclodextrin, triacetyl-β-cyclodextrin, peracetylated-β-cyclodextrin, carboxymethyl-β-cyclodextrin, hydroxyethyl-β-cyclodextrin, 2-hydroxy-3-(trimethylammonio)propyl-β-cyclodextrin, glucosyl-β-cyclodextrin, sulphated β-cyclodextrin (S-β-CD), maltosyl-β-cyclodextrin, β-cyclodextrin sulphobutyl ether, branched-β-cyclodextrin, hydroxypropyl-γ-cyclodextrin, randomly methylated-γ-cyclodextrin, and trimethyl-γ-cyclodextrin, and mixtures thereof.

Any suitable chelating agent can be used. Examples of a suitable chelating agent include those selected from the group consisting of ethylenediaminetetraacetic acid and metal salts thereof, disodium edetate, trisodium edetate, and tetrasodium edetate, and mixtures thereof.

Any suitable preservative can be used. Examples of a preservative include those selected from the group consisting of quaternary ammonium salts such as benzalkonium halides (preferably benzalkonium chloride), chlorhexidine gluconate, benzethonium chloride, cetyl pyridinium chloride, benzyl bromide, phenylmercury nitrate, phenylmercury acetate, phenylmercury neodecanoate, merthiolate, methylparaben, propylparaben, sorbic acid, potassium sorbate, sodium benzoate, sodium propionate, ethyl p-hydroxybenzoate, propylaminopropyl biguanide, and butyl-p-hydroxybenzoate, and sorbic acid, and mixtures thereof.

The aqueous vehicle may also include a tonicity agent to adjust the tonicity (osmotic pressure). The tonicity agent can be selected from the group consisting of a glycol (such as propylene glycol, diethylene glycol, triethylene glycol), glycerol, dextrose, glycerin, mannitol, potassium chloride, and sodium chloride, and a mixture thereof.

The aqueous vehicle may also contain a viscosity/suspending agent. Suitable viscosity/suspending agents include those selected from the group consisting of cellulose derivatives, such as methyl cellulose, ethyl cellulose, hydroxyethylcellulose, polyethylene glycols (such as polyethylene glycol 300, polyethylene glycol 400), carboxymethyl cellulose, hydroxypropylmethyl cellulose, and cross-linked acrylic acid polymers (carbomers), such as polymers of acrylic acid cross-linked with polyalkenyl ethers or divinyl glycol (Carbopols—such as Carbopol 934, Carbopol 934P, Carbopol 971, Carbopol 974 and Carbopol 974P), and a mixture thereof.

In order to adjust the formulation to an acceptable pH (typically a pH range of about 5.0 to about 9.0, more preferably about 5.5 to about 8.5, particularly about 6.0 to about 8.5, about 7.0 to about 8.5, about 7.2 to about 7.7, about 7.1 to about 7.9, or about 7.5 to about 8.0), the formulation may contain a pH modifying agent. The pH modifying agent is typically a mineral acid or metal hydroxide base, selected from the group of potassium hydroxide, sodium hydroxide, and hydrochloric acid, and mixtures thereof, and preferably sodium hydroxide and/or hydrochloric acid. These acidic and/or basic pH modifying agents are added to adjust the formulation to the target acceptable pH range. Hence it may not be necessary to use both acid and base—depending on the formulation, the addition of one of the acid or base may be sufficient to bring the mixture to the desired pH range.

The aqueous vehicle may also contain a buffering agent to stabilise the pH. When used, the buffer is selected from the group consisting of a phosphate buffer (such as sodium dihydrogen phosphate and disodium hydrogen phosphate), a borate buffer (such as boric acid, or salts thereof including disodium tetraborate), a citrate buffer (such as citric acid, or salts thereof including sodium citrate), and ε-aminocaproic acid, and mixtures thereof.

The formulation may further comprise a wetting agent. Suitable classes of wetting agents include those selected from the group consisting of polyoxypropylene-polyoxyethylene block copolymers (poloxamers), polyethoxylated ethers of castor oils, polyoxyethylenated sorbitan esters (polysorbates), polymers of oxyethylated octyl phenol (Tyloxapol), polyoxyl 40 stearate, fatty acid glycol esters, fatty acid glyceryl esters, sucrose fatty esters, and polyoxyethylene fatty esters, and mixtures thereof.

According to a further aspect of the disclosure there is provided a pharmaceutical composition which comprises a compound of the disclosure as defined hereinbefore, or a pharmaceutically acceptable salt, hydrate or solvate thereof, in association with a pharmaceutically acceptable diluent or carrier.

The compositions of the disclosure may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular, intraperitoneal or intramuscular dosing or as a suppository for rectal dosing).

The compositions of the disclosure may be obtained by conventional procedures using conventional pharmaceutical excipients, well known in the art. Thus, compositions intended for oral use may contain, for example, one or more colouring, sweetening, flavouring and/or preservative agents.

An effective amount of a compound of the present disclosure for use in therapy is an amount sufficient to treat or prevent a sleep disorder related condition referred to herein, slow its progression and/or reduce the symptoms associated with the condition.

An effective amount of a compound of the present disclosure for use in therapy is an amount sufficient to treat a sleep disorder related condition referred to herein, slow its progression and/or reduce the symptoms associated with the condition.

The size of the dose for therapeutic or prophylactic purposes of a compound of Formula (I), (II), and (II') will naturally vary according to the nature and severity of the conditions, the age and sex of the animal or subject and the route of administration, according to well-known principles of medicine.

Methods of Use

Sleep fragmentation, a condition in humans characterized by poor sleep consolidation, includes frequent brief arousals or microarousals (defined by the American Academy of Sleep Medicine as episodes of cortical EEG activation lasting at least 2 seconds and up to 16 seconds in duration and interrupting sleep) and frequent transitions to lighter stages of sleep, which can result in significant daytime impairment, secondary morbidity, and mortality when sleep fragmentation is a concomitant of pain, sleep disordered breathing, and other disease states. Daytime impairment may include impaired attention and concentration, excessive sleepiness, impaired judgement, impaired memory and learning, and increased risk of accidents. Subjects suffering from sleep fragmentation are typically unaware of the hundreds of brief arousals that may occur during the night, and primarily complain of severe daytime impairment. Sleep fragmentation subjects often complain that their sleep is not beneficial or refreshing.

The diagnosis of sleep fragmentation and its methods of treatment are different from insomnia, which is a separate and distinct medical diagnosis. Insomnia is typically characterized by subject awareness dissatisfaction with their sleep. Most insomnia patients have a hyperarousal disorder that makes it difficult to fall asleep and/or difficult to stay asleep, but enable them to function well during the daytime. Insomnia is diagnosed by measuring the latency to persistent sleep (LPS of ≥30 minutes satisfies the definition of sleep-onset insomnia) and/or measuring the amount of time awake after sleep onset (WASO of ≥50 minutes satisfies the definition of sleep-maintenance insomnia). It is common for insomnia patients, and particularly the elderly, to awaken in the middle of the night and be unable to return to sleep. Unlike subjects suffering from sleep fragmentation, insomnia patients are almost always highly aware of their inability to fall asleep or stay asleep at night and complain about their nighttime experience, and typically do not complain about daytime impairment.

The embodiments herein pertain to the identification of pharmacological compound classes that are especially well suited to treat sleep disorders characterized in whole or in part by sleep fragmentation. The compounds of the present disclosure may be described as having dual $H_1$ receptor inverse agonist and 5-$HT_{2A}$ receptor antagonist activity to improve sleep fragmentation as evidenced by reduced number of arousals (measured as reduced number of transitions to wake per hour), increased sleep continuity/consolidation (measured by average sleep bout duration per hour), and increased depth of sleep (measured preclinically by electroencephalograph (EEG) spectral analyses to identify power in the EEG frequency band of 0.5-4.0 hertz (EEG "delta power").

Molecules with the requisite $H_1$ inverse agonist and 5-$HT_{2A}$ antagonist receptor pharmacology may be studied for their effects on EEG sleep-wakefulness, locomotor activity, drink- and food-related activity and body temperature in laboratory rats using an improved and expanded version of SCORE-2000®, a sophisticated sleep-wake bioassay and analysis system which shall henceforth be referred to as "SCORE™".

The technology is well suited for sleep-wake efficacy and physiological and behavioral side effect assessment. Associated with this technology is an extensive pharmacological database with standardized sleep-wake, physiological, and behavioral data for over 500 distinct molecules.

The standardized nature of the experimental designs, data quality control, and data analysis methods enable direct comparisons between molecules Rat and Human Sleep The present disclosure provides a pre-clinical drug evaluation using rats. Without wishing to be bound by theory, rat sleep and human sleep have all of the necessary fundamental similarities to permit the rat to be used as a preclinical model. As such, compounds that are soporific in a human may have soporific effects in a rat, and compounds that are soporific in a rat may have soporific effects in a human. Both rat and human exhibit robust circadian modulation of sleep tendency and sleep architecture.

The "homeostatic" control of sleep shares similarity across mammalian species, including humans, in that loss of sleep increases a homeostatic drive for sleep evidenced by a reduction in latency to sleep onset, increase in the depth of sleep that can be reflected by the amount of low-frequency "delta" EEG ("EEG slow waves") during nonREM, an increase in sleep consolidation as measured by sleep bout duration, or an increase in total sleep time. Sleep deprivation in a subject may cause the subject to fall asleep faster, sleep deeper, sleep more efficiently (e.g., more consolidation of bouts of sleep), or sleep more (e.g., an increase of sleep time) until the homeostatic drive for sleep becomes adequately discharged through the sleeping process.

Uninterrupted, well consolidated sleep can determine sleep quality in both a rat and a human. Without wishing to be bound by theory, no matter how much a subject sleeps or what frequency of EEG dominates during sleep, the beneficial work of the sleeping process requires that sleep is not fragmented (interrupted) by frequent arousals.

Without wishing to be bound by theory, compounds of the present disclosure which affect NREM sleep by decreasing the latency to sleep onset, increasing sleep time, increasing the depth and/or consolidation of sleep, reducing arousals, or a combination of the aforementioned effects in a subject, have the same effects in a different subject. The compounds of the present disclosure, which affect NREM sleep by decreasing the latency to sleep onset effects in a subject, may have the same effects on a subject of a different species. The compounds of the present disclosure, which affect NREM sleep by decreasing the latency to sleep onset effects in rats, may have the same effects on a subject of different species. The compounds of the present disclosure, which affect NREM sleep by decreasing the latency to sleep onset effects in rats, may have the same effects on a human.

Without wishing to be bound by theory, compounds of the present disclosure which affect NREM sleep by increasing sleep time in a subject, have the same effects on a different subject. The compounds of the present disclosure which affect NREM sleep by increasing sleep time in a subject, may have the same effects on a subject of a different species. The compounds of the present disclosure which affect NREM sleep by increasing sleep time in rats, may have the same effects on a subject of a different species. The compounds of the present disclosure which affect NREM sleep by increasing sleep time in rats, may have the same effects on a human.

Without wishing to be bound by theory, compounds of the present disclosure which affect NREM sleep by increasing the depth and/or consolidation of sleep in a subject, have the same effects in a different subject. Compounds of the present disclosure which affect NREM sleep by increasing the depth and/or consolidation of sleep in a subject, may have the same effects in a subject of a different species. Compounds of the present disclosure which affect NREM sleep by increasing the depth and/or consolidation of sleep in rats, may have the same effects in a subject of a different species. Compounds of the present disclosure which affect NREM sleep by increasing the depth and/or consolidation of sleep in rats, may have the same effects in a human.

Without wishing to be bound by theory, compounds of the present disclosure which affect NREM sleep by increasing the depth and consolidation of sleep in a subject, have the same effects in a different subject. Compounds of the present disclosure which affect NREM sleep by increasing the depth and consolidation of sleep in a subject, may have the same effects in a subject of a different species. Compounds of the present disclosure which affect NREM sleep by increasing the depth and consolidation of sleep in rats, may have the same effects in a subject of a different species. Compounds of the present disclosure which affect NREM sleep by increasing the depth and consolidation of sleep in rats, may have the same effects in a human.

Without wishing to be bound by theory, compounds of the present disclosure which affect NREM sleep by increasing the depth or consolidation of sleep in a subject, have the same effects in a different subject. Compounds of the present disclosure which affect NREM sleep by increasing the depth or consolidation of sleep in a subject, may have the same effects in a subject of a different species. Compounds of the present disclosure which affect NREM sleep by increasing the depth or consolidation of sleep in rats, may have the same effects in a subject of a different species. Compounds of the present disclosure which affect NREM sleep by increasing the depth or consolidation of sleep in rats, may have the same effects in a human.

Without wishing to be bound by theory, compounds of the present disclosure which affect NREM sleep by increasing the depth of sleep in a subject, have the same effects in a different subject. Compounds of the present disclosure which affect NREM sleep by increasing the depth of sleep in a subject, may have the same effects in a subject of a different species. Compounds of the present disclosure which affect NREM sleep by increasing the depth of sleep in rats, may have the same effects in a subject of a different species. Compounds of the present disclosure which affect NREM sleep by increasing the depth of sleep in rats, may have the same effects in a human.

Without wishing to be bound by theory, compounds of the present disclosure which affect NREM sleep by increasing the consolidation of sleep in a subject, have the same effects in a different subject. Compounds of the present disclosure which affect NREM sleep by increasing the consolidation of sleep in a subject, may have the same effects in a subject of a different species. Compounds of the present disclosure which affect NREM sleep by increasing the consolidation of sleep in rats, may have the same effects in a subject of a different species. Compounds of the present disclosure which affect NREM sleep by increasing the consolidation of sleep in rats, may have the same effects in a human.

Without wishing to be bound by theory, compounds of the present disclosure which affect NREM sleep by reducing arousals in a subject, have the same effects in a different subject. Compounds of the present disclosure which affect NREM sleep by reducing arousals in a subject, have the same effects in a subject of a different species. Compounds of the present disclosure which affect NREM sleep by reducing arousals in rats, have the same effects in a subject of a different species. Compounds of the present disclosure which affect NREM sleep by reducing arousals in rats, have the same effects in a human.

Without wishing to be bound by theory, compounds of the present disclosure which affect REM sleep by decreasing the latency to sleep onset, increasing sleep time, increasing the depth and/or consolidation of sleep, reducing arousals, or a combination of the aforementioned effects in a subject, have the same effects in a different subject. The compounds of the present disclosure, which affect REM sleep by decreasing the latency to sleep onset effects in a subject, may have the same effects on a subject of a different species. The compounds of the present disclosure, which affect REM sleep by decreasing the latency to sleep onset effects in rats, may have the same effects on a subject of different species. The compounds of the present disclosure, which affect REM sleep by decreasing the latency to sleep onset effects in rats, may have the same effects on a human.

Without wishing to be bound by theory, compounds of the present disclosure which affect REM sleep by increasing sleep time in a subject, have the same effects on a different subject. The compounds of the present disclosure which affect REM sleep by increasing sleep time in a subject, may have the same effects on a subject of a different species. The compounds of the present disclosure which affect REM sleep by increasing sleep time in rats, may have the same effects on a subject of a different species. The compounds of the present disclosure which affect REM sleep by increasing sleep time in rats, may have the same effects on a human.

Without wishing to be bound by theory, compounds of the present disclosure which affect REM sleep by increasing the depth and/or consolidation of sleep in a subject, have the same effects in a different subject. Compounds of the present disclosure which affect REM sleep by increasing the depth and/or consolidation of sleep in a subject, may have the same effects in a subject of a different species. Compounds of the present disclosure which affect REM sleep by increasing the depth and/or consolidation of sleep in rats, may have the same effects in a subject of a different species. Compounds of the present disclosure which affect REM sleep by increasing the depth and/or consolidation of sleep in rats, may have the same effects in a human.

Without wishing to be bound by theory, compounds of the present disclosure which affect REM sleep by increasing the depth and consolidation of sleep in a subject, have the same effects in a different subject. Compounds of the present disclosure which affect REM sleep by increasing the depth and consolidation of sleep in a subject, may have the same effects in a subject of a different species. Compounds of the present disclosure which affect REM sleep by increasing the depth and consolidation of sleep in rats, may have the same effects in a subject of a different species. Compounds of the present disclosure which affect REM sleep by increasing the depth and consolidation of sleep in rats, may have the same effects in a human.

Without wishing to be bound by theory, compounds of the present disclosure which affect REM sleep by increasing the depth or consolidation of sleep in a subject, have the same effects in a different subject. Compounds of the present disclosure which affect REM sleep by increasing the depth or consolidation of sleep in a subject, may have the same effects in a subject of a different species. Compounds of the present disclosure which affect REM sleep by increasing the depth or consolidation of sleep in rats, may have the same effects in a subject of a different species. Compounds of the present disclosure which affect REM sleep by increasing the depth or consolidation of sleep in rats, may have the same effects in a human.

Without wishing to be bound by theory, compounds of the present disclosure which affect REM sleep by increasing the depth of sleep in a subject, have the same effects in a different subject. Compounds of the present disclosure which affect REM sleep by increasing the depth of sleep in a subject, may have the same effects in a subject of a different species. Compounds of the present disclosure which affect REM sleep by increasing the depth of sleep in rats, may have the same effects in a subject of a different species. Compounds of the present disclosure which affect REM sleep by increasing the depth of sleep in rats, may have the same effects in a human.

Without wishing to be bound by theory, compounds of the present disclosure which affect REM sleep by increasing the consolidation of sleep in a subject, have the same effects in a different subject. Compounds of the present disclosure which affect REM sleep by increasing the consolidation of sleep in a subject, may have the same effects in a subject of a different species. Compounds of the present disclosure which affect REM sleep by increasing the consolidation of sleep in rats, may have the same effects in a subject of a different species. Compounds of the present disclosure which affect REM sleep by increasing the consolidation of sleep in rats, may have the same effects in a human.

Without wishing to be bound by theory, compounds of the present disclosure which affect REM sleep by reducing arousals in a subject, have the same effects in a different subject. Compounds of the present disclosure which affect REM sleep by reducing arousals in a subject, have the same effects in a subject of a different species. Compounds of the present disclosure which affect REM sleep by reducing arousals in rats, have the same effects in a subject of a different species. Compounds of the present disclosure which affect REM sleep by reducing arousals in rats, have the same effects in a human.

Without wishing to be bound by theory, sleep continuity can be measured as the duration of NREM "bouts" or the duration of REM bouts, or the duration NREM+REM "bouts", wherein an arousal or bout of wakefulness interrupts the NREM-REM cycle.

In some embodiments, sleep bout can be comprised of NREM, REM, or NREM+REM.

In some embodiments, sleep bout can be comprised of NREM. In some embodiments, sleep bout can be comprised of REM. In some embodiments, sleep bout can be comprised of NREM+REM.

In some embodiments, NREM and REM sleep alternate in what may be called the NREM-REM cycle. In some embodiments NREM precedes REM.

In some embodiments, the proportion of time spent in NREM versus REM is the same for different subjects. In some embodiments, the proportion of time spent in NREM versus REM is the same for different subjects of different species. In some embodiments, the proportion of time spent in NREM versus REM is the same for a rat and a subject of a different species. In some embodiments, the proportion of time spent in NREM versus REM is the same for a rat and a human.

In some embodiments, the proportion of time spent in NREM versus REM is about 5:1. In some embodiments, the proportion of time spent in NREM versus REM is about 4:1. In some embodiments, the proportion of time spent in NREM versus REM is about 3:1. In some embodiments, the proportion of time spent in NREM versus REM is about 2:1.

In some embodiments, the proportion of time spent in NREM versus REM is from about 100:1 to about 1:1. In some embodiments, the proportion of time spent in NREM versus REM is from about 90:1 to about 1:1. In some embodiments, the proportion of time spent in NREM versus REM is from about 80:1 to about 1:1. In some embodiments, the proportion of time spent in NREM versus REM is from about 70:1 to about 1:1. In some embodiments, the proportion of time spent in NREM versus REM is from about 60:1 to about 1:1. In some embodiments, the proportion of time spent in NREM versus REM is from about 50:1 to about 1:1. In some embodiments, the proportion of time spent in NREM versus REM is from about 40:1 to about 1:1. In some embodiments, the proportion of time spent in NREM versus REM is from about 30:1 to about 1:1. In some embodiments, the proportion of time spent in NREM versus REM is from about 20:1 to about 1:1. In some embodiments, the proportion of time spent in NREM versus REM is from about 10:1 to about 1:1. In some embodiments, the proportion of time spent in NREM versus REM is from about 5:1 to about 1:1. In some embodiments, the species is a mouse. In some embodiments, the species is a hoofed animal. In some embodiments, the hoofed animal is a horse or cow. In some embodiments, the species is not a laboratory rat. In some embodiments, the species is not a human.

In some embodiments, hypnotics reduce REM sleep to some degree, and several classes of sleep disorder medicines can strongly suppress REM sleep. Without wishing to be bound by theory, REM sleep suppression may be relevant to learning, memory, and/or psychiatric health.

Without wishing to be bound by theory, the relative effect of some classes of medicines for sleep disorders, neuropsychiatric disorders, and cardiovascular disease that either inhibit or stimulate REM sleep translates from a subject to a different subject. The relative effect of some classes of medicines for sleep disorders, neuropsychiatric disorders, and cardiovascular disease that either inhibit or stimulate REM sleep translates from a subject to a subject of a different species. The relative effect of some classes of medicines for sleep disorders, neuropsychiatric disorders, and cardiovascular disease that either inhibit or stimulate REM sleep translates from rat to a subject of a different species. The relative effect of some classes of medicines for sleep disorders that either inhibit or stimulate REM sleep may translate from laboratory rats to a human.

There are two differences which may be present between rat and human sleep. First, rats are night-active, whereas humans are day-active. This difference may have no importance per se for testing drug effects on sleep and wakefulness. The timing of the dose relative to the normal sleep period can be relied upon when evaluating drug efficacy on sleep related variables (e.g., inhibition of REM sleep) when comparing rat and human sleep. The difference between rats and humans is sleep-bout length, also referred to as "sleep continuity." Further, humans may consolidate sleep into a single period per day, interrupted only by short (e.g., less than 2 hours, less than 1 hour, less than 45 minutes, less than 30 minutes, less than 25 minutes, less than 20 minutes, less than 15 minutes, less than 10 minutes, less than 5 minutes, or less than 1 minute) bouts of wakefulness. The abnormal conditions may result in human sleep becoming fragmented, diminishing the restorative benefits of sleep. Rats may have shorter bouts of sleep that occur throughout the 24-hour day (e.g., on average, every 20 minutes, a rat completes a sleep-wake cycle). During darkness (when the rat may be most active), sleep typically occupies about ⅓ of each 20-minute cycle, and REM sleep is rare. During the day (lights-on), the rat typically sleeps about ⅔ of each 20-minute cycle. The polyphasic nature of sleep and shorter spontaneous sleep bout durations in the rat, enables highly sensitive assessments of drug effects, such as those that increase sleep consolidation (sleep bout duration), decrease the number of arousals (number of wake bouts), and a variety of secondary but desirable measures of sleep quality, for example EEG slow wave activity in nonREM sleep, and measures of wake maintenance as measured by wake bout duration. Sleep bout-length may also be a sensitive measure of physiological sleepiness and may be a pre-clinical predictor of soporific efficacy in humans.

Timing of Treatment

Empirical optimization can be performed by assessing sleep-related compounds by administering such compounds at two circadian times of day, CT-18 and CT-5, wherein CT-0 is defined as lights-on. CT-18 is the mid-point of the activity phase of the rat's circadian cycle, 6 hours after lights-off, and may be sensitive to soporific drug effects on sleep bout length, although such effects can be observed at both CT-18 and CT-5. CT-5 begins several hours of peak abundance of REM sleep and thus is a sensitive time to reveal drug-related inhibition of REM sleep. Both CT-18 and CT-5 are suitable times of the day for the assessment of drug effects on sleep fragmentation as measured by arousals (number of wake bouts or the number of transitions to wake), sleep consolidation (sleep bout duration), as well as assessments of maintenance of wakefulness (wake bout length) and drug-related side effects.

Preclinical effects observed at either CT-5 (treatments administered at a time of day corresponding to 5 hours after lights-on) and/or CT-18 (treatments administered at a time of day corresponding to 18 hours after lights-on or 6 hours after light-off when animals are housed in a 24 hour light dark cycle consisting of 12-hours of light and 12 hours of dark) are considered sufficient for purposes of identifying compounds which may reduce sleep fragmentation.

Methods of Use

In some embodiments, the present disclosure provides a method of modulating H1/5-HT$_{2A}$ function (e.g., dual acting H1 inverse agonist and 5-HT$_{2A}$ antagonist activity, e.g., in vitro or in vivo), comprising contacting a cell with an effective amount of a compound of the present disclosure or a pharmaceutically acceptable salt thereof. In some embodiments, the present disclosure provides a method of alleviating a symptom of, treating or preventing a disease or disorder disclosed herein in a subject in need thereof, by administering to the subject a therapeutically effective amount of a compound of the present disclosure or a pharmaceutically acceptable salt thereof, or a pharmaceutical composition of the present disclosure.

In some embodiments, modulating H1/5-HT$_{2A}$ function (e.g., dual acting H1 inverse agonist and 5-HT$_{2A}$ antagonist activity, e.g., in vitro or in vivo) alleviates a symptom of, treats, or prevents a sleep disorder.

In some embodiments, modulating H1/5-HT$_{2A}$ function (e.g., dual acting H1 inverse agonist and 5-HT$_{2A}$ antagonist activity, e.g., in vitro or in vivo) alleviates a symptom of or treats a sleep disorder.

In some embodiments, modulating H1/5-HT$_{2A}$ function (e.g., dual acting H1 inverse agonist and 5-HT$_{2A}$ antagonist activity, e.g., in vitro or in vivo) treats a sleep disorder.

In some aspects, the present disclosure provides a method of alleviating a symptom of, treating or preventing a sleep disorder.

In some embodiments, the present disclosure provides a method of treating or preventing a disease or disorder disclosed herein in a subject in need thereof, by administering to the subject a therapeutically effective amount of a compound of the present disclosure or a pharmaceutically acceptable salt thereof, or a pharmaceutical composition of the present disclosure.

In some embodiments, the present disclosure provides a method of treating a disease or disorder disclosed herein in a subject in need thereof, by administering to the subject a therapeutically effective amount of a compound of the present disclosure or a pharmaceutically acceptable salt thereof, or a pharmaceutical composition of the present disclosure.

In some embodiments, the present disclosure provides use of a compound of the present disclosure, or a pharmaceutically acceptable salt thereof for treating or preventing a disease or disorder.

In some embodiments, the present disclosure provides use of a compound of the present disclosure, or a pharmaceutically acceptable salt thereof for treating a disease or disorder.

In some embodiments, the present disclosure provides use of a compound of the present disclosure, or a pharmaceutically acceptable salt thereof in the manufacture of a medicament for treating or preventing a disease or disorder.

In some embodiments, the present disclosure provides use of a compound of the present disclosure, or a pharmaceutically acceptable salt thereof in the manufacture of a medicament for treating a disease or disorder.

In some embodiments, the present disclosure provides a compound of the present disclosure, or a pharmaceutically acceptable salt thereof for use in treating or preventing a disease or disorder.

In some embodiments, the present disclosure provides a compound of the present disclosure, or a pharmaceutically acceptable salt thereof for use in treating a disease or disorder.

In some embodiments, the disease or disorder is a sleep disorder.

In some embodiments, the sleep disorder is increased disturbed sleep, increased sleep fragmentation, increased arousals, or decreased arousal threshold.

In some embodiments, the sleep fragmentation is co-morbid with a medical condition.

In some embodiments, the sleep disorder is caused by or co-morbid with a medical condition, wherein the medical condition causes or worsens the sleep disorder.

In some embodiments, the sleep disorder is caused by a medical condition, wherein the medical condition causes or worsens the sleep disorder.

In some embodiments, the sleep disorder is co-morbid with a medical condition, wherein the medical condition causes or worsens the sleep disorder.

In some aspects, the present disclosure provides a method of alleviating a symptom of, treating or preventing a sleep disorder in a subject in need thereof, by administering to the subject a therapeutically effective amount of a compound of the present disclosure or a pharmaceutically acceptable salt thereof, or a pharmaceutical composition of the present disclosure.

In some aspects, the present disclosure provides a method of treating or preventing a sleep disorder in a subject in need thereof, by administering to the subject a therapeutically effective amount of a compound of the present disclosure or a pharmaceutically acceptable salt thereof, or a pharmaceutical composition of the present disclosure.

In some aspects, the present disclosure provides a method of treating a sleep disorder in a subject in need thereof, by administering to the subject a therapeutically effective amount of a compound of the present disclosure or a pharmaceutically acceptable salt thereof, or a pharmaceutical composition of the present disclosure.

In some aspects, the present disclosure provides use of a compound of the present disclosure or a pharmaceutically acceptable salt thereof for alleviating a symptom of, treating or preventing a sleep disorder.

In some aspects, the present disclosure provides use of a compound of the present disclosure or a pharmaceutically acceptable salt thereof for alleviating a symptom of or treating a sleep disorder.

In some aspects, the present disclosure provides use of a compound of the present disclosure or a pharmaceutically acceptable salt thereof for treating a sleep disorder.

In some aspects, the present disclosure provides use of a compound of the present disclosure or a pharmaceutically acceptable salt thereof in the manufacture of a medicament for alleviating a symptom of, treating or preventing a sleep disorder.

In some aspects, the present disclosure provides use of a compound of the present disclosure or a pharmaceutically acceptable salt thereof in the manufacture of a medicament for alleviating a symptom of or treating a sleep disorder.

In some aspects, the present disclosure provides use of a compound of the present disclosure or a pharmaceutically acceptable salt thereof in the manufacture of a medicament for treating a sleep disorder.

In some aspects, the present disclosure provides a compound of the present disclosure or a pharmaceutically acceptable salt thereof for use in alleviating a symptom of, treating or preventing a sleep disorder.

In some aspects, the present disclosure provides a compound of the present disclosure or a pharmaceutically acceptable salt thereof for use in alleviating a symptom of or treating a sleep disorder.

In some aspects, the present disclosure provides a compound of the present disclosure or a pharmaceutically acceptable salt thereof for use in treating a sleep disorder.

In some embodiments, modulating $H1/5\text{-}HT_{2A}$ function (e.g., dual acting H1 inverse agonist and $5\text{-}HT_{2A}$ antagonist activity, e.g., in vitro or in vivo) alleviates a symptom of, treats, or prevents a sleep disorder.

In some embodiments, modulating $H1/5\text{-}HT_{2A}$ function (e.g., dual acting H1 inverse agonist and $5\text{-}HT_{2A}$ antagonist activity, e.g., in vitro or in vivo) alleviates a symptom of or treats a sleep disorder.

In some embodiments, modulating $H1/5\text{-}HT_{2A}$ function (e.g., dual acting H1 inverse agonist and $5\text{-}HT_{2A}$ antagonist activity, e.g., in vitro or in vivo) treats a sleep disorder.

In some embodiments, the present disclosure provides a method of modulating $H1/5\text{-}HT_{2A}$ function (e.g., dual acting H1 inverse agonist and $5\text{-}HT_{2A}$ antagonist activity, e.g., in vitro or in vivo) by administering a compound of the present disclosure or a pharmaceutically acceptable salt thereof.

In some embodiments, the present disclosure provides use of a compound of the present disclosure or a pharmaceutically acceptable salt thereof for modulating $H1/5\text{-}HT_{2A}$ function (e.g., dual acting H1 inverse agonist and $5\text{-}HT_{2A}$ antagonist activity, e.g., in vitro or in vivo).

In some embodiments, the present disclosure provides use of a compound of the present disclosure or a pharmaceutically acceptable salt thereof, in the manufacture of a medicament, for modulating $H1/5\text{-}HT_{2A}$ function (e.g., dual acting H1 inverse agonist and $5\text{-}HT_{2A}$ antagonist activity, e.g., in vitro or in vivo).

In some embodiments, the present disclosure provides a compound of the present disclosure or a pharmaceutically acceptable salt thereof for use in modulating $H1/5\text{-}HT_{2A}$ function (e.g., dual acting H1 inverse agonist and $5\text{-}HT_{2A}$ antagonist activity, e.g., in vitro or in vivo).

In some embodiments, the $H1/5\text{-}HT_{2A}$ receptor regulates sleep. In some embodiments, the modulation of $H1/5\text{-}HT_{2A}$ function improves a sleep disorder. In some embodiments, the modulation of $H1/5\text{-}HT_{2A}$ function improves disturbed sleep. In some embodiments, the modulation of $H1/5\text{-}HT_{2A}$ function improves sleep fragmentation. In some embodiments, the modulation of $H1/5\text{-}HT_{2A}$ function improves sleep arousals. In some embodiments, the modulation of $H1/5\text{-}HT_{2A}$ function improves arousal threshold. In some embodiments, the $H1/5\text{-}HT_{2A}$ receptor is up-regulated. In some embodiments, the $H1/5\text{-}HT_{2A}$ receptor is down-regulated In some embodiments, the present disclosure provides a method of modulating $H1/5\text{-}HT_{2A}$ function (e.g., a dual acting H1 inverse agonist and $5\text{-}HT_{2A}$ antagonist activity, e.g., in vitro or in vivo), by administering to the subject a therapeutically effective amount of a compound of Formula (I), (II), or (II') or a pharmaceutically acceptable salt thereof, or a pharmaceutical composition of the present disclosure.

In some embodiments, the present disclosure provides the use of a compound of Formula (I), (II), or (II') or a pharmaceutically acceptable salt thereof, or a pharmaceutical composition of the present disclosure, for modulating $H1/5\text{-}HT_{2A}$ function (e.g., a dual acting H1 inverse agonist and $5\text{-}HT_{2A}$ antagonist activity, e.g., in vitro or in vivo).

In some embodiments, the present disclosure provides the use of a compound of Formula (I), (II), or (II') or a pharmaceutically acceptable salt thereof, or a pharmaceutical composition of the present disclosure, in the manufacture of a medicament, for modulating $H1/5\text{-}HT_{2A}$ function (e.g., a dual acting H1 inverse agonist and $5\text{-}HT_{2A}$ antagonist activity, e.g., in vitro or in vivo).

In some embodiments, the present disclosure provides a compound of Formula (I), (II), or (II') or a pharmaceutically acceptable salt thereof, or a pharmaceutical composition of the present disclosure, for use in modulating $H1/5\text{-}HT_{2A}$ function (e.g., a dual acting H1 inverse agonist and $5\text{-}HT_{2A}$ antagonist activity, e.g., in vitro or in vivo).

In some embodiments, a compound of Formula (I), (II), or (II'), or a pharmaceutically acceptable salt thereof is provided herein for treating a sleep disorder. In some embodiments, a compound of Formula (I), or a pharmaceutically acceptable salt thereof is provided herein for treating a sleep disorder. In some embodiments, a compound of Formula (II), or a pharmaceutically acceptable salt thereof is provided herein for treating a sleep disorder. In some embodiments, a compound of Formula (II'), or a pharmaceutically acceptable salt thereof is provided herein for treating a sleep disorder.

In some embodiments, a compound of Formula (I), (II), or (II'), or a pharmaceutically acceptable salt thereof is provided for treating a sleep disorder in a subject with a co-morbid medical condition. In some embodiments, a compound of Formula (I), or a pharmaceutically acceptable salt thereof is provided for treating a sleep disorder in a subject with a co-morbid medical condition. In some embodiments, a compound of Formula (II), or a pharmaceutically acceptable salt thereof is provided for treating a sleep disorder in a subject with a co-morbid medical condition. In some embodiments, a compound of Formula (II'), or a pharmaceutically acceptable salt thereof is provided for treating a sleep disorder in a subject with a co-morbid medical condition.

In some embodiments, the present disclosure provides use of a compound of Formula (I), (II), or (II'), or a pharmaceutically acceptable salt thereof for the treatment of a sleep disorder. In some embodiments, the present disclosure provides use of a compound of Formula (I), or a pharmaceutically acceptable salt thereof for the treatment of a sleep disorder. In some embodiments, the present disclosure provides use of a compound of Formula (II), or a pharmaceutically acceptable salt thereof for the treatment of a sleep disorder. In some embodiments, the present disclosure provides use of a compound of Formula (II'), or a pharmaceutically acceptable salt thereof for the treatment of a sleep disorder.

In some embodiments, the present disclosure provides use of a compound of Formula (I), (II), or (II'), or a pharmaceutically acceptable salt thereof for the treatment of a sleep disorder in a subject with a co-morbid medical condition. In some embodiments, the present disclosure provides use of a compound of Formula (I), or a pharmaceutically acceptable salt thereof for the treatment of a sleep disorder in a subject with a co-morbid medical condition. In some embodiments, the present disclosure provides use of a compound of Formula (II), or a pharmaceutically acceptable salt thereof for the treatment of a sleep disorder in a subject with a co-morbid medical condition. In some embodiments, the present disclosure provides use of a compound of Formula (II'), or a pharmaceutically acceptable salt thereof for the treatment of a sleep disorder in a subject with a co-morbid medical condition.

In some embodiments, the present disclosure provides use of a compound of Formula (I), (II), or (II'), or a pharmaceutically acceptable salt thereof in the manufacture of a medicament for the treatment of a sleep disorder. In some embodiments, the present disclosure provides use of a compound of Formula (I), or a pharmaceutically acceptable salt thereof in the manufacture of a medicament for the treatment of a sleep disorder. In some embodiments, the present disclosure provides use of a compound of Formula (II), or a pharmaceutically acceptable salt thereof in the manufacture of a medicament for the treatment of a sleep disorder. In some embodiments, the present disclosure provides use of a compound of Formula (II'), or a pharmaceutically acceptable salt thereof in the manufacture of a medicament for the treatment of a sleep disorder.

In some embodiments, the present disclosure provides use of a compound of Formula (I), (II), or (II'), or a pharmaceutically acceptable salt thereof in the manufacture of a medicament for the treatment of a sleep disorder in a subject with a co-morbid medical condition. In some embodiments, the present disclosure provides use of a compound of Formula (I), or a pharmaceutically acceptable salt thereof in the manufacture of a medicament for the treatment of a sleep disorder in a subject with a co-morbid medical condition. In some embodiments, the present disclosure provides use of a compound of Formula (II), or a pharmaceutically acceptable salt thereof in the manufacture of a medicament for the treatment of a sleep disorder in a subject with a co-morbid medical condition. In some embodiments, the present disclosure provides use of a compound of Formula (II'), or a pharmaceutically acceptable salt thereof in the manufacture of a medicament for the treatment of a sleep disorder in a subject with a co-morbid medical condition.

In some embodiments, the present disclosure provides a compound of Formula (I), (II), or (II'), or a pharmaceutically acceptable salt thereof for use in treating a sleep disorder. In some embodiments, the present disclosure provides a compound of Formula (I), or a pharmaceutically acceptable salt thereof for use in treating a sleep disorder. In some embodiments, the present disclosure provides a compound of Formula (II), or a pharmaceutically acceptable salt thereof for use in treating a sleep disorder. In some embodiments, the present disclosure provides a compound of Formula (II'), or a pharmaceutically acceptable salt thereof for use in treating a sleep disorder.

In some embodiments, the present disclosure provides a compound of Formula (I), (II), or (II'), or a pharmaceutically acceptable salt thereof for use in treating a sleep disorder in a subject with a co-morbid medical condition. In some embodiments, the present disclosure provides a compound of Formula (I), or a pharmaceutically acceptable salt thereof for use in treating a sleep disorder in a subject with a co-morbid medical condition. In some embodiments, the present disclosure provides a compound of Formula (II), or a pharmaceutically acceptable salt thereof for use in treating a sleep disorder in a subject with a co-morbid medical condition. In some embodiments, the present disclosure provides a compound of Formula (II'), or a pharmaceutically acceptable salt thereof for use in treating a sleep disorder in a subject with a co-morbid medical condition.

In some embodiments, the present disclosure provides a method of modulating H1/5-HT$_{2A}$ function (e.g., a dual acting H1 inverse agonist and 5-HT$_{2A}$ antagonist activity, e.g., in vitro or in vivo), by administering to the subject a therapeutically effective amount of compound 30, 31, 34, or 35, or a pharmaceutically acceptable salt thereof.

In some embodiments, the present disclosure provides use of compound 30, 31, 34, or 35, or a pharmaceutically acceptable salt thereof for modulating H1/5-HT$_{2A}$ function (e.g., a dual acting H1 inverse agonist and 5-HT$_{2A}$ antagonist activity, e.g., in vitro or in vivo).

In some embodiments, the present disclosure provides use of compound 30, 31, 34, or 35, or a pharmaceutically acceptable salt thereof, in the manufacture of a medicament, for modulating H1/5-HT$_{2A}$ function (e.g., a dual acting H1 inverse agonist and 5-HT$_{2A}$ antagonist activity, e.g., in vitro or in vivo).

In some embodiments, the present disclosure provides a compound 30, 31, 34, or 35, or a pharmaceutically acceptable salt thereof for use in modulating H1/5-HT$_{2A}$ function (e.g., a dual acting H1 inverse agonist and 5-HT$_{2A}$ antagonist activity, e.g., in vitro or in vivo).

In some embodiments, the present disclosure provides a method of alleviating a symptom of, treating, or preventing a sleep disorder, by administering to the subject a therapeutically effective amount of compound 30, 31, 34, or 35, or a pharmaceutically acceptable salt thereof.

In some embodiments, the present disclosure provides a method of alleviating a symptom of or treating a sleep disorder, by administering to the subject a therapeutically effective amount of compound 30, 31, 34, or 35, or a pharmaceutically acceptable salt thereof.

In some embodiments, the present disclosure provides a method of treating a sleep disorder, by administering to the subject a therapeutically effective amount of compound 30, 31, 34, or 35, or a pharmaceutically acceptable salt thereof.

In some embodiments, the present disclosure provides use of compound 30, 31, 34, or 35, or a pharmaceutically acceptable salt thereof for alleviating a symptom of, treating, or preventing a sleep disorder.

In some embodiments, the present disclosure provides use of compound 30, 31, 34, or 35, or a pharmaceutically acceptable salt thereof for alleviating a symptom of or treating a sleep disorder.

In some embodiments, the present disclosure provides use of compound 30, 31, 34, or 35, or a pharmaceutically acceptable salt thereof for treating a sleep disorder.

In some embodiments, the present disclosure provides use of compound 30, 31, 34, or 35, or a pharmaceutically acceptable salt thereof, in the manufacture of a medicament, for alleviating a symptom of, treating, or preventing a sleep disorder.

In some embodiments, the present disclosure provides use of compound 30, 31, 34, or 35, or a pharmaceutically acceptable salt thereof, in the manufacture of a medicament, for alleviating a symptom of or treating a sleep disorder.

In some embodiments, the present disclosure provides use of compound 30, 31, 34, or 35, or a pharmaceutically acceptable salt thereof, in the manufacture of a medicament, for treating a sleep disorder.

In some embodiments, the present disclosure provides a compound 30, 31, 34, or 35, or a pharmaceutically acceptable salt thereof for use in alleviating a symptom of, treating, or preventing a sleep disorder.

In some embodiments, the present disclosure provides a compound 30, 31, 34, or 35, or a pharmaceutically acceptable salt thereof for use in alleviative a symptom of or treating a sleep disorder.

In some embodiments, the present disclosure provides a compound 30, 31, 34, or 35, or a pharmaceutically acceptable salt thereof for use in treating a sleep disorder.

In some embodiments, the present disclosure is directed to alleviating a symptom of, treating, or preventing a sleep disorder wherein the sleep disorder is increased disturbed sleep, increased sleep fragmentation, increased arousals, or decreased arousal threshold in a subject, wherein the sleep disorder is caused by or co-morbid with sleep apnea, restless legs syndrome, a high respiratory disturbance index (RDI), a neurological disease, a circadian rhythm disorder, pain, periodic leg movement disorder (PLMD), REM behavior disorder, elderly fragmented sleep, age-related sleep fragmentation, post-menopausal sleep disorder, substance abuse, substance abuse withdrawal, narcolepsy, a mental disorder, an increased sensitivity to pain, cardiovascular disease, hypertension, non-restorative sleep, a stroke, a metabolic disorder, or cognitive impairment.

In some embodiments, the present disclosure is directed to alleviating a symptom of, treating, or preventing a sleep disorder wherein the sleep disorder is increased disturbed sleep, increased sleep fragmentation, increased arousals, or decreased arousal threshold in a subject, wherein the sleep disorder is caused by sleep apnea, restless legs syndrome, a high respiratory disturbance index (RDI), a neurological disease, a circadian rhythm disorder, pain, periodic leg movement disorder (PLMD), REM behavior disorder, elderly fragmented sleep, age-related sleep fragmentation, post-menopausal sleep disorder, substance abuse, substance abuse withdrawal, narcolepsy, a mental disorder, an increased sensitivity to pain, cardiovascular disease, hypertension, non-restorative sleep, a stroke, a metabolic disorder, or cognitive impairment.

In some embodiments, the present disclosure is directed to alleviating a symptom of, treating, or preventing a sleep disorder wherein the sleep disorder is increased disturbed sleep, increased sleep fragmentation, increased arousals, or decreased arousal threshold in a subject, wherein the sleep disorder is co-morbid with sleep apnea, restless legs syndrome, high respiratory disturbance index (RDI), a neurological disease, a circadian rhythm disorder, pain, periodic leg movement disorder (PLMD), REM behavior disorder, elderly fragmented sleep, age-related sleep fragmentation, post-menopausal sleep disorder, substance abuse, substance abuse withdrawal, narcolepsy, a mental disorder, an increased sensitivity to pain, cardiovascular disease, hypertension, non-restorative sleep, a stroke, a metabolic disorder, or cognitive impairment.

In some embodiments, the present disclosure is directed to alleviating a symptom of, treating, or preventing a sleep disorder wherein the sleep disorder is increased disturbed sleep, increased sleep fragmentation, increased arousals, or decreased arousal threshold in a subject, wherein the sleep disorder is caused by or co-morbid with sleep apnea, restless legs syndrome, a high respiratory disturbance index (RDI), a neurological disease, a circadian rhythm disorder, pain, periodic leg movement disorder (PLMD), REM behavior disorder, elderly fragmented sleep, age-related sleep fragmentation, post-menopausal sleep disorder, substance abuse, substance abuse withdrawal, narcolepsy, a mental disorder, or non-restorative sleep.

In some embodiments, the present disclosure is directed to alleviating a symptom of, treating, or preventing a sleep disorder wherein the sleep disorder is increased disturbed sleep, increased sleep fragmentation, increased arousals, or decreased arousal threshold in a subject, wherein the sleep disorder is caused by sleep apnea, restless legs syndrome, a high respiratory disturbance index (RDI), a neurological disease, a circadian rhythm disorder, pain, periodic leg movement disorder (PLMD), REM behavior disorder, elderly fragmented sleep, age-related sleep fragmentation, post-menopausal sleep disorder, substance abuse, substance abuse withdrawal, narcolepsy, a mental disorder, or non-restorative sleep.

In some embodiments, the present disclosure is directed to alleviating a symptom of, treating, or preventing a sleep disorder wherein the sleep disorder is increased disturbed sleep, increased sleep fragmentation, increased arousals, or decreased arousal threshold in a subject, wherein the sleep disorder is co-morbid with sleep apnea, restless legs syndrome, high respiratory disturbance index (RDI), a neurological disease, a circadian rhythm disorder, pain, periodic leg movement disorder (PLMD), REM behavior disorder, elderly fragmented sleep, age-related sleep fragmentation, post-menopausal sleep disorder, substance abuse, substance abuse withdrawal, narcolepsy, a mental disorder, or non-restorative sleep.

In some embodiments, the sleep disorder is caused by or co-morbid with one or more type of pain.

In some embodiments, the sleep disorder is caused by one or more type of pain.

In some embodiments, the sleep disorder is co-morbid with one or more type of pain.

In some embodiments, the pain is selected from inflammatory pain, nociceptive pain, neuropathic pain, mixed nociceptive and neuropathic pain, post-operative pain, post-herpetic pain, traumatic pain, phantom-limb pain, fibromyalgia, back pain, cancer pain, and osteoarthritic pain.

In some embodiments, the pain is chronic pain.

In some embodiments, the pain is arthritic pain.

In some embodiments, the pain is an inflammatory pain.

In some embodiments, the inflammatory pain is arthritis. In some embodiments, the arthritis is rheumatoid arthritis. In some embodiments, the arthritis is osteoarthritis.

In some embodiments, the pain is a nociceptive pain. In some embodiments, the nociceptive pain is acute. In some embodiments, the nociceptive pain is chronic. In some embodiments, the nociceptive pain is caused by a cancer therapy. In some embodiments, the nociceptive pain is caused by a surgery.

In some embodiments, the pain is a neuropathic pain. In some embodiments, the neuropathic pain is chronic. In some embodiments, the neuropathic pain is acute. In some embodiments, the neuropathic pain is back pain. In some embodiments, the neuropathic pain is caused by a spinal cord injury. In some embodiments, the neuropathic pain is caused by multiple sclerosis. In some embodiments, the neuropathic pain is caused by a stroke. In some embodiments, the neuropathic pain is caused by diabetes. In some embodiments, the neuropathic pain is caused by a metabolic condition.

In some embodiments, the pain is a mixed nociceptive and neuropathic pain.

In some embodiments, the pain is a post-operative pain.

In some embodiments, the pain is a post-herpetic pain.

In some embodiments, the pain is a traumatic pain. In some embodiments, traumatic pain is caused by causalgia.

In some embodiments, the pain is a phantom-limb pain.

In some embodiments, the pain is a fibromyalgia.

In some embodiments, the pain is a back pain. In some embodiments, the pain is a low back pain.

In some embodiments, the pain is a cancer pain. In some embodiments, the cancer pain is cancer. In some embodiments, the cancer pain is caused by a tumor. In some embodiments, the cancer pain is caused by a cancer treatment. In some embodiments, the cancer pain is caused by chemotherapy. In some embodiments, the cancer pain is radiation therapy. In some embodiments, the cancer pain is caused by surgery.

In some embodiments, the pain is an osteoarthritic pain.

In some embodiments, the pain may be characterized by a change in mood.

In some embodiments, the sleep disorder is caused by or co-morbid with sleep apnea.

In some embodiments, the sleep disorder is caused by sleep apnea.

In some embodiments, the sleep disorder is co-morbid with sleep apnea.

In some embodiments, sleep apnea is obstructive sleep apnea.

In some embodiments, sleep apnea is obstructive sleep apnea is due to a high respiratory disturbance index (RDI) associated with an elevated respiratory event related arousal (RERA) with or without a concomitant apnea.

In some embodiments, sleep apnea is obstructive sleep apnea due to a high respiratory disturbance index (RDI) associated with an elevated respiratory event related arousal (RERA) with a concomitant apnea.

In some embodiments, sleep apnea is obstructive sleep apnea due to a high respiratory disturbance index (RDI) associated with an elevated respiratory event related arousal (RERA) with or without a concomitant hypopnea.

In some embodiments, sleep apnea is obstructive sleep apnea due to a high respiratory disturbance index (RDI) associated with an elevated respiratory event related arousal (RERA) with a concomitant hypopnea.

In some embodiments, sleep apnea is obstructive sleep apnea due to a high respiratory disturbance index (RDI) associated with an elevated respiratory event related arousal (RERA) with or without concomitant acute hemoglobin desaturation.

In some embodiments, sleep apnea is obstructive sleep apnea due to a high respiratory disturbance index (RDI) associated with an elevated respiratory event related arousal (RERA) with concomitant acute hemoglobin desaturation.

In some embodiments, the obstructive sleep apnea may be characterized by excessive daytime sleepiness.

In some embodiments, the obstructive sleep apnea may be characterized by the presence of cardiovascular biomarkers.

In some embodiments, sleep apnea is central sleep apnea.

In some embodiments, sleep apnea is low-arousal threshold sleep apnea.

In some embodiments, sleep apnea is hypopnea.

In some embodiments, the sleep disorder is caused by or co-morbid with restless legs syndrome.

In some embodiments, the sleep disorder is caused by restless legs syndrome.

In some embodiments, the sleep disorder is co-morbid with restless legs syndrome.

In some embodiments, the sleep disorder is caused by or co-morbid with a high respiratory disturbance index (RDI).

In some embodiments, the sleep disorder is caused by a high respiratory disturbance index (RDI).

In some embodiments, the sleep disorder is co-morbid with a high respiratory disturbance index (RDI).

In some embodiments, the RDI is associated with an elevated respiratory event related arousal (RERA) with or without a concomitant apnea.

In some embodiments, the RDI is associated with an elevated respiratory event related arousal (RERA) with a concomitant apnea.

In some embodiments, the RDI is associated with an elevated respiratory event related arousal (RERA) with or without a concomitant hypopnea.

In some embodiments, the RDI is associated with an elevated respiratory event related arousal (RERA) with a concomitant hypopnea.

In some embodiments, the RDI is associated with an elevated respiratory event related arousal (RERA) with or without concomitant acute hemoglobin desaturation.

In some embodiments, the RDI is associated with an elevated respiratory event related arousal (RERA) with concomitant acute hemoglobin desaturation.

In some embodiments, the RDI is associated with an elevated respiratory event related arousal (RERA) with or without concomitant hemoglobin desaturation.

In some embodiments, the RDI is associated with an elevated respiratory event related arousal (RERA) with concomitant hemoglobin desaturation.

In some embodiments, the sleep disorder is caused by or co-morbid with a mental disorder.

In some embodiments, the sleep disorder is caused by a mental disorder.

In some embodiments, the sleep disorder is co-morbid with a mental disorder.

In some embodiments, the mental disorder is depression, major depressive disorder, post-traumatic stress disorder, anxiety disorder, bipolar disorder, or schizophrenia.

In some embodiments, the mental disorder is depression. In some embodiments, the mental disorder is major depressive disorder. In some embodiments, the mental disorder is post-traumatic stress disorder. In some embodiments, the mental disorder is anxiety disorder. In some embodiments, the mental disorder is bipolar disorder. In some embodiments, the mental disorder is schizophrenia.

In some embodiments, the post-traumatic stress disorder may be characterized by the occurrence of a nightmare.

In some embodiments, the post-traumatic stress disorder may be characterized by the decrease in sleep quality.

In some embodiments, the post-traumatic stress disorder may be characterized by disruptive night-time behaviors.

In some embodiments, the post-traumatic stress disorder may be co-morbid with depression.

In some embodiments, the post-traumatic stress disorder may be co-morbid with anxiety.

In some embodiments, the sleep disorder is caused by or co-morbid with a neurological disease.

In some embodiments, the sleep disorder is caused by a neurological disease.

In some embodiments, the sleep disorder is co-morbid with a neurological disease.

In some embodiments, the neurological disease is a neurodegenerative disease.

In some embodiments, the neurodegenerative disease is Lewy body disease (i.e., Lewy body dementia). In some embodiments, the Lewy body disease is diffuse.

In some embodiments, the neurodegenerative disease is amyotrophic lateral sclerosis (ALS). In some embodiments, the neurodegenerative disease is Huntington's disease. In some embodiments, the neurodegenerative disease is Parkinson's disease. In some embodiments, the neurodegenerative disease is Alzheimer's disease. In some embodiments, the neurodegenerative disease is a synucleinopathy.

In some embodiments, a synucleinopathy is Alzheimer's disease, Parkinson's disease, or Lewy body dementia. In some embodiments, a synucleinopathy is Alzheimer's disease. In some embodiments, a synucleinopathy is Parkinson's disease. In some embodiments, a synucleinopathy is dementia with Lewy bodies. In some embodiments, a synucleinopathy is multiple system atrophy.

In some embodiments, the Parkinson's disease may be characterized by Parkinson's disease-related sleep disturbances.

In some embodiments, the Parkinson's disease may be characterized by the occurrence of nightmares.

In some embodiments, the Parkinson's disease may be characterized by the occurrence of hallucinations.

In some embodiments, the Parkinson's disease may be characterized by excessive daytime sleepiness.

In some embodiments, the Alzheimer's disease may be characterized by Alzheimer's disease-related sleep disorders.

In some embodiments, the Alzheimer's disease may be characterized by night-time wandering.

In some embodiments, the neurological disease is a neurodevelopmental disease. In some embodiments, the neurodevelopmental disease is autism. In some embodiments, the neurological disease is a muscular dystonia. In some embodiments, the dystonia is neuromuscular dystonia. In some embodiments, the neuromuscular dystonia is spasmodic torticollis.

In some embodiments, the neurological disease is multiple sclerosis (MS).

In some embodiments, the sleep disorder is caused by or co-morbid with a circadian rhythm disorder.

In some embodiments, the sleep disorder is caused by a circadian rhythm disorder.

In some embodiments, the sleep disorder is co-morbid with a circadian rhythm disorder.

In some embodiments, the circadian rhythm disorder is advanced sleep-wake phase disorder. In some embodiments, the circadian rhythm disorder is irregular sleep-wake rhythm disorder. In some embodiments, the circadian rhythm disorder is jet lag. In some embodiments, the circadian rhythm disorder is shift work sleep disorder. In some embodiments, the circadian rhythm disorder is delayed sleep phase syndrome. In some embodiments, the circadian rhythm disorder is non-24 hour rhythm disorder.

In some embodiments, the sleep disorder is caused by or co-morbid with elderly fragmented sleep.

In some embodiments, the sleep disorder is caused by elderly fragmented sleep.

In some embodiments, sleep disorder is co-morbid with elderly fragmented sleep.

In some embodiments, the sleep disorder is caused by or co-morbid with age-related sleep fragmentation.

In some embodiments, the sleep disorder is caused by age-related sleep fragmentation.

In some embodiments, the sleep disorder is co-morbid with age-related sleep fragmentation.

In some embodiments, the sleep disorder is caused by or co-morbid with post-menopausal sleep disorder.

In some embodiments, the sleep caused by post-menopausal sleep disorder.

In some embodiments, the sleep disorder is co-morbid with post-menopausal sleep disorder.

In some embodiments, the sleep disorder is caused by or co-morbid with substance abuse.

In some embodiments, the sleep disorder is caused by substance abuse.

In some embodiments, the sleep disorder is co-morbid with substance abuse.

In some embodiments, the substance abuse is opioid abuse or alcoholism. In some embodiments, the substance abuse is opioid abuse. In some embodiments, the substance abuse is alcoholism.

In some embodiments, the sleep disorder is caused by or co-morbid with substance abuse withdrawal.

In some embodiments, the sleep disorder is caused by substance abuse withdrawal.

In some embodiments, the sleep disorder is co-morbid with substance abuse withdrawal.

In some embodiments, the substance abuse withdrawal is opioid withdrawal or alcohol withdrawal. In some embodiments, the substance abuse withdrawal is opioid withdrawal.

In some embodiments, the substance abuse is alcohol withdrawal.

In some embodiments, the sleep disorder is caused by or co-morbid with narcolepsy.

In some embodiments, the sleep disorder is caused by narcolepsy.

In some embodiments, the sleep disorder is co-morbid with narcolepsy.

In some embodiments, the sleep disorder is caused by or co-morbid with periodic leg movement disorder (PLMD).

In some embodiments, the sleep disorder is caused by periodic leg movement disorder (PLMD).

In some embodiments, the sleep disorder is co-morbid with periodic leg movement disorder (PLMD).

In some embodiments, the sleep disorder is caused by or co-morbid with REM behavior disorder.

In some embodiments, the sleep disorder is caused by REM behavior disorder.

In some embodiments, the sleep disorder is co-morbid with REM behavior disorder.

In some embodiments, the sleep disorder is caused by or co-morbid with elderly fragmented sleep.

In some embodiments, the sleep disorder is caused by elderly fragmented sleep.

In some embodiments, the sleep disorder is co-morbid with elderly fragmented sleep.

In some embodiments, the sleep disorder is caused by or co-morbid with idiopathic hypersomnia.

In some embodiments, the sleep disorder is caused by idiopathic hypersomnia.

In some embodiments, the sleep disorder is co-morbid with idiopathic hypersomnia.

In some embodiments, the sleep disorder is caused by or co-morbid with non-restorative sleep.

In some embodiments, the sleep disorder is caused by non-restorative sleep.

In some embodiments, the sleep disorder is co-morbid with non-restorative sleep.

In some embodiments, the sleep disorder is caused by or co-morbid with snoring.

In some embodiments, the sleep disorder is caused by snoring.

In some embodiments, sleep disorder is co-morbid with snoring.

In some embodiments, the sleep disorder is caused by or co-morbid with an increased sensitivity to pain.

In some embodiments, the sleep disorder is caused by an increased sensitivity to pain.

In some embodiments, the sleep disorder is co-morbid with an increased sensitivity to pain.

In some embodiments, the sleep disorder is caused by or co-morbid with cardiovascular disease.

In some embodiments, the sleep disorder is caused by cardiovascular disease.

In some embodiments, the sleep disorder is co-morbid with cardiovascular disease.

In some embodiments, the sleep disorder is caused by or co-morbid with hypertension.

In some embodiments, the sleep disorder is caused by hypertension.

In some embodiments, the sleep disorder is co-morbid with hypertension.

In some embodiments, the sleep disorder is caused by or co-morbid with a stroke.

In some embodiments, the sleep disorder is caused by a stroke.

In some embodiments, the sleep disorder is co-morbid with a stroke.

In some embodiments, the sleep disorder is caused by or co-morbid with a metabolic disorder.

In some embodiments, the sleep disorder is caused by a metabolic disorder.

In some embodiments, the sleep disorder is co-morbid with a metabolic disorder.

In some embodiments, the metabolic disorder is diabetes.

In some embodiments, the sleep disorder is caused by or co-morbid with cognitive impairment.

In some embodiments, the sleep disorder is caused by cognitive impairment.

In some embodiments, the sleep disorder is co-morbid with cognitive impairment.

The present disclosure provides compounds that function as modulators of H1/5-HT$_{2A}$ function. The present disclosure therefore provides a method of modulating H1 inverse agonism and 5-HT$_{2A}$ antagonism in vitro or in vivo. The method comprises contacting a cell with an effective amount of a compound, or a pharmaceutically acceptable salt thereof, as defined herein.

Effectiveness of compounds of the disclosure can be determined by industry-accepted assays or disease models according to standard practices of elucidating the same as described in the art and are found in the current general knowledge.

The present disclosure also provides a method of treating a disease or disorder in which H1/5-HT$_{2A}$ function is implicated in a subject in need of such treatment, said method by administering to said subject a therapeutically effective amount of a compound, or a pharmaceutically acceptable salt thereof, or a pharmaceutical composition as defined herein.

A compound of the present disclosure, or pharmaceutically acceptable salt thereof, may be administered alone as a sole therapy or may be administered in addition with one or more other substances and/or treatments. In some embodiments, the one or more other substance and/or treatment and a compound of the present disclosure, or a pharmaceutically acceptable salt thereof, may be administered in temporal proximity. Such conjoint treatment may be achieved by way of the simultaneous, sequential or separate administration of the individual components of the treatment.

In some embodiments, a method of the present disclosure involves administering to a subject a compound of the present disclosure and additional active agent. In some embodiments, the additional active agent may, for example, be a sedative-hypnotic.

In some embodiments, a method of the present disclosure comprises administering a compound of the present disclosure, or a pharmaceutically acceptable derivative thereof alone.

In some embodiments, a method of the present disclosure comprises administering a compound of the present disclosure, or a pharmaceutically acceptable derivative thereof in combination with a single additional active agent.

In some embodiments, a method of the present disclosure comprises administering a compound of the present disclosure, or a pharmaceutically acceptable derivative thereof, and a combination of active agents.

In some embodiments, a method of the present disclosure involves administering a compound of the present disclosure, if present, either hora somni, h.s. (at bedtime) or between 0 to about 4 hours before bedtime.

In some embodiments, a method of the present disclosure involves administering a compound of the present disclosure, if present, at hora somni, h.s. (at bedtime).

In some embodiments, a method of the present disclosure involves administering a compound of the present disclosure and any additional active agents between 0 to about 4 hours before bedtime.

In some embodiments, a method of the present disclosure involves administering a compound of the present disclosure and any additional active agents about 1 hour before bedtime.

In some embodiments, a method of the present disclosure involves administering a compound of the present disclosure and any additional active agents about 2 hours before bedtime.

In some embodiments, a method of the present disclosure involves administering a compound of the present disclosure and any additional active agents about 3 hours before bedtime.

In some embodiments, a method of the present disclosure involves administering a compound of the present disclosure and any additional active agents about 4 hours before bedtime.

For example, therapeutic effectiveness may be enhanced by administration of an adjuvant (i.e. by itself the adjuvant may only have minimal therapeutic benefit, but in combination with another therapeutic agent, the overall therapeutic benefit to the individual is enhanced).

Alternatively, by way of example only, the benefit experienced by an individual may be increased by administering the compound of Formula (I), (II), or (II') with another therapeutic agent (which also includes a therapeutic regimen) that also has therapeutic benefit.

In the instances where the compound of the present disclosure is administered in combination with other therapeutic agents, the compound of the disclosure need not be administered via the same route as other therapeutic agents, and may, because of different physical and chemical characteristics, be administered by a different route. For example, the compound of the disclosure may be administered orally to generate and maintain good blood levels thereof, while the other therapeutic agent may be administered intravenously. The initial administration may be made according to established protocols known in the art, and then, based upon the observed effects, the dosage, modes of administration and times of administration can be modified by the skilled clinician.

The particular choice of other therapeutic agent will depend upon the diagnosis of the attending physicians and their judgment of the condition of the individual and the appropriate treatment protocol. According to this aspect of the disclosure there is provided a combination for use in the treatment of a sleep disorder comprising a compound of the disclosure as defined hereinbefore, or a pharmaceutically acceptable salt thereof, and another suitable agent.

According to a further aspect of the disclosure there is provided a pharmaceutical composition which comprises a compound of the disclosure, or a pharmaceutically acceptable salt thereof, in combination with a suitable, in association with a pharmaceutically acceptable diluent or carrier.

In addition to its use in therapeutic medicine, compounds of Formula (I), (II), or (II') and pharmaceutically acceptable salts thereof are also useful as pharmacological tools in the development and standardisation of in vitro and in vivo test systems for the evaluation of the effects of H1/5-$HT_{2A}$ function in laboratory animals such as dogs, rabbits, monkeys, rats and mice, as part of the search for new therapeutic agents.

In some embodiments, a method of the present disclosure comprises administering a compound of the present disclosure, or a pharmaceutically acceptable salt thereof, either alone, or in combination with a single additional active agent.

In some embodiments, a method of the present disclosure comprises administering a compound of the present disclosure, or a pharmaceutically acceptable salt thereof, in combination with a single additional active agent.

In some embodiments, a method of the present disclosure comprises administering a compound of the present disclosure, or a pharmaceutically acceptable salt thereof, and a combination of active agents.

In some embodiments, a method of the present disclosure comprises administering to a subject a compound of the present disclosure, or a pharmaceutically acceptable salt thereof as a co-therapy with a medical device based treatment.

In some embodiments, a method of the present disclosure comprises administering to a subject a compound of the present disclosure, or a pharmaceutically acceptable salt thereof as a co-therapy with a medical device based treatment such as continuous positive airway pressure (CPAP) technologies, or transcranial magnetic stimulation or transcranial electromagnetic stimulation technologies.

In some embodiments, a method of the present disclosure comprises administering a compound of Formula (I), (II), or (II'), or a pharmaceutically acceptable salt thereof, either alone, or in combination with a single additional active agent.

In some embodiments, a method of the present disclosure comprises administering a compound of Formula (I), (II), or (II'), or a pharmaceutically acceptable salt thereof, in combination with a single additional active agent.

In some embodiments, a method of the present disclosure comprises administering a compound of Formula (I), (II), or (II'), or a pharmaceutically acceptable salt thereof, and a combination of active agents.

In some embodiments, a method of the present disclosure comprises administering to a subject a compound of Formula (I), Formula (II), or Formula (II'), or a pharmaceutically acceptable salt thereof as a co-therapy with a medical device based treatment.

In some embodiments, a method of the present disclosure comprises administering to a subject a compound of Formula (I), (II), or (II'), or a pharmaceutically acceptable salt thereof as a co-therapy with a medical device based treatment such as continuous positive airway pressure (CPAP) technologies, or transcranial magnetic stimulation or transcranial electromagnetic stimulation technologies.

In some embodiments, a method of the present disclosure comprises administering a compound of Formula (I) or (II), or a pharmaceutically acceptable salt thereof, either alone, or in combination with a single additional active agent.

In some embodiments, a method of the present disclosure comprises administering a compound of Formula (I) or (II), or a pharmaceutically acceptable salt thereof, in combination with a single additional active agent.

In some embodiments, a method of the present disclosure comprises administering a compound of Formula (I) or (II), or a pharmaceutically acceptable salt thereof, and a combination of active agents.

In some embodiments, a method of the present disclosure comprises administering to a subject a compound of Formula (I) or Formula (II), or a pharmaceutically acceptable salt thereof as a co-therapy with a medical device based treatment.

In some embodiments, a method of the present disclosure comprises administering to a subject a compound of Formula (I) or (II), or a pharmaceutically acceptable salt thereof as a co-therapy with a medical device based treatment such as continuous positive airway pressure (CPAP) technologies, or transcranial magnetic stimulation or transcranial electromagnetic stimulation technologies.

In some embodiments, a method of the present disclosure comprises administering a compound 30, 31, 34, or 35, or a pharmaceutically acceptable salt thereof, either alone, or in combination with a single additional active agent.

In some embodiments, a method of the present disclosure comprises administering a compound 30, 31, 34, or 35, or a pharmaceutically acceptable salt thereof, in combination with a single additional active agent.

In some embodiments, a method of the present disclosure comprises administering a compound 30, 31, 34, or 35, or a pharmaceutically acceptable salt thereof, and a combination of active agents.

In some embodiments, a method of the present disclosure comprises administering to a subject a compound 30, 31, 34, or 35, or a pharmaceutically acceptable salt thereof as a co-therapy with a medical device based treatment.

In some embodiments, a method of the present disclosure comprises administering to a subject a compound 30, 31, 34, or 35, or a pharmaceutically acceptable salt thereof as a co-therapy with a medical device based treatment such as continuous positive airway pressure (CPAP) technologies, or transcranial magnetic stimulation or transcranial electromagnetic stimulation technologies.

In some embodiments, the medical device based treatment is a continuous positive airway pressure (CPAP) technology, transcranial magnetic stimulation technology, or transcranial electromagnetic stimulation technology.

In some embodiments, the medical device based treatment is a continuous positive airway pressure (CPAP) technology.

In some embodiments, the medical device based treatment is a transcranial magnetic stimulation technology.

In some embodiments, the medical device based treatment is a transcranial electromagnetic stimulation technology.

In some embodiments, a method of the present disclosure comprises administering to a subject a compound of Formula (I) or Formula (II) as a co-therapy with cognitive behavioral therapy (CBT).

In some embodiments, the CBT is brief cognitive behavioral therapy (BCBT), cognitive emotional behavioral therapy (CEBT), structure cognitive behavioral training (SCBT), moral reconation therapy, stress inoculation training, or activity-guided CBT.

In some embodiments, the CBT is brief cognitive behavioral therapy (BCBT).

In some embodiments, the CBT is cognitive emotional behavioural therapy (CEBT).

In some embodiments, the CBT is structure cognitive behavioural training (SCBT).

In some embodiments, the CBT is moral reconation therapy.

In some embodiments, the CBT is stress inoculation training.

In some embodiments, the CBT is activity-guided CBT.

In some embodiments, a compound of the present disclosure may improve sleep fragmentation.

Sleep fragmentation may be assessed by evaluating polysomnography-derived sleep architecture and depth of sleep endpoints, including the number of arousals (measured by the number of transitions from sleep to wakefulness), sleep continuity/consolidation (as measured by the average duration of sleep bouts), and depth of sleep as measured by EEG delta power (Fourier analysis derived power in the 0.5-4.0 Hz band in the cortical EEG during nonREM sleep).

Sleep fragmentation may be assessed by evaluating polysomnography-derived sleep architecture and depth of sleep endpoints, including the number of arousals (measured by the number of transitions from sleep to wakefulness). Sleep fragmentation may be assessed by evaluating polysomnography-derived sleep architecture and depth of sleep endpoints, including sleep continuity/consolidation (as measured by the average duration of sleep bouts). Sleep fragmentation may be assessed by evaluating polysomnography-derived sleep architecture and depth of sleep endpoints, including depth of sleep as measured by EEG delta power (Fourier analysis derived power in the 0.5-4.0 Hz band in the cortical EEG during nonREM sleep).

In some embodiments, a compound of the present disclosure satisfies the minimum co-requisite preclinical endpoints for identifying molecules that reduce sleep fragmentation.

In some embodiments, a compound of the present disclosure may improve other measures of sleep quality indicative of molecules that facilitate sleep maintenance.

In some embodiments, a compound of the present disclosure may improve other measures of sleep quality indicative of molecules that facilitate sleep maintenance as demonstrated by increased depth of sleep as measured by EEG or indirectly using other behavioral parameters.

In some embodiments, the compounds of the present disclosure may improve sleep fragmentation without producing certain unwanted side effects. In some embodiments, an unwanted side effect is selected from myorelaxation, impaired motor function, lack of rebound insomnia, and a significant change in sleep stage architecture (e.g., percentages of sleep stages per unit time).

In some embodiments, the unwanted side effect is myorelaxation.

In some embodiments, the unwanted side effect is impaired motor function.

In some embodiments, the unwanted side effect is rebound insomnia.

In some embodiments, the unwanted side effect is a significant change in sleep stage architecture.

In any of the above-mentioned pharmaceutical composition, process, method, use, medicament, and manufacturing features of the instant disclosure, any of the alternate embodiments of macromolecules of the present disclosure described herein also apply.

Routes of Administration

The compounds of the disclosure or pharmaceutical compositions comprising these compounds may be administered to a subject by any convenient route of administration, whether systemically/peripherally or topically (i.e., at the site of desired action).

Routes of administration include, but are not limited to, oral (e.g. by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eye drops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intra-arterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

EXEMPLARY EMBODIMENTS

Embodiment No. 1. A compound of Formula (I):

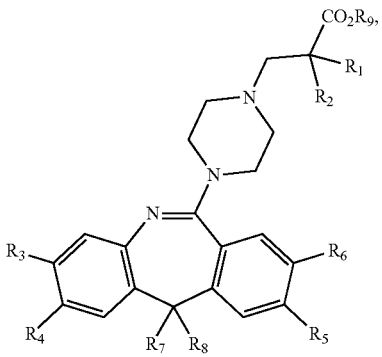

or a prodrug, solvate, or pharmaceutically acceptable salt thereof, wherein:

$R_1$ is $C_1$-$C_6$ alkyl, $C_2$-$C_6$ alkenyl, $C_2$-$C_6$ alkynyl, $C_1$-$C_6$ haloalkyl, $C_1$-$C_6$ alkoxyl, or $C_3$-$C_6$ cycloalkyl;

$R_2$ is $C_1$-$C_6$ alkyl, $C_2$-$C_6$ alkenyl, $C_2$-$C_6$ alkynyl, $C_1$-$C_6$ haloalkyl, $C_1$-$C_6$ alkoxyl, or $C_3$-$C_6$ cycloalkyl; or $R_1$ and $R_2$ together with the atoms to which they are attached form a $C_3$-$C_6$ saturated or partially unsaturated cycloalkyl or a 3- to 14-membered saturated or partially unsaturated heterocycle comprising 1-5 heteroatoms selected from N, O, and S;

$R_3$ is H, halogen, —S($C_1$-$C_6$ alkyl), —N($C_1$-$C_6$ alkyl)$_2$, —NH($C_1$-$C_6$ alkyl), —NH$_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxyl, $C_1$-$C_6$ haloalkoxyl, or $C_3$-$C_6$ cycloalkyl;

$R_4$ is H, halogen, —S($C_1$-$C_6$ alkyl), —N($C_1$-$C_6$ alkyl)$_2$, —NH($C_1$-$C_6$ alkyl), —NH$_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxyl, $C_1$-$C_6$ haloalkoxyl, or $C_3$-$C_6$ cycloalkyl;

$R_5$ is H, halogen, —S($C_1$-$C_6$ alkyl), —N($C_1$-$C_6$ alkyl)$_2$, —NH($C_1$-$C_6$ alkyl), —NH$_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxyl, $C_1$-$C_6$ haloalkoxyl, or $C_3$-$C_6$ cycloalkyl;

$R_6$ is H, halogen, —S($C_1$-$C_6$ alkyl), —N($C_1$-$C_6$ alkyl)$_2$, —NH($C_1$-$C_6$ alkyl), —NH$_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxyl, $C_1$-$C_6$ haloalkoxyl, or $C_3$-$C_6$ cycloalkyl;

$R_7$ is H, deuterium, $C_1$-$C_6$ alkyl, $C_2$-$C_6$ alkenyl, or $C_2$-$C_6$ alkynyl;

$R_8$ is H, deuterium, $C_1$-$C_6$ alkyl, $C_2$-$C_6$ alkenyl, or $C_2$-$C_6$ alkynyl; and $R_9$ is H, $C_1$-$C_6$ alkyl, $C_2$-$C_6$ alkenyl, $C_2$-$C_6$ alkynyl, $C_1$-$C_6$ haloalkyl, or $C_3$-$C_6$ cycloalkyl, provided that at least one of $R_3$, $R_4$, $R_5$, and $R_6$ is H.

Embodiment No. 2. A compound of Formula (II):

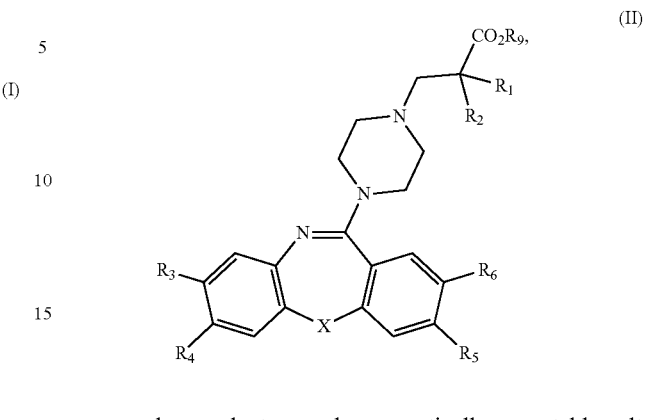

or a prodrug, solvate, or pharmaceutically acceptable salt thereof, wherein:

X is $CR_7R_8$, O, S, or $NR_7$;

$R_1$ is $C_1$-$C_6$ alkyl, $C_2$-$C_6$ alkenyl, $C_2$-$C_6$ alkynyl, $C_1$-$C_6$ haloalkyl, $C_1$-$C_6$ alkoxyl, or $C_3$-$C_6$ cycloalkyl;

$R_2$ is $C_1$-$C_6$ alkyl, $C_2$-$C_6$ alkenyl, $C_2$-$C_6$ alkynyl, $C_1$-$C_6$ haloalkyl, $C_1$-$C_6$ alkoxyl, or $C_3$-$C_6$ cycloalkyl; or $R_1$ and $R_2$ together with the atoms to which they are attached form a $C_3$-$C_6$ saturated or partially unsaturated cycloalkyl or a 3- to 14-membered saturated or partially unsaturated heterocycle comprising 1-5 heteroatoms selected from N, O, and S;

$R_3$ is H, halogen, —S($C_1$-$C_6$ alkyl), —N($C_1$-$C_6$ alkyl)$_2$, —NH($C_1$-$C_6$ alkyl), —NH$_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxyl, $C_1$-$C_6$ haloalkoxyl, or $C_3$-$C_6$ cycloalkyl;

$R_4$ is H, halogen, —S($C_1$-$C_6$ alkyl), —N($C_1$-$C_6$ alkyl)$_2$, —NH($C_1$-$C_6$ alkyl), —NH$_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxyl, $C_1$-$C_6$ haloalkoxyl, or $C_3$-$C_6$ cycloalkyl;

$R_5$ is H, halogen, —S($C_1$-$C_6$ alkyl), —N($C_1$-$C_6$ alkyl)$_2$, —NH($C_1$-$C_6$ alkyl), —NH$_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxyl, $C_1$-$C_6$ haloalkoxyl, or $C_3$-$C_6$ cycloalkyl;

$R_6$ is H, halogen, —S($C_1$-$C_6$ alkyl), —N($C_1$-$C_6$ alkyl)$_2$, —NH($C_1$-$C_6$ alkyl), —NH$_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxyl, $C_1$-$C_6$ haloalkoxyl, or $C_3$-$C_6$ cycloalkyl;

$R_7$ is H, deuterium, $C_1$-$C_6$ alkyl, $C_2$-$C_6$ alkenyl, or $C_2$-$C_6$ alkynyl;

$R_8$ is H, deuterium, $C_1$-$C_6$ alkyl, $C_2$-$C_6$ alkenyl, or $C_2$-$C_6$ alkynyl; and $R_9$ is H, $C_1$-$C_6$ alkyl, $C_2$-$C_6$ alkenyl, $C_2$-$C_6$ alkynyl, $C_1$-$C_6$ haloalkyl, or $C_3$-$C_6$ cycloalkyl, provided that:

(a) when $R_5$ is H, X is $CR_7R_8$ or S;

(b) when $R_5$ halogen and $R_4$ is H, then $R_3$ is not methyl, methoxyl, or Br and X is $CR_7R_8$ or S; and (c) when $R_5$ is methoxyl or methyl, $R_4$ is not H.

Embodiment No. 3. A compound of Formula (II'):

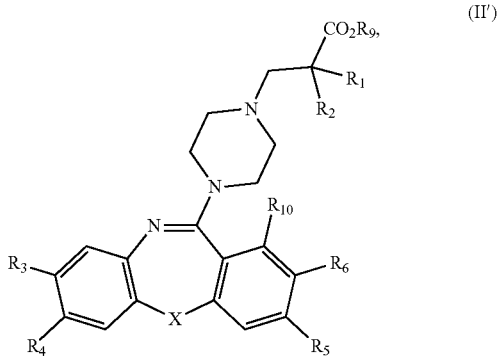

or a prodrug, solvate, or pharmaceutically acceptable salt thereof, wherein:

X is $CR_7R_8$, O, S, or $NR_7$;

$R_1$ is $C_1$-$C_6$ alkyl, $C_2$-$C_6$ alkenyl, $C_2$-$C_6$ alkynyl, $C_1$-$C_6$ haloalkyl, $C_1$-$C_6$ alkoxyl, or $C_3$-$C_6$ cycloalkyl;

$R_2$ is $C_1$-$C_6$ alkyl, $C_2$-$C_6$ alkenyl, $C_2$-$C_6$ alkynyl, $C_1$-$C_6$ haloalkyl, $C_1$-$C_6$ alkoxyl, or $C_3$-$C_6$ cycloalkyl; or $R_1$ and $R_2$ together with the atoms to which they are attached form a $C_3$-$C_6$ saturated or partially unsaturated cycloalkyl or a 3- to 14-membered saturated or partially unsaturated heterocycle comprising 1-5 heteroatoms selected from N, O, and S;

$R_3$ is H, halogen, —S($C_1$-$C_6$ alkyl), —N($C_1$-$C_6$ alkyl)$_2$, —NH($C_1$-$C_6$ alkyl), —NH$_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxyl, $C_1$-$C_6$ haloalkoxyl, or $C_3$-$C_6$ cycloalkyl;

$R_4$ is H, halogen, —S($C_1$-$C_6$ alkyl), —N($C_1$-$C_6$ alkyl)$_2$, —NH($C_1$-$C_6$ alkyl), —NH$_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxyl, $C_1$-$C_6$ haloalkoxyl, or $C_3$-$C_6$ cycloalkyl;

$R_5$ is H, halogen, —S($C_1$-$C_6$ alkyl), —N($C_1$-$C_6$ alkyl)$_2$, —NH($C_1$-$C_6$ alkyl), —NH$_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxyl, $C_1$-$C_6$ haloalkoxyl, or $C_3$-$C_6$ cycloalkyl;

$R_6$ is H, halogen, —S($C_1$-$C_6$ alkyl), —N($C_1$-$C_6$ alkyl)$_2$, —NH($C_1$-$C_6$ alkyl), —NH$_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxyl, $C_1$-$C_6$ haloalkoxyl, or $C_3$-$C_6$ cycloalkyl;

$R_7$ is H, deuterium, $C_1$-$C_6$ alkyl, $C_2$-$C_6$ alkenyl, or $C_2$-$C_6$ alkynyl;

$R_8$ is H, deuterium, $C_1$-$C_6$ alkyl, $C_2$-$C_6$ alkenyl, or $C_2$-$C_6$ alkynyl;

$R_9$ is H, $C_1$-$C_6$ alkyl, $C_2$-$C_6$ alkenyl, $C_2$-$C_6$ alkynyl, $C_1$-$C_6$ haloalkyl, or $C_3$-$C_6$ cycloalkyl; and $R_{10}$ is H or halogen, provided that:

(a) (i) when $R_5$ is H then X is $CR_7R_8$ or S, or (ii) when $R_5$ is H and $R_{10}$ is halogen then X is O;

(b) when $R_5$ halogen, $R_4$ is H, then $R_3$ is not methyl, methoxyl, or Br and X is $CR_7R_8$ or S; and (c) when $R_5$ is methoxyl or methyl then $R_4$ is not H.

Embodiment No. 4. The compound of embodiment 2, wherein X is O or $CR_7R_8$.

Embodiment No. 5. The compound of embodiment 2, wherein X is O.

Embodiment No. 6. The compound of embodiment 2, wherein X is $CH_2$.

Embodiment No. 7. The compound of any one of the preceding embodiments, wherein $R_1$ is $C_1$-$C_6$ alkyl.

Embodiment No. 8. The compound of any one of the preceding embodiments, wherein $R_1$ is methyl.

Embodiment No. 9. The compound of any one of the preceding embodiments, wherein $R_2$ is $C_1$-$C_6$ alkyl.

Embodiment No. 10. The compound of any one of the preceding embodiments, wherein $R_2$ is methyl.

Embodiment No. 11. The compound of any one of the preceding embodiments, wherein $R_1$ and $R_2$ together with the atoms to which they are attached form a $C_3$-$C_6$ saturated or partially unsaturated cycloalkyl or a 3- to 14-membered saturated or partially unsaturated heterocycle comprising 1-5 heteroatoms selected from N, O, and S.

Embodiment No. 12. The compound of any one of the preceding embodiments, wherein $R_1$ and $R_2$ together with the atoms to which they are attached form a cyclopropyl.

Embodiment No. 13. The compound of any one of the preceding embodiments, wherein $R_3$ is H, halogen, $C_1$-$C_6$ alkyl, or $C_1$-$C_6$ alkoxyl.

Embodiment No. 14. The compound of any one of the preceding embodiments, wherein $R_3$ is H, F, Cl, methyl, or methoxyl.

Embodiment No. 15. The compound of any one of the preceding embodiments, wherein $R_3$ is H.

Embodiment No. 16. The compound of any one of the preceding embodiments, wherein $R_3$ is F.

Embodiment No. 17. The compound of any one of the preceding embodiments, wherein $R_3$ is Cl.

Embodiment No. 18. The compound of any one of the preceding embodiments, wherein $R_3$ is methyl.

Embodiment No. 19. The compound of any one of the preceding embodiments, wherein $R_3$ is methoxyl.

Embodiment No. 20. The compound of any one of the preceding embodiments, wherein $R_4$ is H, halogen, $C_1$-$C_6$ alkyl, or $C_1$-$C_6$ haloalkyl.

Embodiment No. 21. The compound of anyone of the preceding embodiments, wherein $R_4$ is H, F, Cl, methyl, or $CHF_2$.

Embodiment No. 22. The compound of any one of the preceding embodiments, wherein $R_4$ is H.

Embodiment No. 23. The compound of any one of the preceding embodiments, wherein $R_4$ is F.

Embodiment No. 24. The compound of any one of the preceding embodiments, wherein $R_4$ is Cl.

Embodiment No. 25. The compound of any one of the preceding embodiments, wherein $R_4$ is methyl.

Embodiment No. 26. The compound of any one of the preceding embodiments, wherein $R_4$ is $CHF_2$.

Embodiment No. 27. The compound of any one of the preceding embodiments, wherein $R_5$ is H, halogen, $C_1$-$C_6$ alkyl, $C_1$-$C_6$ alkoxyl, S($C_1$-$C_6$ alkyl), or $C_1$-$C_6$ haloalkyl.

Embodiment No. 28. The compound of any one of the preceding embodiments, wherein $R_5$ is H, F, Cl, methyl, ethyl, iso-propyl, n-propyl, methoxyl, —$SCH_3$, or $CHF_2$.

Embodiment No. 29. The compound of any one of the preceding embodiments, wherein $R_5$ is H.

Embodiment No. 30. The compound of any one of the preceding embodiments, wherein $R_5$ is F.

Embodiment No. 31. The compound of any one of the preceding embodiments, wherein $R_5$ is Cl.

Embodiment No. 32. The compound of any one of the preceding embodiments, wherein $R_5$ is methyl.

Embodiment No. 33. The compound of any one of the preceding embodiments, wherein $R_5$ is ethyl.

Embodiment No. 34. The compound of any one of the preceding embodiments, wherein $R_5$ is iso-propyl.

Embodiment No. 35. The compound of any one of the preceding embodiments, wherein $R_5$ is n-propyl.

Embodiment No. 36. The compound of any one of the preceding embodiments, wherein $R_5$ is methoxyl.

Embodiment No. 37. The compound of any one of the preceding embodiments, wherein $R_5$ is methylthiyl.

Embodiment No. 38. The compound of any one of the preceding embodiments, wherein $R_5$ is $CHF_2$.

Embodiment No. 39. The compound of any one of the preceding embodiments, wherein $R_6$ is H, $C_1$-$C_6$ alkyl, or $C_1$-$C_6$ alkoxyl.

Embodiment No. 40. The compound of any one of the preceding embodiments, wherein $R_6$ is H, methyl, or methoxyl.

Embodiment No. 41. The compound of anyone of the preceding embodiments, wherein $R_6$ is H.

Embodiment No. 42. The compound of any one of the preceding embodiments, wherein $R_6$ is methyl.

Embodiment No. 43. The compound of any one of the preceding embodiments, wherein $R_6$ is methoxyl.

Embodiment No. 44. The compound of any one of the preceding embodiments, wherein $R_7$ is H.

Embodiment No. 45. The compound of any one of the preceding embodiments, wherein $R_8$ is H.

Embodiment No. 46. The compound of any one of the preceding embodiments, wherein $R_9$ is H.

Embodiment No. 47. The compound of any one of the preceding embodiments, wherein $R_{10}$ is H.

Embodiment No. 48. The compound of any one of the preceding embodiments, wherein $R_{10}$ is F.

Embodiment No. 49. The compound of any one of the preceding embodiments, wherein the compound is of Formula (Ia):

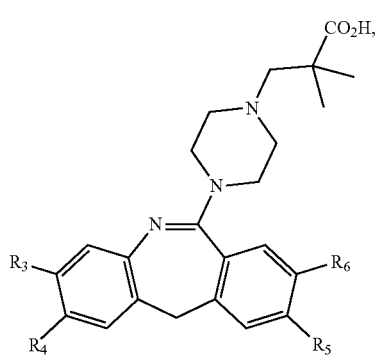

(Ia)

or a prodrug, solvate, or pharmaceutically acceptable salt thereof, wherein, wherein $R_3$, $R_4$, $R_5$, and $R_6$ are as described herein.

Embodiment No. 50. The compound of any one of the preceding embodiments, wherein the compound is of Formula (Ib):

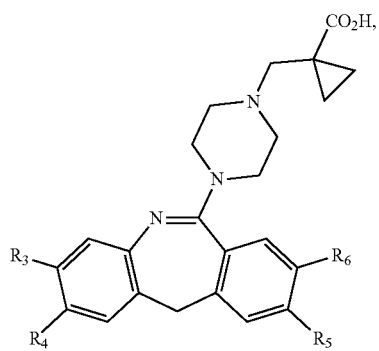

(Ib)

or a prodrug, solvate, or pharmaceutically acceptable salt thereof, wherein, wherein $R_3$, $R_4$, $R_5$, and $R_6$ are as described herein.

Embodiment No. 51. The compound of any one of the preceding embodiments, wherein the compound is of Formula (IIa):

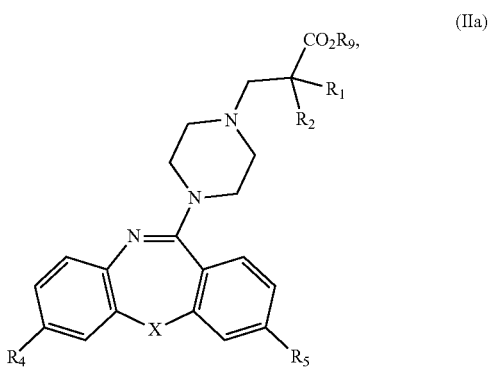

(IIa)

or a prodrug, solvate, or pharmaceutically acceptable salt thereof, wherein, wherein X, $R_1$, $R_2$, $R_4$, $R_5$, and $R_9$ are as described herein.

Embodiment No. 52. The compound of any one of the preceding embodiments, wherein the compound is of Formula (IIa-1):

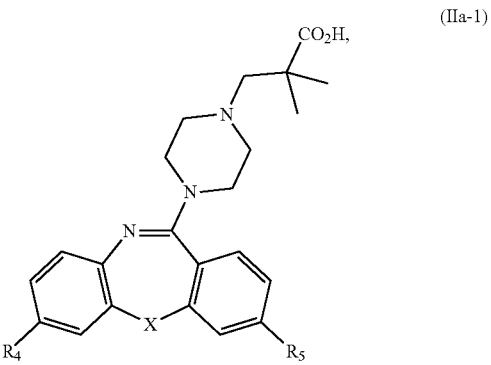

(IIa-1)

or a prodrug, solvate, or pharmaceutically acceptable salt thereof, wherein, wherein X, $R_4$, and $R_5$ are as described herein.

Embodiment No. 53. The compound of any one of the preceding embodiments, wherein the compound is of Formula (IIa-2):

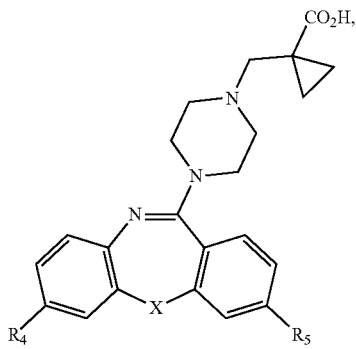

or a prodrug, solvate, or pharmaceutically acceptable salt thereof, wherein, wherein X, $R_4$, and $R_5$ are as described herein.

Embodiment No. 54. The compound of any one of the preceding embodiments, wherein the compound is of Formula (IIb):

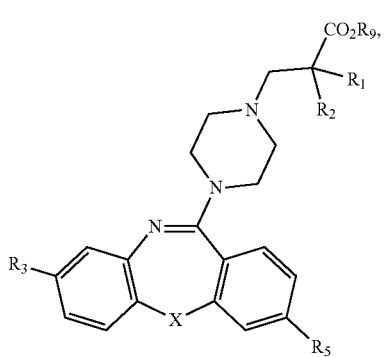

or a prodrug, solvate, or pharmaceutically acceptable salt thereof, wherein, wherein X, $R_1$, $R_2$, $R_3$, $R_5$, and $R_9$ are as described herein.

Embodiment No. 55. The compound of any one of the preceding embodiments, wherein the compound is of Formula (IIb-1):

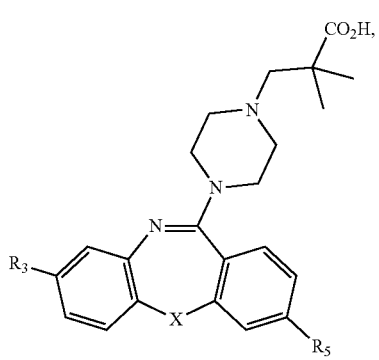

or a prodrug, solvate, or pharmaceutically acceptable salt thereof, wherein, wherein X, $R_3$, and $R_5$ are as described herein.

Embodiment No. 56. The compound of any one of the preceding embodiments, wherein the compound is of Formula (IIb-2):

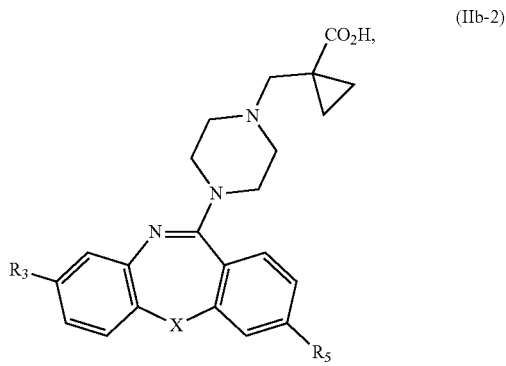

or a prodrug, solvate, or pharmaceutically acceptable salt thereof, wherein, wherein X, $R_3$, and $R_5$ are as described herein.

Embodiment No. 57. The compound of any one of the preceding embodiments, wherein the compound is of Formula (IIc):

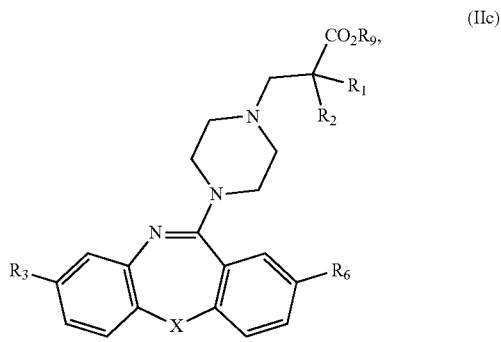

or a prodrug, solvate, or pharmaceutically acceptable salt thereof, wherein, wherein X, $R_1$, $R_2$, $R_3$, $R_6$, and $R_9$ are as described herein.

Embodiment No. 58. The compound of any one of the preceding embodiments, wherein the compound is of Formula (IIc-1):

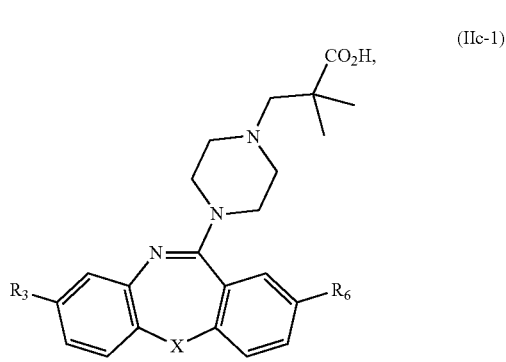

or a prodrug, solvate, or pharmaceutically acceptable salt thereof, wherein, wherein X, R$_3$, and R$_6$ are as described herein.

Embodiment No. 59. The compound of any one of the preceding embodiments, wherein the compound is of Formula (IIc-2):

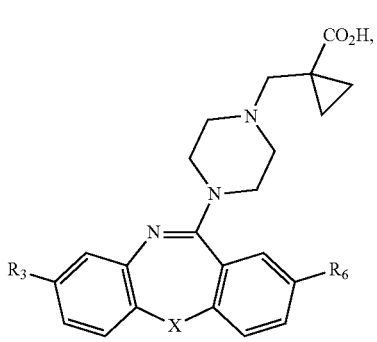

(IIc-2)

or a prodrug, solvate, or pharmaceutically acceptable salt thereof, wherein, wherein X, R$_3$, and R$_6$ are as described herein.

Embodiment No. 60. The compound of any one of the preceding embodiments, wherein the compound is of Formula (II'a)

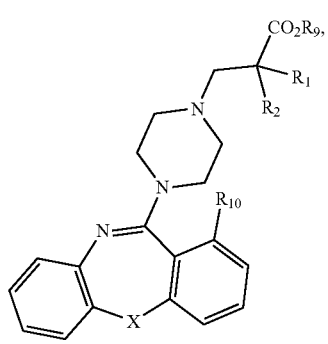

(II'a)

or a prodrug, solvate, or pharmaceutically acceptable salt thereof, wherein X, R$_1$, R$_2$, R$_9$, and R$_{10}$ are as described herein for Formula (II')

Embodiment No. 61. The compound of any one of the embodiments 1-60, being selected from Compound Nos. 1-39, prodrugs and pharmaceutically acceptable salts thereof.

Embodiment No. 62. The compound of any one of embodiments 1-60, being selected from Compound Nos. 1-39 and pharmaceutically acceptable salts thereof.

Embodiment No. 63. The compound of any one of embodiments 1-60, being selected from Compound Nos. 1-39.

Embodiment No. 64. The compound of any one of embodiments 1-60, being selected from Compound Nos. 30, 31, 34, and 35.

Embodiment No. 65. A compound obtainable by, or obtained by, a method described herein; optionally, the method comprises one or more steps described in Schemes 1-3.

Embodiment No. 66. A pharmaceutical composition comprising the compound of any one of embodiments 1-65 or a pharmaceutically acceptable salt thereof, and a pharmaceutically acceptable diluent or carrier.

Embodiment No. 67. The pharmaceutical composition of embodiment 66, wherein the compound is selected from Compound Nos. 1-39.

Embodiment No. 68. A method of alleviating a symptom of, treating, or preventing a sleep disorder in a subject by administering a compound of any one of embodiments 1-65 or a pharmaceutical composition of embodiment 66 or 67 to a subject in need thereof.

Embodiment No. 69. The method of embodiment 68, wherein the sleep disorder is increased sleep fragmentation.

Embodiment No. 70. The method of embodiment 68 or 69, wherein the compound is a H1/5-HT$_{2A}$ receptor modulator.

Embodiment No. 71. The method of embodiment 68 or 69, wherein the sleep disorder is caused by or co-morbid with sleep apnea, restless legs syndrome, a high respiratory disturbance index (RDI), neurological disease, circadian rhythm disorder, pain, periodic leg movement disorder (PLMD), REM behavior disorder, elderly fragmented sleep, age-related sleep fragmentation, post-menopausal sleep disorder, substance abuse, substance abuse withdrawal, narcolepsy, mental disorder, an increased sensitivity to pain, cardiovascular disease, hypertension, non-restorative sleep, a stroke, a metabolic disorder, or cognitive impairment.

Embodiment No. 72. The method of embodiment 71, wherein the sleep apnea is obstructive sleep apnea due to a high respiratory disturbance index (RDI) associated with an elevated respiratory event related arousal (RERA) with or without a concomitant apnea, hypopnea, or acute hemoglobin desaturation.

Embodiment No. 73. The method of embodiment 71, wherein the neurological disease is Alzheimer's disease, Parkinson's disease, Huntington's disease, or Lewy body dementia.

Embodiment No. 74. The method of embodiment 71, wherein the neurological disease is a neurodegenerative disease.

Embodiment No. 75. The method of embodiment 74, wherein the neurodegenerative disease is synucleinopathy.

Embodiment No. 76. The method of embodiment 75, wherein the synucleinopathy is Alzheimer's disease, Parkinson's disease, or dementia with Lewy bodies.

Embodiment No. 77. The method of embodiment 74, wherein the neurodegenerative disease is Lewy body disease, amyotrophic lateral sclerosis, Parkinson's disease, Alzheimer's disease, or Huntington's disease.

Embodiment No. 78. The method of embodiment 71, wherein the pain is acute nociceptive pain, chronic neuropathic pain, inflammatory pain, arthritic pain, cancer pain, or mixed nociceptive and neuropathic pain.

Embodiment No. 79. The method of embodiment 78, wherein the mixed nociceptive and neuropathic pain is low back pain.

Embodiment No. 80. The method of embodiment 71, wherein the circadian rhythm disorder is jet-lag, shift-work, delayed sleep phase disorder, or non-24 hour rhythm disorder.

Embodiment No. 81. The method of embodiment 71, wherein the substance abuse is opioid abuse or alcoholism.

Embodiment No. 82. The method of embodiment 71, wherein substance abuse withdrawal is opioid withdrawal or alcohol withdrawal.

Embodiment No. 83. The method of embodiment 71, wherein the mental disorder is depression, major depressive disorder, post-traumatic stress disorder, anxiety disorder, bipolar disorder, or schizophrenia.

Embodiment No. 84. The method of any one of embodiments 68-83, wherein the compound is administered in combination with an additional active agent.

Embodiment No. 85. The method embodiment 84, wherein the additional active agent is a sedative-hypnotic.

Embodiment No. 86. The method of any one of embodiments 68-85, wherein the compound, and any additional active agent, if present, is administered either hora somni, h.s. (at bedtime) or between about 0-4 hours before bedtime.

Embodiment No. 87. A compound of any one of embodiments 1-65 or the pharmaceutical composition of embodiment 66 or 67, for use in alleviating a symptom of, treating, or preventing a sleep disorder.

Embodiment No. 88. The compound or pharmaceutical composition for use of embodiment 87, wherein the sleep disorder is increased sleep fragmentation.

Embodiment No. 89. The compound or pharmaceutical composition for use of embodiment 87 or 88, wherein the compound or pharmaceutical composition is a H1/5-HT$_{2A}$ receptor modulator.

Embodiment No. 90. The compound or pharmaceutical composition for use of embodiment 87 or 88, wherein the sleep disorder is caused by or co-morbid with sleep apnea, restless legs syndrome, a high respiratory disturbance index (RDI), neurological disease, circadian rhythm disorder, pain, periodic leg movement disorder (PLMD), REM behavior disorder, elderly fragmented sleep, age-related sleep fragmentation, post-menopausal sleep disorder, substance abuse, substance abuse withdrawal, narcolepsy, mental disorder, an increased sensitivity to pain, cardiovascular disease, hypertension, non-restorative sleep, a stroke, a metabolic disorder, or cognitive impairment.

Embodiment No. 91. The compound or pharmaceutical composition for use of embodiment 90, wherein the sleep apnea is obstructive sleep apnea due to a high respiratory disturbance index (RDI) associated with an elevated respiratory event related arousal (RERA) with or without a concomitant apnea, hypopnea, or acute hemoglobin desaturation.

Embodiment No. 92. The compound or pharmaceutical composition for use of embodiment 90, wherein the neurological disease is Alzheimer's disease, Parkinson's disease, Huntington's disease, or Lewy body dementia.

Embodiment No. 93. The compound or pharmaceutical composition for use of embodiment 90, wherein the neurological disease is a neurodegenerative disease.

Embodiment No. 94. The compound or pharmaceutical composition for use of embodiment 93, wherein the neurodegenerative disease is synucleinopathy.

Embodiment No. 95. The compound or pharmaceutical composition for use of embodiment 94, wherein the synucleinopathy is Alzheimer's disease, Parkinson's disease, or dementia with Lewy bodies.

Embodiment No. 96. The compound or pharmaceutical composition for use of embodiment 93, wherein the neurodegenerative disease is Lewy body disease, amyotrophic lateral sclerosis, Parkinson's disease, Alzheimer's disease, or Huntington's disease.

Embodiment No. 97. The compound or pharmaceutical composition for use of embodiment 90, wherein the pain is acute nociceptive pain, chronic neuropathic pain, inflammatory pain, arthritic pain, cancer pain, or mixed nociceptive and neuropathic pain.

Embodiment No. 98. The compound or pharmaceutical composition for use of embodiment 97, wherein the mixed nociceptive and neuropathic pain is low back pain.

Embodiment No. 99. The compound or pharmaceutical composition for use of embodiment 90, wherein the circadian rhythm disorder is jet-lag, shift-work, delayed sleep phase disorder, or non-24 hour rhythm disorder.

Embodiment No. 100. The compound or pharmaceutical composition for use of embodiment 90, wherein the substance abuse is opioid abuse or alcoholism.

Embodiment No. 101. The compound or pharmaceutical composition for use of embodiment 90, wherein substance abuse withdrawal is opioid withdrawal or alcohol withdrawal.

Embodiment No. 102. The compound or pharmaceutical composition for use of embodiment 90, wherein the mental disorder is depression, major depressive disorder, post-traumatic stress disorder, anxiety disorder, bipolar disorder, or schizophrenia.

Embodiment No. 103. The compound or pharmaceutical composition for use of any one of embodiments 87-102, wherein the compound is administered in combination with an additional active agent.

Embodiment No. 104. The compound or pharmaceutical composition for use of embodiment 103, wherein the additional active agent is a sedative-hypnotic.

Embodiment No. 105. The compound or pharmaceutical composition for use of any one of embodiments 87-104, wherein the compound, and any additional active agent, if present, is administered either hora somni, h.s. (at bedtime) or between about 0-4 hours before bedtime.

Embodiment No. 106. Use of the compound of any one of embodiments 1-65, or a pharmaceutical composition of embodiment 66 or 67, in the manufacture of a medicament for alleviating a symptom of, treating, or preventing a sleep disorder.

Embodiment No. 107. The use of a compound or pharmaceutical composition in the manufacture of a medicament of embodiment 106, wherein the sleep disorder is increased sleep fragmentation.

Embodiment No. 108. The use of a compound or pharmaceutical composition in the manufacture of a medicament of embodiment 106 or 107, wherein the compound or pharmaceutical composition is a H1/5-HT$_{2A}$ receptor modulator.

Embodiment No. 109. The use of a compound or pharmaceutical composition in the manufacture of a medicament of embodiment 106 or 107, wherein the sleep disorder is caused by or co-morbid with sleep apnea, restless legs syndrome, a high respiratory disturbance index (RDI), neurological disease, circadian rhythm disorder, pain, periodic leg movement disorder (PLMD), REM behavior disorder, elderly fragmented sleep, age-related sleep fragmentation, post-menopausal sleep disorder, substance abuse, substance abuse withdrawal, narcolepsy, mental disorder, an increased sensitivity to pain, cardiovascular disease, hypertension, non-restorative sleep, a stroke, a metabolic disorder, or cognitive impairment.

Embodiment No. 110. The use of a compound or pharmaceutical composition in the manufacture of a medicament of embodiment 109, wherein the sleep apnea is obstructive sleep apnea due to a high respiratory disturbance index (RDI) associated with an elevated respiratory event related arousal (RERA) with or without a concomitant apnea, hypopnea, or acute hemoglobin desaturation.

Embodiment No. 111. The use of a compound or pharmaceutical composition in the manufacture of a medicament of embodiment 109, wherein the neurological disease is Alzheimer's disease, Parkinson's disease, Huntington's disease, or Lewy body dementia.

Embodiment No. 112. The use of a compound or pharmaceutical composition in the manufacture of a medicament of embodiment 109, wherein the neurological disease is a neurodegenerative disease.

Embodiment No. 113. The use of a compound or pharmaceutical composition in the manufacture of a medicament of embodiment 112, wherein the neurodegenerative disease is synucleinopathy.

Embodiment No. 114. The use of a compound or pharmaceutical composition in the manufacture of a medicament of embodiment 113, wherein the synucleinopathy is Alzheimer's disease, Parkinson's disease, or dementia with Lewy bodies.

Embodiment No. 115. The use of a compound or pharmaceutical composition in the manufacture of a medicament of embodiment 112, wherein the neurodegenerative disease is Lewy body disease, amyotrophic lateral sclerosis, Parkinson's disease, Alzheimer's disease, or Huntington's disease.

Embodiment No. 116. The use of a compound or pharmaceutical composition in the manufacture of a medicament of embodiment 109, wherein the pain is acute nociceptive pain, chronic neuropathic pain, inflammatory pain, arthritic pain, cancer pain, or mixed nociceptive and neuropathic pain.

Embodiment No. 117. The use of a compound or pharmaceutical composition in the manufacture of a medicament of embodiment 116, wherein the mixed nociceptive and neuropathic pain is low back pain.

Embodiment No. 118. The method of embodiment 109, wherein the circadian rhythm disorder is jet-lag, shift-work, delayed sleep phase disorder, or non-24 hour rhythm disorder.

Embodiment No. 119. The use of a compound or pharmaceutical composition in the manufacture of a medicament of embodiment 109, wherein the substance abuse is opioid abuse or alcoholism.

Embodiment No. 120. The use of a compound or pharmaceutical composition in the manufacture of a medicament of embodiment 109, wherein substance abuse withdrawal is opioid withdrawal or alcohol withdrawal.

Embodiment No. 121. The use of a compound or pharmaceutical composition in the manufacture of a medicament of embodiment 109, wherein the mental disorder is depression, major depressive disorder, post-traumatic stress disorder, anxiety disorder, bipolar disorder, or schizophrenia.

Embodiment No. 122. The use of a compound or pharmaceutical composition in the manufacture of a medicament of any one of embodiments 106-121, wherein the compound is administered in combination with an additional active agent.

Embodiment No. 123. The use of a compound or pharmaceutical composition in the manufacture of a medicament of embodiment 122, wherein the additional active agent is a sedative-hypnotic.

Embodiment No. 124. The use of a compound or pharmaceutical composition in the manufacture of a medicament of any one of embodiments 106-123, wherein the compound, and any additional active agent, if present, is administered either hora somni, h.s. (at bedtime) or between about 0-4 hours before bedtime.

Embodiment No. 125. Use of a compound of any one of embodiments 1-65 or a pharmaceutical composition of embodiment 66 or 67, for alleviating a symptom of, treating, or preventing a sleep disorder.

Embodiment No. 126. The use of embodiment 125, wherein the sleep disorder is increased sleep fragmentation.

Embodiment No. 127. The compound or pharmaceutical composition of embodiment 125 or 127, wherein the compound or pharmaceutical composition is a H1/5-HT$_{2A}$ receptor modulator.

Embodiment No. 128. The use of embodiment 125 or 126, wherein the sleep disorder is caused by or co-morbid with sleep apnea, restless legs syndrome, a high respiratory disturbance index (RDI), neurological disease, circadian rhythm disorder, pain, periodic leg movement disorder (PLMD), REM behavior disorder, elderly fragmented sleep, age-related sleep fragmentation, post-menopausal sleep disorder, substance abuse, substance abuse withdrawal, narcolepsy, mental disorder, an increased sensitivity to pain, cardiovascular disease, hypertension, non-restorative sleep, a stroke, a metabolic disorder, or cognitive impairment.

Embodiment No. 129. The use of embodiment 128, wherein the sleep apnea is obstructive sleep apnea due to a high respiratory disturbance index (RDI) associated with an elevated respiratory event related arousal (RERA) with or without a concomitant apnea, hypopnea, or acute hemoglobin desaturation.

Embodiment No. 130. The use of embodiment 128, wherein the neurological disease is Alzheimer's disease, Parkinson's disease, Huntington's disease, or Lewy body dementia.

Embodiment No. 131. The use of embodiment 128, wherein the neurological disease is a neurodegenerative disease.

Embodiment No. 132. The use of embodiment 129, wherein the neurodegenerative disease is synucleinopathy.

Embodiment No. 133. The use of embodiment 130, wherein the synucleinopathy is Alzheimer's disease, Parkinson's disease, or dementia with Lewy bodies.

Embodiment No. 134. The use of embodiment 129, wherein the neurodegenerative disease is Lewy body disease, amyotrophic lateral sclerosis, Parkinson's disease, Alzheimer's disease, or Huntington's disease.

Embodiment No. 135. The use of embodiment 128, wherein the pain is acute nociceptive pain, chronic neuropathic pain, inflammatory pain, arthritic pain, cancer pain, or mixed nociceptive and neuropathic pain.

Embodiment No. 136. The use of embodiment 135, wherein the mixed nociceptive and neuropathic pain is low back pain.

Embodiment No. 137. The use of embodiment 128, wherein the circadian rhythm disorder is jet-lag, shift-work, delayed sleep phase disorder, or non-24 hour rhythm disorder.

Embodiment No. 138. The use of embodiment 128, wherein the substance abuse is opioid abuse or alcoholism.

Embodiment No. 139. The use of embodiment 128, wherein substance abuse withdrawal is opioid withdrawal or alcohol withdrawal.

Embodiment No. 140. The use of embodiment 128, wherein the mental disorder is depression, major depressive disorder, post-traumatic stress disorder, anxiety disorder, bipolar disorder, or schizophrenia.

Embodiment No. 141. The use of any one of embodiments 125-140, wherein the compound is administered in combination with an additional active agent.

Embodiment No. 142. The use embodiment 141, wherein the additional active agent is a sedative-hypnotic.

Embodiment No. 143. The use of any one of embodiments 125-142, wherein the compound, and any additional active agent, if present, is administered either hora somni, h.s. (at bedtime) or between about 0-4 hours before bedtime.

EXAMPLES

For exemplary purpose, neutral compounds of Formula (I) and (II) are synthesized and tested in the examples. It is understood that the neutral compounds of Formula (I) and (II) may be converted to the corresponding pharmaceutically acceptable salts of the compounds using routine techniques in the art (e.g., by saponification of an ester to the carboxylic acid salt, or by hydrolyzing an amide to form a corresponding carboxylic acid and then converting the carboxylic acid to a carboxylic acid salt).

Nuclear magnetic resonance (NMR) spectra were recorded at 400 MHz or 300 MHz as stated; the chemical shifts (δ) are reported in parts per million (ppm). Spectra were recorded using a Bruker or Varian instrument with 8, 16 or 32 scans.

LC-MS chromatograms and spectra were recorded using an Agilent 1200 or Shimadzu LC-20 AD&MS 2020 instrument using a C-18 column such as a Xtimate C18 2.1×30 mm, 3 um, in 2 min chromatography, unless otherwise stated. Injection volumes were 0.7-8.0 μl and the flow rates were typically 0.8 or 1.2 ml/min. Detection methods were diode array (DAD) or evaporative light scattering (ELSD) as well as positive ion electrospray ionisation. MS range was 100-1000 Da. Solvents were gradients of water and acetonitrile both containing a modifier (typically 0.01-0.04%) such as trifluoroacetic acid or ammonium carbonate.

Abbreviations:
ACN Acetonitrile
CDCl$_3$ Chloroform-d
DCM Dichloromethane
DMF N,N-dimethylformamide
DMP Dess-Martin periodinane
DMSO dimethylsulphoxide
DMSO-d$_6$ Hexadeuterodimethylsulphoxide
dppf 1,1'-bis(diphenylphosphino)ferrocene
eq. Equivalents
ESI Electrospray ionisation
EtOAc ethyl acetate
FA Formic acid
FCC flash column chromatography
h hour(s)
$^1$H NMR Proton nuclear magnetic resonance spectroscopy
HATU 1-[Bis(dimethylamino)methylene]-1H-1,2,3-triazolo[4,5-b]pyridinium 3-oxid hexafluorophosphate
HPβCD (2-hydroxypropyl)-β-cyclodextrin
HPLC high performance liquid chromatography
LC-MS Liquid chromatography-mass spectrometry
MeOD Methanol-d$_4$
MeOH Methanol
min minute(s)
NaOAc Sodium acetate
PE petroleum ether
ppm parts per million
r.t. room temperature
R$_f$ retention factor
RM reaction mixture
R$_t$ retention time
TEA Triethylamine
TFA trifluoroacetic acid
THF Tetrahydrofuran
TLC thin layer chromatography
Y Yield Example 1. 3-(4-(7-chloro-3-methyldibenzo[b,f][1,4]oxazepin-11-yl)piperazin-1-yl)-2,2-dimethylpropanoic acid (Compound No. 1)

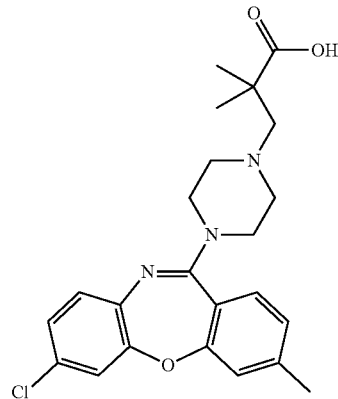 [SMILES: Cc1ccc2c(c1)Oc1cc(Cl)ccc1N=C2N1CCN(CC(C)(C)C(=O)O)CC1]

Step 1: Synthesis of 2-fluoro-4-methylbenzoyl chloride

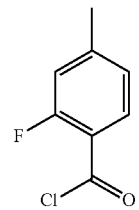

To a solution of 2-fluoro-4-methylbenzoic acid (10.00 g, 64.88 mmol, 1 eq.) in SOCl$_2$ (40 mL) was added DMF (48 mg, 648.80 μmol, 49.92 μL, 0.01 eq.). The mixture was stirred at 80° C. for 2 hrs. The reaction was concentrated to dryness. The residue was used to next step directly. 2-Fluoro-4-methylbenzoyl chloride (11.00 g, crude) was obtained as a yellow solid.

Step 2: N-(4-chloro-2-hydroxyphenyl)-2-fluoro-4-methylbenzamide

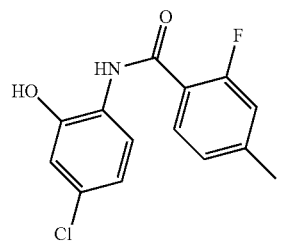 [SMILES: Cc1ccc(C(=O)Nc2ccc(Cl)cc2O)c(F)c1]

To a solution of 2-amino-5-chloro-phenol (9.15 g, 63.74 mmol, 1 eq.) and TEA (12.90 g, 127.47 mmol, 17.7 mL, 2 eq.) in TH (120 mL) was added 2-fluoro-4-methylbenzoyl chloride (11.00 g, 63.74 mmol, 1 eq.) in portions at 0° C. The mixture was stirred at 25° C. for 16 hrs. The reaction mixture was quenched with 2N HCl (200 mL) and extracted with EtOAc (300 mL*2). The combined organic layers were washed with brine (200 mL), dried over $N_2SO_4$, filtered and concentrated to give a residue. The residue was purified by silica gel combi flash ($SiO_2$, Petroleum ether/Ethyl acetate=3:1). N-(4-chloro-2-hydroxyphenyl)-2-fluoro-4-methylbenzamide (8.60 g, 26.49 mmol, 41.57% yield, 86.16% purity) was obtained as a brown solid. $^1$H NMR ($CDCl_3$, 400 MHz) $\delta_H$=9.05 (s, 1H), 8.73 (d, J=18.0 Hz, 1H), 8.08 (t, J=8.4 Hz, 1H), 7.15 (d, J=8.0 Hz, 1H), 7.10-7.02 (m, 3H), 6.93-6.87 (m, 1H), 2.45 (s, 3H).

Step 3: Synthesis of 7-chloro-3-methyldibenzo[b,f][1,4]oxazepin-11(10H)-one

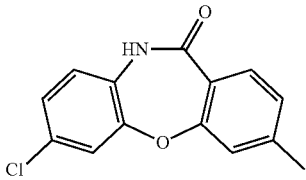 [SMILES: Cc1ccc2c(c1)Oc1cc(Cl)ccc1NC2=O]

To a solution of N-(4-chloro-2-hydroxyphenyl)-2-fluoro-4-methylbenzamide (8.30 g, 29.68 mmol, 1 eq.) in DMF (150 mL) was added t-BuOK (6.66 g, 59.36 mmol, 2 eq.). The mixture was stirred at 140° C. for 2 hrs. The mixture was poured into $H_2O$ (200 mL) slowly. The precipitate was filtered. The filtered cake was dried under reduced pressure. The product was used to the next step directly without purification. 7-chloro-3-methyldibenzo[b,f][1,4]oxazepin-11(10H)-one (4.10 g, 15.79 mmol, 53.19% yield) was obtained as a brown solid. $^1$H NMR ($CDCl_3$, 400 MHz) $\delta_H$=8.62 (brs, 1H), 7.82 (d, J=8.0 Hz, 1H), 7.28-7.23 (m, 1H), 7.13-7.04 (m, 3H), 7.01-6.99 (m, 1H), 2.40 (s, 3H).

Step 4: Synthesis of 7,11-dichloro-3-methyldibenzo[b][1,4]oxazepine

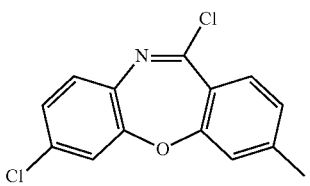 [SMILES: Cc1ccc2c(c1)Oc1cc(Cl)ccc1N=C2Cl]

A mixture of 7-chloro-3-methyldibenzo[b,f][1,4]oxazepin-11(10H)-one (1.00 g, 3.85 mmol, 1 eq.) in $POCl_3$ (57.75 g, 376.64 mmol, 35 mL, 97.81 eq.) was stirred at 100° C. for 3 hrs. The mixture was concentrated to give crude product. The crude product was used directly to the next step without further purification. 7,11-dichloro-3-methyldibenzo[b,f][1,4]oxazepine (1.00 g, crude) was obtained as a light yellow solid.

Step 5: Synthesis of 7-chloro-3-methyl-1-(piperazin-1-yl)dibenzo[b,f][1,4]oxazepine

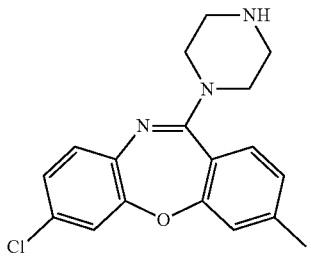 [SMILES: Cc1ccc2c(c1)Oc1cc(Cl)ccc1N=C2N1CCNCC1]

A mixture of 7,11-dichloro-3-methyldibenzo[b,f][1,4]oxazepine (1.00 g, 3.60 mmol, 1 eq.) and piperazine (3.10 g, 35.95 mmol, 10 eq.) in 1, 4-dioxane (50 mL) was stirred at 120° C. for 10 hrs. The mixture was diluted with $H_2O$ (300 mL), and extracted with EtOAc (200 mL*3). The combined organic layer was concentrated to give crude product. The crude product was purified by column chromatography on silica gel (DCM:MeOH=3:1). 7-chloro-3-methyl-11-(piperazin-1-yl)dibenzo[b,f][1,4]oxazepine (300 mg, 665.33 μmol, 18.51% yield, 72.7% purity) was obtained as a light yellow solid. LCMS $R_t$=0.784 min in 1.5 min chromatography (Merk RP18e 25-3 mm, purity 72.7%). MS ESI calcd. for 327.11 [M+H]$^+$ 328.11, found 327.9.

Step 6: Synthesis of methyl 3-(4-(7-chloro-3-methyldibenzo[b,f][1,4]oxazepin-11-yl) piperazin-1-yl)-2,2-dimethylpropanoate

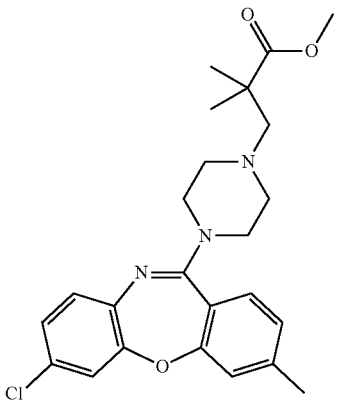 [SMILES: COC(=O)C(C)(C)CN1CCN(C2=Nc3ccc(Cl)cc3Oc3cc(C)ccc32)CC1]

To a mixture of 7,11-dichloro-3-methyldibenzo[b,f][1,4]oxazepine (300 mg, 915.17 μmol, 1 eq.) and methyl 2,2-dimethyl-3-oxo-propanoate (1.79 g, 13.73 mmol, 15 eq.) in DCM (5 mL) was added $NaBH(OAc)_3$ (969.8 mg, 4.58 mmol, 5 eq.). The resulting mixture was stirred at 25° C. for 10 hrs. The mixture was diluted with DCM (30 mL), and washed with saturated aqueous $NaHCO_3$ (30 mL*5). The combined organic layer was concentrated to give crude product. The crude product was purified by column chromatography on silica gel (PE:EtOAc=6:1). methyl 3-(4-(7-chloro-3-methyldibenzo[b,f][1,4]oxazepin-11-yl) piperazin-1-yl)-2,2-dimethylpropanoate (200 mg, 452.54 μmol, 49.45% yield, 100% purity) was obtained as a yellow oil. $^1$H NMR (DMSO-$d_6$, 400 MHz) $\delta_H$=7.28-7.21 (m, 3H), 7.15-

7.09 (m, 2H), 7.00 (d, J=8.4 Hz, 1H), 3.60 (s, 3H), 3.51-3.35 (m, 6H), 2.60-2.52 (m, 4H), 2.34 (s, 3H), 1.13 (s, 6H).

Step 7: Synthesis of 3-(4-(7-chloro-3-methyl-dibenzo[b,f][1,4]oxazepin-11-yl)piperazin-1-yl)-2,2-dimethylpropanoic acid To a mixture of methyl 3-(4-(7-chloro-3-methyldibenzo[b,f][1,4]oxazepin-11-yl) piperazin-1-yl)-2,2-dimethylpropanoate (200 mg, 452.54 µmol, 1 eq.) in MeOH (4 mL) and H$_2$O (2 mL) was added NaOH (54 mg, 1.36 mmol, 3 eq.). The resulting mixture was stirred at 35° C. for 10 hrs. The mixture was concentrated to remove MeOH, and the pH of the mixture was adjusted to around 5 with HCOOH. The crude product was purified by prep-HPLC (column: Xtimate C18 150*40 mm*10 um; mobile phase: [water (0.225% FA)-ACN]; B %: 29%-59%, 8 min). 3-(4-(7-chloro-3-methyldibenzo[b,f][1,4]oxazepin-11-yl)piperazin-1-yl)-2,2-dimethylpropanoic acid (11.9 mg, 24.67 µmol, 5.45% yield, 98.26% purity, FA) was obtained as a white solid. $^1$H NMR (DMSO-d$_6$, 400 MHz) δ$_H$=7.28-7.26 (m, 2H), 7.22 (s, 1H), 7.15-7.09 (m, 2H), 7.01 (d, J=8.8 Hz, 1H), 3.54-3.38 (m, 6H), 2.55-2.50 (m, 4H), 2.34 (s, 3H), 1.06 (s, 6H). HPLC R$_t$=4.73 min in 8 min chromatography, Utimate 3.0*50 mm, purity 98.50%. LCMS R$_t$=1.245 min in 2 min chromatography, Xtimate C18 2.1*30 mm, purity 100%, MS ESI calcd. for 427.17 [M+H]$^+$ 428.17, found 428.0.

Example 2. 3-(4-(7-fluoro-3-methyldibenzo[b,f][1,4]oxazepin-11-yl)piperazin-1-yl)-2,2-dimethylpropanoic acid (Compound No. 6)

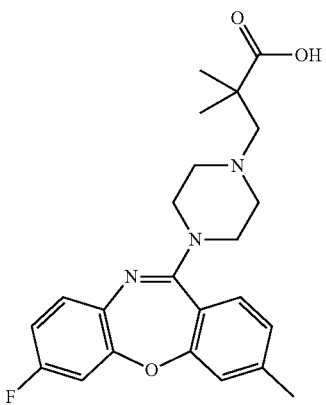 [SMILES: Cc1ccc2c(c1)Oc1cc(F)ccc1N=C2N1CCN(CC(C)(C)C(=O)O)CC1]

Step 1: Synthesis of 4-bromo-2-fluorobenzoyl chloride

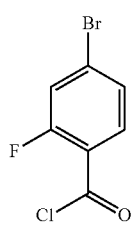

To a mixture of 4-bromo-2-fluorobenzoic acid (10.0 g, 45.66 mmol, 1 eq.) in SOCl$_2$ (98.40 g, 827.10 mmol, 60 mL, 18.11 eq.) was added DMF (334 mg, 4.57 mmol, 351.32 µL, 0.1 eq.). The mixture was stirred at 80° C. for 2 hrs. The mixture was concentrated to give a residue. The filtrate was concentrated to give crude product. The crude product was used directly to the next step without further purification. 4-Bromo-2-fluorobenzoyl chloride (10 g, 42.11 mmol, 92.23% yield) was obtained as a light yellow oil.

Step 2: 4-bromo-2-fluoro-N-(4-fluoro-2-hydroxyphenyl)benzamide

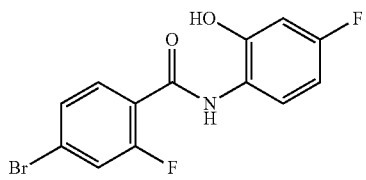 [SMILES: O=C(Nc1ccc(F)cc1O)c1ccc(Br)cc1F]

To a mixture of 2-amino-5-fluorophenol (6.42 g, 50.54 mmol, 1.2 eq.) and TEA (12.78 g, 126.34 mmol, 17.59 mL, 3 eq.) in THF (80 mL) was added a solution of 4-bromo-2-fluorobenzoyl chloride (10.0 g, 42.11 mmol, 1 eq.) in THF (20 mL) dropwise at 0° C. The resulting mixture was allowed to warm up to 25° C. and stirred for 2 hrs. The mixture was diluted EtOAc (500 mL), an washed with brine (800 mL*8). The combined organic layer was dried over Na$_2$SO$_4$, and concentrated to give crude product. The product was purified by column chromatography on silica gel (PE:EtOAc=7:3). 4-bromo-2-fluoro-N-(4-fluoro-2-hydroxyphenyl)benzamide (5.5 g, 13.62 mmol, 32.35% yield, 81.27% purity) was obtained as a brown solid. $^1$H NMR (DMSO-d$_6$, 400 MHz) δ$_H$=10.52 (brs, 1H), 9.47 (d, J=6.0 Hz, 1H), 7.90 (dd, J=2.8, 12.4 Hz, 1H), 7.76-7.72 (m, 3H), 7.60-7.57 (m, 1H), 6.74-6.67 (m, 2H).

Step 3: Synthesis of 3-bromo-7-fluorodibenzo[b,f][1,4]oxazepin-11(10H)-one

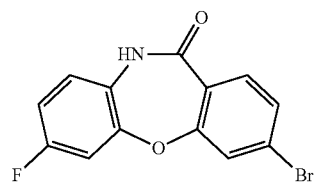 [SMILES: O=C1Nc2ccc(F)cc2Oc2cc(Br)ccc21]

To a mixture of 4-bromo-2-fluoro-N-(4-fluoro-2-hydroxyphenyl)benzamide (5.20 g, 15.85 mmol, 1 eq.) in DMSO (100 mL) was added t-BuOK (3.56 g, 31.70 mmol, 2 eq.). The mixture was stirred at 140° C. for 2 hrs. The mixture was diluted DCM (800 mL), and washed with brine (1000 mL*3). The combined organic layer was concentrated to give crude product. The product was purified by column chromatography on silica gel (DCM:MeOH=4:1). 3-bromo-7-fluorodibenzo[b,f][1,4]oxazepin-11(10H)-one (2.4 g, 6.68 mmol, 42.18% yield, 85.81% purity) was obtained as a brown solid. $^1$H NMR (DMSO-d$_6$, 400 MHz) δ$_H$=10.62 (s, 1H), 7.72-7.69 (m, 2H), 7.57 (dd, J=2.0, 8.4 Hz, 1H), 7.36 (dd, J=2.8, 9.2 Hz, 1H), 7.21-7.17 (m, 1H), 7.14-7.08 (m, 1H).

Step 4: Synthesis of 7-fluoro-3-methyldibenzo[b,f][1,4]oxazepin-11(10H)-one

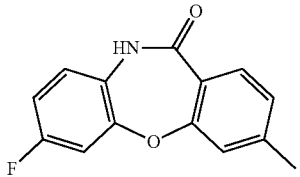 [SMILES: Cc1ccc2c(c1)Oc1cc(F)ccc1NC2=O]

To a mixture of 3-bromo-7-fluorodibenzo[b,f][1,4]oxazepin-11(10H)-one (500 mg, 1.62 mmol, 1 eq.) and MeBF$_3$K (396 mg, 3.25 mmol, 2 eq.) in H$_2$O (1 mL) and 1,4-dioxane (4 mL) was added Pd(dppf)Cl$_2$ (238 mg, 324.57 μmol, 0.2 eq.) and Cs$_2$CO$_3$ (1.06 g, 3.25 mmol, 2 eq.). The mixture was stirred at 80° C. for 2 hrs. The mixture was diluted EtOAc (100 mL), and washed with brine (200 mL*3). The combined organic layer was dried over Na$_2$SO$_4$, and concentrated to give crude product. The product was purified by column chromatography on silica gel (PE:EtOAc=7:3). 7-fluoro-3-methyldibenzo[b,f][1,4]oxazepin-11(10H)-one (260 mg, 975.94 μmol, 60.14% yield, 91.30% purity) was obtained as a brown solid. LCMS R$_t$=1.497 min in 2 min chromatography, Xtimate C18 2.1*30 mm, purity 77.40%, MS ESI calcd. for 243.07 [M+H]$^+$ 244.07, found 244.1.

Step 5: Synthesis of 11-chloro-7-fluoro-3-methyldibenzo[b,f][1,4]oxazepine

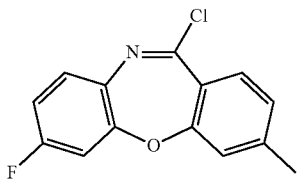

A mixture of 7-fluoro-3-methyldibenzo[b,f][1,4]oxazepin-11(10H)-one (260 mg, 1.07 mmol, 1 eq.) in POCl$_3$ (33.00 g, 215.22 mmol, 20 mL, 201.34 eq.) was stirred at 100° C. for 5 hrs. The mixture was concentrated to give crude product. The product was used directly to the next step without further purification. 11-chloro-7-fluoro-3-methyldibenzo[b,f][1,4]oxazepine (260 mg, 993.59 μmol, 92.95% yield) was obtained as a light yellow solid.

Step 5: Synthesis of methyl 3-(4-(7-fluoro-3-methyldibenzo[b,f][1,4]oxazepin-11-yl)piperazin-1-yl)-2,2-dimethylpropanoate

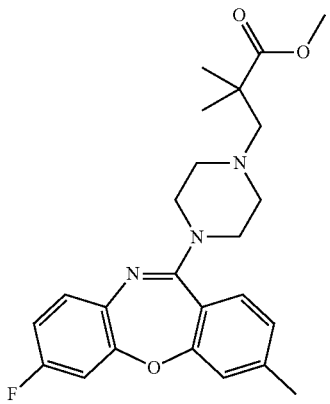

To a mixture of 11-chloro-7-fluoro-3-methyldibenzo[b,f][1,4]oxazepine (250 mg, 955.37 μmol, 1 eq.) and TEA (967 mg, 9.55 mmol, 1.33 mL, 10 eq.) in dioxane (15 mL) was added methyl 2,2-dimethyl-3-(piperazin-1-yl)propanoate (392 mg, 1.43 mmol, 1.5 eq., 2HCl). The mixture was stirred at 110° C. for 10 hrs. The mixture was diluted EtOAc (100 mL), and washed with brine (500 mL*3). The combined organic layer was dried over Na$_2$SO$_4$, and concentrated to give crude product. The product was purified by column chromatography on silica gel (PE:EtOAc=4:1). methyl 3-(4-(7-fluoro-3-methyldibenzo[b,f][1,4]oxazepin-11-yl)piperazin-1-yl)-2,2-dimethylpropanoate (250 mg, 587.55 μmol, 61.50% yield, 100% purity) was obtained as a yellow oil. LCMS R$_t$=1.196 min in 2 min chromatography, Xtimate C18 2.1*30 mm, purity 100%, MS ESI calcd. for 425.21 [M+H]$^+$ 426.21, found 426.2.

Step 6: Synthesis of 3-(4-(7-fluoro-3-methyldibenzo[b,f][1,4]oxazepin-11-yl)piperazin-1-yl)-2,2-dimethylpropanoic acid To a mixture of methyl 3-(4-(7-fluoro-3-methyldibenzo[b,f][1,4]oxazepin-11-yl)piperazin-1-yl)-2,2-dimethylpropanoate (250 mg, 587.55 μmol, 1 eq) in MeOH (6 mL) and H$_2$O (3 mL) was added NaOH (71 mg, 1.76 mmol, 3 eq.). The mixture was stirred at 60° C. for 10 hrs. The mixture was concentrated to remove MeOH. The pH of the mixture was adjusted to around 5 with HCOOH. The product was purified by prep-HPLC (column: Welch Xtimate C18 100*25 mm*3 um; mobile phase: [water (0.225% FA)-ACN]; B %: 24%-34%, 12 min). 3-(4-(7-fluoro-3-methyldibenzo[b,f][1,4]oxazepin-11-yl)piperazin-1-yl)-2,2-dimethylpropanoic acid (63.2 mg, 138.14 μmol, 23.51% yield, 100% purity, FA) was obtained as a white solid. $^1$H NMR (DMSO-d$_6$, 400 MHz) δ$_H$=7.27 (d, J=8.0 Hz, 1H), 7.19 (s, 1H), 7.13 (d, J=8.0 Hz, 1H), 7.09 (dd, J=2.8, 8.8 Hz, 1H), 7.05-7.00 (m, 1H), 6.96-6.92 (m, 1H), 3.45-3.36 (m, 6H), 2.64-2.53 (m, 4H), 2.34 (s, 3H), 1.10 (s, 6H). HPLC R$_t$=3.95 min in 8 min chromatography, Utimate 3.0*50 mm, purity 100%. LCMS R$_t$=1.306 min in 2.0 min chromatography, Xtimate C18 2.1*30 mm, purity 100%, MS ESI calcd. for 411.20 [M+H]$^+$ 412.20, found 412.3.

Example 3. 3-(4-(3,7-dimethyldibenzo[b,f][1,4]oxazepin-11-yl)piperazin-1-yl)-2,2-dimethylpropanoic acid (Compound No. 7)

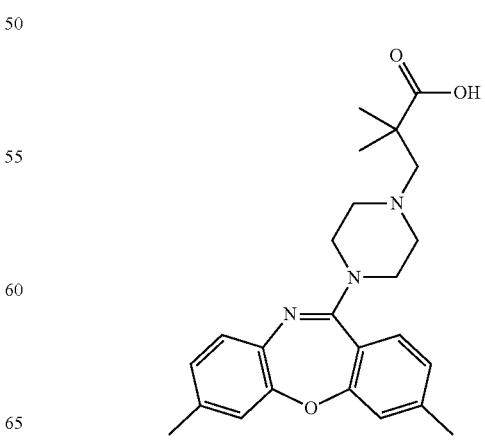

Step 1: Synthesis of 3,7-dimethyldibenzo[b,f][1,4]oxazepin-11(10H)-one

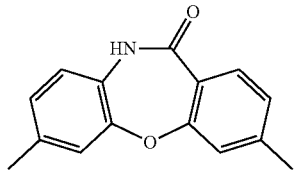

A mixture of 7-bromo-3-methyldibenzo[b,f][1,4]oxazepin-11(10H)-one (576 mg, 1.89 mmol, 1 eq.), MeBF$_3$K (462 mg, 3.79 mmol, 2 eq.), Cs$_2$CO$_3$ (1.85 g, 5.68 mmol, 3 eq.) and Pd(dppf)Cl$_2$ (139 mg, 189.29 µmol, 0.1 eq.) in 1,4-dioxane (15 mL) and H$_2$O (6 mL) was degassed and purged with N$_2$ for 3 times, and then the mixture was stirred at 100° C. for 3 hrs under N$_2$ atmosphere. The mixture was diluted with EtOAc (500 mL), and washed with brine (200 mL*3). The combined organic layer was concentrated to give crude product. The crude product was purified by column chromatography on silica gel (PE:EtOAc=6:1). 3,7-dimethyldibenzo[b,f][1,4]oxazepin-11(10H)-one (507 mg, 1.86 mmol, 98.23% yield, 87.75% purity) was obtained as a yellow solid. LCMS R$_t$=0.899 min in 1.5 min chromatography, Merk RP18e 25-3 mm, purity 87.75%, MS ESI calcd. for 239.09 [M+H]$^+$ 240.09, found 239.9.

Step 2: Synthesis of 11-chloro-3,7-dimethyldibenzo[b,f][1,4]oxazepine

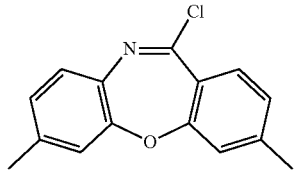

A mixture of 3,7-dimethyldibenzo[b,f][1,4]oxazepin-11(10H)-one (500 mg, 2.09 mmol, 1 eq.) in POCl$_3$ (33.00 g, 215.22 mmol, 20 mL, 102.99 eq.) was stirred at 110° C. for 3 hrs. The mixture was concentrated to give crude product. The crude product was used directly to the next step without further purification. 11-chloro-3,7-dimethyldibenzo[b,f][1,4]oxazepine (500 mg, 1.94 mmol, 92.84% yield) was obtained as a yellow solid.

Step 3: Synthesis of methyl 3-(4-(3,7-dimethyldibenzo[b,f][1,4]oxazepin-11-yl)piperazin-1-yl)-2,2-dimethylpropanoate

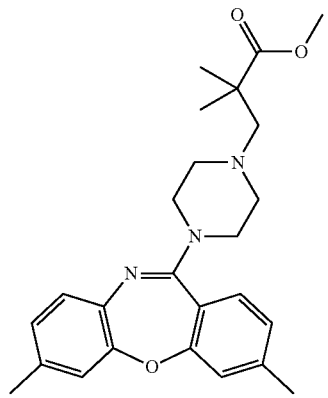

To a mixture of 11-chloro-3,7-dimethyldibenzo[b,f][1,4]oxazepine (500 mg, 1.94 mmol, 1 eq.) and TEA (1.96 g, 19.40 mmol, 2.70 mL, 10 eq.) in 1,4-dioxane (20 mL) was added methyl 2,2-dimethyl-3-piperazin-1-yl-propanoate (795 mg, 2.91 mmol, 1.5 eq., 2HCl). The resulting mixture was stirred at 110° C. for 10 hrs. The mixture was diluted with EtOAc (100 mL), washed with brine (50 mL*3). The combined organic layer was concentrated to give crude product. The product was purified by column chromatography on silica gel (PE:EtOAc=6:1). methyl 3-(4-(3,7-dimethyldibenzo[b,f][1,4]oxazepin-11-yl)piperazin-1-yl)-2,2-dimethylpropanoate (300 mg, 711.69 µmol, 36.68% yield) was obtained as a yellow oil. $^1$H NMR (DMSO-d$_6$, 400 MHz) δ$_H$=7.24 (d, J=8.0 Hz, 1H), 7.14 (s, 1H), 7.09 (d, J=8.4 Hz, 1H), 6.96 (s, 1H), 6.91-6.85 (m, 2H), 3.60 (s, 3H), 3.45-3.36 (m, 6H), 2.56-2.52 (m, 4H), 2.33 (s, 3H), 2.22 (s, 3H), 1.13 (s, 6H).

Step 4: Synthesis of 3-(4-(3,7-dimethyldibenzo[b,f][1,4]oxazepin-11-yl)piperazin-1-yl)-2,2-dimethylpropanoic acid To a mixture of methyl 3-(4-(3,7-dimethyldibenzo[b,f][1,4]oxazepin-11-yl)piperazin-1-yl)-2,2-dimethylpropanoate (300 mg, 711.69 µmol, 1 eq.) in MeOH (10 mL) and H$_2$O (4 mL) was added NaOH (86 mg, 2.14 mmol, 3 eq.). The resulting mixture was stirred at 60° C. for 10 hrs. The mixture was concentrated to remove MeOH. The pH of the mixture was adjusted to around 5 with HCOOH. The product was purified by prep-HPLC (column: Welch Xtimate C18 150*30 mm*5 um; mobile phase: [water (0.225% FA)-ACN]; B %: 20%-40%, 8 min). 3-(4-(3,7-dimethyldibenzo[b,f][1,4]oxazepin-11-yl)piperazin-1-yl)-2,2-dimethylpropanoic acid (115 mg, 253.57 µmol, 35.63% yield, 100% purity, FA) was obtained as a white solid. $^1$H NMR (DMSO-d$_6$, 400 MHz) δ$_H$=7.24 (d, J=8.0 Hz, 1H), 7.14 (s, 1H), 7.09 (d, J=8.0 Hz, 1H), 6.96 (d, J=1.2 Hz, 1H), 6.92-6.84 (m, 2H), 3.76-3.42 (m, 6H), 2.64-2.52 (m, 4H), 2.33 (s, 3H), 2.22 (s, 3H), 1.10 (s, 6H). HPLC R$_t$=3.93 min in 8 min chromatography, Utimate 3.0*50 mm, purity 100%. LCMS R$_t$=1.117 min in 2 min chromatography, Xtimate C18 2.1*30 mm, purity 100%, MS ESI calcd. for 407.22 [M+H]$^+$ 408.22, found 408.2.

Example 4. 3-(4-(7-chloro-3-propyldibenzo[b,f][1,4]oxazepin-11-yl)piperazin-1-yl)-2,2-dimethylpropanoic acid (Compound No. 5)

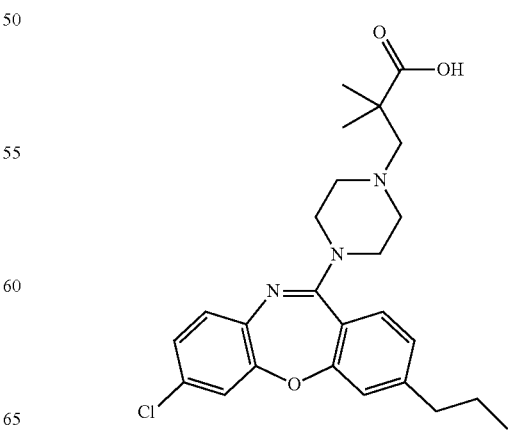

Step 1: Synthesis of methyl (E)-2-fluoro-4-(prop-1-en-1-yl)benzoate

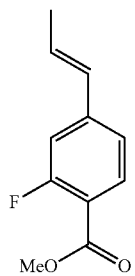

A mixture of methyl 4-bromo-2-fluorobenzoate (10.0 g, 42.91 mmol, 1 eq.), potassium hydride; trifluoro-[(E)-prop-1-enyl]boron (9.52 g, 64.37 mmol, 1.5 eq.), $Cs_2CO_3$ (41.94 g, 128.74 mmol, 3 eq.) and $Pd(dppf)Cl_2$ (3.14 g, 4.29 mmol, 0.1 eq.) in 1,4-dioxane (100 mL) and $H_2O$ (40 mL) was degassed and purged with $N_2$ for 3 times, and then the mixture was stirred at 100° C. for 1 hr under $N_2$ atmosphere. The mixture was diluted with EtOAc (100 mL), and washed with brine (50 mL*3). The combined organic layer was concentrated to give crude product. The crude product was purified by column chromatography on silica gel (PE:E-tOAc=10:1). methyl (E)-2-fluoro-4-(prop-1-en-1-yl)benzoate (8.2 g, 42.22 mmol, 98.40% yield) was obtained as a white solid. $^1$H NMR (DMSO-$d_6$, 400 MHz) $\delta_H$=7.86 (t, J=8.0 Hz, 1H), 7.13 (dd, J=1.6, 8.4 Hz, 1H), 7.07 (dd, J=1.6, 12.4 Hz, 1H), 6.41-6.36 (m, 2H), 3.92 (s, 3H), 1.92 (d, J=4.8 Hz, 3H).

Step 2: Synthesis of methyl 2-fluoro-4-propylbenzoate

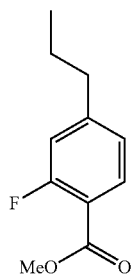

To a mixture of methyl (E)-2-fluoro-4-(prop-1-en-1-yl)benzoate (9.0 g, 46.34 mmol, 1 eq.) in MeOH (90 mL) was added Pd/C (1.0 g, 10% purity) under $N_2$. The suspension was degassed and purged with H2 several times. The mixture was stirred at 25° C. for 16 hrs under H2 atmosphere (15 psi). The reaction mixture was filtered and the filtrate was concentrated. The crude product was used for next step directly without purification. Methyl 2-fluoro-4-propylbenzoate (8.92 g, 45.46 mmol, 98.09% yield) was obtained as a yellow oil. $^1$H NMR (DMSO-$d_6$, 400 MHz) $\delta_H$=7.76 (t, J=8.4 Hz, 1H), 6.92 (dd, J=1.6, 8.0 Hz, 1H), 6.89-6.83 (m, 1H), 3.83 (s, 3H), 2.59-2.49 (m, 2H), 1.57 (q, J=7.6 Hz, 2H), 0.86 (t, J=7.2 Hz, 3H).

Step 3: Synthesis of 2-fluoro-4-propylbenzoic acid

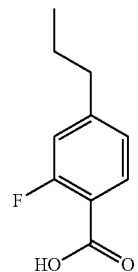

To a mixture of methyl 2-fluoro-4-propylbenzoate (8.92 g, 45.46 mmol, 1 eq.) in MeOH (100 mL), $H_2O$ (100 mL) and THF (100 mL) was added LiOH $H_2O$ (5.72 g, 136.38 mmol, 3 eq.). The mixture was stirred at 25° C. for 4 hrs. The mixture was concentrated to remove MeOH. The pH of the mixture was adjusted to around 1 with 1N HCl. The mixture was filtered via a filter paper, the filter cake was dried under reduced pressure. The product was used directly to the next step without further purification. 2-fluoro-4-propylbenzoic acid (7.88 g, 43.25 mmol, 95.14% yield) was obtained as a white solid. $^1$H NMR (DMSO-$d_6$, 400 MHz) $\delta_H$=7.94 (t, J=8.0 Hz, 1H), 7.06 (dd, J=1.6, 8.0 Hz, 1H), 7.02-6.95 (m, 1H), 2.69-2.61 (m, 2H), 1.68 (q, J=7.6 Hz, 2H), 0.96 (t, J=7.2 Hz, 3H).

Step 4: Synthesis of 2-fluoro-4-propylbenzoyl chloride

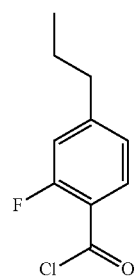

A mixture of 2-fluoro-4-propylbenzoic acid (7.88 g, 43.25 mmol, 1 eq.) in $SOCl_2$ (131.20 g, 1.10 mol, 80 mL, 25.50 eq.) was degassed and purged with $N_2$ for 3 times, and then the mixture was stirred at 80° C. for 2 hr under $N_2$ atmosphere. The reaction mixture was concentrated to dryness. The product was used directly to the next step without further purification. 2-fluoro-4-propylbenzoyl chloride (9.31 g, crude) was obtained as a brown oil.

Step 5: Synthesis of N-(4-chloro-2-hydroxyphenyl)-2-fluoro-4-propylbenzamide

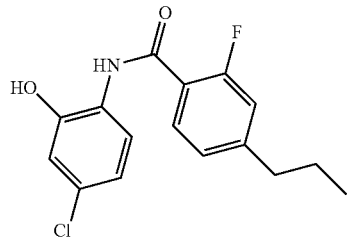 [SMILES: CCCc1ccc(C(=O)Nc2ccc(Cl)cc2O)c(F)c1]

To a mixture of 2-fluoro-4-propylbenzoyl chloride (7.99 g, 55.68 mmol, 1.2 eq.) and TEA (14.09 g, 139.21 mmol, 19.38 mL, 3 eq.) in THF (130 mL) was added a solution of 2-fluoro-4-propyl-benzoyl chloride (9.31 g, 46.40 mmol, 1 eq.) in THF (20 mL) dropwise at 0° C. The resulting mixture was stirred at 25° C. for 3 hrs. The mixture was diluted with EtOAc (200 mL), and washed with brine (200 mL*3). The combined organic layer was concentrated to give crude product. The crude product was purified by column chromatography on silica gel (PE:EtOAc=10% 100%). The product was triturated with EtOAc (30 mL). N-(4-chloro-2-hydroxyphenyl)-2-fluoro-4-propylbenzamide (13.16 g, 42.76 mmol, 92.16% yield) was obtained as a brown solid. $^1$H NMR (DMSO-$d_6$, 400 MHz) $\delta_H$=9.05-9.01 (m, 1H), 8.08 (t, J=8.0 Hz, 1H), 7.21 (d, J=8.4 Hz, 1H), 7.14 (dd, J=1.6, 8.4 Hz, 1H), 7.04-6.98 (m, 1H), 6.89 (dd, J=2.4, 8.4 Hz, 1H), 6.81-6.68 (m, 1H), 2.72-2.59 (m, 2H), 1.72-1.64 (m, 2H), 0.96 (t, J=7.6 Hz, 3H).

Step 6: Synthesis of 7-chloro-3-propyldibenzo[b,f][1,4]oxazepin-11(10H)-one

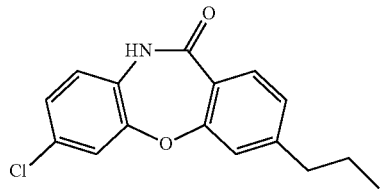 [SMILES: CCCc1ccc2c(c1)Oc1cc(Cl)ccc1NC2=O]

A mixture of N-(4-chloro-2-hydroxyphenyl)-2-fluoro-4-propylbenzamide (13.0 g, 42.24 mmol, 1 eq.) and tBuOK (9.48 g, 84.49 mmol, 2 eq.) in DMF (170 mL) was degassed and purged with $N_2$ for 3 times, and then the mixture was stirred at 140° C. for 2 hrs under $N_2$ atmosphere. The mixture was poured into $H_2O$ (400 mL) slowly. The mixture was filtered via a filter paper, and the filter cake was dried under reduced pressure. The crude product was purified by column chromatography on silica gel (PE:EtOAc=6% 20%). 7-chloro-3-propyldibenzo[b,f][1,4]oxazepin-11(10H)-one (3 g, 8.84 mmol, 20.92% yield, 84.74% purity) was obtained as a yellow solid. $^1$H NMR (DMSO-$d_6$, 400 MHz) $\delta_H$=8.48 (s, 1H), 7.77 (d, J=8.0 Hz, 1H), 7.20 (d, J=2.4 Hz, 1H), 7.03 (d, J=2.4 Hz, 1H), 6.97 (s, 1H), 6.92 (d, J=8.4 Hz, 1H), 2.60-2.51 (m, 2H), 1.60 (q, J=7.6 Hz, 2H), 0.88 (t, J=7.2 Hz, 3H)

Step 7: Synthesis of 7,11-dichloro-3-propyldibenzo[b,f][1,4]oxazepine

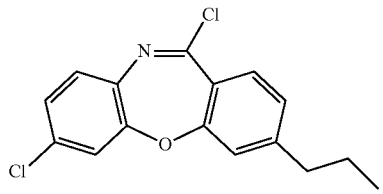 [SMILES: CCCc1ccc2c(c1)Oc1cc(Cl)ccc1N=C2Cl]

A mixture of 7-chloro-3-propyldibenzo[b,f][1,4]oxazepin-11(10H)-one (300 mg, 1.04 mmol, 1 eq) in $POCl_3$ (15 mL) was stirred at 100° C. for 5 hour. The reaction mixture was concentrated under reduce pressure. The residue was diluted with DCM (30 mL), washed with brine (20 mL*2). The combined organic layer was dried over $Na_2SO_4$, filtered and concentrated to give a residue. The crude product was used for next step directly without purification. 7,11-dichloro-3-propyldibenzo[b,f][1,4]oxazepine (350 mg, crude) was obtained as a yellow oil. LCMS $R_t$=1.105 min in 1.5 min chromatography, Agilent Pursult C18 2.1*30 mm, purity 78.871%, MS ESI calcd. for 305.04 [M+H]$^+$ 306.04, found 305.9.

Step 8: Synthesis of methyl 3-(4-(7-chloro-3-propyldibenzo[b,f][1,4]oxazepin-11-yl)piperazin-1-yl)-2,2-dimethylpropanoate

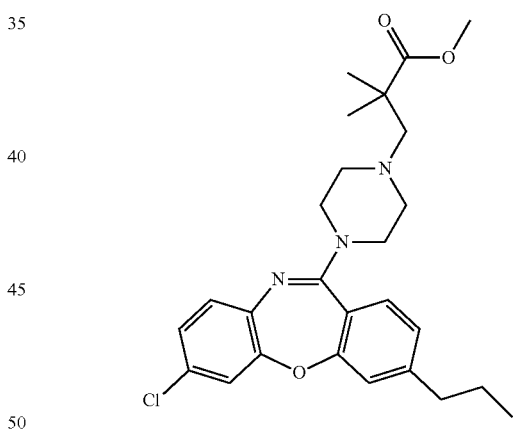

To a mixture of 7,11-dichloro-3-propyldibenzo[b,f][1,4]oxazepine (300 mg, 979.80 μmol, 1 eq.) in dioxane (10 mL) was added TEA (496 mg, 4.90 mmol, 681.88 μL, 5 eq.) and methyl 2,2-dimethyl-3-piperazin-1-yl-propanoate (589 mg, 2.94 mmol, 3 eq.). The mixture was stirred at 110° C. for 10 hr under $N_2$ atmosphere. The mixture was diluted with EtOAc (500 mL), washed with brine (200 mL*3). The combined organic layer was concentrated to give crude product. The crude product was purified by column chromatography on silica gel (PE:EtOAc=10% 20%). methyl 3-(4-(7-chloro-3-propyldibenzo[b,f][1,4]oxazepin-11-yl)piperazin-1-yl)-2,2-dimethylpropanoate (290 mg, 607.40 μmol, 61.99% yield, 98.441% purity) was obtained as a yellow oil. LCMS $R_t$=1.503 min in 2 min chromatography, Xtimate C18 2.1*30 mm, purity 98.441%, MS ESI calcd. for 469.21 [M+H]$^+$ 470.21, found 470.3.

Step 9: Synthesis of 3-(4-(7-chloro-3-propyldibenzo[b,f][1,4]oxazepin-11-yl)piperazin-1-yl)-2,2-dimethylpropanoic acid To a mixture of methyl 3-(4-(7-chloro-3-propyldibenzo[b,f][1,4]oxazepin-11-yl)piperazin-1-yl)-2,2-dimethylpropanoate (250 mg, 531.91 µmol, 1 eq) in MeOH (6 mL) and H₂O (2 mL) was added NaOH (64 mg, 1.60 mmol, 3 eq), and then the mixture was stirred at 60° C. for 10 hr under N₂ atmosphere. The mixture was concentrated to remove MeOH. The pH of the mixture was adjusted to around 5 with HCOOH. The crude product was purified by prep-HPLC (column: Welch Xtimate C18 150*25 mm*5 um; mobile phase: [water (0.225% FA)-ACN]; B %: 32%-52%, 7 min). 3-(4-(7-chloro-3-propyldibenzo[b,f][1,4]oxazepin-11-yl)piperazin-1-yl)-2,2-dimethylpropanoic acid (70.1 mg, 149.29 µmol, 28.07% yield, 97.11% purity) was obtained as a white solid. ¹H NMR (DMSO-d₆, 400 MHz) $\delta_H$=7.22 (d, J=8.4 Hz, 1H), 7.16-7.13 (m, 1H), 7.09-7.02 (m, 4H), 3.77-3.56 (m, 4H), 2.96-2.84 (m, 4H), 2.66-2.58 (m, 4H), 1.68 (q, J=7.2 Hz, 2H), 1.28 (s, 6H), 0.98 (t, J=7.6 Hz, 3H). HPLC $R_t$=5.34 min in 8 min chromatography, Utimate 3.0*50 mm, purity 97.11%. LCMS $R_t$=1.489 min in 2 min chromatography, Xtimate C18 2.1*30 mm, purity 96.89%, MS ESI calcd. for 455.20 [M+H]⁺ 456.20, found 456.3.

Example 5. 3-(4-(11H-dibenzo[b,e]azepin-6-yl)piperazin-1-yl)-2,2-dimethylpropanoic acid (Compound No. 8)

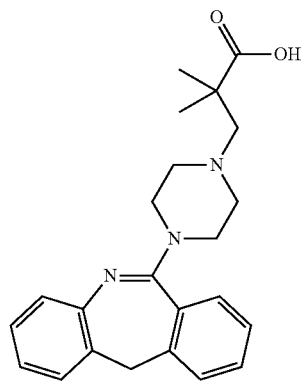 [SMILES: CC(C)(CN1CCN(C2=Nc3ccccc3Cc3ccccc32)CC1)C(=O)O]

Step 1: Synthesis of 5,11-dihydro-6H-dibenzo[b,e]azepin-6-one

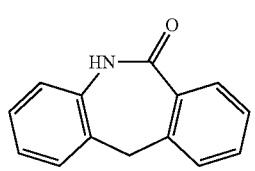 [SMILES: O=C1Nc2ccccc2Cc2ccccc21]

To a mixture of 5H-dibenzo[b,e]azepine-6,11-dione (4.9 g, 21.95 mmol, 1 eq.) in TFA (200 mL) was added triethylsilane (25.52 g, 219.51 mmol, 35.06 mL, 10 eq.). The mixture was stirred at 25° C. for 10 hrs. The mixture was concentrated to give a residue. The product was purified by column chromatography on silica gel (PE:EtOAc=6:1). 5,11-dihydro-6H-dibenzo[b,e]azepin-6-one (5.3 g, 21.79 mmol, 99.27% yield, 86.03% purity) was obtained as a white solid. ¹H NMR (DMSO-d₆, 400 MHz) $\delta_H$=10.44 (s, 1H), 7.71 (d, J=7.2 Hz, 1H), 7.52-7.44 (m, 1H), 7.40-7.29 (m, 3H), 7.21-7.15 (m, 1H), 7.15-7.10 (m, 1H), 7.10-7.04 (m, 1H), 3.90 (s, 2H).

Step 2: Synthesis of 6-chloro-11H-dibenzo[b,e]azepine

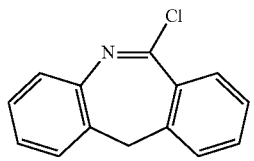 [SMILES: ClC1=Nc2ccccc2Cc2ccccc21]

A mixture of 5,11-dihydro-6H-dibenzo[b,e]azepin-6-one (300 mg, 1.43 mmol, 1 eq.) in POCl₃ (20 mL) was degassed and purged with N₂ for 3 times, and then the mixture was stirred at 110° C. for 3 hr under N₂ atmosphere. The reaction mixture was quenched by addition water (50 mL), and then extracted with DCM (50 mL*2). The combined organic layers were washed with brine (50 mL*2), dried over anhydrous Na₂SO₄, filtered and concentrated under reduced pressure to give a residue. The residue was used into next step without further purification. 6-chloro-11H-dibenzo[b,e]azepine (300 mg, 1.32 mmol, 91.90% yield) was obtained as a brown oil.

Step 3: methyl 3-(4-(H-dibenzo[b,e]azepin-6-yl)piperazin-1-yl)-2,2-dimethylpropanoate

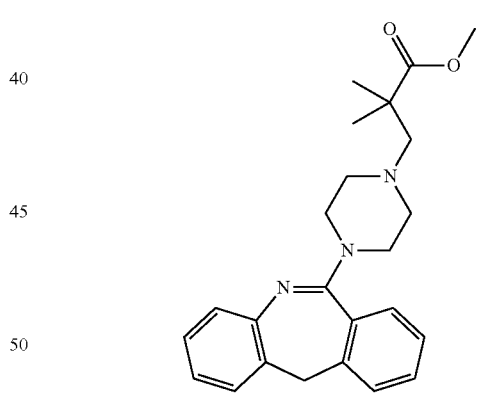

To a mixture of 6-chloro-11H-dibenzo[b,e]azepine (300 mg, 1.32 mmol, 1 eq.) and TEA (1.33 g, 13.18 mmol, 1.83 mL, 10 eq.) in dioxane (20 mL) was added methyl 2,2-dimethyl-3-piperazin-1-yl-propanoate (540 mg, 1.98 mmol, 1.5 eq., 2HCl). The mixture was stirred at 110° C. for 20 hrs. The mixture was diluted EtOAc (100 mL), washed with brine (200 mL*3). The combined organic layer was dried over Na₂SO₄, and concentrated to give crude product. The product was purified by column chromatography on silica gel (PE:EtOAc=4:1). methyl 3-(4-(11H-dibenzo[b,e]azepin-6-yl)piperazin-1-yl)-2,2-dimethylpropanoate (250 mg, 584.92 µmol, 44.39% yield, 91.60% purity) was obtained as a yellow oil. ¹H NMR (DMSO-d₆, 400 MHz) $\delta_H$=7.41-7.37 (m, 2H), 7.36-7.31 (m, 1H), 7.31-7.25 (m, 1H), 7.18 (d, J=7.2 Hz, 1H), 7.10-7.02 (m, 1H), 6.95-6.86 (m, 2H), 3.68 (d, J=14.8 Hz, 1H), 3.59 (s, 3H), 3.45 (d, J=10.0 Hz, 1H), 3.43-3.35 (m, 6H), 2.58-2.56 (m, 2H), 2.55-2.52 (m, 2H), 1.12 (s, 6H)

Step 4: Synthesis of 3-(4-(H-dibenzo[b,e]azepin-6-yl)piperazin-1-yl)-2,2-dimethylpropanoic acid To a mixture of methyl 3-(4-(11H-dibenzo[b,e]azepin-6-yl)piperazin-1-yl)-2,2-dimethylpropanoate (250 mg, 638.56 μmol, 1 eq.) in MeOH (6 mL) and $H_2O$ (3 mL) was added NaOH (77 mg, 1.92 mmol, 3 eq.). The mixture was stirred at 60° C. for 10 hrs. The mixture was concentrated to remove MeOH. The pH of the mixture was adjusted to around 5 with HCOOH. The product was purified by prep-HPLC (column: Welch Xtimate C18 150*30 mm*5 um; mobile phase: [water (0.225% FA)-ACN]; B %: 15%-40%, 6 min). 3-(4-(11H-dibenzo[b,e]azepin-6-yl)piperazin-1-yl)-2,2-dimethylpropanoic acid (118.3 mg, 279.34 μmol, 43.74% yield, 100% purity, FA) was obtained as a white solid. $^1$H NMR (DMSO-$d_6$, 400 MHz) $\delta_H$=12.39 (s, 1H), 8.15 (s, 0.14H), 7.45-7.25 (m, 2H), 7.19 (d, J=7.2 Hz, 1H), 7.06 (t, J=7.6 Hz, 1H), 6.97-6.86 (m, 2H), 3.68 (d, J=13.2 Hz, 1H), 3.52-3.37 (m, 7H), 2.72-2.57 (m, 3H), 1.10 (s, 6H). HPLC $R_t$=3.14 min in 8 min chromatography, Utimate 3.0*50 mm, purity 99.92%. LCMS $R_t$=0.978 min in 2 min chromatography, Xtimate C18 2.1*30 mm, purity 100%, MS ESI calcd. for 377.21 [M+H]$^+$ 378.21, found 378.2.

Example 6. 1-((4-(7-chloro-3-methyldibenzo[b,f][1,4]oxazepin-11-yl)piperazin-1-yl)methyl)cyclopropane-1-carboxylic acid (Compound No. 13)

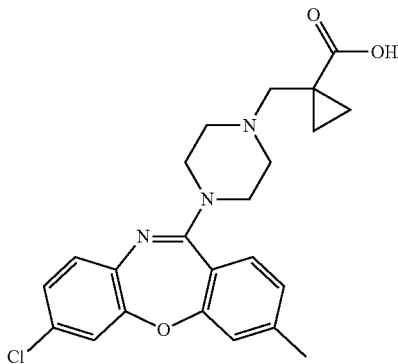 [SMILES: Cc1ccc2c(c1)Oc1cc(Cl)ccc1N=C2N1CCN(CC2(C(=O)O)CC2)CC1]

Step 1: Synthesis of methyl 1-((4-(7-chloro-3-methyldibenzo[b,f][1,4]oxazepin-11-yl)piperazin-1-yl)methyl)cyclopropane-1-carboxylate

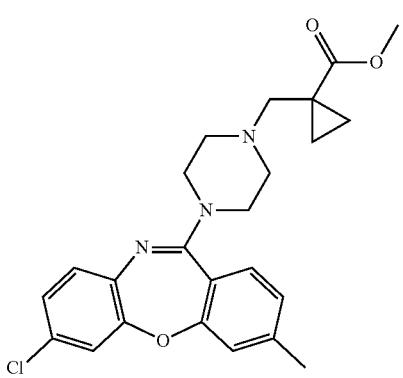 [SMILES: COC(=O)C1(CN2CCN(C3=Nc4ccc(Cl)cc4Oc4cc(C)ccc43)CC2)CC1]

To a mixture of 7-chloro-3-methyl-11-(piperazin-1-yl)dibenzo[b,f][1,4]oxazepine (150 mg, 457.59 μmol, 1 eq.) and methyl 1-formylcyclopropane-1-carboxylate (293 mg, 2.29 mmol, 5 eq.) in DCM (5 mL) was added NaBH(OAc)$_3$ (485 mg, 2.29 mmol, 5 eq.). The resulting mixture was stirred at 25° C. for 2 hrs. The mixture was diluted with EtOAc (100 mL), washed with brine (50 mL*3). The combined organic layer was concentrated to give crude product. The crude product was purified by column chromatography on silica gel (PE:EtOAc=1:1). methyl 1-((4-(7-chloro-3-methyldibenzo[b,f][1,4]oxazepin-11-yl)piperazin-1-yl)methyl)cyclopropane-1-carboxylate (120 mg, 248.38 μmol, 54.28% yield, 91.06% purity) was obtained as a yellow oil. LCMS $R_t$=1.431 min in 2 min chromatography, Xtimate C18 2.1*30 mm, purity 91.06%, MS ESI calcd. for 439.17 [M+H]$^+$ 440.17, found 440.3.

Step 2: Synthesis of 1-((4-(7-chloro-3-methyldibenzo[b,f][1,4]oxazepin-11-yl)piperazin-1-yl)methyl)cyclopropane-1-carboxylic acid To a mixture of methyl 1-((4-(7-chloro-3-methyldibenzo[b,f][1,4]oxazepin-11-yl)piperazin-1-yl)methyl)cyclopropane-1-carboxylate (120 mg, 272.77 μmol, 1 eq.) in MeOH (6 mL) and $H_2O$ (4 mL) was added NaOH (33 mg, 818.30 μmol, 3 eq.). The resulting mixture was stirred at 60° C. for 10 hrs. The mixture was concentrated to remove MeOH. The pH of the mixture was adjusted to around 5 with HCOOH. The product was purified by prep-HPLC (column: Venusil ASB Phenyl 150*30 mm*5 um; mobile phase: [water (0.05% HCl)-ACN]; B %: 36%-66%, 9 min). 1-((4-(7-chloro-3-methyldibenzo[b,f][1,4]oxazepin-11-yl)piperazin-1-yl)methyl)cyclopropane-1-carboxylic acid (35.5 mg, 75.08 μmol, 27.53% yield, 97.79% purity, HCl) was obtained as a light yellow solid. $^1$H NMR (DMSO-$d_6$, 400 MHz) $\delta_H$=10.83 (brs, 1H), 7.56-7.44 (m, 2H), 7.39-7.21 (m, 4H), 4.20-4.07 (m, 4H), 3.68-3.15 (m, 6H), 2.39 (s, 3H), 1.46-1.40 (m, 2H), 1.36-1.29 (m, 2H). HPLC $R_t$=4.62 min in 8 min chromatography, Utimate 3.0*50 mm, purity 97.79%. LCMS $R_t$=1.224 min in 2 min chromatography, Xtimate C18 2.1*30 mm, purity 100%, MS ESI calcd. for 425.15 [M+H]$^+$ 425.15, found 426.2.

Example 7. 3-(4-(7-(difluoromethyl)-3-methyldibenzo[b,f][1,4]oxazepin-11-yl)piperazin-1-yl)-2,2-dimethylpropanoic acid (Compound No. 16)

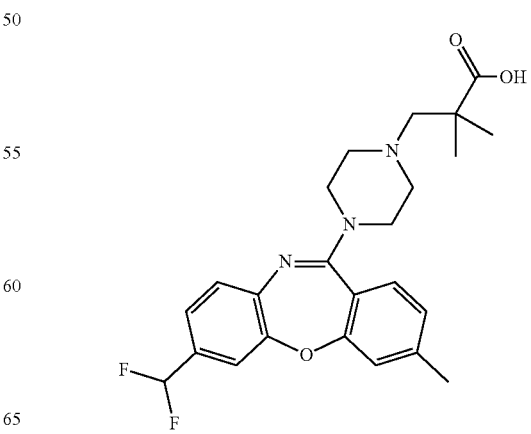

Step 1: Synthesis of 3-methyl-7-vinyldibenzo[b,f][1,4]oxazepin-11(10H)-one

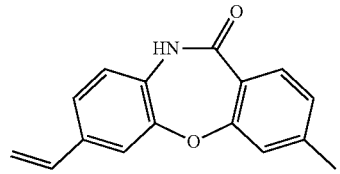 [SMILES: C=Cc1ccc2c(c1)Oc1cc(C)ccc1C(=O)N2]

A mixture of 7-bromo-3-methyldibenzo[b,f][1,4]oxazepin-11(10H)-one (1 g, 3.29 mmol, 1 eq.), potassium vinyltrifluoroborate (1.01 g, 6.58 mmol, 2 eq.), Cs$_2$CO$_3$ (2.14 g, 6.58 mmol, 2 eq.), Pd(dppf)Cl$_2$ (241 mg, 328.80 μmol, 0.1 eq.) in H$_2$O (2 mL) and dioxane (10 mL) was degassed and purged with N$_2$ for 3 times, and then the mixture was stirred at 100° C. for 2 hr under N$_2$ atmosphere. The reaction mixture was diluted with water (100 mL) and extracted with EtOAc (100 mL*2). The combined organic layers were washed with brine (100 mL*2), dried over anhydrous Na$_2$SO$_4$, filtered and concentrated. The residue was purified by flash silica gel chromatography (Silica Flash Column, Eluent of 0$_1$5% Ethyl acetate/Petroleum ether). 3-methyl-7-vinyldibenzo[b,f][1,4]oxazepin-11(10H)-one (600 mg, 2.13 mmol, 64.92% yield, 89.39% purity) was obtained as a yellow solid. LCMS R$_t$=0.910 min in 1.5 min chromatography, Merk RP18e 25-3 mm, purity 89.39%, MS ESI calcd. for 251.09 [M+H]$^+$ 252.09, found 252.

Step 2: Synthesis of 3-methyl-1-oxo-10, 11-dihydrodibenzo [b,f][1, 4] oxazepine-7-carbaldehyde

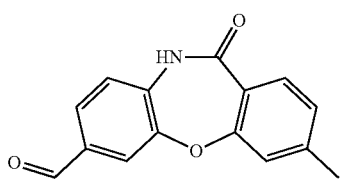 [SMILES: Cc1ccc2c(c1)Oc1cc(C=O)ccc1NC2=O]

To a mixture of 3-methyl-7-vinyldibenzo[b,f][1,4]oxazepin-11(10H)-one (600 mg, 2.39 mmol, 1 eq.) in THF (10 mL) and H$_2$O (3 mL) was added OsO$_4$ (30 mg, 119.50 μmol, 6.19 μL, 0.05 eq.) at −5° C. After stirring at −5° C. for 10 min, a solution of NaIO$_4$ (1.02 g, 4.78 mmol, 265 μL, 2 eq.) in H$_2$O (10 mL) was added at −5° C., and then the mixture was stirred at −5° C. for 2 hr. The reaction mixture was quenched by addition sat.Na$_2$SO$_3$ (100 mL), and then extracted with EtOAc (100 mL*2). The combined organic layers were washed with brine (100 mL*2), dried over anhydrous Na$_2$SO$_4$, filtered and concentrated under reduced pressure to give a residue. The residue was purified by flash silica gel chromatography (Silica Flash Column, Eluent of 030% Ethyl acetate/Petroleum ether). 3-methyl-1-oxo-10,11-dihydrodibenzo[b,f][1,4]oxazepine-7-carbaldehyde (500 mg, 1.92 mmol, 80.30% yield, 97.21% purity) was obtained as a yellow solid. LCMS R$_t$=0.784 min in 1.5 min chromatography, Agilent Pursult 5 C18 20*2.0 mm, purity 97.21%, MS ESI calcd. for 253.07 [M+H]$^+$ 254.07, found 253.8.

Step 3: Synthesis of 7-(difluoromethyl)-3-methyldibenzo [b, f] [1, 4] oxazepin-11(10H)-one

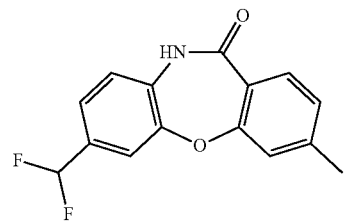 [SMILES: Cc1ccc2c(c1)Oc1cc(C(F)F)ccc1NC2=O]

To a mixture of 3-methyl-1-oxo-10,11-dihydrodibenzo[b,f][1,4]oxazepine-7-carbaldehyde (500 mg, 1.97 mmol, 1 eq.) in DCM (10 mL) was added DAST (955 mg, 5.92 mmol, 783 μL, 3 eq.) at −5° C., and then the mixture was stirred at −5° C. for 16 hr under N$_2$ atmosphere. The reaction mixture was quenched by addition sat.NaHCO$_3$(100 mL), and then extracted with DCM (100 mL*2). The combined organic layers were washed with brine (100 mL*2), dried over anhydrous Na$_2$SO$_4$, and concentrated. The residue was purified by flash silica gel chromatography (Silica Flash Column, Eluent of 0-15% Ethyl acetate/Petroleum ether). 7-(difluoromethyl)-3-methyldibenzo[b,f][1,4]oxazepin-11(10H)-one (500 mg, crude) was obtained as a yellow solid. $^1$H NMR (CDCl$_3$, 400 MHz) δ$_H$=8.43 (s, 1H), 7.88-7.80 (m, 1H), 7.43 (s, 1H), 7.18-7.03 (m, 4H), 6.62 (t, J=56.4 Hz, 1H), 2.41 (s, 3H).

Step 4: Synthesis of 11-chloro-7-(difluoromethyl)-3-methyldibenzo [b, f] [1, 4]oxazepine

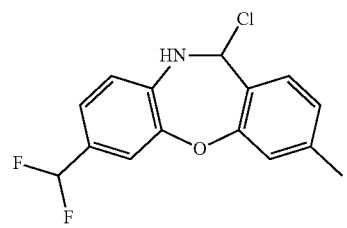 [SMILES: Cc1ccc2c(c1)Oc1cc(C(F)F)ccc1NC2Cl]

A mixture of 7-(difluoromethyl)-3-methyldibenzo[b,f][1,4]oxazepin-11(10H)-one (170 mg, 617.62 μmol, 1 eq.) in POCl$_3$ (20 mL) was degassed and purged with N$_2$ 3 times, and then the mixture was stirred at 100° C. for 3 hr under N$_2$ atmosphere. The reaction mixture was evaporated, and the residue was diluted with DCM (100 mL*2), washed with brine (100 mL*2). The combined organic layer was dried over anhydrous Na$_2$SO$_4$, filtered and concentrated under reduced pressure. The crude product was used into next step without further purification. 11-chloro-7-(difluoromethyl)-3-methyldibenzo[b,f][1,4]oxazepine (150 mg, 510.73 μmol, 82.69% yield) was obtained as a yellow oil.

Step 5: Synthesis of methyl 3-(4-(7-(difluoromethyl)-3-methyldibenzo[b, f][1,4]oxazepin-11-yl)piperazin-1-yl)-2, 2-dimethylpropanoate

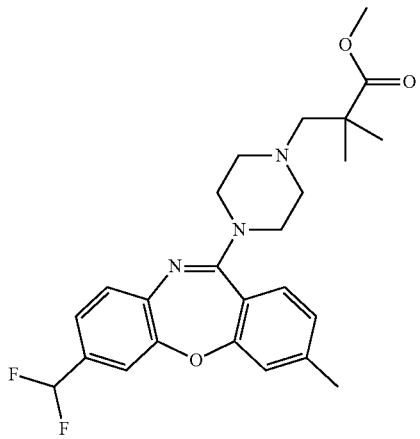 [SMILES: COC(=O)C(C)(C)CN1CCN(C2=Nc3ccc(C(F)F)cc3Oc3cc(C)ccc32)CC1]

A mixture of 11-chloro-7-(difluoromethyl)-3-methyl-dibenzo[b,f][1,4]oxazepine (150 mg, 510.73 μmol, 1 eq.), methyl 2,2-dimethyl-3-piperazin-1-yl-propanoate (307 mg, 1.53 mmol, 3 eq.), TEA (258 mg, 2.55 mmol, 355 μL, 5 eq.) in 1,4-dioxane (10 mL) was degassed and purged with $N_2$ for 3 times, and then the mixture was stirred at 120° C. for 16 hr under $N_2$ atmosphere. The reaction mixture was quenched by addition water 100 mL, and then was extracted with EtOAc (50 mL*2). The combined organic layers were washed with brine (100 mL*2), dried over anhydrous $Na_2SO_4$, filtered and concentrated. The residue was purified by flash silica gel chromatography (Silica Flash Column, Eluent of $0_{20}$% Ethyl acetate/Petroleum ether). Methyl 3-(4-(7-(difluoromethyl)-3-methyldibenzo[b,f][1,4]oxazepin-11-yl)piperazin-1-yl)-2,2-dimethylpropanoate (150 mg, 208.45 μmol, 40.81% yield, 63.58% purity) was obtained as a yellow oil. LCMS $R_t$=0.803 min in 1.5 min chromatography, Agilent Pursult 5 C18 20*2.0 mm, purity 63.58%, MS ESI calcd. for 457.22 $[M+H]^+$ 458.22, found 458.1.

Step 6: Synthesis of 3-(4-(7-(difluoromethyl)-3-methyldibenzo [b, f] [1, 4] oxazepin-1-yl) piperazin-1-yl)-2, 2-dimethylpropanoic acid A mixture of methyl 3-(4-(7-(difluoromethyl)-3-methyldibenzo[b,f][1,4]oxazepin-11-yl)piperazin-1-yl)-2,2-dimethylpropanoate (150 mg, 327.86 μmol, 1 eq.), NaOH (39 mg, 983.58 μmol, 3 eq.), in MeOH (5 mL) and $H_2O$ (2 mL) was degassed and purged with $N_2$ 3 times, and then the mixture was stirred at 60° C. for 16 hr under $N_2$ atmosphere. The reaction mixture was acidified with HCOOH to pH=5, and then concentrated. The residue was purified by prep-HPLC (column: Welch Xtimate C18 150*25 mm*5 um; mobile phase: [water (0.225% FA)-ACN]; B %: 30%-60%, 8 min). 3-(4-(7-(difluoromethyl)-3-methyldibenzo[b,f][1,4]oxazepin-11-yl)piperazin-1-yl)-2,2-dimethylpropanoic acid (41 mg, 91.94 μmol, 28.04% yield, 99.45% purity) was obtained as a light yellow solid. $^1$H NMR (CDCl$_3$, 400 MHz) $\delta_H$=7.31-7.29 (m, 1H), 7.25-7.16 (m, 3H), 7.13-7.10 (m, 1H), 7.04 (d, J=7.6 Hz, 1H), 6.60 (t, J=56.4 Hz, 1H), 3.95-3.46 (m, 4H), 3.02-2.78 (m, 4H), 2.63 (s, 2H), 2.40 (s, 3H), 1.28 (s, 6H). HPLC $R_t$=4.47 min in 8 min chromatography, Ultimate 3.0*50 mm 3 um, purity 99.45%. LCMS $R_t$=1.180 min in 2 min chromatography, Xtimate C18 2.1*30 mm, purity 100%, MS ESI calcd. for 443.20 $[M+H]^+$ 444.20, found 444.3.

Example 8. 3-(4-(3-(difluoromethyl)-7-methyl-dibenzo[b,f][1,4]oxazepin-11-yl)piperazin-1-yl)-2,2-dimethylpropanoic acid (Compound No. 15)

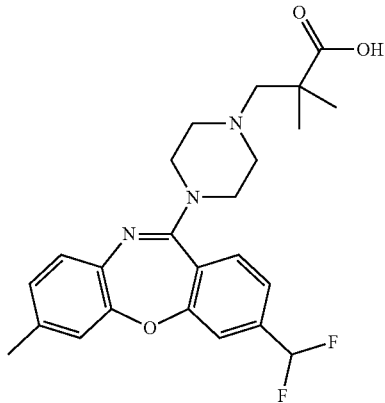 [SMILES: Cc1ccc2c(c1)Oc1cc(C(F)F)ccc1C(N1CCN(CC(C)(C)C(=O)O)CC1)=N2]

Step 1: Synthesis of 7-methyl-11-oxo-10, 11-dihydrodibenzo [b, f] [1, 4] oxazepine-3-carbaldehyde

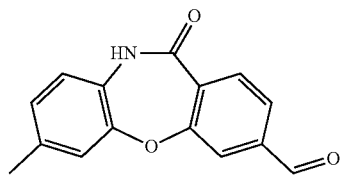 [SMILES: Cc1ccc2c(c1)Oc1cc(C=O)ccc1C(=O)N2]

To a solution of 7-methyl-3-vinyldibenzo[b,f][1,4]oxazepin-11(10H)-one (1.4 g, 5.57 mmol, 1 eq.) in THF (30 mL) was added OsO$_4$ (71 mg, 278.57 μmol, 14.45 μL, 0.05 eq.) in H$_2$O (5 mL). The mixture was stirred at 0° C. for 10 min. To the mixture was added NaIO$_4$ (4.77 g, 22.29 mmol, 1.23 mL, 4 eq.) in H$_2$O (5 mL). And then the mixture was allowed to warm up to 25° C. and stirred for 1 hr. The reaction mixture was quenched with saturated aqueous Na$_2$S$_2$O$_3$ (30 mL) and the mixture was stirred at 0° C. for another 1 hour, and extracted with EtOAc (50 mL*3). The combined organic layers were washed with brine (50 mL), dried over Na$_2$SO$_4$, filtered and concentrated. The residue was purified by column chromatography (SiO$_2$, EtOAc/(PE:DCM= 1:1)=0 to 20%). 7-methyl-1-oxo-10,11-dihydrodibenzo[b,f][1,4]oxazepine-3-carbaldehyde (1 g, 3.95 mmol, 70.87% yield) was obtained as a white solid. $^1$H NMR (400 MHz, CDCl$_3$) $\delta$=10.06 (s, 1H), 8.49 (s, 1H), 8.10 (d, J=8.8 Hz, 1H), 7.77-7.71 (m, 2H), 7.13 (s, 1H), 7.00-6.90 (m, 2H), 2.33 (s, 3H).

Step 2: Synthesis of 3-(difluoromethyl)-7-methyl-dibenzo[b, f] [1, 4]oxazepin-11(10H)-one

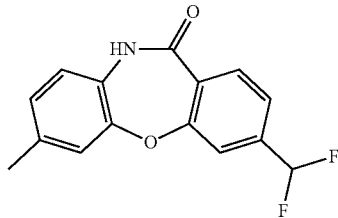 [SMILES: Cc1ccc2c(c1)Oc1cc(C(F)F)ccc1C(=O)N2]

To a mixture of 7-methyl-1-oxo-10,11-dihydrodibenzo[b,f][1,4]oxazepine-3-carbaldehyde (500 mg, 1.97 mmol, 1 eq.) in DCM (10 mL) was added DAST (955 mg, 5.92 mmol, 782.55 µL, 3 eq.) at −5° C. under $N_2$ atmosphere, and then the mixture was allowed to warm up to 25° C. and stirred for 16 hr. The reaction mixture was quenched by addition saturated aqueous $NaHCO_3$(100 mL), and then extracted with EtOAc (100 mL*2). The combined organic layers were washed with brine (100 mL*2), dried over anhydrous $Na_2SO_4$, filtered and concentrated under reduced pressure. The residue was purified by flash silica gel chromatography (Silica Flash Column, Eluent of 025% Ethyl acetate/Petroleum ether). 3-(difluoromethyl)-7-methyl-dibenzo[b,f][1,4]oxazepin-11(10H)-one (190 mg, 687.38 µmol, 34.82% yield, 99.58% purity) was obtained as a white solid. $^1$H NMR (400 MHz, $CDCl_3$) δ=8.05-7.95 (m, 2H), 7.45-7.35 (m, 2H), 7.15-7.05 (m, 1H), 7.01-6.86 (m, 2H), 6.65 (t, J=56 Hz, 1H), 2.33 (s, 3H).

Step 3: Synthesis of 11-chloro-3-(difluoromethyl)-7-methyl-10,11-dihydrodibenzo[b,f][1,4]oxazepine

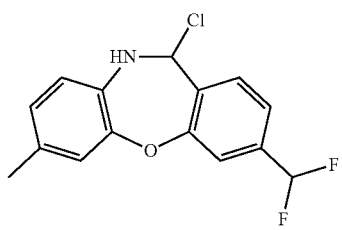 [SMILES: Cc1ccc2c(c1)Oc1cc(C(F)F)ccc1C(Cl)N2]

A mixture of 3-(difluoromethyl)-7-methyldibenzo[b,f][1,4]oxazepin-11(10H)-one (190 mg, 690.28 mmol, 1 eq.) in $POCl_3$ (40 mL) was stirred at 110° C. for 5 hr. The reaction mixture was dried under reduced pressure. Then it was dissolved with DCM (100 mL) and extracted with $H_2O$ (100 mL). The organic layers were washed with brine (100 mL), dried over $Na_2SO_4$, filtered and concentrated under reduced pressure. The product was used for next step directly without further purification. 11-chloro-3-(difluoromethyl)-7-methyl-10,11-dihydrodibenzo[b,f][1,4]oxazepine (250 mg, crude) was obtained as a yellow oil.

Step 4: Synthesis of methyl 3-(4-(3-(difluoromethyl)-7-methyldibenzo[b,f][1,4]oxazepin-11-yl) piperazin-1-yl)-2,2-dimethylpropanoate

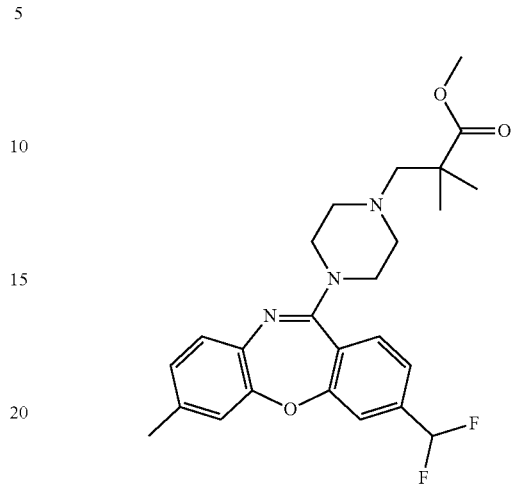

A mixture of methyl 2,2-dimethyl-3-(piperazin-1-yl)propanoate (271 mg, 1.35 mmol, 2 eq.), 11-chloro-3-(difluoromethyl)-7-methyl-10,11-dihydrodibenzo[b,f][1,4]oxazepine (200 mg, 676.34 µmol, 1 eq.), and TEA (685 mg, 6.76 mmol, 941.38 µL, 10 eq.) in dioxane (10 mL) and DMSO (2 mL) was stirred at 120° C. for 16 hr. The reaction mixture was diluted with $H_2O$ (50 mL) and extracted with DCM (100 mL*3). The combined organic layers were washed with brine (100 mL), dried over $Na_2SO_4$, filtered and concentrated under reduced pressure to give a residue. The residue was purified by column chromatography ($SiO_2$, EtOAc/PE=0 to 20%). Methyl 3-(4-(3-(difluoromethyl)-7-methyldibenzo[b,f][1,4]oxazepin-11-yl)piperazin-1-yl)-2,2-dimethylpropanoate (100 mg, 216.02 µmol, 31.94% yield, 98.83% purity) was obtained as a yellow oil. LCMS $R_t$=1.220 min in 2 min chromatography, Xtimate C18 2.1*30 mm, purity 67.53%, MS ESI calcd. for 457.51 [M+H]$^+$ 458.51, found 458.2.

Step 5: Synthesis of 3-(4-(3-(difluoromethyl)-7-methyldibenzo [b, f] [1,4]oxazepin-11-yl)piperazin-1-yl)-2,2-dimethylpropanoic acid A mixture of methyl 3-(4-(3-(difluoromethyl)-7-methyldibenzo[b,f][1,4]oxazepin-11-yl)piperazin-1-yl)-2,2-dimethylpropanoate (100 mg, 218.57 µmol, 1 eq.), and NaOH (26 mg, 655.72 µmol, 3 eq.) in MeOH (10 mL) and $H_2O$ (3 mL) was stirred at 60° C. for 16 hr. The reaction mixture was concentrated to remove MeOH. The pH of the mixture was adjusted to around 5 with HCOOH. The residue was purified by prep-HPLC (column: Welch Xtimate C18 150*30 mm*5 um; mobile phase: [water (0.225% FA)-ACN]; B %: 22%-52%, 8 min). 3-(4-(3-(difluoromethyl)-7-methyldibenzo[b,f][1,4]oxazepin-11-yl)piperazin-1-yl)-2,2-dimethylpropanoic acid (67.8 mg, 152.88 µmol, 69.94% yield, 100% purity) was obtained as a white solid. $^1$H NMR (400 MHz, DMSO-$d_6$) δ=7.60-7.45 (m, 3H), 7.07 (t, J=55.6 Hz, 1H), 7.04 (s, 1H), 7.94-6.87 (m, 2H), 3.42-3.37 (m, 6H), 2.65-2.53 (m, 4H), 2.23 (s, 3H), 1.09 (s, 6H). HPLC $R_t$=4.36 min in 8 min chromatography, Ultimate 3.0*50 mm 3 um, purity 100%. LCMS $R_t$=1.188 min in 2 min chromatography, Xtimate C18 2.1*30 mm, purity 100%, MS ESI calcd. for 443.49 [M+H]$^+$ 444.49, found 444.2.

Example 9. 1-((4-(3,7-difluorodibenzo[b,f][1,4]oxazepin-11-yl)piperazin-1-yl)methyl)cyclopropane-1-carboxylic acid (Compound No. 10)

Step 1: Synthesis of 11-chloro-3,7-difluorodibenzo[b,f][1,4]oxazepine

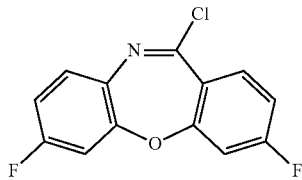

A mixture of 3,7-difluorodibenzo[b,f][1,4]oxazepin-11(10H)-one (500 mg, 2.02 mmol, 1 eq.) in $POCl_3$ (24.69 g, 161.06 mmol, 14.97 mL, 79.63 eq.) was stirred at 110° C. for 4 hrs. The mixture was concentrated to give a residue. The residue was diluted with DCM (100 mL), washed with brine (50 mL*3). The combined organic layer was dried over $Na_2SO_4$, and concentrated to give crude product. The crude product was used directly to the next step without further purification. 11-chloro-3,7-difluorodibenzo[b,f][1,4]oxazepine (500 mg, 1.88 mmol, 93.06% yield) was obtained as a brown solid.

Step 2: Synthesis of methyl 1-((4-(3,7-difluorodibenzo[b,f][1,4]oxazepin-II-yl)piperazin-1-yl)methyl)cyclopropanecarboxylate

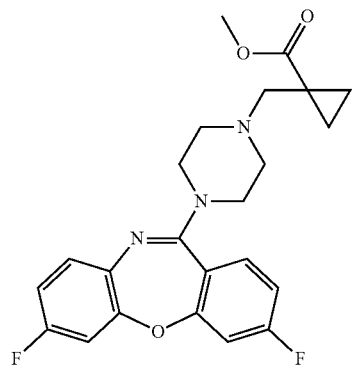 [SMILES: COC(=O)C1(CN2CCN(C3=Nc4ccc(F)cc4Oc4cc(F)ccc43)CC2)CC1]

To a mixture of 11-chloro-3,7-difluorodibenzo[b,f][1,4]oxazepine (400 mg, 1.51 mmol, 1 eq.) and TEA (1.52 g, 15.06 mmol, 2.10 mL, 10 eq.) in dioxane (50 mL) was added methyl 1-(piperazin-1-ylmethyl)cyclopropane-1-carboxylate (597.08 mg, 3.01 mmol, 2 eq.). The mixture was stirred at 110° C. for 10 hrs. The mixture was diluted EtOAc (300 mL), washed with brine (500 mL*3). The combined organic layer was dried over $Na_2SO_4$, and concentrated to give crude product. The product was purified by column chromatography on silica gel (PE:EtOAc=3:2). methyl 1-((4-(3,7-difluorodibenzo[b,f][1,4]oxazepin-11-yl)piperazin-1-yl)methyl)cyclopropane-1-carboxylate (290 mg, 549.07 μmol, 36.46% yield, 80.93% purity) was obtained as a yellow oil. LCMS $R_t$=1.397 min in 2 min chromatography, Xtimate C18 2.1*30 mm, purity 80%, MS ESI calcd. for 427.44 [M+H]$^+$ 428.17, found 428.3.

Step 3: Synthesis of 1-((4-(3,7-difluorodibenzo[b,f][1,4]oxazepin-1-yl)piperazin-1-yl)methyl)cyclopropanecarboxylic acid To a mixture of methyl 1-((4-(3,7-difluorodibenzo[b,f][1,4]oxazepin-11-yl)piperazin-1-yl)methyl)cyclopropane-1-carboxylate (290 mg, 678.45 μmol, 1 eq.) in $H_2O$ (1 mL) and MeOH (3 mL) was added LiOH $H_2O$ (142 mg, 3.39 mmol, 5 eq.). The mixture was stirred at 60° C. for 10 hrs. The mixture was concentrated to remove MeOH. The pH of the mixture was adjusted to around 5 with HCOOH. The mixture was diluted DCM (80 mL), washed with brine (100 mL*2), and concentrated to give crude product. The product was purified by prep-HPLC (column: Welch Xtimate C18 150*30 mm*5 um; mobile phase: [water (0.225% FA)-ACN]; B %: 26%-42%, 8 min). 1-((4-(3,7-difluorodibenzo[b,f][1,4]oxazepin-11-yl)piperazin-1-yl)methyl)cyclopropane-1-carboxylic acid (142 mg, 337.47 μmol, 49.74% yield, 98.25% purity) was obtained as a white solid. $^1$H NMR (DMSO-$d_6$, 400 MHz) $\delta_H$=7.51-7.45 (m, 1H), 7.37 (dd, J=2.4, 9.2 Hz, 1H), 7.23 (td, J=2.4 Hz, 8.4 Hz, 1H), 7.15 (dd, J=2.8 Hz, 8.8 Hz, 1H), 7.10-7.05 (m, 1H), 7.00-6.95 (m, 1H), 3.50-3.42 (m, 4H), 2.77-2.61 (m, 6H), 1.12-1.06 (m, 2H), 0.79-0.73 (m, 2H). HPLC $R_t$=4.11 min in 8 min chromatography, Utimate 3.0*50 mm, purity 98.25%. LCMS $R_t$=1.129 min in 2.0 min chromatography, Xtimate C18 2.1*30 mm, purity 100%, MS ESI calcd. for 413.42 [M+H]$^+$ 414.16, found 414.2.

Example 10. 1-((4-(3,7-dimethyldibenzo[b,f][1,4]oxazepin-11-yl)piperazin-1-yl)methyl)cyclopropane-1-carboxylic acid (Compound No. 9)

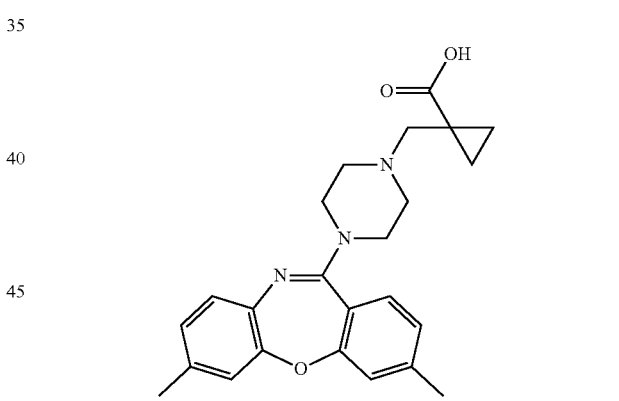

Step 1: Synthesis of 3,7-dimethyldibenzo[b,f][1,4]oxazepin-11(10H)-one

To a mixture of 7-bromo-3-methyldibenzo[b,f][1,4]oxazepin-11(10H)-one (1 g, 3.29 mmol, 1 eq.) in $H_2O$ (4 mL) and dioxane (20 mL) was added Pd(dppf)Cl$_2$ (481 mg, 657.60 μmol, 0.2 eq.), MeBF$_4$K (1.20 g, 9.86 mmol, 3 eq.) and Cs$_2$CO$_3$ (2.14 g, 6.58 mmol, 2 eq.). The mixture was protected by N₂ and stirred at 110° C. for 10 hrs. The mixture was diluted EtOAc (500 mL), washed with brine (800 mL*3). The combined organic layer was dried over Na₂SO₄, and concentrated to give crude product. The product was purified by column chromatography on silica gel (PE:E-tOAc=7:3). 3,7-dimethyldibenzo[b,f][1,4]oxazepin-11 (10H)-one (740 mg, 2.12 mmol, 64.52% yield, 68.59% purity) was obtained as a yellow solid. LCMS $R_t$=1.342 min in 2 min chromatography, Xtimate C18 2.1*30 mm, purity 91.06%, MS ESI calcd. for 239.09 [M+H]⁺ 240.09, found 239.9.

Step 2: Synthesis of 11-chloro-3,7-dimethyldibenzo [b,f][1,4]oxazepine

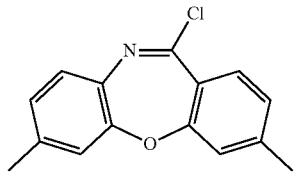

A mixture of 3,7-dimethyldibenzo[b,f][1,4]oxazepin-11 (10H)-one (500 mg, 2.09 mmol, 1 eq.) in POCl₃ (25.51 g, 166.39 mmol, 15.46 mL, 79.63 eq.) was stirred at 110° C. for 4 hrs. The mixture was concentrated to give a residue. The residue was diluted with DCM (100 mL), washed with brine (50 mL*3). The combined organic layer was dried over Na₂SO₄, and concentrated to give crude product. The crude product was used directly to the next step without further purification. 11-chloro-3,7-dimethyldibenzo[b,f][1,4] oxazepine (500 mg, 1.94 mmol, 92.84% yield) was obtained as a brown solid.

Step 3: Synthesis of methyl 1-((4-(3,7-dimethyl-dibenzo[b,f][1,4]oxazepin-11-yl)piperazin-1-yl) methyl)cyclopropanecarboxylate

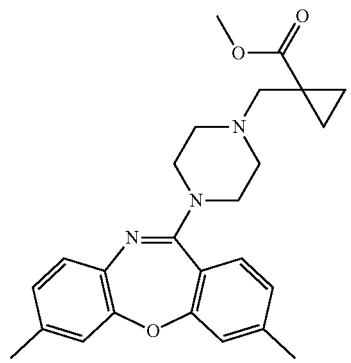 [SMILES: COC(=O)C1(CN2CCN(C3=Nc4ccc(C)cc4Oc4cc(C)ccc43)CC2)CC1]

To a mixture of 11-chloro-3,7-dimethyldibenzo[b,f][1,4] oxazepine (400 mg, 1.55 mmol, 1 eq.) in 1,4-dioxane (10 mL) and DMSO (3 mL) was added TEA (1.57 g, 15.52 mmol, 2.16 mL, 10 eq.) and methyl 1-(piperazin-1-ylmethyl)cyclopropanecarboxylate (616 mg, 3.10 mmol, 2 eq.). The resulting mixture was stirred at 110° C. for 10 hrs. The mixture was diluted with EtOAc (500 mL), washed with brine (300 mL*3). The combined organic layer was concentrated to give crude product. The crude product was purified by column chromatography on silica gel (PE:E-tOAc=3:1). Methyl 1-((4-(3,7-dimethyldibenzo[b,f][1,4] oxazepin-11-yl)piperazin-1-yl)methyl)cyclopropane-1-carboxylate (350 mg, 698.89 μmol, 45.03% yield, 83.77% purity) was obtained as a light yellow oil. ¹H NMR (DMSO-d₆, 400 MHz) $δ_H$=7.27-7.23 (m, 1H), 7.15 (s, 1H), 7.13-7.09 (m, 1H), 6.97-6.94 (m, 1H), 6.92-6.88 (m, 1H), 6.86-6.84 (m, 1H), 3.65 (s, 3H), 3.47-3.33 (m, 4H), 2.63 (s, 2H), 2.57-2.52 (m, 4H), 2.33 (s, 3H), 2.22 (s, 3H), 1.15-1.10 (m, 2H), 0.92-0.84 (m, 2H).

Step 4: Synthesis of 1-((4-(3,7-dimethyldibenzo[b,f] [1,4]oxazepin-11-yl)piperazin-1-yl)methyl)cyclopropanecarboxylic acid To a mixture of methyl 1-((4-(3,7-dimethyldibenzo[b,f] [1,4]oxazepin-11-yl)piperazin-1-yl)methyl)cyclopropane-1-carboxylate (350 mg, 834.30 μmol, 1 eq.) in MeOH (20 mL) and H₂O (5 mL) was added LiOH H₂O (175 mg, 4.17 mmol, 5 eq.). The resulting mixture was stirred at 60° C. for 10 hrs. The mixture was concentrated to remove MeOH. The pH of the mixture was adjusted to around 5 with HCOOH. The product was purified by prep-HPLC (column: Welch Xtimate C18 150*30 mm*5 um; mobile phase: [water (0.225% FA)-ACN]; B %: 26%-31%, 8 min). 1-((4-(3,7-dimethyl-dibenzo[b,f][1,4]oxazepin-11-yl)piperazin-1-yl)methyl)cyclopropane-1-carboxylic acid (105.3 mg, 233.22 μmol, 27.95% yield, 100% purity, FA) was obtained as a white solid. ¹H NMR (DMSO-d₆, 400 MHz) $δ_H$=7.27 (d, J=7.6 Hz, 1H), 7.16 (s, 1H), 7.11 (d, J=8.0 Hz, 1H), 6.97 (s, 1H), 6.94-6.86 (m, 2H), 3.60-3.37 (m, 4H), 2.83-2.62 (m, 6H), 2.34 (s, 3H), 2.29 (s, 3H), 1.12-1.05 (m, 2H), 0.79-0.72 (m, 2H). HPLC $R_t$=3.86 min in 8 min chromatography, Utimate 3.0*50 mm, purity 98.94%. LCMS $R_t$=1.289 min in 2 min chromatography, Xtimate C18 2.1*30 mm, purity 100%, MS ESI calcd. for 405.21 [M+H]⁺ 406.21, found 406.3.

Example 11. 3-(4-(7-chloro-3-isopropyldibenzo[b,f] [1,4]oxazepin-11-yl)piperazin-1-yl)-2,2-dimethyl-propanoic acid (Compound No. 2)

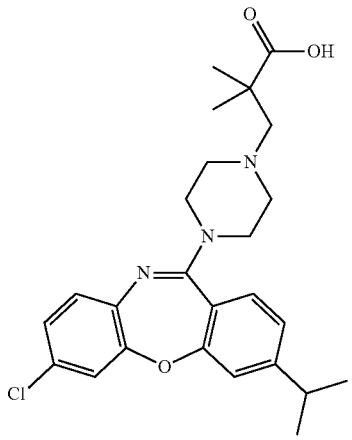 [SMILES: CC(C)c1ccc2c(c1)Oc1cc(Cl)ccc1N=C2N1CCN(CC(C)(C)C(=O)O)CC1]

Step 9: synthesis of 3-(4-(7-chloro-3-isopropy-ldibenzo [b, f] [1, 4] oxazepin-11-yl) piperazin-1-yl)-2, 2-dimethylpropanoic acid A mixture of methyl 3-(4-(7-chloro-3-isopropyldibenzo [b,f][1,4]oxazepin-11-yl)piperazin-1-yl)-2,2-dimethylpropanoate (3 g, 6.38 mmol, 1 eq.), NaOH (766 mg, 19.15 mmol, 3 eq.) in H$_2$O (10 mL) and MeOH (30 mL) was degassed and purged with N$_2$ for 3 times, and then the mixture was stirred at 60° C. for 16 hr under N$_2$ atmosphere. The reaction mixture was acidified with HCOOH to pH=5. The mixture was diluted with water (100 mL) and extracted with DCM (100 mL*2). The combined organic layers were washed with brine (100 mL*2), dried over anhydrous Na$_2$SO$_4$, filtered and concentrated. The crude product was triturated from acetonitrile, which was further purified by prep-HPLC (column: Welch Xtimate C18 150*40 mm*10 um; mobile phase: [water (0.2% FA)-ACN]; B %: 35%-75%, 8 min). 3-(4-(7-chloro-3-isopropyldibenzo[b,f][1,4]oxazepin-11-yl)piperazin-1-yl)-2,2-dimethylpropanoic acid (1.5 g, 3.17 mmol, 49.60% yield, 96.24% purity) was obtained as a white solid. $^1$H NMR (CDCl$_3$, 400 MHz) $\delta_H$=7.24 (d, J=8.0 Hz, 1H), 7.17-7.14 (m, 1H), 7.12-7.05 (m, 4H), 3.82-3.54 (m, 4H), 3.02-2.82 (m, 5H), 2.63 (s, 2H), 1.31-1.24 (m, 12H). HPLC R$_f$=4.13 min in 8 min chromatography, Ultimate XB-C18 3.0*50 mm, 3 um, purity 96.24%. LCMS R$_f$=1.064 min in 2 min chromatography, Xtimate C18 2.1*30 mm, purity 100%, MS ESI calcd. for 455.20 [M+H]$^+$ 456.20, found 456.2.

Example 12. 1-((4-(11H-dibenzo[b,e]azepin-6-yl)piperazin-1-yl)methyl)cyclopropane-1-carboxylic acid (Compound No. 12)

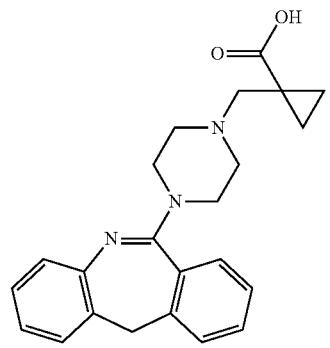 [SMILES: O=C(O)C1(CN2CCN(C3=Nc4ccccc4Cc4ccccc43)CC2)CC1]

Step 1: Synthesis of 6-chloro-11H-dibenzo[b,e]azepine

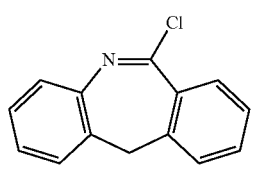

A mixture of 5,11-dihydro-6H-dibenzo[b,e]azepin-6-one (500 mg, 2.39 mmol, 1 eq.) in POCl$_3$ (33.00 g, 215.22 mmol, 20 mL, 90.07 eq.) was stirred at 110° C. for 3 hrs. The mixture was concentrated to give a residue. The residue was diluted with DCM (100 mL), washed with brine (50 mL*3). The combined organic layer was dried over Na$_2$SO$_4$, and concentrated to give crude product. The crude product was used directly to the next step without further purification. 6-chloro-11H-dibenzo[b,e]azepine (500 mg, 2.20 mmol, 91.90% yield) was obtained as a brown solid.

Step 2: Synthesis of methyl 1-((4-(H-dibenzo[b,e]azepin-6-yl)piperazin-1-yl)methyl)cyclopropanecarboxylate

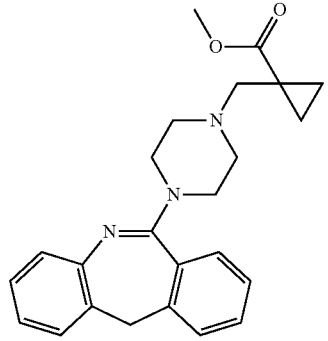 [SMILES: COC(=O)C1(CN2CCN(C3=Nc4ccccc4Cc4ccccc43)CC2)CC1]

To a mixture of 6-chloro-11H-dibenzo[b,e]azepine (400.00 mg, 1.76 mmol, 1 eq.) and TEA (1.78 g, 17.57 mmol, 2.45 mL, 10 eq.) in dioxane (50 mL) was added methyl 1-(piperazin-1-ylmethyl)cyclopropane-1-carboxylate (697 mg, 3.51 mmol, 2 eq.). The mixture was stirred at 110° C. for 10 hrs. The mixture was concentrated to give a residue. The residue was dissolved in DMSO (50 mL), and then TEA (2 mL) and methyl 1-(piperazin-1-ylmethyl)cyclopropane-1-carboxylate (349 mg, 1.76 mmol, 1 eq.) was added. The mixture was stirred at 140° C. for 10 hrs. The mixture was diluted EtOAc (300 mL), washed with brine (500 mL*3). The combined organic layer was dried over Na$_2$SO$_4$, and concentrated to give crude product. The product was purified by column chromatography on silica gel (PE:EtOAc=3:2). Methyl 1-((4-(11H-dibenzo[b,e]azepin-6-yl)piperazin-1-yl)methyl)cyclopropane-1-carboxylate (500 mg, 1.13 mmol, 64.52% yield, 88.29% purity) was obtained as a yellow oil. LCMS R$_f$=0.681 min in 1.5 min chromatography, Xtimate C18 2.0*20 mm, purity 93.15%, MS ESI calcd. for 389.21 [M+H]+ 390.21, found 390.1.

Step 3: Synthesis of 1-((4-(H-dibenzo[b,e]azepin-6-yl)piperazin-1-yl)methyl)cyclopropanecarboxylic acid To a mixture of methyl 1-((4-(11H-dibenzo[b,e]azepin-6-yl)piperazin-1-yl)methyl)cyclopropane-1-carboxylate (500 mg, 1.28 mmol, 1 eq) in H$_2$O (3 mL) and MeOH (6 mL) was added LiOH H$_2$O (154 mg, 6.42 mmol, 5 eq.). The mixture was stirred at 60° C. for 10 hrs. The mixture was concentrated to remove MeOH. The pH of the mixture was adjusted to around 5 with HCOOH. The product was purified by prep-HPLC (column: Welch Xtimate C18 150*25 mm*5 um; mobile phase: [water (0.225% FA)-MeOH]; B %: 17%-47%, 7.8 min). 1-((4-(11H-dibenzo[b,e]azepin-6-yl)piperazin-1-yl)methyl)cyclopropane-1-carboxylic acid (114.4 mg, 302.80 μmol, 23.59% yield, 99.38% purity) was obtained as a white solid. $^1$H NMR (DMSO-d$_6$, 400 MHz) $\delta_H$=8.198 (s, 0.41H), 7.46-7.35 (m, 3H), 7.33-7.27 (m, 1H), 7.20 (d, J=6.4 Hz, 1H), 7.10-7.05 (m, 1H), 6.97-6.89 (m, 2H), 3.69 (d, J=12.8 Hz, 1H), 3.49-3.40 (m, 5H), 2.80-2.71 (m 2H), 2.70-2.61 (m, 4H), 1.10-1.00 (m, 2H), 0.77-0.73 (m, 2H). HPLC R$_f$=6.61 min in 15 min chromatography, Utimate 4.6*150 mm, purity 99.38%. LCMS R$_f$=1.101 min in 2.0 min chromatography, Xtimate C18 2.1*30 mm, purity 100%, MS ESI calcd. for 375.19 [M+H]+ 376.20, found 376.3.

Example 13. 3-(4-(3,7-difluorodibenzo[b,f][1,4]oxazepin-11-yl)piperazin-1-yl)-2,2-dimethylpropanoic acid (Compound No. 11)

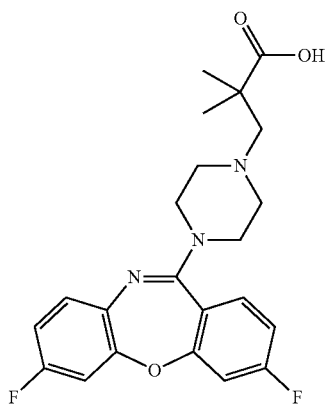

Step 1: Synthesis of 2,4-difluorobenzoyl chloride

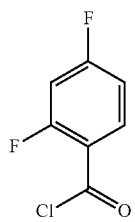

To a mixture of 2,4-difluorobenzoic acid (10.00 g, 63.25 mmol, 1 eq.) in SOCl₂ (100 mL) was added DMF (462 mg, 6.33 mmol, 486.65 μL, 0.1 eq.). The mixture was stirred at 80° C. for 3 hrs. The mixture was concentrated to give a residue. The crude product was used directly to the next step without further purification. 2,4-difluorobenzoyl chloride (11 g, 62.31 mmol, 98.51% yield) was obtained as a yellow oil.

Step 2: Synthesis of 2,4-difluoro-N-(4-fluoro-2-hydroxyphenyl)benzamide

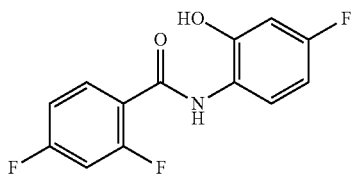 [SMILES: O=C(Nc1ccc(F)cc1O)c1ccc(F)cc1F]

To a mixture of 2-amino-5-fluorophenol (9.90 g, 77.88 mmol, 1.25 eq.) and TEA (18.91 g, 186.92 mmol, 26.02 mL, 3 eq.) in THF (160 mL) was added a solution of 2,4-difluorobenzoyl chloride (11 g, 62.31 mmol, 7.64 mL, 1 eq) in THF (40 mL) dropwise at 0° C. The resulting mixture was allowed to warm up to 25° C. and stirred for 2 hrs. The mixture was diluted EtOAc (1000 mL), washed with 2N HCl (500 mL*1) and brine (1500 mL*3). The combined organic layer was dried over Na₂SO₄, and concentrated to give crude product. The product was used directly to the next step without further purification. 2,4-difluoro-N-(4-fluoro-2-hydroxyphenyl)benzamide (10.9 g, 40.79 mmol, 65.47% yield) was obtained as a brown solid. ¹H NMR (DMSO-d₆, 400 MHz) $\delta_H$=10.52 (brs, 1H), 9.42 (d, J=6.4 Hz, 1H), 7.97-7.88 (m, 2H), 7.49-7.38 (m, 1H), 7.25 (td, J=2.0 Hz, 8.4 Hz, 1H), 6.76-6.63 (m, 2H).

Step 3: Synthesis of 3,7-difluorodibenzo[b,f][1,4]oxazepin-11(10H)-one

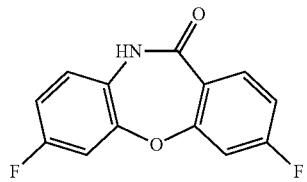 [SMILES: O=C1Nc2ccc(F)cc2Oc2cc(F)ccc21]

To a mixture of 2,4-difluoro-N-(4-fluoro-2-hydroxyphenyl)benzamide (10.4 g, 38.92 mmol, 1 eq.) in DMF (100 mL) was added t-BuOK (8.73 g, 77.84 mmol, 2 eq.). The mixture was stirred at 130° C. for 4 hrs. The mixture was poured into H₂O (300 mL) slowly. The mixture was filtered via a filter paper, and the filter cake was dried under reduced pressure. The product was purified by column chromatography on silica gel (DCM:MeOH=9:1). 3,7-difluorodibenzo[b,f][1,4]oxazepin-11(10H)-one (3.08 g, 6.19 mmol, 15.90% yield, 49.66% purity) was obtained as a red-brown solid. ¹H NMR (DMSO-d₆, 400 MHz) $\delta_H$=10.57 (s, 1H), 7.87-7.84 (m, 1H), 7.34-7.30 (M, 2H), 7.26-7.17 (m, 2H), 7.14-7.08 (m, 1H).

Step 4: Synthesis of 11-chloro-3,7-difluorodibenzo[b,f][1,4]oxazepine

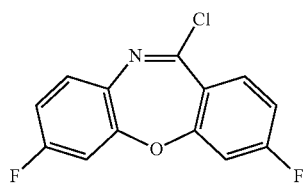 [SMILES: Fc1ccc2c(c1)Oc1cc(F)ccc1C(Cl)=N2]

A mixture of 3,7-difluorodibenzo[b,f][1,4]oxazepin-11(10H)-one (500 mg, 2.02 mmol, 1 eq.) in POCl₃ (49.50 g, 322.83 mmol, 30 mL, 159.60 eq.) was stirred at 110° C. for 3 hrs. The mixture was concentrated to give a residue. The residue was diluted with DCM (100 mL), washed with brine (50 mL*3). The combined organic layer was dried over Na₂SO₄, and concentrated to give crude product. The crude product was used directly to the next step without further purification. 11-chloro-3,7-difluorodibenzo[b,f][1,4]oxazepine (500 mg, 1.88 mmol, 93.06% yield) was obtained as a yellow solid.

Step 5: Synthesis of methyl 3-(4-(3,7-difluorodibenzo[b,f][1,4]oxazepin-11-yl)piperazin-1-yl)-2,2-dimethylpropanoate

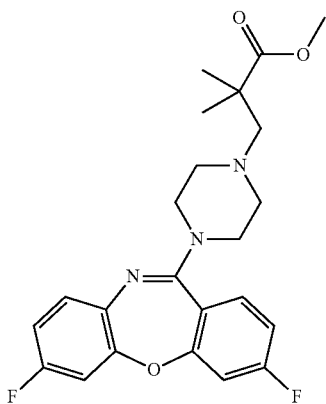 [SMILES: COC(=O)C(C)(C)CN1CCN(C2=Nc3ccc(F)cc3Oc3cc(F)ccc32)CC1]

To a mixture of 11-chloro-3,7-difluorodibenzo[b,f][1,4]oxazepine (500 mg, 1.88 mmol, 1 eq) and TEA (1.90 g, 18.82 mmol, 2.62 mL, 10 eq.) in dioxane (50 mL) was added methyl 2,2-dimethyl-3-(piperazin-1-yl)propanoate (1.03 g, 3.76 mmol, 2 eq., 2HCl). The mixture was stirred at 110° C. for 10 hrs. The mixture was diluted EtOAc (300 mL), washed with brine (500 mL*3). The combined organic layer was dried over $Na_2SO_4$, and concentrated to give crude product. The product was purified by column chromatography on silica gel (PE:EtOAc=4:1). methyl 3-(4-(3,7-difluorodibenzo[b,f][1,4]oxazepin-11-yl)piperazin-1-yl)-2,2-dimethylpropanoate (190 mg, 442.42 μmol, 23.50% yield, 100% purity) was obtained as a yellow oil. $^1$H NMR (DMSO-$d_6$, 400 MHz) $\delta_H$=7.48-7.41 (m, 1H), 7.35 (dd, J=2.4 Hz, 9.2 Hz, 1H), 7.21 (td, J=2.4 Hz, 8.4 Hz, 1H), 7.13 (dd, J=2.8, 9.2 Hz, 1H), 7.08-7.02 (m, 1H), 7.00-6.94 (m, 1H), 3.60 (s, 3H), 3.46-3.34 (m, 4H), 2.58-2.52 (m, 4H), 1.12 (s, 6H).

Step 6: Synthesis of 3-(4-(3,7-difluorodibenzo[b,f][1,4]oxazepin-11-yl)piperazin-1-yl)-2,2-dimethylpropanoic acid To a mixture of methyl 3-(4-(3,7-difluorodibenzo[b,f][1,4]oxazepin-11-yl)piperazin-1-yl)-2,2-dimethylpropanoate (190 mg, 442.42 μmol, 1 eq.) in $H_2O$ (5 mL) and THF (5 mL) was added NaOH (53 mg, 1.33 mmol, 3 eq.). The mixture was stirred at 60° C. for 10 hrs. The mixture was concentrated to remove MeOH. The pH of the mixture was adjusted to around 5 with HCOOH. The mixture was diluted with DCM (80 mL), washed with brine (100 mL*2). The combined organic layer was concentrated to give crude product. The product was purified by prep-HPLC (column: Welch Xtimate C18 150*30 mm*5 um; mobile phase: [water (0.225% FA)-ACN]; B %: 20%-50%, 8 min). 3-(4-(3,7-difluorodibenzo[b,f][1,4]oxazepin-11-yl)piperazin-1-yl)-2,2-dimethylpropanoic acid (110.7 mg, 237.35 μmol, 53.65% yield, 98.94% purity, FA) was obtained as a white solid. $^1$H NMR (DMSO-$d_6$, 400 MHz) $\delta_H$=7.48-7.43 (m, 1H), 7.35 (dd, J=2.8 Hz, 9.6 Hz, 1H), 7.21 (td, J=2.8 Hz, 8.4 Hz, 1H), 7.14 (dd, J=2.8 Hz, 9.2 Hz, 1H), 7.08-7.02 (m, 1H), 7.00-6.94 (m, 1H), 3.46-3.34 (m, 4H), 2.64-2.52 (m, 6H), 1.10 (s, 6H). HPLC $R_t$=4.17 min in 8 min chromatography, Utimate 3.0*50 mm, purity 98.94%. LCMS $R_t$=1.360 min in 2.0 min chromatography, Xtimate C18 2.1*30 mm, purity 100%, MS ESI calcd. for 415.43 [M+H]$^+$ 416.17, found 416.3.

Example 14. 1-((4-(3-ethyl-7-methyldibenzo[b,f][1,4]oxazepin-11-yl)piperazin-1-yl)methyl)cyclopropane-1-carboxylic acid (Compound No. 14)

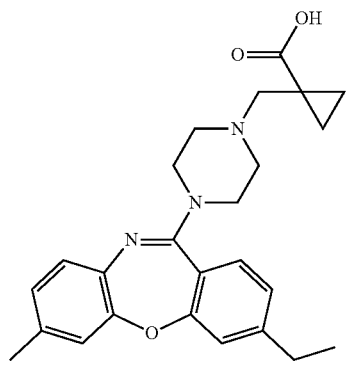 [SMILES: CCc1ccc2c(c1)Oc1cc(C)ccc1N=C2N1CCN(CC2(C(=O)O)CC2)CC1]

Step 1: Synthesis of methyl 4-bromo-2-(5-methyl-2-nitrophenoxy)benzoate

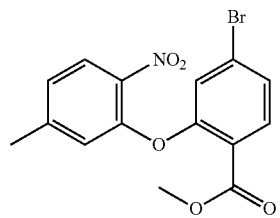 [SMILES: COC(=O)c1ccc(Br)cc1Oc1cc(C)ccc1[N+](=O)[O-]]

A mixture of methyl 4-bromo-2-hydroxybenzoate (10 g, 43.28 mmol, 1 eq.), 2-fluoro-4-methyl-1-nitro-benzene (6.71 g, 43.28 mmol, 1 eq.), $K_2CO_3$ (17.95 g, 129.85 mmol, 3 eq.) in DMF (200 mL) was stirred at 90° C. for 6 hr. The reaction mixture was diluted with $H_2O$ (150 mL) and extracted with EtOAc (150 mL*3). The combined organic layers were washed with brine (100 mL), dried over $Na_2SO_4$, filtered and concentrated under reduced pressure to give a residue. The residue was purified by column chromatography ($SiO_2$, Ethyl acetate/Petroleum ether=0 to 20%). Methyl 4-bromo-2-(5-methyl-2-nitrophenoxy)benzoate (10 g, 27.31 mmol, 63.10% yield) was obtained as a white solid. $^1$H NMR (400 MHz, $CDCl_3$) $\delta$=7.93 (d, J=8.4 Hz, 1H), 7.86 (d, J=8.8 Hz, 1H), 7.41 (dd, J=2.0 Hz, 8.4 Hz, 1H), 7.16-7.15 (m, 1H), 7.05-7.00 (m, 1H), 6.71-6.66 (m, 1H), 3.78 (s, 3H), 2.35 (s, 3H).

Step 2: Synthesis of 3-bromo-7-methyldibenzo [b,f][1,4]oxazepin-11(10H)-one

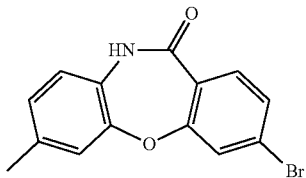 [SMILES: Cc1ccc2c(c1)Oc1cc(Br)ccc1C(=O)N2]

A mixture of methyl 4-bromo-2-(5-methyl-2-nitrophenoxy)benzoate (17 g, 46.43 mmol, 1 eq.), Fe (15.56 g, 278.56 mmol, 6 eq.) in $CH_3COOH$ (340 mL) was stirred at 120° C. for 2 hr. The reaction mixture was filtered through the celite pad. The cake was washed with EtOAc (1000 mL*3). The combined filtrate was washed with $H_2O$ (1000 mL*2) and sat.aq.$NaHCO_3$(1000 mL*2), then washed with brine (1000 mL). The organic layer was dried over $Na_2SO_4$, and concentrated in vacuum. The residue was triturated with EtOAc (200 mL). 3-bromo-7-methyldibenzo[b,f][1,4]oxazepin-11(10H)-one (11.3 g, 37.15 mmol, 80.03% yield) was obtained as a white solid. $^1$H NMR (400 MHz, $CDCl_3$) δ=8.14 (s, 1H), 7.80 (d, J=8.4 Hz, 1H), 7.45-7.35 (m, 2H), 7.10-7.05 (m, 1H), 7.00-6.87 (m, 2H), 2.32 (s, 3H).

Step 3: Synthesis of 7-methyl-3-vinyldibenzo [b,f][1,4]oxazepin-11(10H)-one

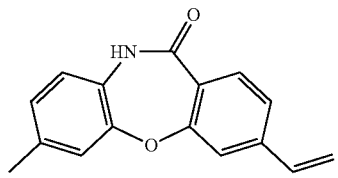 [SMILES: C=Cc1ccc2c(c1)Oc1cc(C)ccc1NC2=O]

A mixture of 3-bromo-7-methyldibenzo[b,f][1,4]oxazepin-11(10H)-one (1 g, 3.29 mmol, 1 eq.), trifluoro-[(Z)-vinylboranylidene-fluoranyl]potassium (1.01 g, 6.58 mmol, 2 eq.), Pd(dppf)$Cl_2$ (240.58 mg, 328.80 μmol, 0.1 eq.), $Cs_2CO_3$ (2.14 g, 6.58 mmol, 2 eq.) in dioxane (30 mL) and $H_2O$ (3 mL) was degassed and purged with $N_2$ for 3 times, and then the mixture was stirred at 100° C. for 2 hr under $N_2$ atmosphere. The reaction mixture was filtered through the Celites. Then it was concentrated to dryness. The residue was purified by column chromatography ($SiO_2$, EtOAc/PE=0 to 30%). 7-methyl-3-vinyldibenzo[b,f][1,4]oxazepin-11(10H)-one (760 mg, 3.02 mmol, 91.99% yield) was obtained as a white solid. $^1$H NMR (400 MHz, $CDCl_3$) δ=7.88 (d, J=8.0 Hz, 1H), 7.83 (s, 1H), 7.25-7.24 (m, 2H), 7.13-7.05 (m, 1H), 6.97-6.86 (m, 2H), 6.76-6.64 (m, 1H), 5.87 (d, J=17.6 Hz, 1H), 5.41 (d, J=10.8 Hz, 1H), 2.32 (s, 3H).

Step 4: Synthesis of 3-ethyl-7-methyldibenzo [b,f][1,4]oxazepin-11(10H)-one

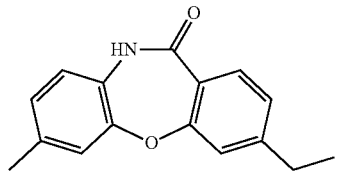 [SMILES: CCc1ccc2c(c1)Oc1cc(C)ccc1NC2=O]

A mixture of 7-methyl-3-vinyldibenzo[b,f][1,4]oxazepin-11(10H)-one (760 mg, 3.02 mmol, 1 eq.), Pd/C (0.4 g, 3.02 mmol, 10% purity, 1 eq.) in MeOH (10 mL) was stirred at 25° C. for 2 hr under H2 (15 psi) atmosphere. The reaction mixture was filtered through celite. The cake was washed with DCM (100 mL*3). The combined filtrate was concentrated in vacuum. The product was used for next step directly without further purification. 3-ethyl-7-methyldibenzo[b,f][1,4]oxazepin-11(10H)-one (760 mg, 2.94 mmol, 97.04% yield, 97.82% purity) was obtained as a white solid. $^1$H NMR (400 MHz, $CDCl_3$) δ=7.90-7.80 (m, 2H), 7.09-7.04 (m, 3H), 6.96-6.90 (m, 1H), 6.89-6.85 (m, 1H), 2.68 (q, J=8.0 Hz, 2H), 2.32 (s, 3H), 1.25 (t, J=7.6 Hz, 3H).

Step 5: Synthesis of 11-chloro-3-ethyl-7-methyldibenzo [b, f] [1, 4] oxazepine

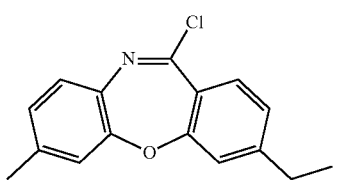 [SMILES: CCc1ccc2c(c1)Oc1cc(C)ccc1N=C2Cl]

A mixture of 3-ethyl-7-methyldibenzo[b,f][1,4]oxazepin-11(10H)-one (300 mg, 1.18 mmol, 1 eq.) in $POCl_3$ (40 mL) was stirred at 110° C. for 5 hr. The reaction mixture was dried under reduced pressure. Then it was diluted with DCM (100 mL) and washed with $H_2O$ (100 mL*2). The combined organic layers were washed with brine (100 mL), dried over $Na_2SO_4$, filtered and concentrated under reduced pressure to give a residue. The product was used for next step directly without further purification. 11-chloro-3-ethyl-7-methyldibenzo[b,f][1,4]oxazepine (200 mg, crude) was obtained as a yellow oil.

Step 6: Synthesis of methyl 1-((4-(3-ethyl-7-methyldibenzo[b,f][1,4]oxazepin-11-yl)piperazin-1-yl)methyl)cyclopropanecarboxylate

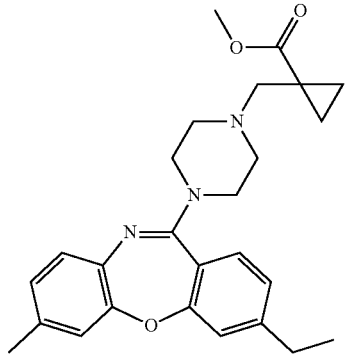 [SMILES: CCc1ccc2c(c1)Oc1cc(C)ccc1N=C2N1CCN(CC2(C(=O)OC)CC2)CC1]

A mixture of 11-chloro-3-ethyl-7-methyldibenzo[b,f][1,4]oxazepine (200 mg, 736.00 mmol, 1 eq.), methyl 1-(piperazin-1-ylmethyl)cyclopropane-1-carboxylate (292 mg, 1.47 mmol, 2 eq.), TEA (745 mg, 7.36 mmol, 1.02 mL, 10 eq.) in dioxane (6 mL) and DMSO (6 mL) was stirred at 120° C. for 16 hr. The reaction mixture was diluted with $H_2O$ (100 mL) and extracted with EtOAc (100 mL*3). The combined organic layers were washed with brine (100 mL), dried over $Na_2SO_4$, filtered and concentrated under reduced pressure to give a residue. The residue was purified by column chromatography ($SiO_2$, EtOAc/PE=0 to 35%). methyl 1-((4-(3-ethyl-7-methyldibenzo[b,f][1,4]oxazepin-11-yl)piperazin-1-yl)methyl)cyclopropane-1-carboxylate (250 mg, 544.99 μmol, 74.05% yield, 94.51% purity) was obtained as a colorless oil. LCMS $R_t$=2.069 min in 3 min chromatography, Xtimate C18 2.1*30 mm, purity 47.58%, MS ESI calcd. for 433.54 [M+H]$^+$ 434.54, found 434.3.

Step 7: Synthesis of 1-((4-(3-ethyl-7-methyldibenzo[b, f][1,4]oxazepin-11-yl)piperazin-1-yl)methyl)cyclopropanecarboxylic acid A mixture of methyl 1-((4-(3-ethyl-7-methyldibenzo[b,f][1,4]oxazepin-11-yl)piperazin-1-yl)methyl)cyclopropane-1-carboxylate (250 mg, 576.65 μmol, 1 eq.) and NaOH (69 mg, 1.73 mmol, 3 eq.) in MeOH (15 mL) and $H_2O$ (5 mL) was stirred at 60° C. for 6 hr. The reaction mixture was concentrated to remove MeOH. The pH of the mixture was adjusted to around 5 with HCOOH. The residue was purified by prep-HPLC (column: Welch Xtimate C18 150*25 mm*5 um; mobile phase: [water (0.225% FA)-ACN]; B %: 15%-45%, 8 min). 1-((4-(3-ethyl-7-methyldibenzo[b,f][1,4]oxazepin-11-yl)piperazin-1-yl)methyl)cyclopropane-1-carboxylic acid (147.5 mg, 351.60 μmol, 60.97% yield, 100% purity) was obtained as a white solid. $^1$H NMR (400 MHz, DMSO-$d_6$) δ=8.17 (s, 0.3H), 7.29 (d, J=8.0 Hz, 1H), 7.20-7.10 (m, 2H), 7.02-6.96 (m, 1H), 6.95-6.85 (m, 2H), 3.50-3.42 (m, 4H), 2.78-2.58 (m, 8H), 2.23 (s, 3H), 1.18 (t, J=8 Hz, 3H), 1.11-1.04 (m, 2H), 0.80-0.70 (m, 2H). HPLC $R_t$=4.09 min in 8 min chromatography, Ultimate 3.0*50 mm 3 um, purity 99.83%. LCMS $R_t$=1.133 min in 2 min chromatography, Xtimate C18 2.1*30 mm, purity 100%, MS ESI calcd. for 419.52 [M+H]+ 420.52, found 420.2.

Example 15. 1-((4-(7-fluoro-3-methyldibenzo[b,f][1,4]oxazepin-11-yl)piperazin-1-yl)methyl)cyclopropane-1-carboxylic acid (Compound No. 18)

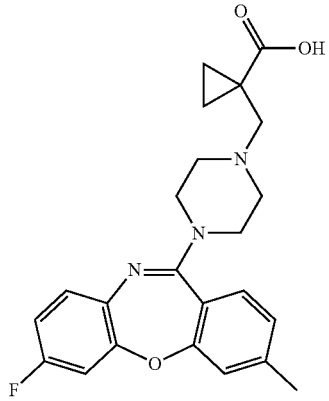 [SMILES: Cc1ccc2c(c1)Oc1cc(F)ccc1N=C2N1CCN(CC2(C(=O)O)CC2)CC1]

Step 1: Synthesis of 2-fluoro-4-methylbenzoyl chloride

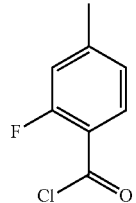

To a mixture of 2-fluoro-4-methylbenzoic acid (5 g, 32.44 mmol, 1 eq.) in $SOCl_2$ (50 mL) was added DMF (237 mg, 3.24 mmol, 249.58 μL, 0.1 eq.). The mixture was stirred at 80° C. for 4 hrs. The mixture was concentrated to give a residue. The crude product was used directly to the next step without further purification. 2-fluoro-4-methylbenzoyl chloride (5 g, 28.97 mmol, 89.31% yield) was obtained as a yellow oil.

Step 2: Synthesis of 2-fluoro-N-(4-fluoro-2-hydroxyphenyl)-4-methylbenzamide

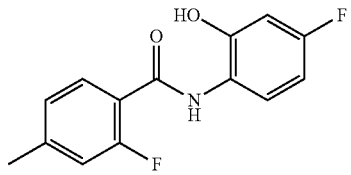 [SMILES: Cc1ccc(C(=O)Nc2ccc(F)cc2O)c(F)c1]

To a mixture of 2-amino-5-fluorophenol (4.60 g, 36.21 mmol, 1.25 eq.) and TEA (8.79 g, 86.91 mmol, 12.10 mL, 3 eq.) in THF (60 mL) was added a solution of 2-fluoro-4-methylbenzoyl chloride (5 g, 28.97 mmol, 1 eq.) in THF (40 mL) dropwise at 0° C. The resulting mixture was allowed to warm up to 25° C. and stirred for 4 hrs. The mixture was diluted EtOAc (500 mL), washed with brine (500 mL*3).

The combined organic layer was dried over Na₂SO₄, and concentrated to give crude product. The product was purified by column chromatography on silica gel (PE:EtOAc=7:3) and triturated with EtOAc (100 mL). 2-fluoro-N-(4-fluoro-2-hydroxyphenyl)-4-methylbenzamide (5 g, 18.99 mmol, 65.56% yield) was obtained as a brown solid. ¹H NMR (DMSO-d₆, 400 MHz) δ$_H$=10.61 (s, 1H), 9.30 (d, J=9.6 Hz, 1H), 8.05-8.01 (m, 1H), 7.80 (t, J=8.0 Hz, 1H), 7.25-7.14 (m, 2H), 6.76-6.63 (m, 2H), 2.39 (s, 3H).

Step 3: Synthesis of 7-fluoro-3-methyldibenzo[b,f][1,4]oxazepin-11(10H)-one

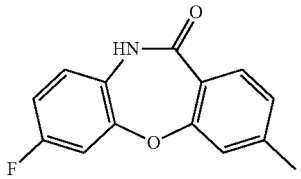 [SMILES: Cc1ccc2c(c1)Oc1cc(F)ccc1NC2=O]

To a mixture of 2-fluoro-N-(4-fluoro-2-hydroxyphenyl)-4-methylbenzamide (3.8 g, 14.44 mmol, 1 eq.) in DMSO (38 mL) was added t-BuOK (3.24 g, 28.87 mmol, 2 eq.). The mixture was stirred at 140° C. for 4 hrs. The mixture was filtered via a celite pad, the pad was washed with EtOAc (300 mL*3). The mixture was washed with brine (500 mL*2). The combined organic layer was dried over Na₂SO₄, and concentrated to give crude product. The product was used directly to the next step without further purification. 7-fluoro-3-methyldibenzo[b,f][1,4]oxazepin-11(10H)-one (2.91 g, 10.98 mmol, 76.05% yield, 91.76% purity) was obtained as a red-brown solid. ¹H NMR (DMSO-d₆, 400 MHz) δ$_H$=10.44 (s, 1H), 7.66 (d, J=8.0 Hz, 1H), 7.27 (dd, J=2.8 Hz, 9.2 Hz, 1H), 7.21-7.12 (m, 3H), 7.07 (td, J=2.8 Hz, 8.4 Hz, 1H), 2.35 (s, 3H).

Step 4: Synthesis of 11-chloro-7-fluoro-3-methydibenzo[b,f][1,4]oxazepine

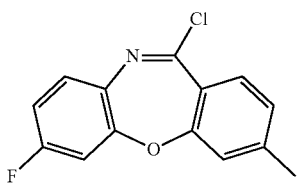 [SMILES: Cc1ccc2c(c1)Oc1cc(F)ccc1N=C2Cl]

A mixture of 7-fluoro-3-methyldibenzo[b,f][1,4]oxazepin-11(10H)-one (900 mg, 3.70 mmol, 1 eq.) in POCl₃ (49.50 g, 322.83 mmol, 30 mL, 87.25 eq.) was stirred at 110° C. for 3 hrs. The mixture was concentrated to give a residue. The residue was diluted with DCM (100 mL), washed with brine (50 mL*3). The combined organic layer was dried over Na₂SO₄, and concentrated to give crude product. 11-chloro-7-fluoro-3-methyldibenzo[b,f][1,4]oxazepine (900 mg, 3.44 mmol, 92.95% yield) was obtained as a brown solid.

Step 5: Synthesis of methyl 1-((4-(7-fluoro-3-methydibenzo[b,f][1,4]oxazepin-11-yl)piperazin-1-yl)methyl)cyclopropanecarboxylate

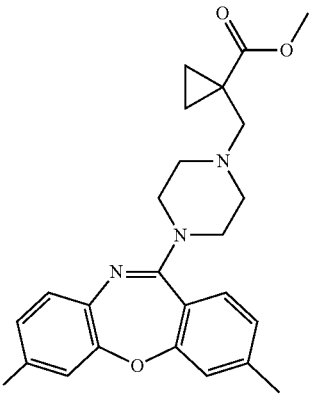

To a mixture of 11-chloro-7-fluoro-3-methyldibenzo[b,f][1,4]oxazepine (500 mg, 1.91 mmol, 1 eq.) and TEA (1.93 g, 19.11 mmol, 2.66 mL, 10 eq.) in dioxane (15 mL) was added methyl 1-(piperazin-1-ylmethyl)cyclopropane-1-carboxylate (379 mg, 1.91 mmol, 1 eq.). The mixture was stirred at 110° C. for 10 hrs. The mixture was diluted EtOAc (200 mL), washed with brine (300 mL*3). The combined organic layer was dried over Na₂SO₄, and concentrated to give crude product. The product was purified by column chromatography on silica gel (PE:EtOAc=7:3). methyl 1-((4-(7-fluoro-3-methyldibenzo[b,f][1,4]oxazepin-11-yl)piperazin-1-yl)methyl)cyclopropane-1-carboxylate (300 mg, 708.42 μmol, 37.08% yield, 100% purity) was obtained as a yellow oil. LCMS R$_t$=1.139 min in 2 min chromatography, Xtimate C18 2.1*30 mm, purity 100%, MS ESI calcd. for 423.48 [M+H]⁺ 424.20, found 424.1.

Step 6: Synthesis of 1-((4-(7-fluoro-3-methyl-dibenzo[b,f][1,4]oxazepin-11-yl)piperazin-1-yl) methyl)cyclopropanecarboxylic acid To a mixture of methyl 1-((4-(7-fluoro-3-methyldibenzo[b,f][1,4]oxazepin-11-yl)piperazin-1-yl)methyl)cyclopropane-1-carboxylate (300 mg, 708.42 μmol, 1 eq.) in H₂O (5 mL) and MeOH (4 mL) was added NaOH (85 mg, 2.13 mmol, 3 eq.). The mixture was stirred at 60° C. for 10 hrs. The mixture was concentrated to remove MeOH. The pH of the mixture was adjusted to around 5 with HCOOH. The product was purified by prep-HPLC (column: Welch Xtimate C18 150*25 mm*5 um; mobile phase: [water (0.05% HCl)-ACN]; B %: 10%-40%, 8.5 min). 1-((4-(7-fluoro-3-methyldibenzo[b,f][1,4]oxazepin-11-yl)piperazin-1-yl)methyl)cyclopropane-1-carboxylic acid (40 mg, 97.69 μmol, 13.79% yield, 100% purity) was obtained as a yellow solid. ¹H NMR (DMSO-d₆, 400 MHz) δ$_H$=11.04 (s, 1H), 7.63 (d, J=8.0 Hz, 1H), 7.49 (t, J=6.4 Hz, 1H), 7.42-7.34 (m, 2H), 7.28 (d, J=7.6 Hz, 1H), 7.16 (td, J=2.8 Hz, 8.4 Hz, 1H), 3.80-3.25 (m, 6H), 2.56-2.51 (m, 4H), 2.40 (s, 3H), 1.48-1.43 (m, 2H), 1.36-1.31 (m, 2H). HPLC R$_t$=2.65 min in 4 min chromatography, Utimate 3.0*50 mm, purity 98.12%. LCMS R$_t$=3.325 min in 7 min chromatography, Xtimate C18 2.1*30 mm, purity 100%, MS ESI calcd. for 409.45 [M+H]⁺ 410.18, found 410.1.

Example 16. 3-(4-(7-chloro-3-methoxydibenzo[b,f][1,4]oxazepin-11-yl)piperazin-1-yl)-2,2-dimethylpropanoic acid (Compound No. 20)

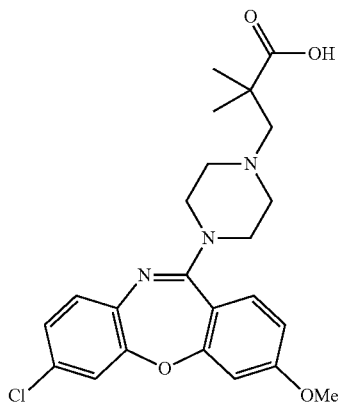 [SMILES: COc1ccc2c(c1)Oc1cc(Cl)ccc1N=C2N1CCN(CC(C)(C)C(=O)O)CC1]

Step 1: Synthesis of methyl 3-(4-(7-chloro-3-methoxydibenzo[b,f][1,4]oxazepin-11-yl)piperazin-1-yl)-2,2-dimethylpropanoate

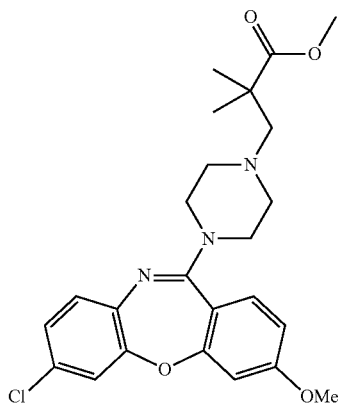 [SMILES: COC(=O)C(C)(C)CN1CCN(C2=Nc3ccc(Cl)cc3Oc3cc(OC)ccc32)CC1]

To a mixture of 7,11-dichloro-3-methoxydibenzo[b,f][1,4]oxazepine (400 mg, 1.36 mmol, 1 eq.) in TEA (1.38 g, 13.60 mmol, 1.89 mL, 10 eq.) and dioxane (10 mL) was added methyl 2,2-dimethyl-3-piperazin-1-yl-propanoate (545 mg, 2.72 mmol, 2 eq.). The mixture was stirred at 120° C. for 10 hrs. The mixture was diluted with DCM (200 mL), washed with brine (200 mL*3). The combined organic layer was dried over $Na_2SO_4$, and concentrated to give crude product. The product was purified by column chromatography on silica gel (PE:EtOAc=6:1). methyl 3-(4-(7-chloro-3-methoxydibenzo[b,f][1,4]oxazepin-11-yl)-2,2-dimethylpropanoate (400 mg, 873.46 μmol, 64.23% yield, 100% purity) was obtained as a colorless solid. LCMS $R_t$=0.820 min in 1.5 min chromatography, Xtimate C18 2.1*30 mm, purity 100%, MS ESI calcd. for 457.18 $[M+H]^+$ 458.18, found 458.0.

Step 2: Synthesis of 3-(4-(7-chloro-3-methoxydibenzo[b,f][1,4]oxazepin-11-yl)piperazin-1-yl)-2,2-dimethylpropanoic acid To a mixture of methyl 3-(4-(7-chloro-3-methoxydibenzo[b,f][1,4]oxazepin-11-yl)piperazin-1-yl)-2,2-dimethylpropanoate (380 mg, 829.79 μmol, 1 eq.) in MeOH (3 mL), $H_2O$ (4 mL) and THF (3 mL) was added NaOH (67 mg, 1.66 mmol, 2.00 eq.). The mixture was stirred at 60° C. for 4 hrs. The mixture was concentrated to remove MeOH. The pH of the mixture was adjusted to around 5 with HCOOH. The mixture was diluted with DMSO (6 mL), $H_2O$ (30 mL) and MeOH (10 mL). The mixture was filtered via a filter paper, the filter cake was dissolved in $CH_3CN$ (10 mL) and $H_2O$ (40 mL), and lyophilized. 3-(4-(7-chloro-3-methoxydibenzo[b,f][1,4]oxazepin-11-yl)piperazin-1-yl)-2,2-dimethylpropanoic acid (218 mg, 491.08 μmol, 59.18% yield, 100% purity) was obtained as a white solid. $^1$H NMR (DMSO-$d_6$, 400 MHz) $\delta_H$=7.32-7.27 (m, 2H), 7.12 (dd, J=2.4 Hz, 8.4 Hz, 1H), 7.03-6.99 (m, 2H), 6.95 (dd, J=2.8 Hz, 8.8 Hz, 1H), 3.81 (s, 3H), 3.43-3.37 (m, 4H), 2.60-2.50 (m, 6H), 1.10 (s, 6H). HPLC $R_t$=2.83 min in 4 min chromatography, Ultimate 3.0*50 mm 3 um, purity 100.00%. LCMS $R_t$=3.684 min in 7 min chromatography, Xtimate C18 2.1*30 mm, purity 94.11%, MS ESI calcd. for 443.16 $[M+H]^+$ 444.16, found 444.1.

Example 17. 1-((4-(3-fluoro-7-methyldibenzo[b,f][1,4]oxazepin-11-yl)piperazin-1-yl)methyl)cyclopropane-1-carboxylic acid (Compound No. 19)

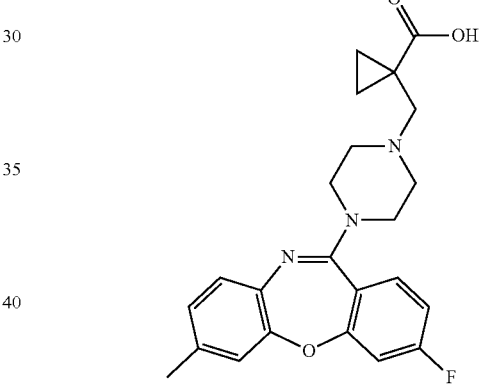

Step 1: Synthesis of 11-chloro-3-fluoro-7-methyldibenzo[b,f][1,4]oxazepine

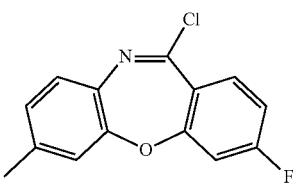 [SMILES: Cc1ccc2c(c1)Oc1cc(F)ccc1C(Cl)=N2]

A mixture of 3-fluoro-7-methyldibenzo[b,f][1,4]oxazepin-11(10H)-one (600 mg, 2.47 mmol, 1 eq.) in $POCl_3$ (33.00 g, 215.22 mmol, 20 mL, 87.25 eq.) was stirred at 110° C. for 3 hrs. The mixture was concentrated to give a residue. The residue was diluted with DCM (100 mL), washed with brine (50 mL*3). The combined organic layer was dried over $Na_2SO_4$, and concentrated to give crude product. The product was used directly to the next step without further purification. 11-chloro-3-fluoro-7-methyldibenzo[b,f][1,4]oxazepine (600 mg, 2.29 mmol, 92.95% yield) was obtained as a brown solid.

Step 2: Synthesis of methyl 1-((4-(3-fluoro-7-methyldibenzo[b,f][1,4]oxazepin-11-yl)piperazin-1-yl)methyl)cyclopropanecarboxylate

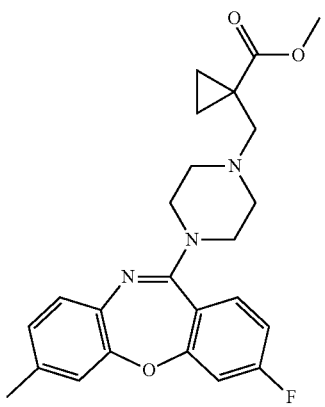

To a mixture of 11-chloro-3-fluoro-7-methyldibenzo[b,f][1,4]oxazepine (300 mg, 1.15 mmol, 1 eq.) in TEA (1.16 g, 11.46 mmol, 1.60 mL, 10 eq.) and dioxane (10 mL) was added methyl 2,2-dimethyl-3-piperazin-1-yl-propanoate (459 mg, 2.29 mmol, 2 eq.). The mixture was stirred at 110° C. for 10 hrs. The reaction mixture was diluted with EtOAc (100 mL), washed with brine (50 mL*3). The combined organic layer was dried over $Na_2SO_4$, and concentrated to give crude product. The product was purified by column chromatography on silica gel (PE:EtOAc=3:1). methyl 1-((4-(3-fluoro-7-methyldibenzo[b,f][1,4]oxazepin-11-yl)piperazin-1-yl)methyl)cyclopropane-1-carboxylate (220 mg, 519.51 μmol, 45.17% yield, 100% purity) was obtained as a yellow solid. $^1$H NMR ($CDCl_3$, 400 MHz) $\delta_H$=7.37-7.20 (m, 1H), 7.05-7.02 (m, 1H), 6.99-6.95 (m, 1H), 6.94-6.88 (m, 3H), 3.69 (s, 3H), 3.53-3.37 (m, 4H), 2.72 (s, 2H), 2.66-2.55 (m, 4H), 2.30 (s, 3H), 1.33-1.24 (m, 2H), 0.91-0.82 (m, 2H).

Step 3: Synthesis of 1-((4-(3-fluoro-7-methyldibenzo[b,f][1,4]oxazepin-11-yl)piperazin-1-yl)methyl)cyclopropanecarboxylic acid To a mixture of methyl 1-((4-(3-fluoro-7-methyldibenzo[b,f][1,4]oxazepin-11-yl)piperazin-1-yl)methyl)cyclopropane-1-carboxylate (200 mg, 472.28 μmol, 1 eq.) in MeOH (3 mL), $H_2O$ (4 mL) and THF (3 mL) was added NaOH (38 mg, 944.56 μmol, 2 eq.). The mixture was stirred at 60° C. for 4 hrs. The reaction mixture was concentrated to remove MeOH. The pH of the mixture was adjusted to around 5 with HCOOH. The residue was purified by prep-HPLC (column: Welch Xtimate C18 150*25 mm*5 um; mobile phase: [water (0.05% HCl)-ACN]; $^B$ %: 10%-40%, 8.5 min). 1-((4-(3-fluoro-7-methyldibenzo[b,f][1,4]oxazepin-11-yl)piperazin-1-yl)methyl)cyclopropane-1-carboxylic acid (60.5 mg, 147.76 μmol, 31.29% yield, 100.00% purity) was obtained as a yellow solid. $^1$H NMR (DMSO-$d_6$, 400 MHz) $\delta_H$=7.68 (t, J=7.2 Hz, 1H), 7.45 (d, J=8.8 Hz, 1H), 7.33-7.25 (m, 1H), 7.19-7.12 (m, 2H), 7.03 (d, J=8.0 Hz, 1H), 3.50-3.45 (m, 4H), 2.50-2.49 (m, 6H), 2.28 (s, 3H), 1.44-1.32 (m, 4H). HPLC $R_t$=2.66 min in 4 min chromatography, Ultimate 3.0*50 mm 3 um, purity 98.62%. LCMS $R_t$=3.515 min in 7 min chromatography, Xtimate C18 2.1*30 mm, purity 100.00%, MS ESI calcd. for 409.18 [M+H]$^+$ 410.18, found 410.1.

Example 18. 3-(4-(7-chloro-3-(methylthio)dibenzo[b,f][1,4]oxazepin-11-yl)piperazin-1-yl)-2,2-dimethylpropanoic acid (Compound No. 4)

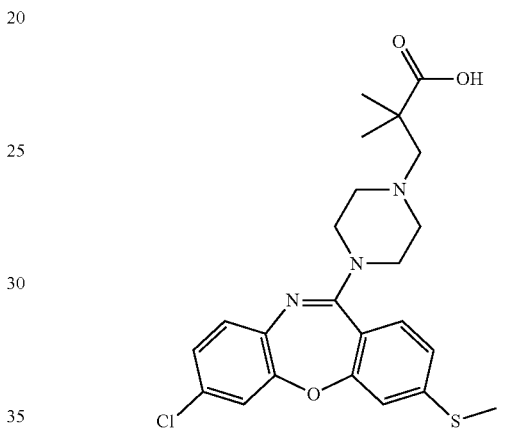

Step 1: Synthesis of 2-fluoro-4-(methylthio)benzoic acid

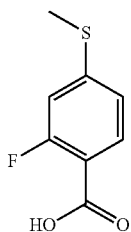

A mixture of 2-fluoro-4-mercaptobenzoic acid (5 g, 29.04 mmol, 1 eq.), MeI (20.61 g, 145.20 mmol, 9.04 mL, 5 eq.), $K_2CO_3$ (20.07 g, 145.20 mmol, 5 eq.) in $CH_3CN$ (50 mL) was degassed and purged with $N_2$ for 3 times, and then the mixture was stirred at 50° C. for 16 hr under $N_2$ atmosphere. The reaction mixture was quenched by addition water (200 mL), and then extracted with EtOAc (200 mL*2). The water layer were acidified with 2N HCl to pH=5, and the mixture was filtered and the filter cake was dried under reduced pressure. 2-fluoro-4-(methylthio)benzoic acid (1.9 g, 10.20 mmol, 35.14% yield) as a light yellow solid. $^1$H NMR ($CDCl_3$, 400 MHz) $\delta_H$=7.93 (t, J=8.4 Hz, 1H), 7.07-6.94 (m, 2H), 2.53 (s, 3H).

Step 2: Synthesis of 2-fluoro-4-(methylthio)benzoyl chloride

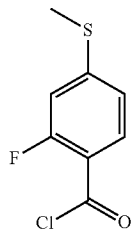

A mixture of 2-fluoro-4-(methylthio)benzoic acid (1.9 g, 10.20 mmol, 1 eq.) in SOCl₂ (20 mL) was degassed and purged with N₂ for 3 times, and then the mixture was stirred at 85° C. for 3 hr under N₂ atmosphere. The reaction mixture was concentrated to dryness. The crude product was used into next step without further purification. 2-fluoro-4-(methylthio)benzoyl chloride (2 g, crude) was obtained as a yellow oil.

Step 3: Synthesis of N-(4-chloro-2-hydroxyphenyl)-2-fluoro-4-(methylthio)benzamide

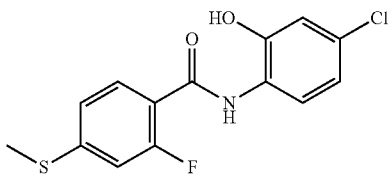 [SMILES: CSc1ccc(C(=O)Nc2ccc(Cl)cc2O)c(F)c1]

To a mixture of 2-amino-5-chloro-phenol (2.00 g, 13.93 mmol, 1.5 eq.), TEA (3.76 g, 37.14 mmol, 5.17 mL, 4 eq.) in THF (20 mL) was added a solution of 2-fluoro-4-(methylthio)benzoyl chloride (1.9 g, 9.28 mmol, 1 eq.) in THF (20 mL) at 0° C., and the mixture was stirred at 25° C. for 16 hr under N₂ atmosphere. The reaction mixture was quenched by addition water (300 mL), and then extracted with EtOAc (300 mL*2). The combined organic layers were washed with brine (300 mL*2), dried over anhydrous Na₂SO₄, filtered and concentrated. The residue was purified by flash silica gel chromatography (Silica Flash Column, Eluent of 080% Ethyl acetate/Petroleum ether). N-(4-chloro-2-hydroxyphenyl)-2-fluoro-4-(methylthio)benzamide (1 g, 3.21 mmol, 34.55% yield) was obtained as a gray solid. ¹H NMR (CDCl₃, 400 MHz) δ$_H$=8.69 (d, J=17.6 Hz, 1H), 8.10 (t, J=8.4 Hz, 1H), 7.28-7.27 (m, 1H), 7.16 (d, J=2.4 Hz, 1H), 7.11-7.09 (m, 2H), 7.03 (d, J=13.6 Hz, 1H), 6.90 (d, J=6.4 Hz, 1H), 2.55 (s, 3H).

Step 4: Synthesis of 7-chloro-3-(methylthio)dibenzo[b, f][1,4]oxazepin-11(10H)-one

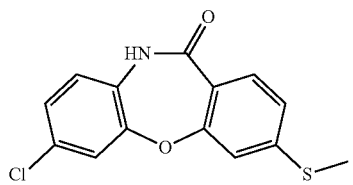 [SMILES: CSc1ccc2c(c1)Oc1cc(Cl)ccc1NC2=O]

A mixture of N-(4-chloro-2-hydroxyphenyl)-2-fluoro-4-(methylthio)benzamide (800 mg, 2.57 mmol, 1 eq.) t-BuOK (576 mg, 5.13 mmol, 2 eq.) in DMF (15 mL) was degassed and purged with N₂ 3 times, and then the mixture was stirred at 140° C. for 3 hr under N₂ atmosphere. After cooling to 25° C., the reaction mixture was poured into ice water, and the suspension solution was filtered, the filter cake was collected. The crude product was evaporated under reduced pressure. The crude product was used into next step without further purification. 7-chloro-3-(methylthio)dibenzo[b,f][1,4]oxazepin-11(10H)-one (400 mg, 1.37 mmol, 53.43% yield) was obtained as a brown solid. ¹H NMR (CDCl₃, 400 MHz) δ$_H$=8.40 (s, 1H), 7.83 (d, J=8.0 Hz, 1H), 7.28 (d, J=2.4 Hz, 1H), 7.16-6.95 (m, 4H), 2.53 (s, 3H).

Step 5: Synthesis of 7, 11-dichloro-3-(methylthio)dibenzo[b, f][1,4]oxazepine

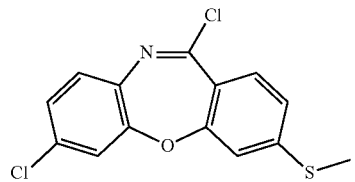 [SMILES: CSc1ccc2c(c1)Oc1cc(Cl)ccc1N=C2Cl]

A mixture of 7-chloro-3-(methylthio)dibenzo[b,f][1,4]oxazepin-11(10H)-one (400 mg, 1.37 mmol, 1 eq.) in POCl₃ (30 mL) was degassed and purged with N₂ 3 times, and then the mixture was stirred at 100° C. for 3 hr under N₂ atmosphere. The reaction mixture was concentrated, and then the residue was extracted with DCM (100 mL). The combined organic layers were washed with brine (100 mL*2), dried over anhydrous Na₂SO₄, filtered and concentrated under reduced pressure. The crude product was used into next step without further purification. 7,11-dichloro-3-(methylthio)dibenzo[b,f][1,4]oxazepine (400 mg, 1.29 mmol, 94.05% yield) was obtained as a brown oil.

Step 6: Synthesis of methyl 3-(4-(7-chloro-3-(methylthio)dibenzo[b, f][1, 4]oxazepin-11-yl)piperazin-1-yl)-2, 2-dimethylpropanoate

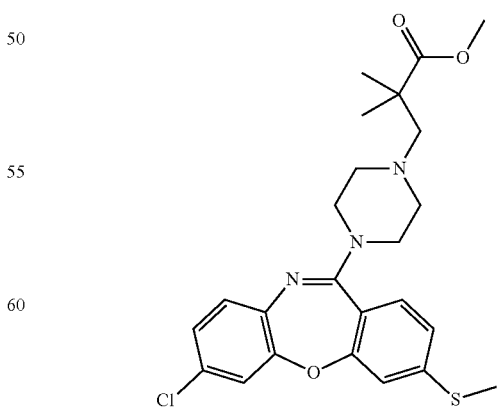

A mixture of 7,11-dichloro-3-(methylthio)dibenzo[b,f][1, 4]oxazepine (400 mg, 1.29 mmol, 1 eq.), methyl 2,2- dimethyl-3-piperazin-1-yl-propanoate (775 mg, 3.87 mmol, 3 eq.) and TEA (652 mg, 6.45 mmol, 897.42 μL, 5 eq.) in dioxane (10 mL) and DMSO (5 mL) was stirred at 120° C. for 16 hr under N₂ atmosphere. This reaction mixture was diluted with water (100 mL) and extracted with EtAOc (100 mL*2). The combined organic layers were washed with brine (100 mL*2), dried over Na₂SO₄ filtered and concentrated under reduced pressure to give a residue. The residue was purified by flash silica gel chromatography (Eluent of 0-15% Ethyl acetate/Petroleum). methyl 3-(4-(7-chloro-3-(methylthio)dibenzo[b,f][1,4]oxazepin-11-yl)piperazin-1-yl)-2,2-dimethylpropanoate (200 mg, 421.93 μmol, 32.72% yield, 100% purity) was obtained as a yellow oil. LCMS R$_t$=1.053 min in 2 min chromatography, Xtimate C18 2.1*30 mm, purity 100%, MS ESI calcd. for 473.15 [M+H]⁺ 474.15, found 474.1.

Step 7: Synthesis of 3-(4-(7-chloro-3-(methylthio) dibenzo [b, f][1,4]oxazepin-1-yl)piperazin-1-yl)-2, 2-dimethylpropanoic acid A mixture of methyl 3-(4-(7-chloro-3-(methylthio) dibenzo[b,f][1,4]oxazepin-11-yl)piperazin-1-yl)-2,2-dimethylpropanoate (200 mg, 421.93 μmol, 1 eq.), NaOH (51 mg, 1.27 mmol, 3 eq.) in MeOH (9 mL) and H₂O (3 mL) was degassed and purged with N₂ for 3 times, and then the mixture was stirred at 60° C. for 16 hr under N₂ atmosphere. The reaction mixture was acidified with HCOOH to pH=6, and concentrated. The residue was purified by prep-HPLC (column: Welch Xtimate C18 150*30 mm*5 um; mobile phase: [water (0.225% FA)-ACN]; B %: 25%-55%, 8 min). 3-(4-(7-chloro-3-(methylthio)dibenzo[b,f][1,4]oxazepin-11-yl)piperazin-1-yl)-2,2-dimethylpropanoic acid (61.3 mg, 133.26 μmol, 31.58% yield, 100% purity) was obtained as a white solid. ¹H NMR (CDCl₃, 400 MHz) δ$_H$=7.19 (d, J=8.0 Hz, 1H), 7.13 (d, J=1.6 Hz, 1H), 7.09-7.01 (m, 4H), 3.78-3.47 (m, 4H), 2.95-2.77 (m, 4H), 2.61 (s, 2H), 2.52 (s, 3H), 1.27 (s, 6H). HPLC R$_t$=4.81 min in 8 min chromatography, Ultimate 3.0*50 mm 3 um, purity 100%. LCMS R$_t$=1.025 min in 2 min chromatography, Xtimate C18 2.1*30 mm, purity 100%, MS ESI calcd. for 459.14 [M+H]⁺ 460.14, found 460.1.

Example 19. 3-(4-(3-fluoro-7-methyldibenzo[b,f][1, 4]oxazepin-11-yl)piperazin-1-yl)-2,2-dimethylpropanoic acid (Compound No. 17)

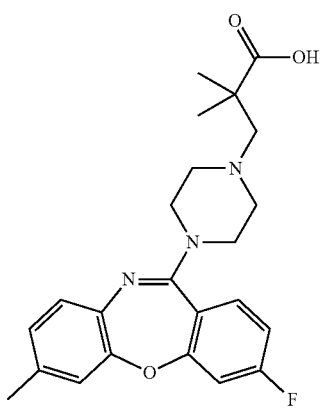 [SMILES: Cc1ccc2c(c1)Oc1cc(F)ccc1C(N1CCN(CC(C)(C)C(=O)O)CC1)=N2]

Step 1: Synthesis of methyl 4-fluoro-2-(5-methyl-2-nitrophenoxy)benzoate

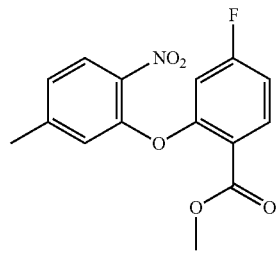 [SMILES: COC(=O)c1ccc(F)cc1Oc1cc(C)ccc1[N+](=O)[O-]]

To a mixture of methyl 4-fluoro-2-hydroxybenzoate (5 g, 29.39 mmol, 1 eq.) and 2-fluoro-4-methyl-1-nitro-benzene (4.56 g, 29.39 mmol, 1 eq.) in DMF (150 mL) was added K₂CO₃ (8.12 g, 58.78 mmol, 2 eq.). The resulting mixture was stirred at 100° C. for 16 hrs. The mixture was diluted with EtOAc (500 mL), washed with brine (400 mL*3). The combined organic layer was dried over Na₂SO₄, and concentrated to give crude product. The crude product was used directly to the next step without further purification. methyl 4-fluoro-2-(5-methyl-2-nitrophenoxy)benzoate (8.5 g, 27.85 mmol, 94.75% yield) was obtained as a yellow solid. ¹H NMR (400 MHz, DMSO-d₆) δ=8.05-7.96 (m, 2H), 7.24-7.21 (m, 1H), 7.17 (d, J=8.4 Hz, 1H), 7.13-7.10 (m, 1H), 6.88 (s, 1H), 3.69 (s, 3H), 2.33 (s, 3H).

Step 2: Synthesis of 3-fluoro-7-methyldibenzo[b,f] [1,4]oxazepin-11(10H)-one

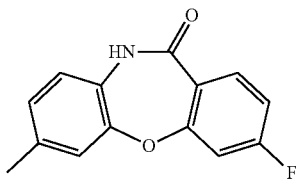 [SMILES: Cc1ccc2c(c1)Oc1cc(F)ccc1C(=O)N2]

To a mixture of methyl 4-fluoro-2-(5-methyl-2-nitrophenoxy)benzoate (22 g, 68.38 mmol, 1 eq.) in HOAc (220 mL) was added Fe (22.91 g, 410.30 mmol, 6 eq.). The mixture was stirred at 120° C. for 2 hrs. The mixture was filtered via a celite pad, and washed with DCM (800 mL*3). The filtrate was washed with brine (500 mL*3). The combined organic layer was dried over Na₂SO₄, and concentrated to give crude product. The crude product was triturated with EtOAc (100 mL). 3-fluoro-7-methyldibenzo[b,f][1,4]oxazepin-11(10H)-one (16 g, 61.61 mmol, 90.10% yield) was obtained as a light yellow solid. ¹H NMR (400 MHz, DMSO-d₆) δ=10.46 (s, 1H), 7.84-7.80 (m, 1H), 7.29-7.26 (m, 1H), 7.23-7.15 (m, 2H), 7.06-6.98 (m, 2H), 2.26 (s, 3H).

Step 3: Synthesis of 11-chloro-3-fluoro-7-methyldibenzo [b, f][1,4]oxazepine

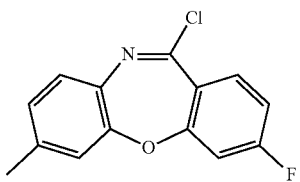 [SMILES: Cc1ccc2c(c1)Oc1cc(F)ccc1C(Cl)=N2]

A mixture of 3-fluoro-7-methyldibenzo[b,f][1,4]oxazepin-11(10H)-one (300 mg, 1.23 mmol, 1 eq.) in POCl$_3$ (20 mL) was degassed and purged with N$_2$ 3 times, and then the mixture was stirred at 100° C. for 3 hr under N$_2$ atmosphere. The reaction mixture was concentrated, and then the residue was diluted with DCM (200 mL), and washed with water (100 mL*2) and brine (100 mL*2). The combined organic layers were dried over anhydrous Na$_2$SO$_4$, filtered and concentrated under reduced pressure. The crude product was used into next step without further purification. 11-chloro-3-fluoro-7-methyldibenzo[b,f][1,4]oxazepine (300 mg, crude) was obtained as a brown oil.

Step 4: Synthesis of methyl 3-(4-(3-fluoro-7-methyldibenzo[b, f][1,4]oxazepin-11-yl)piperazin-1-yl)-2, 2-dimethylpropanoate

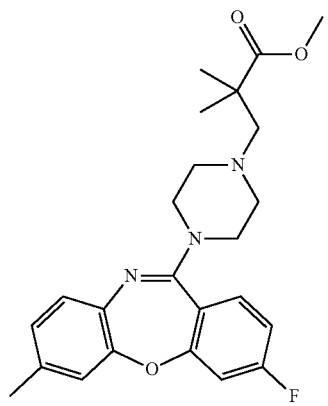

A mixture of 11-chloro-3-fluoro-7-methyldibenzo[b,f][1, 4]oxazepine (300 mg, 1.15 mmol, 1 eq.), methyl 2,2-dimethyl-3-piperazin-1-yl-propanoate (689 mg, 3.44 mmol, 3 eq.) and TEA (580.0 mg, 5.73 mmol, 797.86 µL, 5 eq.) in dioxane (10 mL) and DMSO (5 mL) was stirred at 120° C. for 16 hr under N$_2$ atmosphere. This reaction mixture was diluted with water (100 mL) and extracted with EtAOc (100 mL*2). The combined organic layers were washed with brine (100 mL*2), dried over anhydrous Na$_2$SO$_4$, filtered and concentrated under reduced pressure. The residue was purified by flash silica gel chromatography (Eluent of 0~15% Ethyl acetate/Petroleum). Methyl 3-(4-(3-fluoro-7-methyldibenzo[b,f][1,4]oxazepin-11-yl)piperazin-1-yl)-2,2-dimethylpropanoate (150 mg, 328.73 µmol, 28.67% yield, 93.25% purity) was obtained as a yellow oil. LCMS R$_t$=0.729 min in 1.5 min chromatography, Agilent Pursit 5 C18 20*2.0 mm, purity 93.26%, MS ESI calcd. for 425.21 [M+H]$^+$ 426.21, found 426.1.

Step 5: Synthesis of 3-(4-(3-fluoro-7-methyldibenzo [b, f][1, 4]oxazepin-11-yl)piperazin-1-yl)-2, 2-dimethylpropanoic acid A mixture of methyl 3-(4-(3-fluoro-7-methyldibenzo[b,f][1,4]oxazepin-11-yl)piperazin-1-yl)-2,2-dimethylpropanoate (150 mg, 352.53 µmol, 1 eq.), NaOH (14.0 mg, 352.53 µmol, 1 eq.) in MeOH (10 mL) and H$_2$O (3 mL) was degassed and purged with N$_2$ for 3 times, and then the mixture was stirred at 60° C. for 3 hr under N$_2$ atmosphere. The residue was acidified with HCOOH to pH=6, and concentrated. The residue was purified by prep-HPLC (column: Welch Xtimate C18 150*30 mm*5 um; mobile phase: [water (0.225% FA)-ACN]; B %: 20%-50%, 8 min). 3-(4-(3-fluoro-7-methyldibenzo[b,f][1,4]oxazepin-11-yl)piperazin-1-yl)-2,2-dimethylpropanoic acid (70 mg, 170.12 µmol, 48.26% yield, 100% purity) was obtained as a white solid. $^1$H NMR (CDCl$_3$, 400 MHz) δ$_H$=7.35-7.30 (m, 1H), 7.03 (d, J=7.6 Hz, 1H), 6.98 (dd, J=2.4, 8.8 Hz, 1H), 6.96-6.88 (m, 3H), 3.68-3.53 (m, 4H), 2.93-2.87 (m, 4H), 2.62 (s, 2H), 2.30 (s, 3H), 1.27 (s, 6H). HPLC R$_t$=4.30 min in 8 min chromatography, Ultimate 3.0*50 mm 3 um, purity 100%. LCMS R$_t$=0.920 min in 2 min chromatography, Xtimate C18 2.1*30 mm, purity 100%, MS ESI calcd. for 411.20 [M+H]$^+$ 412.20, found 412.2.

Example 20. 3-(4-(7-fluoro-3-methoxydibenzo[b,f][1,4]oxazepin-11-yl)piperazin-1-yl)-2,2-dimethylpropanoic acid (Compound No. 21)

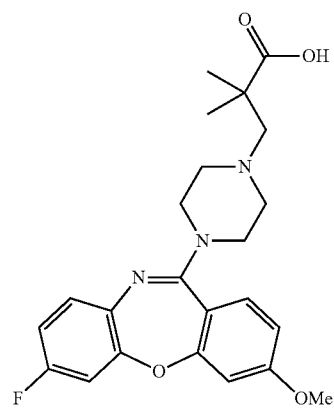 [SMILES: COc1ccc2c(c1)Oc1cc(F)ccc1N=C2N1CCN(CC(C)(C)C(=O)O)CC1]

Step 1: Synthesis of methyl 3-(4-(7-fluoro-3-methoxydibenzo[b,f][1,4]oxazepin-11-yl)piperazin-1-yl)-2,2-dimethylpropanoate

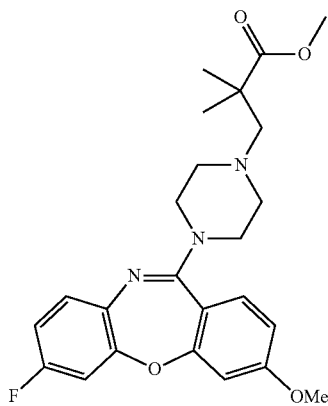 [SMILES: COC(=O)C(C)(C)CN1CCN(C2=Nc3ccc(F)cc3Oc3cc(OC)ccc32)CC1]

To a mixture of 11-chloro-7-fluoro-3-methoxydibenzo[b,f][1,4]oxazepine (400 mg, 1.44 mmol, 1 eq.) in TEA (1.46 g, 14.41 mmol, 2.01 mL, 10 eq.) and dioxane (10 mL) was added methyl 2,2-dimethyl-3-piperazin-1-yl-propanoate (577 mg, 2.88 mmol, 2 eq.). The mixture was stirred at 110° C. for 10 hrs. The mixture was diluted with EtOAc (200 mL), washed with brine (200 mL*3). The combined organic layer was dried over Na$_2$SO$_4$, and concentrated to give crude product. The product was purified by column chromatography on silica gel (PE:EtOAc=3:1). methyl 3-(4-(7-fluoro-3-methoxydibenzo[b,f][1,4]oxazepin-11-yl)piperazin-1-yl)-2,2-dimethylpropanoate (300 mg, 679.51 µmol, 47.17% yield, 100% purity) was obtained as a yellow solid. LCMS R$_t$=1.146 min in 2 min chromatography, Xtimate C18 2.1*30 mm, purity 100.00%, MS ESI calcd. for 441.21 [M+H]$^+$ 442.21, found 442.1.

Step 2: Synthesis of 3-(4-(7-fluoro-3-methoxydibenzo[b,f][1,4]oxazepin-11-yl)piperazin-1-yl)-2,2-dimethylpropanoic acid To a mixture of methyl 3-(4-(7-fluoro-3-methoxydibenzo[b,f][1,4]oxazepin-11-yl)piperazin-1-yl)-2,2-dimethylpropanoate (300 mg, 679.51 µmol, 1 eq.) in MeOH (3 mL), H$_2$O (4 mL) and THF (3 mL) was added NaOH (54 mg, 1.36 mmol, 2 eq.). The mixture was stirred at 60° C. for 4 hrs. The mixture was concentrated to remove MeOH. The pH of the mixture was adjusted to around 5 with HCOOH. The mixture was filtered via a filter paper, the filter cake was dissolved in CH$_3$CN (10 ml) and H$_2$O (40 ml), and lyophilized. 3-(4-(7-fluoro-3-methoxydibenzo[b,f][1,4]oxazepin-11-yl)piperazin-1-yl)-2,2-dimethylpropanoic acid (191.0 mg, 446.82 µmol, 65.76% yield, 100% purity) was obtained as a white solid. $^1$H NMR (DMSO-d$_6$, 400 MHz) δ$_H$=7.29 (d, J=8.8 Hz, 1H), 7.13-7.07 (m, 1H), 7.06-7.00 (m, 1H), 6.98-6.93 (m, 2H), 6.91-6.86 (m, 1H), 3.81 (s, 3H), 3.53-3.35 (m, 4H), 2.78-2.67 (m, 6H), 1.10 (s, 6H). HPLC R$_t$=2.59 min in 4 min chromatography, Ultimate 3.0*50 mm 3 um, purity 99.11%. LCMS R$_t$=3.098 min in 7 min chromatography, Xtimate C18 2.1*30 mm, purity 100%, MS ESI calcd. for 427.19 [M+H]$^+$ 428.19, found 428.1.

Example 21. 3-(4-(3-(difluoromethyl)dibenzo[b,f][1,4]oxazepin-11-yl)piperazin-1-yl)-2,2-dimethylpropanoic acid (Compound No. 36)

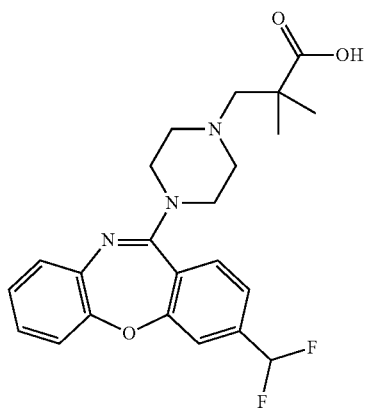 [SMILES: CC(C)(CN1CCN(C2=Nc3ccccc3Oc3cc(C(F)F)ccc32)CC1)C(=O)O]

Step 1: Synthesis of tert-butyl 4-(3-vinyldibenzo[b,f][1,4]oxazepin-11-yl)piperazine-1-carboxylate

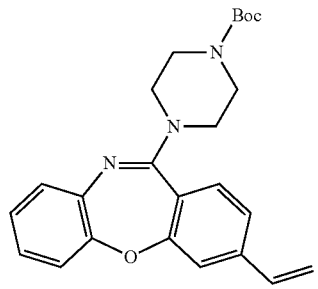 [SMILES: C=Cc1ccc2c(c1)Oc1ccccc1N=C2N1CCN(C(=O)OC(C)(C)C)CC1]

A mixture of tert-butyl 4-(3-bromodibenzo[b,f][1,4]oxazepin-11-yl)piperazine-1-carboxylate (2 g, 4.36 mmol, 1 eq.), potassium hydride; trifluoro(vinyl)boron (1.2 g, 8.73 mmol, 2 eq.), Pd(dppf)Cl$_2$ (319 mg, 436.35 µmol, 0.1 eq.), Cs$_2$CO$_3$ (4.3 g, 13.09 mmol, 3 eq.) in dioxane (15 mL) and H$_2$O (3 mL) was degassed and purged with N$_2$ for 3 times, and then the mixture was stirred at 110° C. for 2 hr under N$_2$ atmosphere. The reaction mixture was quenched by the addition of water (100 mL), and then extracted with EtOAc (100 mL*2). The combined organic layers were washed with brine (100 mL*2), dried over anhydrous Na$_2$SO$_4$, filtered and concentrated under reduced pressure to give a residue. The residue was purified by flash silica gel chromatography (eluent of 0-15% ethyl acetate/petroleum ether). Tert-butyl 4-(3-vinyldibenzo[b,f][1,4]oxazepin-11-yl)piperazine-1-carboxylate (1.37 g, 3.26 mmol, 74.73% yield, 96.51% purity) was obtained as a yellow oil. LCMS R$_t$=0.853 min in 1.5 min chromatography, Merk RP18e 25-3 mm, purity 96.51%, MS ESI calcd. for 405.21 [M+H]$^+$ 406.22, found 406.1.

Step 2: Synthesis of tert-butyl 4-(3-formyldibenzo[b,f][1,4]oxazepin-11-yl)piperazine-1-carboxylate

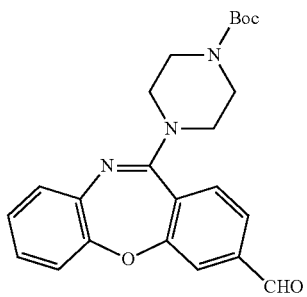 [SMILES: CC(C)(C)OC(=O)N1CCN(C2=Nc3ccccc3Oc3cc(C=O)ccc32)CC1]

A mixture of tert-butyl 4-(3-vinyldibenzo[b,f][1,4]oxazepin-11-yl)piperazine-1-carboxylate (1.37 g, 3.38 mmol, 1 eq.) in MeOH (8 mL) was degassed and purged with O3, and then the mixture was stirred at −78° C. for 0.5 h under O3 atmosphere, then to the mixture was added Me$_2$S (4.20 g, 67.57 mmol, 4.96 mL, 20 eq.) and the mixture was stirred at 25° C. for 15.5 hrs. The reaction mixture was concentrated. The residue was diluted with water (100 mL), and then extracted with EtOAc (100 mL*2). The combined organic layers were washed with brine (100 mL*2). The organic phase was dried over anhydrous Na$_2$SO$_4$, filtered and concentrated. The residue was purified by flash silica gel chromatography (silica flash column, eluent of 0-20% ethyl acetate/petroleum ether). Tert-butyl 4-(3-formyldibenzo[b,f][1,4]oxazepin-11-yl)piperazine-1-carboxylate (220 mg, 527.89 µmol, 15.62% yield, 97.77% purity) was obtained as a yellow oil. LCMS R$_t$=0.848 min in 1.5 min chromatography, Merk RP18e 25-3 mm, purity 68.68%, MS ESI calcd. for 407.18 [M+H]$^+$ 408.18, found 408.1.

Step 3: Synthesis of tert-butyl 4-(3-(difluoromethyl)dibenzo[b,f][1,4]oxazepin-11-yl)piperazine-1-carboxylate

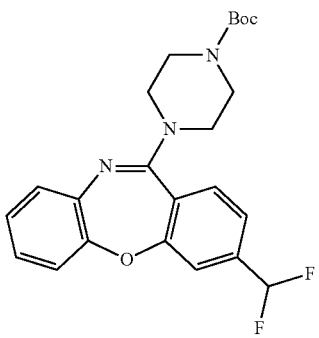 [SMILES: CC(C)(C)OC(=O)N1CCN(C2=Nc3ccccc3Oc3cc(C(F)F)ccc32)CC1]

To a mixture of tert-butyl 4-(3-formyldibenzo[b,f][1,4]oxazepin-11-yl)piperazine-1-carboxylate (220 mg, 539.93 µmol, 1 eq.) in DCM (5 mL) was added DAST (261 mg, 1.62 mmol, 214.01 µL, 3 eq.), and the mixture was degassed and purged with N$_2$ for 3 times, and then the mixture was stirred at −10° C. for 16 hr under N$_2$ atmosphere. The reaction mixture was quenched by the addition of saturated NaHCO$_3$ (100 mL), and then extracted with EtOAc (100 mL*2). The combined organic layers were washed with brine (100 mL*2), dried over anhydrous Na$_2$SO$_4$, filtered and concentrated under reduced pressure to give a residue. The residue was purified by flash silica gel chromatography (silica flash column, eluent of 0-20% ethyl acetate/petroleum ether). Tert-butyl 4-(3-(difluoromethyl)dibenzo[b,f][1,4]oxazepin-11-yl)piperazine-1-carboxylate (200 mg, 465.70 µmol, 86.25% yield, 100% purity) was obtained as a yellow oil. LCMS R$_t$=0.869 min in 1.5 min chromatography, Merk RP18e 25-3 mm, purity 100%, MS ESI calcd. for 429.19 [M+H]$^+$ 430.19, found 430.0.

Step 4: Synthesis of 3-(difluoromethyl)-11-(piperazin-1-yl)dibenzo[b,f][1,4]oxazepine

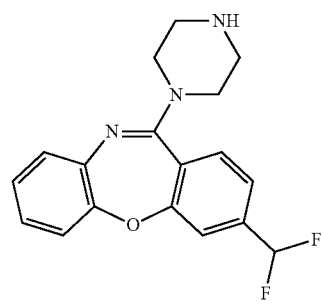 [SMILES: FC(F)c1ccc2c(c1)Oc1ccccc1N=C2N1CCNCC1]

A mixture of tert-butyl 4-(3-(difluoromethyl)dibenzo[b,f][1,4]oxazepin-11-yl)piperazine-1-carboxylate (200 mg, 465.70 µmol, 1 eq.) in HCl/dioxane (4 M, 15 mL) was stirred at 25° C. for 3 hr under N$_2$ atmosphere. The reaction mixture was concentrated to give the crude product. The crude product was used in the next step without further purification. 3-(difluoromethyl)-11-(piperazin-1-yl)dibenzo[b,f][1,4]oxazepine (150 mg, 446.39 µmol, 95.85% yield, 98.01% purity) was obtained as a yellow solid. LCMS R$_t$=0.758 min in 1.5 min chromatography, Merk RP18e 25-3 mm, purity 98.10%, MS ESI calcd. for 329.13 [M+H]$^+$ 330.13, found 329.9.

Step 5: Synthesis of methyl 3-(4-(3-(difluoromethyl)dibenzo[b,f][1,4]oxazepin-II-yl)piperazin-1-yl)-2,2-dimethylpropanoate

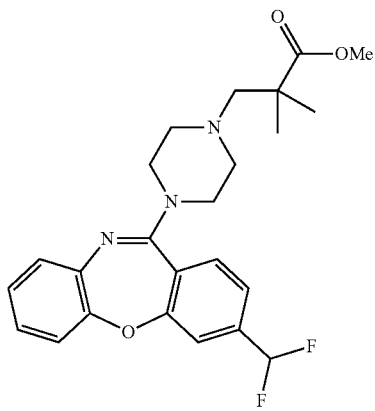 [SMILES: COC(=O)C(C)(C)CN1CCN(C2=Nc3ccccc3Oc3cc(C(F)F)ccc32)CC1]

A mixture of 3-(difluoromethyl)-11-(piperazin-1-yl)dibenzo[b,f][1,4]oxazepine (150 mg, 455.45 µmol, 1 eq.), methyl 2,2-dimethyl-3-oxo-propanoate (593 mg, 4.55 mmol, 10 eq.), NaBH(OAc)$_3$ (483 mg, 2.28 mmol, 5 eq.), and TEA (461 mg, 4.55 mmol, 633.94 μL, 10 eq.) in DCM (10 mL) was degassed and purged with $N_2$ for 3 times, and then the mixture was stirred at 25° C. for 16 hr under $N_2$ atmosphere. The reaction mixture was quenched by the addition of water (100 mL), and then extracted with EtOAc (100 mL*2). The combined organic layers were washed with brine (100 mL*2), dried over anhydrous $Na_2SO_4$, filtered and concentrated under reduced pressure to give a residue. The residue was purified by flash silica gel chromatography (silica flash column, eluent of 0-20% ethyl acetate/petroleum ether). Methyl 3-(4-(3-(difluoromethyl)dibenzo[b,f][1,4]oxazepin-11-yl)piperazin-1-yl)-2,2-dimethylpropanoate (200 mg, 450.97 μmol, 99.02% yield, 100% purity) was obtained as a colorless oil. LCMS $R_t$=0.824 min in 1.5 min chromatography, Merk RP18e 25-3 mm, purity 100%, MS ESI calcd. for 443.20 $[M+H]^+$ 444.20, found 444.1.

Step 6: Synthesis of 3-(4-(3-(difluoromethyl)dibenzo[b,f][1,4]oxazepin-11-yl)piperazin-1-yl)-2,2-dimethylpropanoic acid A mixture of methyl 3-(4-(3-(difluoromethyl)dibenzo[b,f][1,4]oxazepin-11-yl)piperazin-1-yl)-2,2-dimethylpropanoate (200 mg, 450.97 μmol, 1 eq.), NaOH (54 mg, 1.35 mmol, 3 eq.) in MeOH (8 mL) and $H_2O$ (3 mL) was degassed and purged, and then the mixture was stirred at 25° C. for 16 hr under 2 atmosphere. The reaction mixture was concentrated, and the residue was adjusted to pH=5 with HCOOH. The residue was purified by prep-HPLC (column: Welch Xtimate C18 150*30 mm*5 um; mobile phase: [water (0.225% FA)-ACN]; B %: 20%-50%, 8 min). 3-(4-(3-(difluoromethyl)dibenzo[b,f][1,4]oxazepin-11-yl)piperazin-1-yl)-2,2-dimethylpropanoic acid (79 mg, 183.95 μmol, 40.79% yield, 100% purity) was obtained as a white solid. $^1$H NMR ($CDCl_3$, 400 MHz) $\delta_H$=7.48-7.42 (m 2H), 7.40-7.32 (m, 1H), 7.21-7.10 (m, 3H), 7.09-7.03 (m, 1H), 6.65 (t, J=56.0 Hz, 1H), 3.95-3.45 (m, 4H), 3.06-2.89 (m, 4H), 2.71 (s, 2H), 1.31 (s, 6H). HPLC $R_t$=4.28 min in 8 min chromatography, Ultimate 3.0*50 mm 3 um, purity 100%. LCMS $R_t$=1.166 min in 2 min chromatography, Xtimate C18 2.1*30 mm, purity 100%, MS ESI calcd. for 429.19 $[M+H]^+$ 430.19, found 430.3.

Example 22. 2,2-dimethyl-3-(4-(7-methyldibenzo[b,f][1,4]thiazepin-11-yl)piperazin-1-yl)propanoic acid (Compound No. 37)

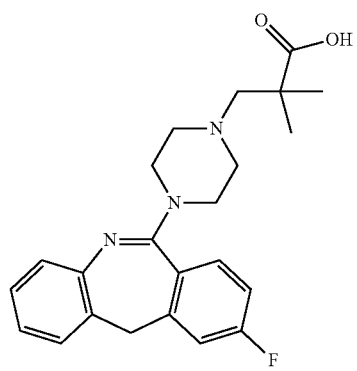 [SMILES: CC(C)(CN1CCN(C2=Nc3ccccc3Cc3cc(F)ccc32)CC1)C(=O)O]

A mixture of methyl 3-(4-(9-fluoro-11H-dibenzo[b,e]azepin-6-yl)piperazin-1-yl)-2,2-dimethylpropanoate (1.3 g, 3.17 mmol, 1 eq.) and $LiOH \cdot H_2O$ (666 mg, 15.87 mmol, 5 eq.) in THF (12 mL), MeOH (3 mL) and $H_2O$ (3 mL) was stirred at 25° C. for 16 hours under $N_2$ atmosphere. The mixture was concentrated to remove MeOH. The pH of the mixture was adjusted to around 4 with HCOOH. The crude product was purified by prep-HPLC (column: Xtimate C18 150*40 mm*5 μm; mobile phase: [water (0.05% HCl)-CAN]; B %: 1%-30%, 10 min) to give 2,2-dimethyl-3-(4-(7-methyldibenzo[b,f][1,4]thiazepin-11-yl)piperazin-1-yl)propanoic acid (1.25 g, 3.16 mmol, 80.90% yield, 100% purity) as a white solid. $^1$H NMR (400 MHz, DMSO-$d_6$) $\delta_H$=10.92 (br s, 1H), 7.81 (s, 1H), 7.57-7.35 (m, 3H), 7.34-7.21 (m, 3H), 4.41-3.75 (m, 2H), 3.55-3.10 (m, 6H), 2.56-2.50 (m, 4H), 1.33 (s, 6H). HPLC $R_t$=3.20 min in 8 min chromatography, Utimate 3.0*50 mm, purity 100%. LCMS $R_t$=0.688 min in 1.5 min chromatography, Xtimate C18 2.0*20 mm, purity 100.00%, MS ESI calcd. for 395.20 $[M+H]^+$ 396.20, found 396.2.

Example 23. 2,2-dimethyl-3-(4-(2-methyl-11H-dibenzo[b,e]azepin-6-yl)piperazin-1-yl)propanoic acid (Compound No. 38)

Step 1: Synthesis of 2-(bromomethyl)-4-methyl-1-nitrobenzene

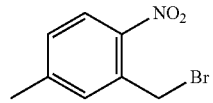

To a mixture of (5-methyl-2-nitrophenyl)methanol (8.7 g, 52.05 mmol, 1 eq.) in DCM (100 mL) was added NBS (13.89 g, 78.07 mmol, 1.5 eq.) and $PPh_3$ (20.48 g, 78.07 mmol, 1.5 eq.) at 0° C. The resulting mixture was allowed to warm up to 25° C. and stirred for 16 hrs. The reaction mixture was diluted with DCM (200 mL), washed with brine (100 mL), dried over $Na_2SO_4$, and concentrated in vacuo. The residue was purified by silica gel combi flash (EtOAc in PE: 0 to 10%). 2-(bromomethyl)-4-methyl-1-nitrobenzene (10 g, 43.47 mmol, 83.52% yield) was obtained as light yellow solid. $^1$H NMR ($CDCl_3$, 400 MHz) $\delta_H$=7.99 (d, J=8.0 Hz, 1H), 7.37 (s, 1H), 7.32-7.22 (m, 1H), 4.84 (s, 2H), 2.46 (s, 3H).

Step 2: Synthesis of methyl 2-(5-methyl-2-nitrobenzyl)benzoate

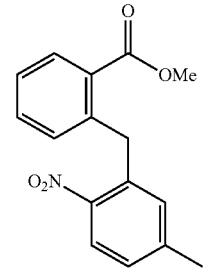 [SMILES: COC(=O)c1ccccc1Cc1cc(C)ccc1[N+](=O)[O-]]

A mixture of 2-(bromomethyl)-4-methyl-1-nitrobenzene (2.0 g, 8.69 mmol, 1 eq.), methyl 2-(4,4,5,5-tetramethyl-1,3,2-dioxaborolan-2-yl)benzoate (4.56 g, 17.39 mmol, 2 eq.), $K_2CO_3$ (3.00 g, 21.73 mmol, 2.5 eq.) and $PdCl_2$ (308 mg, 1.74 mmol, 0.2 eq.) in acetone (30 mL) and H$_2$O (10 mL) was degassed and purged with N$_2$ three times. The reaction mixture was stirred at 25° C. for 16 hours. The reaction was diluted with EtOAc (250 mL), filtered through the celite, washed with brine (250 mL), dried over Na$_2$SO$_4$, and concentrated in vacuo. The residue was purified by silica gel combi flash (EtOAc in PE: 0 to 5%). Methyl 2-(5-methyl-2-nitrobenzyl)benzoate (1.8 g, crude) was obtained as a yellow oil. $^1$H NMR (CDCl$_3$, 400 MHz) δ$_H$=7.91 (dd, J=1.2, 8.0 Hz, 1H), 7.84 (d, J=8.0 Hz, 1H), 7.40-7.35 (m, 1H), 7.29-7.23 (m, 1H), 7.07 (d, J=8.4 Hz, 1H), 7.02 (d, J=7.6 Hz, 1H), 6.76 (s, 1H), 4.59 (s, 2H), 3.72 (s, 3H), 2.24 (s, 3H).

Step 3: Synthesis of 2-methyl-5H-dibenzo[b,e]azepin-6(11H)-one

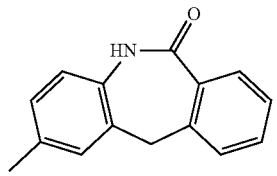 [SMILES: Cc1ccc2c(c1)Cc1ccccc1C(=O)N2]

A mixture of methyl 2-(5-methyl-2-nitrobenzyl)benzoate (1.8 g, 6.31 mmol, 1 eq.) and Fe (2.11 g, 37.86 mmol, 6 eq.) in AcOH (40 mL) was stirred at 120° C. for 3 hour. The reaction mixture was diluted with DCM/MeOH (200 mL, 10:1), and filtered through celite. The filtrate was washed with brine (100 mL*3) and sat. aq. NaHCO$_3$(100 mL*2), dried over Na$_2$SO$_4$, and concentrated in vacuo. The residue was triturated with EtOAc (10 mL) and then filtered. The cake was dried under vacuum. 2-methyl-5H-dibenzo[b,e]azepin-6(11H)-one (800 mg, 3.58 mmol, 56.79% yield) was obtained as a white solid. $^1$H NMR (CDCl$_3$, 400 MHz) δ$_H$=8.35 (br s, 1H), 7.84 (d, J=7.2 Hz, 1H), 7.36 (dt, J=1.2 Hz, 7.6 Hz, 1H), 7.28-7.20 (m, 1H), 7.18-7.16 (m, 1H), 7.02 (s, 1H), 6.97-6.81 (m, 2H), 3.84 (s, 2H), 2.23 (s, 3H).

Step 4: Synthesis of 6-chloro-2-methyl-1H-dibenzo[b,e]azepine

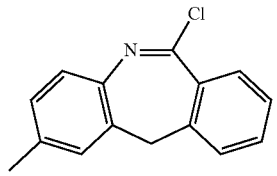 [SMILES: Cc1ccc2c(c1)Cc1ccccc1C(Cl)=N2]

A mixture of 2-methyl-5H-dibenzo[b,e]azepin-6(11H)-one (300 mg, 1.34 mmol, 1 eq.) in POCl$_3$ (15 mL) was degassed and purged with N$_2$ three times, and then the mixture was stirred at 110° C. for 5 hr under N$_2$ atmosphere. The mixture was concentrated to give a residue. The mixture was diluted with DCM (10 mL*2), and concentrated under reduced pressure to give a residue. 6-chloro-2-methyl-11H-dibenzo[b,e]azepine (324 mg, 1.34 mmol, 99.76% yield) was obtained as a brown solid.

Step 5: Synthesis of methyl 2,2-dimethyl-3-(4-(2-methyl-11H-dibenzo[b,e]azepin-6-yl)piperazin-1-yl)propanoate

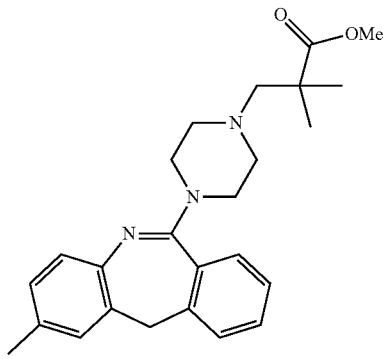 [SMILES: COC(=O)C(C)(C)CN1CCN(C2=Nc3ccc(C)cc3Cc3ccccc32)CC1]

To a solution of 6-chloro-2-methyl-11H-dibenzo[b,e]azepine (324 mg, 1.34 mmol, 1 eq.) in dioxane (20 mL) and TEA (1.36 g, 13.40 mmol, 1.87 mL, 10 eq.) was added methyl 2,2-dimethyl-3-piperazin-1-yl-propanoate (805 mg, 4.02 mmol, 3 eq.). The mixture was stirred at 110° C. for 16 hr. After cooling to room temperature, water (40 mL) was added to the mixture and the aqueous layer was extracted with EtOAc (40 mL×3). The combined organic phase was washed with brine (40 mL), dried over anhydrous Na$_2$SO$_4$, filtered and concentrated under reduced pressure. The residue was purified by flash silica gel chromatography (Eluent of 0 to 94% ethyl acetate/petroleum ether). Methyl 2,2-dimethyl-3-(4-(2-methyl-11H-dibenzo[b,e]azepin-6-yl)piperazin-1-yl)propanoate (65 mg, 128.23 μmol, 9.57% yield, 80% purity) was obtained as a yellow oil. LCMS R$_t$=0.685 min in 1.5 min chromatography, Xtimate C18 2.0*20 mm, purity 80.00%, MS ESI calcd. for 405.24 [M+H]$^+$ 406.24, found 406.1

Step 6: Synthesis of 2,2-dimethyl-3-(4-(2-methyl-11H-dibenzo[b,e]azepin-6-yl)piperazin-1-yl)propanoic acid To a solution of methyl 2,2-dimethyl-3-(4-(2-methyl-11H-dibenzo[b,e]azepin-6-yl)piperazin-1-yl)propanoate (65 mg, 128.23 μmol, 80% purity, 1 eq.) in THF (8 mL), H$_2$O (2 mL) and MeOH (2 mL) was added LiOH.H$_2$O (27 mg, 641.13 μmol, 5 eq.). The mixture was stirred at 25° C. for 16 hr to give a yellow mixture. The reaction mixture was concentrated to give the residue and acidified with HCOOH to a pH of 5. The residue was purified by pre-HPLC (column: 3_Phenomenex Luna C18 75*30 mm*3 μm; mobile phase: [water (0.05% HCl)-ACN]; B %: 5%-35%, 6.5 min). 2,2-dimethyl-3-(4-(2-methyl-11H-dibenzo[b,e]azepin-6-yl)piperazin-1-yl)propanoic acid (10.1 mg, 25.11 μmol, 19.58% yield, 97.34% purity) was obtained as white solid. $^1$H NMR (DMSO-d$_6$, 400 MHz) δ$_H$=10.78 (brs, 1H), 7.69-7.08 (m, 7H), 4.30-4.10 (m, 2H), 3.83 (d, J=12.8 Hz, 1H), 3.70-3.50 (m, 9H), 2.27 (s, 3H), 1.32 (s, 6H). HPLC R$_t$=3.43 min in 8 min chromatography, Utimate 3.0*50 mm, purity 97.34%. LCMS R$_t$=0.639 min in 1.5 min chromatography, Xtimate C18 2.0*20 mm, purity 98.98%, MS ESI calcd. for 391.23 [M+H]$^+$ 392.23, found 392.1.

Example 24. 3-(4-(1-fluorodibenzo[b,f][1,4]oxazepin-11-yl)piperazin-1-yl)-2,2-dimethylpropanoic acid (Compound No. 39)

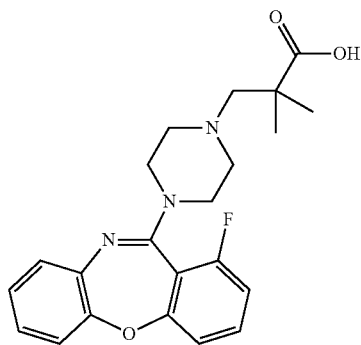 [SMILES: CC(C)(CN1CCN(C2=Nc3ccccc3Oc3cccc(F)c32)CC1)C(=O)O]

Step 1: Synthesis of 2,6-difluorobenzoyl chloride

A solution of 2,6-difluorobenzoic acid (3 g, 18.98 mmol, 1 eq.) in SOCl$_2$ (30 mL) was stirred at 80° C. for two hours under N$_2$ atmosphere. The reaction mixture was concentrated under reduced pressure. The crude product was used for next step directly without purification. 2,6-difluorobenzoyl chloride (3 g, 21.79 mmol, 99.27% yield, 86.03% purity) was obtained as light yellow oil.

Step 3: Synthesis of 2,6-difluoro-N-(2-hydroxyphenyl)benzamide

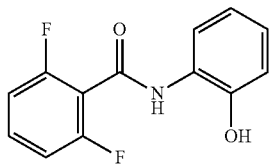 [SMILES: O=C(Nc1ccccc1O)c1c(F)cccc1F]

To a solution of 2-aminophenol (2.41 g, 22.09 mmol, 1.3 eq.) and TEA (5.16 g, 50.98 mmol, 7.10 mL, 3 eq.) in THF (20 mL) was added a solution of 2,6-difluorobenzoyl chloride (3 g, 16.99 mmol, 2.14 mL, 1 eq.) in THF (20 mL) at 0° C. The mixture was allowed to warm up to 25° C. and stirred for 12 hours. The reaction was diluted with EtOAc (200 mL) and washed with H$_2$O (200 mL×3). The mixture was washed with NH$_4$C$_1$ (200 mL×3). The combined organic layers were dried over Na$_2$SO$_4$, filtered and concentrated to dryness. The crude product was triturated with PE/EtOAc (5:1, 200 mL). 2,6-difluoro-N-(2-hydroxyphenyl)benzamide (3.97 g, 15.93 mmol, 93.75% yield, 92.63% purity) was obtained as a brown solid. $^1$H NMR (DMSO-d$_6$, 400 MHz) $\delta_H$=9.96 (s, 1H), 9.81 (s, 1H), 7.85 (dd, J=1.6, 8.0 Hz, 1H), 7.55-7.52 (m, 1H), 7.23-7.14 (m, 2H), 7.06-6.76 (m, 3H).

Step 3: Synthesis of 7-fluoro-5H-benzo[b][1,4]benzoxazepin-6-one

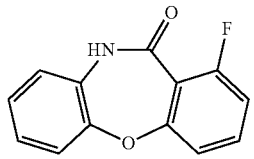 [SMILES: O=C1Nc2ccccc2Oc2cccc(F)c21]

To a mixture of 2,6-difluoro-N-(2-hydroxyphenyl)benzamide (1.5 g, 6.02 mmol, 1 eq.) in DMSO (15 mL) was added NaOH (482 mg, 12.05 mmol, 2 eq.). The mixture was stirred at 120° C. for two hours. The mixture was quenched with H$_2$O (100 mL), diluted with DCM (200 mL), and washed with brine (100 mL×3). The combined organic layers were dried over Na$_2$SO$_4$, and concentrated. The reaction mixture was used for next step directly without purification. 7-fluoro-5H-benzo[b][1,4]benzoxazepin-6-one (1.7 g, crude) was obtained as a brown solid. $^1$H NMR (DMSO-d$_6$, 400 MHz) $\delta_H$=7.67-7.57 (m, 1H), 7.50 (d, J=6.4 Hz, 1H), 7.39-7.28 (m, 1H), 7.27-7.12 (m, 4H), 7.12-7.05 (m, 1H).

Step 4: Synthesis of 6-chloro-7-fluoro-benzo[b][1,4]benzoxazepine

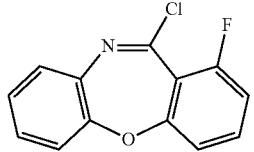 [SMILES: Fc1cccc2c1C(Cl)=Nc1ccccc1O2]

A mixture of 7-fluoro-5H-benzo[b][1,4]benzoxazepin-6-one (1.7 g, 7.42 mmol, 1 eq.) in POCl$_3$ (64.6 g, 421.31 mmol, 39.15 mL, 56.80 eq.) was degassed and purged with N$_2$ three times, and then the mixture was stirred at 110° C. for five hr under N$_2$ atmosphere. The residue was diluted with DCM (300 mL) and washed with H$_2$O (100 mL×2). The combined organic layers were dried over anhydrous Na$_2$SO$_4$, filtered and concentrated under reduced pressure. 6-chloro-7-fluoro-benzo[b][1,4]benzoxazepine (1.6 g, 6.46 mmol, 87.11% yield) was obtained as a black brown solid.

Step 5: Synthesis of methyl 3-[4-(7-fluorobenzo[b][1,4]benzoxazepin-6-yl)piperazin-1-yl]-2,2-dimethyl-propanoate

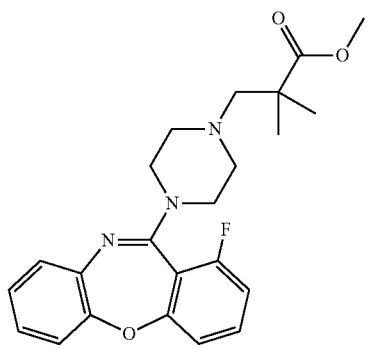 [SMILES: COC(=O)C(C)(C)CN1CCN(C2=Nc3ccccc3Oc3cccc(F)c32)CC1]

A mixture of 6-chloro-7-fluoro-benzo[b][1,4]benzoxazepine (1.6 g, 6.46 mmol, 1 eq.) in TEA (17.45 g, 172.43 mmol, 24 mL, 26.69 eq.) and dioxane (15 mL) and DMSO (5 mL) was added methyl 2,2-dimethyl-3-piperazin-1-yl-propanoate (2.59 g, 12.92 mmol, 2 eq.). The mixture was stirred at 110° C. for 12 hours. The reaction mixture was diluted with EtOAc (200 mL) and washed with brine (200 mL×3). The combined organic layers were dried over $Na_2SO_4$, filtered and concentrated to dryness. The crude product was purified by flash silica gel chromatography, eluent of 0 to 5% EtOAc/PE. Methyl 3-[4-(7-fluorobenzo[b][1,4]benzoxazepin-6-yl)piperazin-1-yl]-2,2-dimethyl-propanoate (597 mg, 1.40 mmol, 21.68% yield, 96.556% purity) was obtained as red oil. $^1$H NMR (DMSO-$d_6$, 400 MHz) $\delta_H$=7.59-7.55 (m, 1H), 7.25-7.12 (m, 3H), 7.07-6.90 (m, 3H), 4.01 (q, J=7.2 Hz, 1H), 2.50 (s, 6H), 2.48-2.39 (m, 4H), 1.97 (s, 2H), 1.10 (s, 6H).

Step 6: Synthesis of 3-[4-(7-fluorobenzo[b][1,4]benzoxazepin-6-yl)piperazin-1-yl]-2,2-dimethyl-propanoic

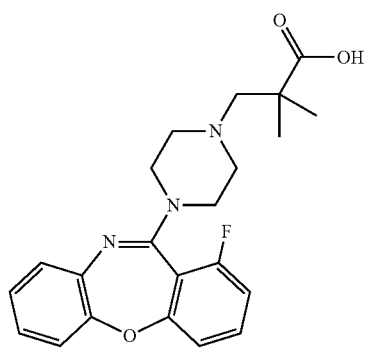 [SMILES: CC(C)(CN1CCN(C2=Nc3ccccc3Oc3cccc(F)c32)CC1)C(=O)O]

To a solution of methyl 3-[4-(7-fluorobenzo[b][1,4]benzoxazepin-6-yl)piperazin-1-yl]-2,2-dimethyl-propanoate (597 mg, 1.45 mmol, 1 eq.) in THF (8 mL), MeOH (2 mL) and $H_2O$ (2 mL) was added $LiOH\cdot H_2O$ (305 mg, 7.27 mmol, 5.01 eq.). The mixture was stirred at 25° C. for 12 hours. The mixture was concentrated to remove MeOH. The pH of the mixture was adjusted to around 5 with HCOOH. The product was purified by prep-HPLC (column: 3_Phenomenex Luna C18 75*30 mm*3 μm; mobile phase: [water (0.05% HCl)-ACN]; B %: 5%-35%, 6.5 min). 3-[4-(7-fluorobenzo[b][1,4]benzoxazepin-6-yl)piperazin-1-yl]-2,2-dimethyl-propanoic (380.6 mg, 954.75 μmol, 65.80% yield, 99.7% purity) was obtained as a white solid. $^1$H NMR (DMSO-$d_6$, 400 MHz) $\delta_H$=7.76-7.62 (m, 1H), 7.32 (d, J=8.4 Hz, 1H), 7.29-7.22 (m, 2H), 7.18-7.10 (m, 2H), 7.09-7.02 (m, 1H), 3.47-3.30 (m, 6H), 2.51-2.51 (m, 4H), 1.30 (d, J=2.4 Hz, 6H). HPLC $R_t$=3.78 min in 8 min chromatography, Utimate 3.0*50 mm, purity 99.70%. LCMS $R_t$=0.741 min in 4 min chromatography, Xtimate C18 2.1*30 mm, purity 99.817%, MS ESI calcd. for 397.18 [M+H]$^+$ 398.18, found 398.2.

Example 25. H1 and 5-HT$_2$A Binding Assay Protocol

The biological activity of the compounds of the present disclosure was determined utilizing the assay described herein.

TABLE A

| Reagents for Example 25 | | | |
|---|---|---|---|
| Target | Host Cell | Source of Membrane | Radio ligand |
| 5-HT$_{2A}$ | HEK293 | Stable cell line | [3H]-Ketanserin |
| H1 | HEK293 | Stable cell line | [3H]pyrilamine |

1M stock was prepared Tris base (Sigma, Cat: T1503-1KG) and adjust pH to 7.4.

TABLE B

| Assay Buffer and Wash Buffer | | |
|---|---|---|
| Target | Assay buffer | Wash buffer |
| 5-HT$_{2A}$ | 50 mM Tris-HCl, pH 7.4 | 50 mM Tris-HCl, pH 7.4 |
| H1 | 50 mM Tris-HCl, pH 7.4 | 50 mM Tris-HCl, pH 7.4 |

TABLE C

| Reference compound information | |
|---|---|
| Target | Reference Compound |
| 5-HT$_{2A}$ | Ketanserin |
| H1 | Pyrilamine |

Membrane Preparation and Ligand Preparation

TABLE D

| Dilute membrane and radioligand with assay buffer | | | | | |
|---|---|---|---|---|---|
| Target | Membrane Stock Conc. (mg/ml) | Final Membrane Conc. (μg/well) | Radio ligand | Radio ligand Stock Conc. (μM) | Final Radio ligand Conc. (nM) |
| 5-HT$_{2A}$ | 1.95 | 5 | [3H]-Ketanserin | 21.14 | 1 |

Compound Preparation

The testing compounds were diluted with DMSO, starting at 2 mM, with 8-points and 5-fold serial dilutions. Ketanserin and Pyrilamine were diluted with DMSO, starting at 0.2 mM, with 8-points and 5-fold serial dilution.

Assay Procedure

1 µl of a compounds of the present disclosure and either reference compound (Table C) were transferred to assay plates. 1 µl of 0.2 mM Ketanserin or Pyrilamine was transferred to an assay plate according to the plate map for nonspecific binding (Low control: LC). 1 µl of DMSO was transferred to an assay plate according to plate map for total binding (High control: HC).

100 µl of membrane stocks were dispensed into the plates, following the plate map. 100 of radio ligand was added. The plates were sealed and shaken at 300 rpm at room temperature for 1 hour. The Unifilter-96 GF/C filter plates were soaked with 50 of 0.3% PEI per well for at least 0.5 hour at room temperature.

When the binding assays were complete, the reaction mixture was filtered through GF/C plates using Perkin Elmer Filtermate Harvester, and then each plate was washed 4 times with cold wash buffer. The filter plates were dried for 1 hour at 50 degrees. After drying, the bottom of the filter plate wells were sealed using Perkin Elmer Unifilter-96 backing seal tape. 50 µl of Perkin Elmer Microscint 20 cocktail was added. The top of the filter plates were sealed with Perkin Elmer TopSeal-A sealing film.

$^3$H trapped on filters were counted using Perkin Elmer MicroBeta2 Reader. Inhibition constants were calculated using the following equation:

$$\% \text{ inhibition} = \left(1 - \frac{\text{Assay well} - \text{Average } LC}{\text{Average } HC - \text{Average } LC}\right) \times 100.$$

The data was analyzed using Prism 5. The model used was "log(inhibitor) vs. response—Variable slope" to fit the data and calculate IC50. The IC50 was then converted to $K_i$ using following equation: $K_i = IC50/(1+L/Kd)$. L is the radioligand concentration in the reaction system; Kd is the affinity of radioligand to the receptor.

Measured $K_i$ values of compounds of the present disclosure are shown in Table E and Table F below ("*" means >1 and ≤25 nM; "" means >25 and ≤50 nM; "*" means >50 nM).

TABLE E

| Compound No. | H1 $K_i$ (nM) | Compound No. | H1 $K_i$ (nM) |
|---|---|---|---|
| 1 | * | 13 | ** |
| 2 | ** | 14 | *** |
| 3 | ** | 15 | *** |
| 4 | * | 16 | *** |
| 5 | ** | 17 | * |
| 6 | * | 18 | * |
| 7 | *** | 19 | ** |
| 8 | ** | 20 | *** |
| 9 | *** | 21 | *** |
| 10 | * | 37 | *** |
| 11 | *** | 38 | *** |
| 12 | * | 39 | *** |

TABLE F

| Compound No. | 5-HT$_{2A}$ $K_i$ (nM) | Compound No. | 5-HT$_{2A}$ $K_i$ (nM) |
|---|---|---|---|
| 1 | * | 13 | * |
| 2 | * | 14 | * |
| 3 | * | 15 | * |

TABLE F-continued

| Compound No. | 5-HT$_{2A}$ $K_i$ (nM) | Compound No. | 5-HT$_{2A}$ $K_i$ (nM) |
|---|---|---|---|
| 4 | * | 16 | *** |
| 5 | * | 17 | * |
| 6 | * | 18 | ** |
| 7 | * | 19 | * |
| 8 | *** | 20 | ** |
| 9 | * | 21 | ** |
| 10 | * | 37 | *** |
| 11 | * | 38 | *** |
| 12 | *** | 39 | *** |

Example 26. Comparison of H1 and 5-HT$_2$A Binding

Compound No. 8 H1 and 5-HT$_{2A}$ binding activity was assessed by comparison of the $K_i$ values with 3-(4-(11H-dibenzo[b,e]azepin-6-yl)piperazin-1-yl)-2-methylpropanoic acid (i.e., Compound A-1). As shown in Table G, Compound No. 8 has a greater H1 and 5-HT$_{2A}$ affinity over 3-(4-(11H-dibenzo[b,e]azepin-6-yl)piperazin-1-yl)-2-methylpropanoic acid.

TABLE G

Comparison of H1 and 5-HT$_{2A}$ $K_i$ values.

| Compound | H1 $K_i$ (nM) | 5-HT$_{2A}$ $K_i$ (nM) |
|---|---|---|
| Compound No. 8 | 46 | 87 |
| A-1 | 104 | 1,376 |

Example 27. 5-HT$_{2C}$ Binding Assay Protocol

The biological activity of the compounds of the present disclosure was determined utilizing the assay described herein.

TABLE H

Reagents for Example 27

| Target | Host Cell | Source of Membrane | Radio ligand |
|---|---|---|---|
| 5-HT$_{2C}$ | HEK293 | Perkin Elmer, Cat# 6116110548400UA | [3H]-Mesulergine |

1M stock of tris base was prepared and adjusted to pH 7.4.

TABLE I

Assay Buffer and Wash Buffer

| Target | Assay Buffer | Wash Buffer |
|---|---|---|
| 5-HT$_{2C}$ | 50 mM Tris-HCl, 10 mM MgCl$_2$, 1 mM EDTA, 0.1% BSA pH 7.4 | 50 mM Tris-HCl, pH 7.4 |

TABLE J

| Reference compound information | |
|---|---|
| Target | Reference Compound |
| 5-HT$_{2C}$ | SB-206553 |

Membrane and Ligand Preparation

TABLE K

Dilution of membrane and radioligand with assay buffer

| Target | Membrane Stock Conc. (mg/mL) | Final Membrane Conc. (μg/well) | Radio ligand | Radio ligand stock Conc. (μM) | Final Radio ligand conc. (nM) |
|---|---|---|---|---|---|
| 5-HT$_{2C}$ | 3.5 | 2.5 | [3H]-Mesulergine | 12.048 | 2 |

Compound Preparation

The testing compounds were diluted with DMSO, starting at 2 mM, with 8-points and 5-fold serial dilutions. SB-206553 was diluted with DMSO, starting at 0.2 mM, with 8-points and 4-fold serial dilutions.

Assay Procedure

1 μL of a compound of the present disclosure the reference compound (Table J) was transferred to an assay plate. 1 μL of 0.2 mM SB-206533 was transferred to an assay plate according to the plate map for nonspecific binding (Low control: LC). 1 μL of DMSO was transferred to an assay plate according to the plate map for total binding (High control: HC).

Unifilter-96 GF/C filter plates were soaked with 50 μL of 0.3% PEI per well for about 0.5 hours at room temperature. When the binding assays were complete, the reaction mixture was filtered through the GF/C filter plates using Perkin Elmer Filtermate Harvester, and each plate was washed 4 times with cold wash buffer. The filter plates were dried for 1 hour at 50° C. After drying, the bottom of the filter plate wells were sealed using Perkin Elmer Unifilter-96 backing seal tape. 50 μL of Perkin Elmer Microscint 20 cocktail was added. The top of the filter plates were sealed with Perkin Elmer TopSeal-A sealing film.

$^3$H trapped on filters were counted using Perkin Elmer MicroBeta2 Reader. Inhibition constants were calculated using the following equation:

$$\% \text{ inhibition} = \left(1 - \frac{\text{Assay well} - \text{Average } LC}{\text{Average } HC - \text{Average } LC}\right) \times 100.$$

The data was analyzed using Prism 5. The model used was "log(inhibitor) vs. response—Variable slope" to fit the data and calculate IC$_{50}$. The IC$_{50}$ was then converted to K$_i$ using the following equation: K$_i$=IC$_{50}$/(1+L/K$_d$), wherein L is the radioligand concentration in the reaction system; K$_d$ is the affinity of radioligand to the receptor.

Measured K$_i$ values of compounds of the present disclosure are shown in Table L below ("*" means ≤100 nM; "" means >100 and ≤500 nM; "*" means >500 nM).

TABLE L

| Compound No. | 5HT$_{2C}$K$_i$ (nM) |
|---|---|
| 1 | *** |
| 6 | *** |
| 7 | *** |
| 8 | *** |
| 28 | ** |
| 29 | * |
| 31 | * |
| 33 | * |
| 34 | * |
| 35 | ** |
| 37 | *** |
| 38 | * |
| 39 | * |

Example 28. Comparison of 5-HT$_{2C}$ and D2 Binding

5-HT$_{2C}$ Binding Assay Protocol

Compound No. 7 for 5-HT$_{2C}$ binding activity was assessed by the comparison of K$_i$ values with 3-(4-(2,8-dimethyldibenzo[b,f][1,4]oxazepin-11-yl)piperazin-1-yl)-2,2-dimethylpropanoic acid (i.e., Compound A-2), 3-(4-(2,7-dimethyldibenzo[b,f][1,4]oxazepin-11-yl)piperazin-1-yl)-2,2-dimethylpropanoic acid (i.e, Compound A-3), 3-(4-(3,8-dimethyldibenzo[b,f][1,4]oxazepin-11-yl)piperazin-1-yl)-2,2-dimethylpropanoic acid (i.e., Compound A-4), and 3-(4-(dibenzo[b,f][1,4]oxazepin-11-yl)piperazin-1-yl)-2,2-dimethylpropanoic acid (i.e., Compound A-5). As shown in Table Q, Compound No. 7 has a lower affinity for 5-HT$_{2C}$ when compared to Compounds A-2, A-3, A-4, and A-5.

D2 Binding Assay Protocol

The biological activity of the compounds of the present disclosure was determined utilizing the assay described herein.

TABLE M

| Reagents for D2 binding assay protocol | | | |
|---|---|---|---|
| Target | Host Cell | Source of Membrane | Radio ligand |
| D2L | HEK293 | WuXi, Cat# PE-NET1169250UC | [3H] 7-OH-DPAT |

TABLE N

| Assay Buffer and Wash Buffer | | |
|---|---|---|
| Target | Assay Buffer | Wash Buffer |
| D2L | 50 mM Tris-HCl, pH 7.4 | 50 mM Tris-HCl, pH 7.4 |

TABLE O

| Reference compound information | |
|---|---|
| Target | Reference Compound |
| D2 | 10 μM droperidol |

TABLE P

Dilution of membrane and radioligand with assay buffer

| Target | Membrane Stock Conc. (mg/mL) | Final Membrane Conc. (µg/well) | Radio ligand | Radio ligand stock Conc. (µM) | Final Radio ligand conc. (nM) |
|---|---|---|---|---|---|
| D2 | 2.9 | 6 | [3H] 7-OH-DPAT | 7.87 | 1 |

Compound Preparation

The testing compounds were diluted with DMSO, starting at 2 mM, with 8-points and 5-fold serial dilutions. droperidol was diluted with DMSO, starting at 0.2 mM, with 8-points and 4-fold serial dilutions.

Assay Procedure

1 µL of a compound of the present disclosure and the reference compound (Table O) was transferred to an assay plate. 1 µL of droperidol was transferred to an assay plate according to the plate map for nonspecific binding (Low control: LC). 1 µL of DMSO was transferred to an assay plate according to the plate map for total binding (High control: HC). Following a plate map, 100 µL of the membrane stock solutions and radio ligand were added into the plate. The plates were sealed and shaken with 300 rpm.

Unifilter-96 GF/C filter plates were soaked with 50 µL of 0.3% PEI per well for about 0.5 hours at room temperature. When the binding assays were complete, the reaction mixture was filtered through the GF/B filter plates using Perkin Elmer Filtermate Harvester, and each plate was washed 4 times with cold wash buffer. The filter plates were dried for 1 hour at 50° C. After drying, the bottom of the filter plate wells were sealed using Perkin Elmer Unifilter-96 backing seal tape. 50 µL of Perkin Elmer Microscint 20 cocktail was added. The top of the filter plates were sealed with Perkin Elmer TopSeal-A sealing film.

$^3$H trapped on filters were counted using Perkin Elmer MicroBeta2 Reader. Inhibition constants were calculated using the following equation:

$$\% \text{ inhibition} = \left(1 - \frac{\text{Assay well} - \text{Average } LC}{\text{Average } HC - \text{Average } LC}\right) \times 100.$$

The data was analyzed using Prism 5. The model used was "log(inhibitor) vs. response—Variable slope" to fit the data and calculate $IC_{50}$. The $IC_{50}$ was then converted to $K_i$ using the following equation: $K_i = IC_{50}/(1+L/K_d)$, wherein L is the radioligand concentration in the reaction system; Kd is the affinity of radioligand to the receptor. As shown in Table Q Compound No. 7 has a lower affinity for D2 when compared to Compounds A-2, A-3, A-4, and A-5.

TABLE Q

Comparison of 5-HT$_{2C}$ and D2 $K_i$ values.

| Compound | 5-HT$_{2C}$ $K_i$ (nM) | D2 $K_i$ (nM) |
|---|---|---|
| Compound No. 7 | 2,220 | > 50,000 |
| A-2 | 265 | 60 |
| A-3 | 125 | 152 |
| A-4 | 772 | 1,902 |
| A-5 | 680 | 2,874 |

Example 29. Human Clearance and Half-life Projections

Projected human clearance (CL) and half-life in humans are shown in Table R below. An allometric scaling method, using a single species scaling from monkey clearance was used to project clearance. Human volume of distribution ($V_d$) was projected from animal $V_d$, adjusted for differences in plasma protein binding and assuming similar unbound $V_d$ across species. Human half-life ($T_{1/2}$) was calculated based on a one-compartmental model, using a relationship of $T_{1/2} = 0.693 \times (\text{predicted } V_d/\text{predicted CL})$.

TABLE R

| Compound No. | CL (mL/min/kg) | $T_{1/2}$ (h) |
|---|---|---|
| 6 | 0.3 | 12-25 |
| 7 | 1.3 | 4-8 |
| 8 | 1.8 | 2-4 |
| 36 | 0.4 | 14-50 |

Example 30. Experimental Details and Methods for Determining Sleep Continuity, Number of Arousals, and Depth of Sleep Treatment detail plots (see, e.g., FIGS. 1-10) depict pre- and post-treatment time series plot ±30 hours before and after treatment at CT-18 (6-hours after lights-off) or pre- and post-treatment time series plots 29 hr before and 31 hr after treatments at CT-5 (5-hours after lights-on). Treatment occurred at the beginning of the hour marked by a triangle on the abscissa of the plot. Variables were computed in hourly bins.

All data were plotted as group mean±SEM (see, e.g., FIGS. 1-10). The gray shaded area encompasses the vehicle treatment mean±SEM. Along the x-axis, time of treatment is marked by a triangle unless noted otherwise. Along the x-axis, light/dark bars indicate lights on/off.

Animal Preparation—Rats

Adult, male Wistar rats (approximately 270 g at time of surgery, Charles River Laboratories) were administered dexmedetomidine 25 µg/kg and anesthetized (2% isoflourane in 95/5 oxygen, to effect) and surgically prepared with a cranial implant that permitted chronic electro-encephalogram (EEG) and electromyogram (EMG) recording. Body temperature and locomotor activity were monitored via a miniature transmitter (Minimitter Series PDT4000 E-Mitter, Bend, Oreg.) surgically placed in the abdomen during the same anesthetic event when the cranial portion was implanted. The cranial implant consisted of miniature stainless steel screws (2 frontal [+3.9 AP from bregma, 2.0 ML], 2 occipital [−6.4 AP, 5.5 ML], and 1 ground placed sagittaly and posterior to lambda) for EEG recording. Two Teflon-coated multi-strand stainless steel wires were positioned under the nuchal trapezoid muscles for EMG recording. All leads were soldered to a miniature connector (Omnetics, Minneapolis, Minn.) and gas sterilized with ethylene oxide prior to surgery. The implant assembly was affixed to the skull by the combination of the EEG recording screws, cyanoacrylate applied between the hermetically sealed implant connector and skull, and a UV-curing dental acrylic. An analgesic (meloxicam 1 mg/kg IP) was administered 1 day prior to surgery and daily for 2 days post-surgery. Neosporin with lidocaine was applied topically to the peri-implant margin. At least three weeks were allowed for surgical recovery prior to any data collection.

Recording Environment

Rats were housed individually within specially modified Innovive® cages equipped with a custom-built ultra-low-torque slip-ring commutator and a customized Innovive® polycarbonate cage-top. These cages were located on shelves of a modified stainless steel animal rack that was pre-wired for physiological and behavioral data collection. Food and water were available ad libitum and the ambient temperature was 22±1° C. A 24-hr light-dark cycle (LD 12:12) was maintained throughout the study using LED lighting strips. Light intensity averaged 35 lux at mid-level inside the cage. Relative humidity averaged 50% approximately. Animals were undisturbed for two days before and after each treatment.

Automated Data Collection.

Sleep and wakefulness were determined using SCORE™—a Linux and Windows-10 real-time computer-based sleep-wake and physiological monitoring system. Validation of the SCORE™ sleep stage identification algorithm in rodents and the system's utility in pre-clinical drug discovery and evaluation have been previously described (Edgar et al. *Psychopharmacology* 1991, 105, 374; Gilmour et al., *Neuropharmacology* 2012, 64, 224; McCarthy et al., 2016, *Neuropharmacology* 108, 415; Olive et al., *J. Pharmacology &Experimental Therapeutics* 1998 285, 1073; Phillips et al, *Neuropharmacology* 2012, 62, 1359; Seidel et al. *J Pharmacology &Experimental Therapeutics* 1995, 275, 263; Van Gelder et al. Sleep 1991, 14, 48). For the studies described herein, the system monitored amplified EEG (×10,000, bandpass 0.7-30 Hz; initial digitization rate 400 Hz [Grass Corp., Quincy, MA]), amplified EMG (×10,000-20,000, bandpass 10-100 Hz, and quantified every 10 seconds using root mean square (RMS) integration. Telemetered body temperature was sampled, and non-specific locomotor activity (LMA) events were counted and values were digitized every minute. Arousal states were classified on-line as NREM sleep, REM sleep, wake, or theta-dominated wake every 10 seconds using EEG period and amplitude feature extraction across a minimum of 48 feature dimensions, integrated EMG threshold criteria, and ranked membership algorithms. Individually taught EEG-arousal-state templates and EMG criteria differentiated states of arousal for each animal. LMA was automatically recorded as counts per minute, and body temperature was recorded each minute. LMA was detected in both horizontal and vertical planes by a customized telemetry receiver (ER4000, Mini-mitter, Bend, Oreg.) beneath the cage.

Telemetry measures (LMA and body temperature) were not part of the SCORE arousal-state determination algorithm; thus, sleep-scoring and telemetry data were concurrent but independent measures. In addition to frequent on-line inspection of the EEG and EMG signals, quality control of the data was assured by expert analysts with a minimum of 4 years of experience using a proprietary suite of quality assurance and analysis programs (SCOREview™ Hypnion, Inc., Lexington, Mass. as further improved by Eli Lilly and Company, Windlesham, Surrey UK, and by Alairion, Inc., Cambridge Mass.) that allowed data quality of all variables to be flexibly scrutinized at the level of (i) individual visual examination of raw EEG and EMG signals, (ii) individual hourly mean timeseries, and (iii) group mean timeseries, using a combination of graphical and statistical assessments. An integrated relational database was updated with data quality control decisions for each individual treatment, and this database controlled all subsequent use of these data. Complete, digitized raw EEG, EMG, and physiological data are permanently archived for all treatments.

Treatments and Drug Preparation

Drug dose, route of administration, and timing of administration are described for each compound and variable within the data exemplifications. Where applicable, (i) methylcellulose vehicle was prepared as a sterile 0.25% solution of methylcellulose (15 centipoise, Sigma, St. Louis, Mo., USA) was delivered orally (PO) at 1 or 2 mL/kg, or (ii) 2-hydroxypropyl-beta-cyclodextrin, 20% (2HPβCD, Sigma, St. Louis, Mo., USA) was prepared and delivered PO and at 2 mL/kg.

Drugs were weighed using an analytical balance (d=0.01 mg). Compound was mixed with vehicle using a sterile 2 mL ground glass pestle and mortar until completely dissolved or well suspended, and then transferred to a sterile Vacutainer (red top) tube. Solutions were thoroughly agitated immediately before being drawn into a syringe. Oral gavage administration (PO) was typically in a volume of 1 or 2 mL/kg. To administer the treatment, each rat was removed from its cage for about 60 seconds to be weighed and treated (the home cage is the recording cage in SCORE™ systems). Note that this procedure caused no prior sleep loss, unlike cases in which the animal must first be acclimated to a special recording chamber. Rats in this experiment lived permanently in their "home cage" within the recording chamber. Prior sleep loss (for instance, the "acclimation" commonly used by other investigators) significantly influences the measurement of sleep-wakefulness responses to drugs.

Study Design

The standard recording duration for SCORE data was not less than 30 hours before and after treatment. The 30 hours pre-treatment baseline recording was itself preceded by at least 24 hours in which the animal was undisturbed in the home/recording cage. Rats were randomly assigned to treatments in parallel groups. Some rats received more than one active treatment, in which cases at least 7 days "washout" elapsed between each treatment.

Statistical Analysis

Statistically significant differences between drug and vehicle were screened using a post-hoc Student's T-test applied to hourly binned data and adjusted for repeated measures.

Example 31. Increased Sleep Continuity/Consolidation, Reduced the Number of Arousals and Increased the Depth of Sleep Sleep Continuity/Consolidation Compound 8 was administered to male Wistar rats at CT-18 (6 hours after light-off, time of treatment indicated by the triangle on the abscissa; FIG. 1), and increased sleep continuity was measured by the average sleep bout duration per hour. Average sleep bout duration was calculated as the mean duration of all sleep bouts initiated in each hour for an individual animal, plotted as the population (N=9) hourly mean SEM 30 hours before (baseline) and after treatment. Differences from methylcellulose vehicle control are indicated by asterisks. 24 hour light-dark cycle (LD 12:12) is indicated on the abscissa (FIG. 1). Compound 8 produced an increase in sleep consolidation as exemplified by an increase in sleep bout-length per hour that was approximately 4-fold greater than the effects observed in vehicle control animals.

Reduced Number of Arousals

Figure 2:
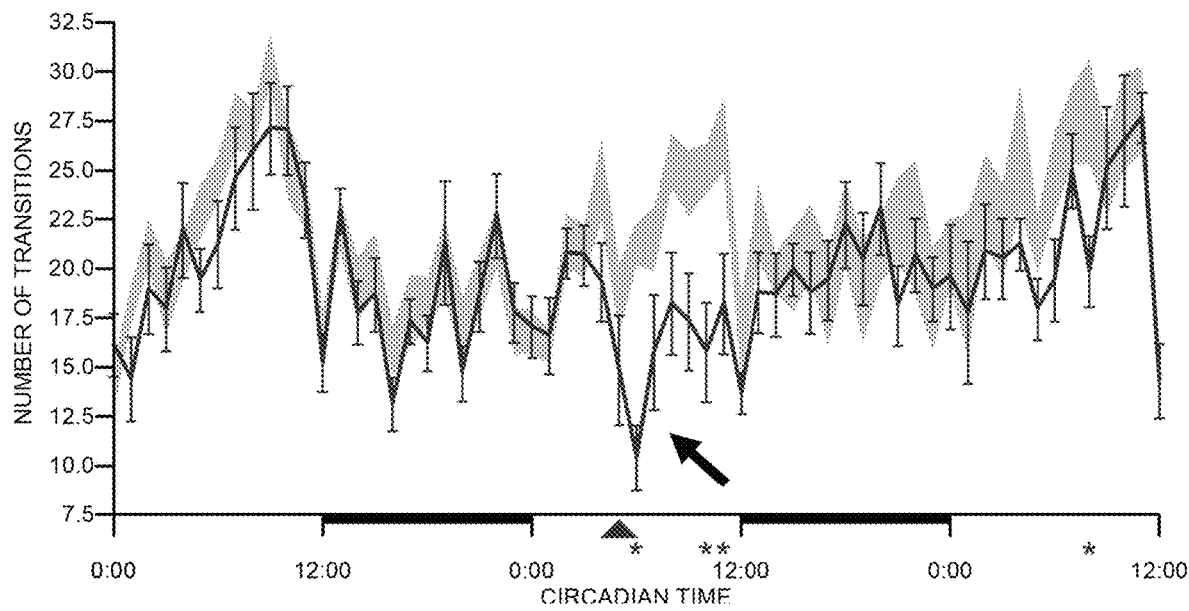
FIG. 2 depicts the number of transitions to wake per hour after administration of compound 8, wherein the thin line depicts compound 8 administration at 10 mg/kg PO (CT-5, n=11), and the thick line depicts administration of the control, methylcellulose, at 1 mL/kg PO (CT-5, n=11).

Compound 8 was administered to male Wistar rats at CT-5 (5 hours after light-on; time of treatment indicated by the triangle on the abscissa; FIG. 2), and reduced the number of arousals, as measured by the number of transitions from sleep to wake. The number of transitions from sleep to wake are plotted as the population (N=11) hourly mean SEM 30 hours before (baseline) and after treatment. Differences from methylcellulose vehicle control are indicated by asterisks. 24 hour light-dark cycle (LD 12:12) is indicated on the abscissa (FIG. 2). Compound 8 produced a reduction in arousals, evidenced by up to 50% reductions in the number of transitions from sleep to wake per hour post-treatment relative to controls.

Increased Depth of Sleep as Measured by EEG Delta Power During nonREM Sleep

Figure 3:
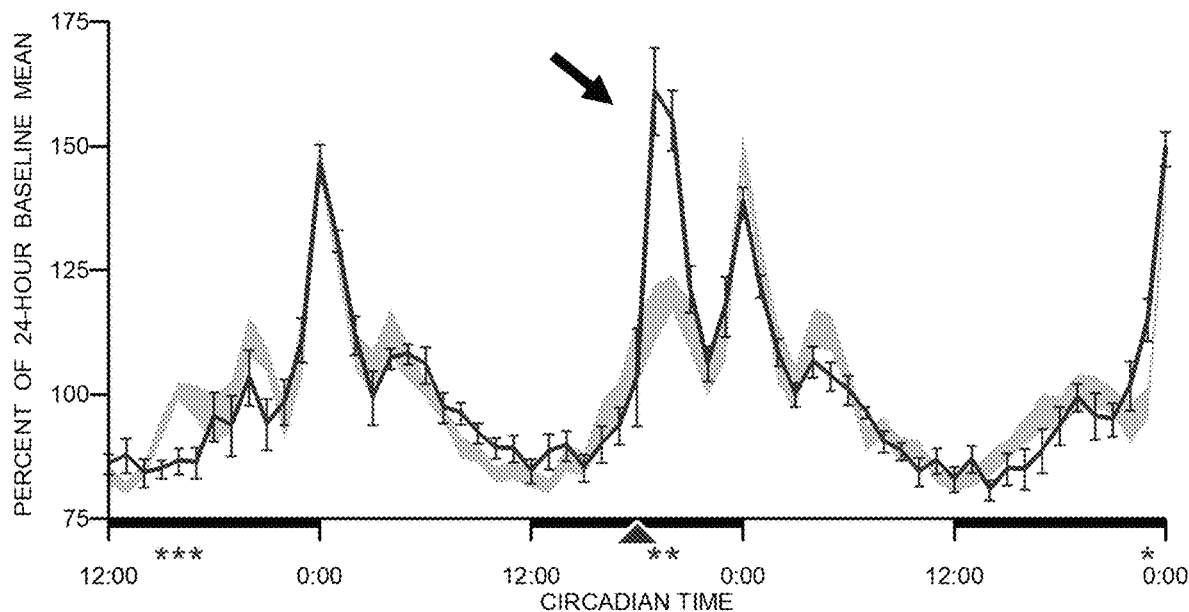
FIG. 3 depicts normalized EEG delta power after administration of compound 8, wherein the thin line depicts compound 8 administration at 3 mg/kg PO (CT-18, n=10), and the thick line depicts administration of the control, methylcellulose, at 1 mL/kg PO (CT-18, n=10).

Compound 8 was administered to male Wistar rats at CT-18 (6 hours after lights-off, time of treatment indicated by the triangle on the abscissa; FIG. 3) and increases in EEG slow wave activity in nonREM sleep were recorded, as measured by the normalized (percent change from baseline) EEG delta power during nonREM sleep per hour. Normalized EEG delta power (power in the EEG at frequencies of 0.5-4.0 Hz, computed using Fourier analysis) is plotted in this example as the population (N=10) hourly mean SEM 30 hours before (baseline) and after treatment. Differences from methylcellulose vehicle control are indicated by asterisk. 24 hour light-dark cycle (LD 12:12) is indicated on the abscissa (FIG. 3). An increase in EEG delta power (slow wave activity) is consistent with an elevation in arousal threshold associated with the compounds ability to reduce sleep fragmentation.

Cumulative Total Sleep Time

Figure 4:
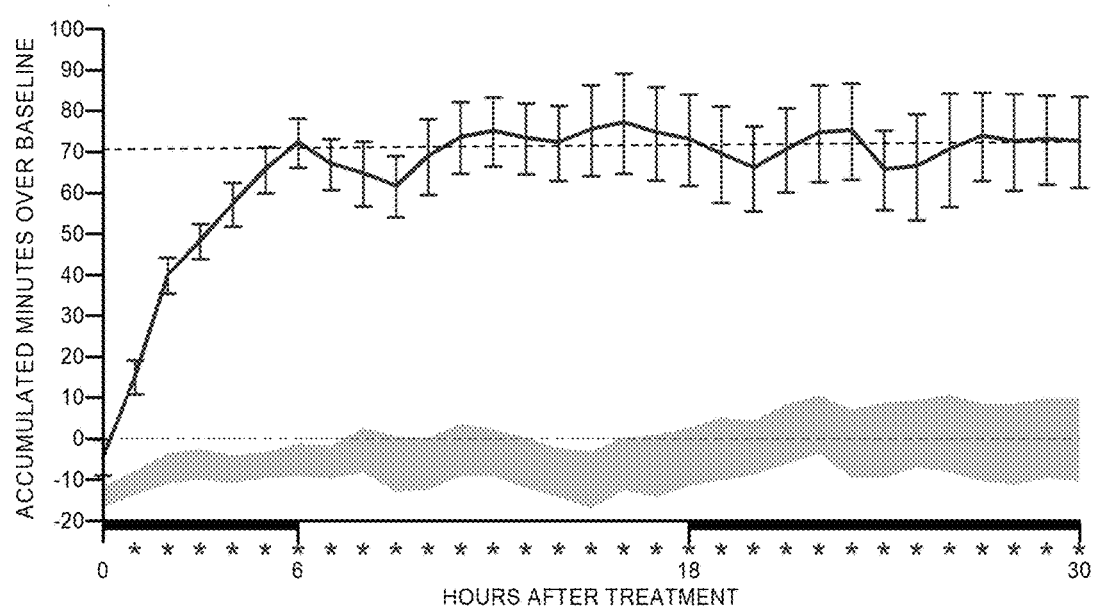
FIG. 4 depicts the hourly accumulation of Total Sleep Time (NREM+REM sleep) after administration of compound 8, measured from the time of treatment (hour 0 on the abscissa) relative to undisturbed baseline 24-hours prior to treatment, wherein the thin line depicts compound 8 administration at 30 mg/kg PO (CT-18, n=12), and the thick line depicts administration of the control, methylcellulose, at 1 mL/kg PO (CT-18, n=15). The dotted line depicts Total Sleep time increased by approximately 70 minutes.

Compound 8 was administered at 30 mg/kg to male Wistar rats at CT-18 (6 hours after light-off, treatment delivered at time=0 on the abscissa; FIG. 4), and the change in Total Sleep Time (NREM+REM sleep) relative to baseline 24-hours earlier was computed hourly as the cumulative sum across each of 30 hours post-treatment for each animal according to methods previously described (Olive et al., *J Pharmacology &Experimental Therapeutics*, 1998, 285: 1073-1083). Data are plotted as the population (N=12) hourly mean SEM during the 30 hours after treatment. Differences from methylcellulose vehicle control (N=15) are indicated by asterisks. Compound 8 produced a 70-minute cumulative increase in Total Sleep Time.

Figure 5:
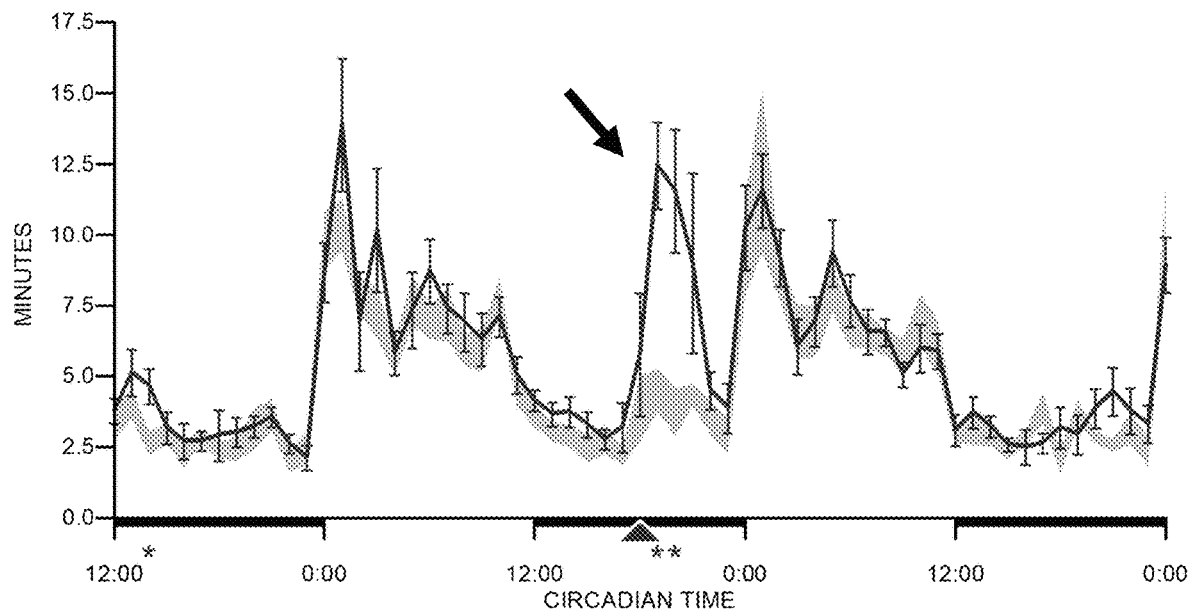
FIG. 5 depicts average aligned sleep bout each hour after administration of compound 7, wherein the thin line depicts compound 7 administration at 30 mg/kg PO (CT-18, n=10), and the thick line depicts administration of the control, methylcellulose, at 1 mL/kg PO (CT-18, n=10)

Example 32. Increased Sleep Continuity/Consolidation, Reduced the Number of Arousals and Increased Depth of Sleep Increased Sleep Continuity/Consolidation Compound 7 was administered to male Wistar rats at CT-18 (6 hours after light-off, time of treatment indicated by the triangle on the abscissa; FIG. 5), and increased sleep continuity was measured by the average sleep bout duration per hour. Average sleep bout duration was calculated as the mean duration of all sleep bouts initiated in each hour for an individual animal, plotted as the population (N=10) hourly mean SEM 30 hours before (baseline) and after treatment. Differences from methylcellulose vehicle control are indicated by asterisks. 24 hour light-dark cycle (LD 12:12) is indicated on the abscissa (FIG. 5). Compound 7 produced an increase in sleep consolidation as exemplified by an increase in sleep bout-length per hour that was approximately 3-4-fold greater than the effects observed in vehicle control animals.

Reduced Number of Arousals

Figure 6:
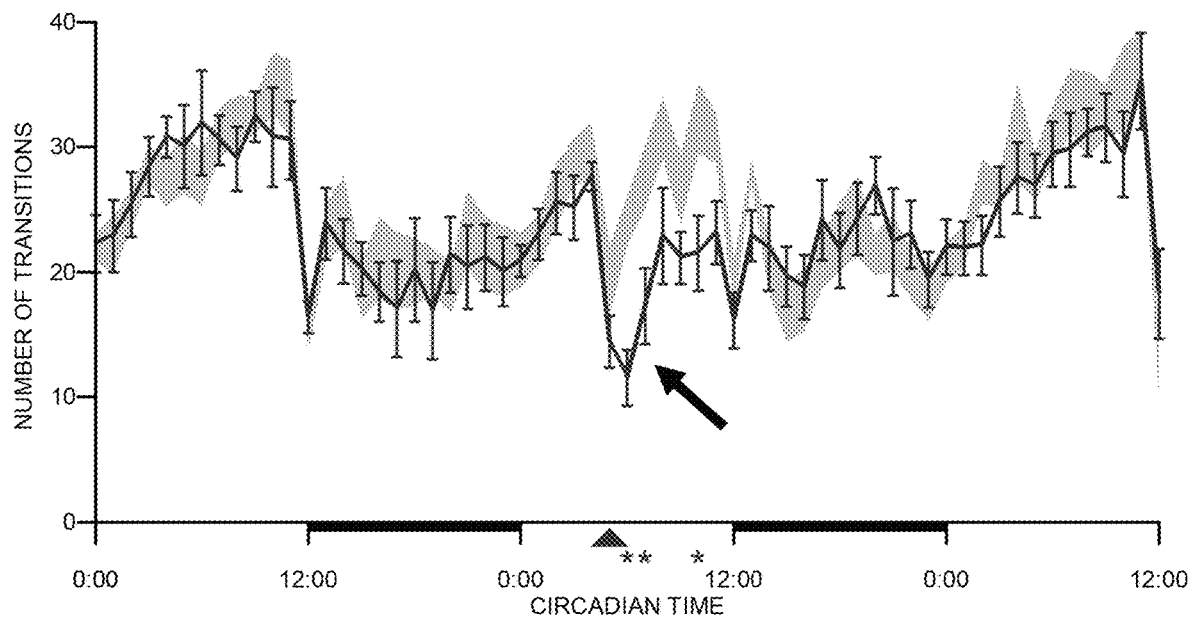
FIG. 6 depicts the number of transitions to wake per hour after administration of compound 7, wherein the thin line depicts compound 7 administration at 30 mg/kg PO (CT-5, n=8), and the thick line depicts administration of the control, 2HPβCD 20%, at 2 mL/kg PO (CT-5, n=10).

Compound 7 was administered to male Wistar rats at CT-5 (5 hours after light-on; time of treatment indicated by the triangle on the abscissa; FIG. 6), and reduced the number of arousals, as measured by the number of transitions from sleep to wake. Number transitions from sleep to wake are plotted as the population (N=8) hourly mean SEM 30 hours before (baseline) and after treatment. Differences from methylcellulose vehicle control are indicated by asterisks. 24 hour light-dark cycle (LD 12:12) is indicated on the abscissa (FIG. 6). Compound 7 produced a reduction in arousals, evidenced by up to 40-50% reductions in the number of transitions from sleep to wake per hour post-treatment relative to controls.

Increased Depth of Sleep as Measured by EEG Delta Power During nonREM Sleep

Figure 7:
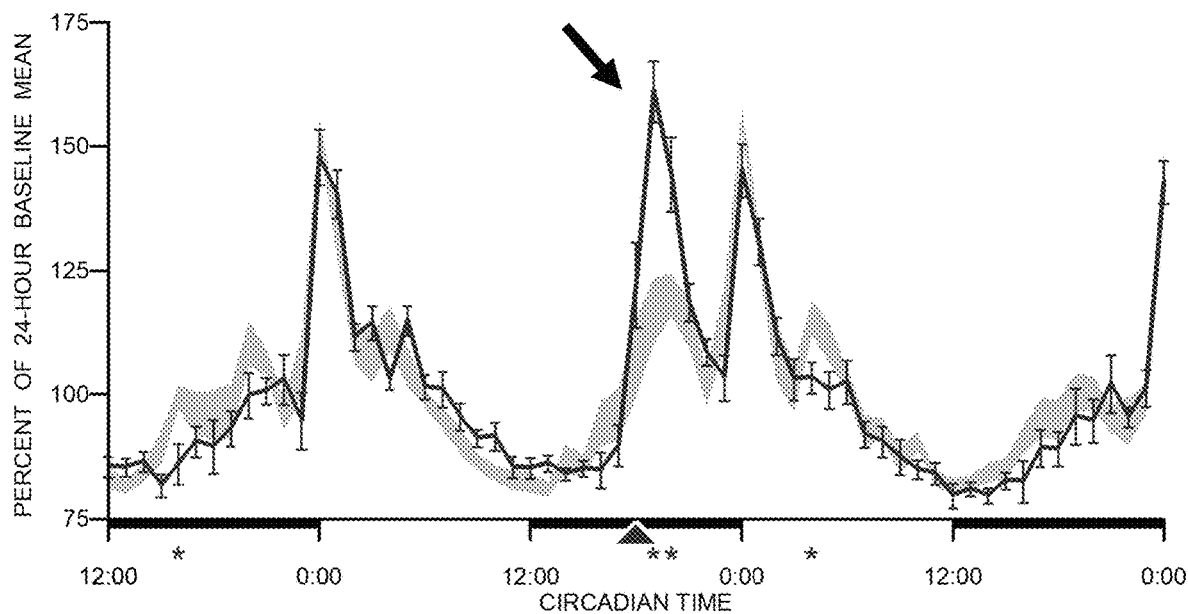
FIG. 7 depicts normalized EEG delta power after administration of compound 7, wherein the thin line depicts compound 7 administration at 30 mg/kg PO (CT-18, n=10), and the thick line depicts administration of the control, methylcellulose, at 1 mL/kg PO (CT-18, n=10).

Compound 7 was administered to male Wistar rats at CT-18 (6 hours after lights-off, time of treatment indicated by the triangle on the abscissa; FIG. 7) increases in EEG slow wave activity in nonREM sleep was recorded, as measured by the normalized (percent change from baseline) EEG delta power during nonREM sleep per hour. Normalized EEG delta power (power in the EEG at frequencies of 0.5-4.0 Hz, computed using Fourier analysis) is plotted in this example as the population (N=10) hourly mean SEM 30 hours before (baseline) and after treatment. Differences from methylcellulose vehicle control are indicated by asterisk. 24 hour light-dark cycle (LD 12:12) is indicated on the abscissa (FIG. 7). An increase in EEG delta power (slow wave activity) is consistent with an elevation in arousal threshold associated with the compounds ability to reduce sleep fragmentation.

Figure 8:
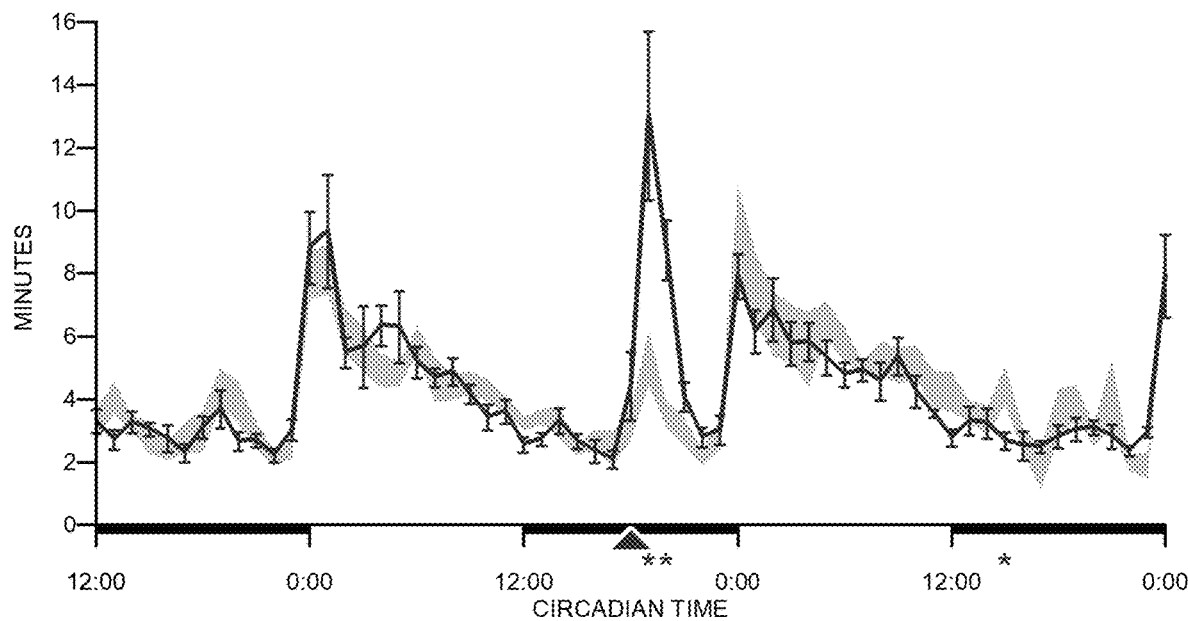
FIG. 8 depicts average aligned sleep bout each hour after administration of compound 15, wherein the thin line depicts compound 15 administration at 30 mg/kg PO (CT-18, n=11), and the thick line depicts administration of the control, 20% 2HPβCD, at 2 mL/kg PO (CT-18, n=11).

Example 33. Increased Sleep Continuity/Consolidation, Reduced the Number of Arousals and Increased Depth of Sleep Sleep Continuity/Consolidation Compound 15 was administered to male Wistar rats at CT-18 (6 hours after light-off, time of treatment indicated by the triangle on the abscissa; FIG. 8), and increased sleep continuity was measured by the average sleep bout duration per hour. Average sleep bout duration was calculated as the mean duration of all sleep bouts initiated in each hour for an individual animal, plotted as the population (N=11) hourly mean SEM 30 hours before (baseline) and after treatment. Differences from 20% HPβCD vehicle control are indicated by asterisks. 24 hour light-dark cycle (LD 12:12) is indicated on the abscissa (FIG. 8). Compound 15 produced an increase in sleep consolidation as exemplified by an increase in sleep bout-length per hour that was approximately 3-fold greater than the effects observed in vehicle control animals.

Reduced Number of Arousals

Figure 9:
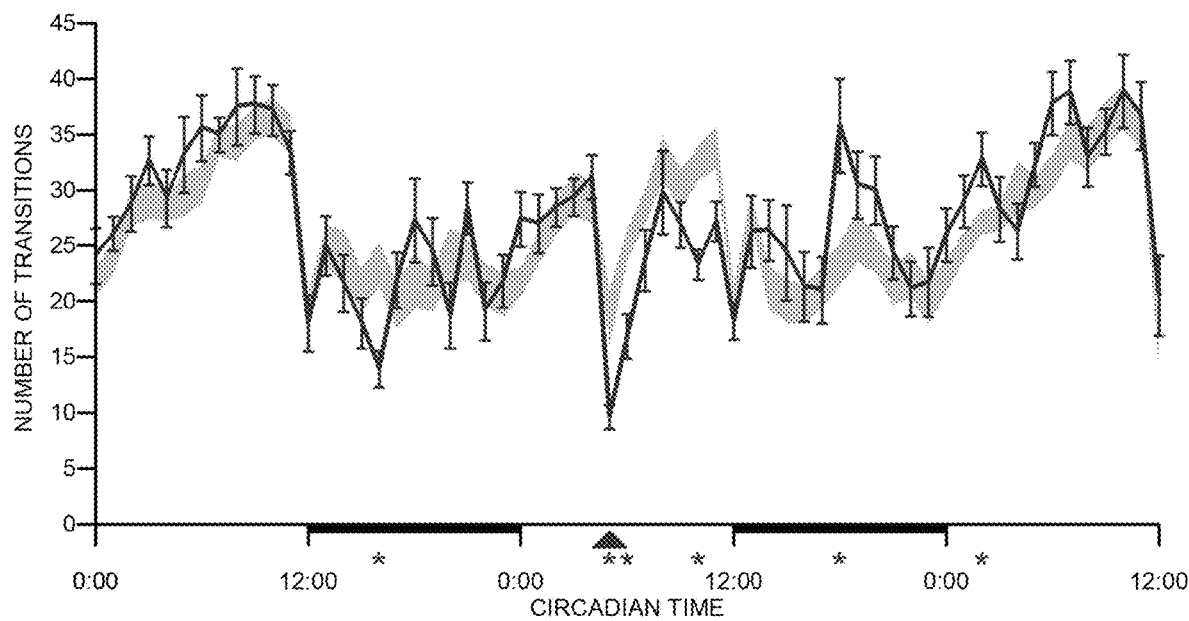
FIG. 9 depicts the number of transitions to wake per hour after administration of compound 15, wherein the thin line depicts compound 15 administration at 30 mg/kg PO (CT-5, n=10), and the thick line depicts administration of the control, 20% 2HPβCD, at 2 mL/kg PO (CT-5, n=20).

Compound 15 was administered to male Wistar rats at CT-5 (5 hours after light-on; time of treatment indicated by the triangle on the abscissa; FIG. 9), and reduced the number of arousals, as measured by the number of transitions from sleep to wake. The number of transitions from sleep to wake are plotted as the population (N=10) hourly mean SEM 30 hours before (baseline) and after treatment. Differences from 20% HPβCD vehicle control are indicated by asterisks. 24 hour light-dark cycle (LD 12:12) is indicated on the abscissa (FIG. 9). Compound 15 produced a reduction in arousals, evidenced by approximately 30% reductions in the number of transitions from sleep to wake per hour post-treatment relative to controls.

Increased Depth of Sleep as Measured by EEG Delta Power During nonREM Sleep

Figure 10:
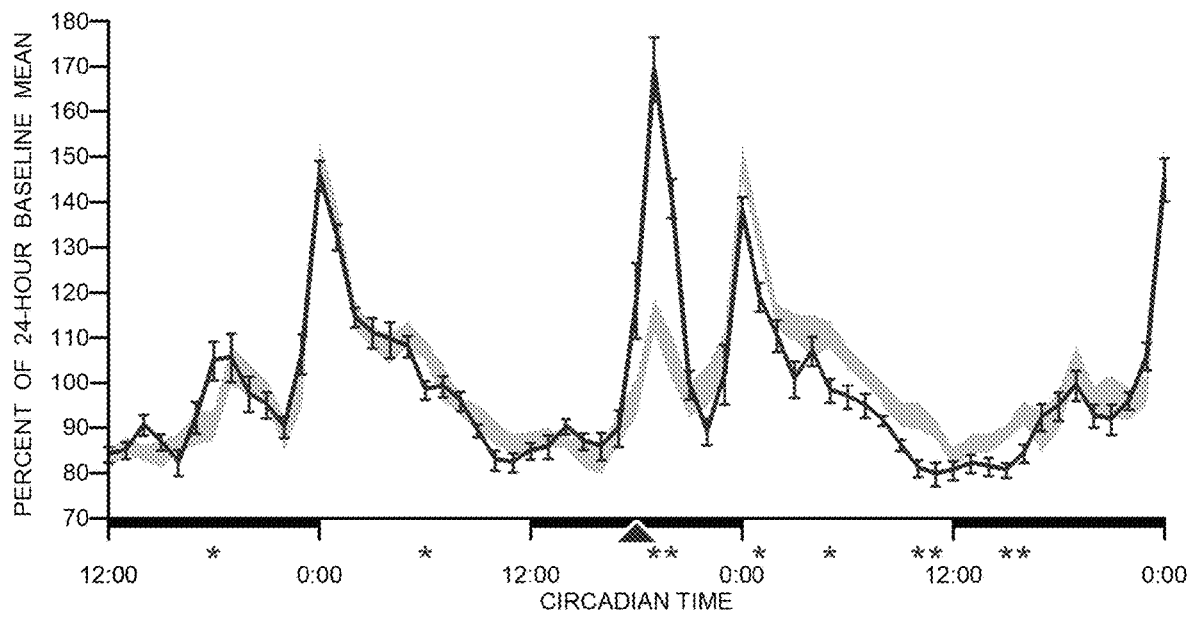
FIG. 10 depicts normalized EEG delta power after administration of compound 15, wherein the thin line depicts compound 15 administration at 30 mg/kg PO (CT-18, n=11), and the thick line depicts administration of the control, 20% 2HPβCD, at 2 mL/kg PO (CT-18, n=11).

Compound 15 was administered to male Wistar rats at CT-18 (6 hours after lights-off, time of treatment indicated by the triangle on the abscissa; FIG. 10) and increases in EEG slow wave activity in nonREM sleep were recorded, as measured by the normalized (percent change from baseline)

EEG delta power during nonREM sleep per hour. Normalized EEG delta power (power in the EEG at frequencies of 0.5-4.0 Hz, computed using Fourier analysis) is plotted in this example as the population (N=11) hourly mean SEM 30 hours before (baseline) and after treatment. Differences from 20% HPβCD vehicle control are indicated by asterisk. 24 hour light-dark cycle (LD 12:12) is indicated on the abscissa (FIG. 10). An increase in EEG delta power (slow wave activity) is consistent with an elevation in arousal threshold associated with the compounds ability to reduce sleep fragmentation.

EQUIVALENTS

The details of one or more embodiments of the disclosure are set forth in the accompanying description above. Although any methods and materials similar or equivalent to those described herein can be used in the practice or testing of the present disclosure, the preferred methods and materials are now described. Other features, objects, and advantages of the disclosure will be apparent from the description and from the claims. In the specification and the appended claims, the singular forms include plural referents unless the context clearly dictates otherwise. Unless defined otherwise, all technical and scientific terms used herein have the same meaning as commonly understood by one of ordinary skill in the art to which this disclosure belongs. All patents and publications cited in this specification are incorporated by reference.

The foregoing description has been presented only for the purposes of illustration and is not intended to limit the disclosure to the precise form disclosed, but by the claims appended hereto.

The invention claimed is:

1. A compound of Formula (I):

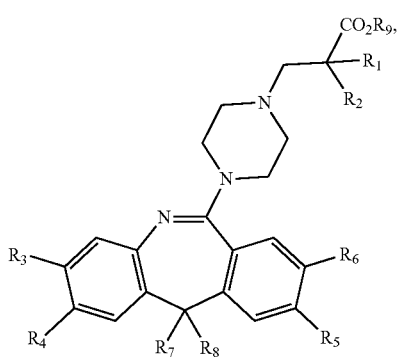

(I)

or a pharmaceutically acceptable salt thereof, wherein:

$R_1$ is $C_1$-$C_6$ alkyl, $C_2$-$C_6$ alkenyl, $C_2$-$C_6$ alkynyl, $C_1$-$C_6$ haloalkyl, $C_1$-$C_6$ alkoxyl, or $C_3$-$C_6$ cycloalkyl;

$R_2$ is $C_1$-$C_6$ alkyl, $C_2$-$C_6$ alkenyl, $C_2$-$C_6$ alkynyl, $C_1$-$C_6$ haloalkyl, $C_1$-$C_6$ alkoxyl, or $C_3$-$C_6$ cycloalkyl; or $R_1$ and $R_2$ together with the atoms to which they are attached form a $C_3$-$C_6$ saturated or partially unsaturated cycloalkyl or a 3- to 14-membered saturated or partially unsaturated heterocycle comprising 1-5 heteroatoms selected from N, O, and S;

$R_3$ is H, halogen, —S($C_1$-$C_6$ alkyl), —N($C_1$-$C_6$ alkyl)$_2$, —NH($C_1$-$C_6$ alkyl), —NH$_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxyl, $C_1$-$C_6$ haloalkoxyl, or $C_3$-$C_6$ cycloalkyl;

$R_4$ is H, halogen, —S($C_1$-$C_6$ alkyl), —N($C_1$-$C_6$ alkyl)$_2$, —NH($C_1$-$C_6$ alkyl), —NH$_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxyl, $C_1$-$C_6$ haloalkoxyl, or $C_3$-$C_6$ cycloalkyl;

$R_5$ is H, halogen, —S($C_1$-$C_6$ alkyl), —N($C_1$-$C_6$ alkyl)$_2$, —NH($C_1$-$C_6$ alkyl), —NH$_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxyl, $C_1$-$C_6$ haloalkoxyl, or $C_3$-$C_6$ cycloalkyl;

$R_6$ is H, halogen, —S($C_1$-$C_6$ alkyl), —N($C_1$-$C_6$ alkyl)$_2$, —NH($C_1$-$C_6$ alkyl), —NH$_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxyl, $C_1$-$C_6$ haloalkoxyl, or $C_3$-$C_6$ cycloalkyl;

$R_7$ is H, deuterium, $C_1$-$C_6$ alkyl, $C_2$-$C_6$ alkenyl, or $C_2$-$C_6$ alkynyl;

$R_8$ is H, deuterium, $C_1$-$C_6$ alkyl, $C_2$-$C_6$ alkenyl, or $C_2$-$C_6$ alkynyl; and $R_9$ is H, $C_1$-$C_6$ alkyl, $C_2$-$C_6$ alkenyl, $C_2$-$C_6$ alkynyl, $C_1$-$C_6$ haloalkyl, or $C_3$-$C_6$ cycloalkyl, provided that at least one of $R_3$, $R_4$, $R_5$, and $R_6$ is H.

2. The compound of claim 1, wherein $R_1$ is $C_1$-$C_6$ alkyl.

3. The compound of claim 1, wherein $R_2$ is $C_1$-$C_6$ alkyl.

4. The compound of claim 1, wherein $R_3$ is H, halogen, $C_1$-$C_6$ alkyl, or $C_1$-$C_6$ alkoxyl.

5. The compound of claim 1, wherein $R_4$ is H, halogen, $C_1$-$C_6$ alkyl, or $C_1$-$C_6$ haloalkyl.

6. The compound of claim 1, wherein $R_5$ is H, halogen, $C_1$-$C_6$ alkyl, $C_1$-$C_6$ alkoxyl, S($C_1$-$C_6$ alkyl), or $C_1$-$C_6$ haloalkyl.

7. The compound of claim 1, wherein $R_6$ is H, $C_1$-$C_6$ alkyl, or $C_1$-$C_6$ alkoxyl.

8. The compound of claim 1, wherein $R_7$, $R_8$, and $R_9$ are H.

9. The compound of claim 1, wherein the compound is of Formula (Ia):

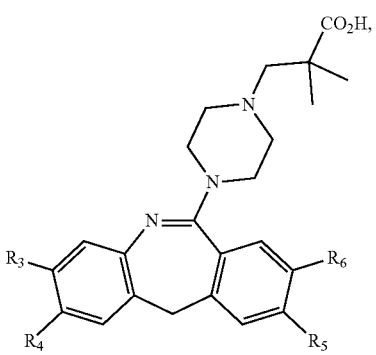

(Ia)

or a pharmaceutically acceptable salt thereof, wherein, $R_3$ is H, halogen, $C_1$-$C_6$ alkyl, or $C_1$-$C_6$ alkoxyl;

$R_4$ is H, halogen, $C_1$-$C_6$ alkyl, or $C_1$-$C_6$ haloalkyl;

$R_5$ is H, halogen, $C_1$-$C_6$ alkyl, $C_1$-$C_6$ alkoxyl, S($C_1$-$C_6$ alkyl), or $C_1$-$C_6$ haloalkyl; and $R_6$ is H, $C_1$-$C_6$ alkyl, or $C_1$-$C_6$ alkoxyl.

10. The compound of claim 1, wherein the compound is:
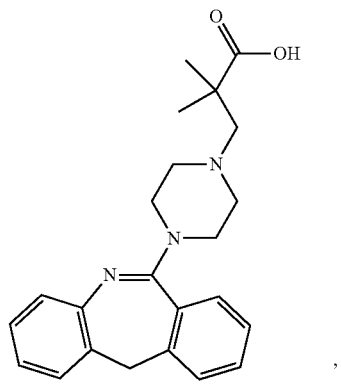
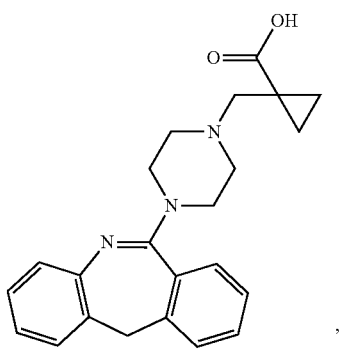
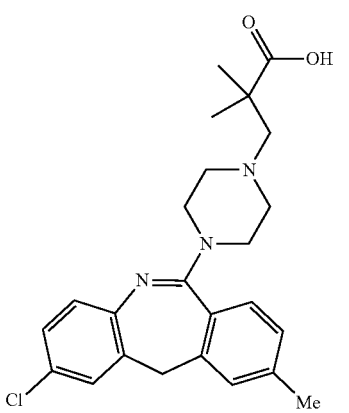
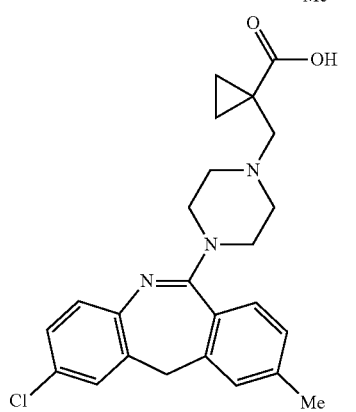
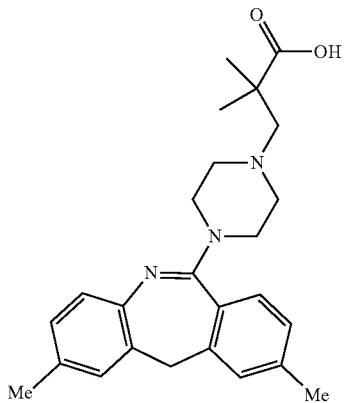
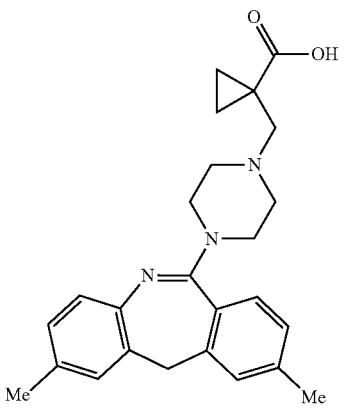
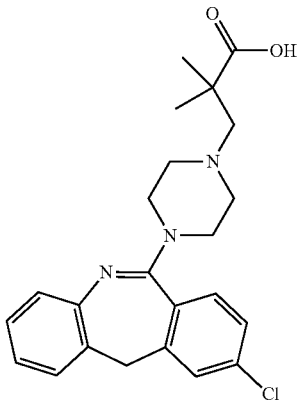
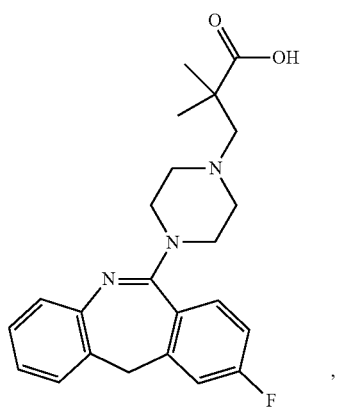, or -continued

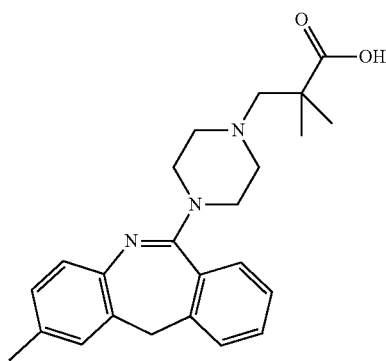

or a pharmaceutically acceptable salt thereof.

11. The compound of claim 1, wherein the compound is:

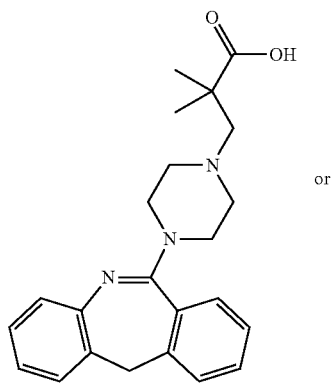 or

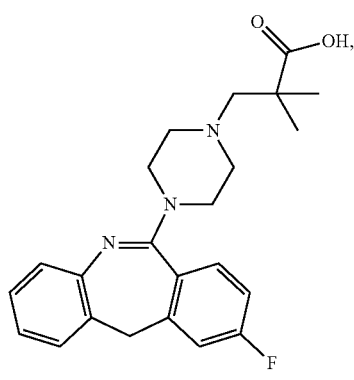

or a pharmaceutically acceptable salt thereof.

12. The compound of claim 1, wherein the compound is:

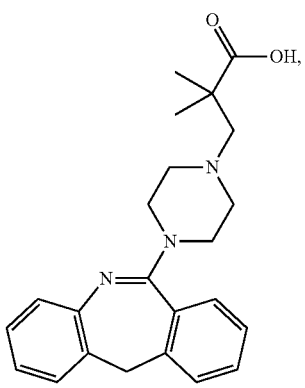 [SMILES: CC(C)(CN1CCN(C2=Nc3ccccc3Cc3ccccc32)CC1)C(=O)O]

or a pharmaceutically acceptable salt thereof.

13. The compound of claim 1, wherein the compound is:

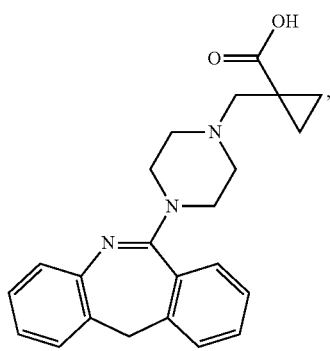 [SMILES: O=C(O)C1(CN2CCN(C3=Nc4ccccc4Cc4ccccc43)CC2)CC1]

or a pharmaceutically acceptable salt thereof.

14. The compound of claim 1, wherein the compound is:

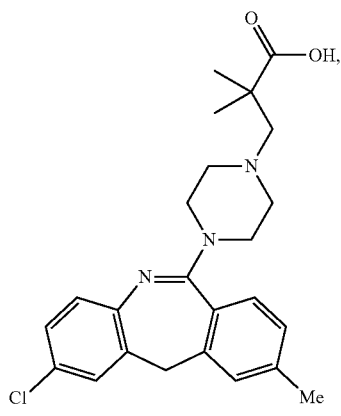 [SMILES: Cc1ccc2c(c1)Cc1cc(Cl)ccc1N=C2N1CCN(CC(C)(C)C(=O)O)CC1]

or a pharmaceutically acceptable salt thereof.

15. The compound of claim 1, wherein the compound is:

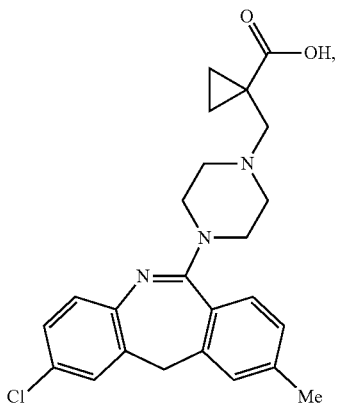 [SMILES: Cc1ccc2c(c1)Cc1cc(Cl)ccc1N=C2N1CCN(CC2(C(=O)O)CC2)CC1]

or a pharmaceutically acceptable salt thereof.

16. The compound of claim 1, wherein the compound is:

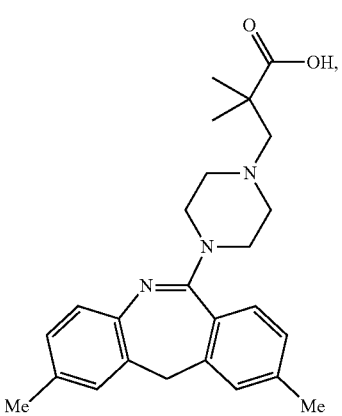 [SMILES: Cc1ccc2c(c1)Cc1cc(C)ccc1C(N1CCN(CC(C)(C)C(=O)O)CC1)=N2]

or a pharmaceutically acceptable salt thereof.

17. The compound of claim 1, wherein the compound is:

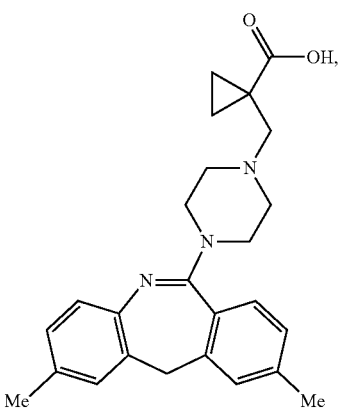

or a pharmaceutically acceptable salt thereof.

18. The compound of claim 1, wherein the compound is:

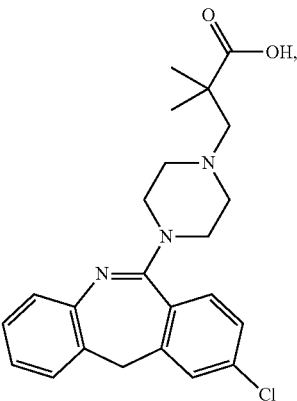 [SMILES: CC(C)(CN1CCN(C2=Nc3ccccc3Cc3cc(Cl)ccc32)CC1)C(=O)O]

or a pharmaceutically acceptable salt thereof.

19. The compound of claim 1, wherein the compound is:

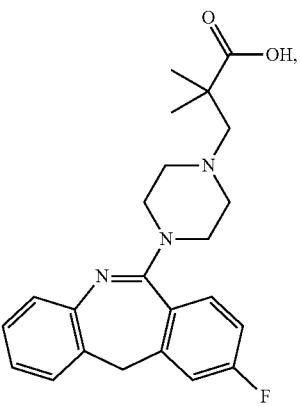 [SMILES: CC(C)(CN1CCN(C2=Nc3ccccc3Cc3cc(F)ccc32)CC1)C(=O)O]

or a pharmaceutically acceptable salt thereof.

20. The compound of claim 1, wherein the compound is:

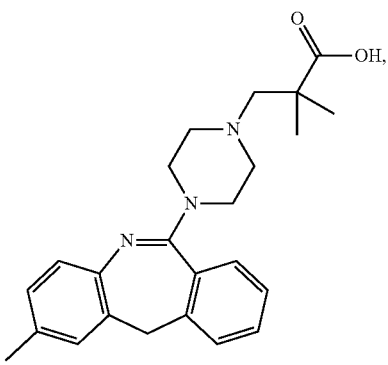 [SMILES: Cc1ccc2c(c1)Cc1ccccc1C(N1CCN(CC(C)(C)C(=O)O)CC1)=N2]

or a pharmaceutically acceptable salt thereof.

21. A pharmaceutical composition comprising the compound of claim 1 or a pharmaceutically acceptable salt thereof, and a pharmaceutically acceptable diluent or carrier.

22. A method of treating increased sleep fragmentation in a subject in need thereof by administering to the subject a compound of claim 1, or a pharmaceutically acceptable salt thereof.

* * * * *

UNITED STATES PATENT AND TRADEMARK OFFICE
CERTIFICATE OF CORRECTION

PATENT NO. : 11,046,651 B2
APPLICATION NO. : 17/075468
DATED : June 29, 2021
INVENTOR(S) : Mark E. Duggan et al.

It is certified that error appears in the above-identified patent and that said Letters Patent is hereby corrected as shown below:

On the Title Page

Page 2, Item (56) References Cited/Other Publications:
"allosteric modulators of the mGlus receptor" should read: -- allosteric modulators of the mGlu$_5$ receptor --.

Signed and Sealed this
Sixteenth Day of August, 2022

Katherine Kelly Vidal
*Director of the United States Patent and Trademark Office*